(12) United States Patent
Quay et al.

(10) Patent No.: US 12,201,591 B2
(45) Date of Patent: Jan. 21, 2025

(54) SUSTAINED RELEASE COMPOSITIONS OF ENDOXIFEN

(71) Applicant: Atossa Therapeutics, Inc., Seattle, WA (US)

(72) Inventors: Steven C. Quay, Seattle, WA (US); Naresh Kumar Reddy Vutukuru, Ann Arbor, MI (US); Srinivasan Shanmugam, Ypsilanti, MI (US)

(73) Assignee: Atossa Therapeutics, Inc., Seattle, WA (US)

( * ) Notice: Subject to any disclaimer, the term of this patent is extended or adjusted under 35 U.S.C. 154(b) by 0 days.

(21) Appl. No.: 17/624,329

(22) PCT Filed: Jul. 2, 2020

(86) PCT No.: PCT/US2020/040757
§ 371 (c)(1),
(2) Date: Dec. 31, 2021

(87) PCT Pub. No.: WO2021/003433
PCT Pub. Date: Jan. 7, 2021

(65) Prior Publication Data
US 2022/0175702 A1 Jun. 9, 2022

Related U.S. Application Data

(60) Provisional application No. 63/021,549, filed on May 7, 2020, provisional application No. 62/989,342, filed on Mar. 13, 2020, provisional application No. 62/870,656, filed on Jul. 3, 2019.

(51) Int. Cl.
| | |
|---|---|
| *A61K 9/28* | (2006.01) |
| *A61K 9/20* | (2006.01) |
| *A61K 31/135* | (2006.01) |
| *A61K 31/138* | (2006.01) |
| *A61K 31/343* | (2006.01) |
| *A61K 31/4525* | (2006.01) |
| *A61K 31/496* | (2006.01) |
| *A61P 35/00* | (2006.01) |

(52) U.S. Cl.
CPC .......... *A61K 31/138* (2013.01); *A61K 9/2013* (2013.01); *A61K 9/2027* (2013.01); *A61K 9/2054* (2013.01); *A61K 9/2095* (2013.01); *A61K 9/2813* (2013.01); *A61K 9/282* (2013.01); *A61K 9/2846* (2013.01); *A61K 31/135* (2013.01); *A61K 31/343* (2013.01); *A61K 31/4525* (2013.01); *A61K 31/496* (2013.01); *A61P 35/00* (2018.01)

(58) Field of Classification Search
CPC ...... A61K 9/20; A61K 9/2004; A61K 9/2009; A61K 9/2013; A61K 9/2018; A61K 9/205; A61K 9/2054; A61K 9/2059; A61K 9/2095
See application file for complete search history.

(56) References Cited

U.S. PATENT DOCUMENTS

| | | |
|---|---|---|
| 3,848,030 A | 11/1974 | Viterbo et al. |
| 4,851,433 A | 7/1989 | Kraus |
| 6,774,122 B2 | 8/2004 | Evans et al. |
| 7,384,418 B2 | 6/2008 | Hung et al. |
| 7,485,623 B2 | 2/2009 | Bua |
| 7,507,769 B2 | 3/2009 | Nestour |
| 7,531,578 B2 | 5/2009 | Forman et al. |
| 7,704,516 B2 | 4/2010 | Drouin et al. |
| 7,705,159 B2 | 4/2010 | MacDonald et al. |
| 7,786,172 B2 | 8/2010 | De et al. |
| 7,968,532 B2 | 6/2011 | Le et al. |
| 8,048,927 B2 | 11/2011 | Le Nestour |
| 8,058,302 B2 | 11/2011 | Solanki et al. |
| 8,063,249 B1 | 11/2011 | Kushner et al. |
| 8,119,695 B2 | 2/2012 | Forman et al. |
| 8,329,680 B2 | 12/2012 | Evans et al. |
| 8,436,029 B2 | 5/2013 | Hickey et al. |
| 8,454,945 B2 | 6/2013 | McCook et al. |
| 8,466,139 B2 | 6/2013 | Evans et al. |
| 8,822,511 B2 | 9/2014 | Combs et al. |
| 8,993,605 B2 | 3/2015 | Combs et al. |
| 9,073,875 B2 | 7/2015 | Boyall et al. |

(Continued)

FOREIGN PATENT DOCUMENTS

| | | |
|---|---|---|
| CN | 101891635 A | 11/2010 |
| CN | 102448467 A | 5/2012 |

(Continued)

OTHER PUBLICATIONS

Ahamad A., et al., "Endoxifen, A New Cornerstone of Breast Cancer Therapy: Demonstration of Safety, Tolerability and Systemic Bioavailability in Healthy Human Subjects," Clinical Pharmacology & Therapeutics, Dec. 2010, vol. 88 (6), pp. 814-817.

(Continued)

*Primary Examiner* — Micah Paul Young
(74) *Attorney, Agent, or Firm* — DLA Piper LLP; Melissa Harwood

(57) ABSTRACT

The present disclosure provides sustained release compositions of (Z)-endoxifen and polymorphs and salts thereof and methods of making sustained release compositions of (Z)-endoxifen and polymorphs and salts thereof. The present disclosure also provides methods for treating disorders susceptible to (Z)-endoxifen, including hormone dependent disorders and mood disorders.

31 Claims, 18 Drawing Sheets

(56) References Cited

U.S. PATENT DOCUMENTS

| | | |
|---|---|---|
| 9,090,640 B2 | 7/2015 | Bierbach et al. |
| 9,200,045 B2 | 12/2015 | Liu et al. |
| 9,220,680 B2 | 12/2015 | Perumal et al. |
| 9,308,181 B2 | 4/2016 | Kisak et al. |
| 9,333,190 B2 | 5/2016 | Ahmad et al. |
| 11,261,151 B2 | 3/2022 | Quay et al. |
| 11,572,334 B2 | 2/2023 | Quay et al. |
| 11,680,036 B1 | 6/2023 | Quay et al. |
| 2002/0025543 A1 | 2/2002 | Serrero |
| 2003/0021787 A1 | 1/2003 | Hung et al. |
| 2003/0099694 A1 | 5/2003 | Cevc et al. |
| 2003/0147950 A1 | 8/2003 | Platteeuw et al. |
| 2004/0092894 A1 | 5/2004 | Hung et al. |
| 2006/0280795 A1* | 12/2006 | Penhasi ............... A61K 9/4891 424/472 |
| 2007/0059288 A1 | 3/2007 | Dinsmore et al. |
| 2007/0161063 A1 | 7/2007 | Love et al. |
| 2007/0190019 A1 | 8/2007 | Guo et al. |
| 2008/0138391 A1 | 6/2008 | Carrara et al. |
| 2008/0319092 A1 | 12/2008 | Singh |
| 2009/0068190 A1 | 3/2009 | Bortz |
| 2009/0098069 A1 | 4/2009 | Vacca |
| 2009/0208944 A1 | 8/2009 | Goetz et al. |
| 2009/0281063 A1 | 11/2009 | Inagi et al. |
| 2009/0291102 A1 | 11/2009 | Fortin |
| 2009/0291134 A1 | 11/2009 | Ahmad et al. |
| 2010/0015195 A1 | 1/2010 | Jain et al. |
| 2010/0015200 A1 | 1/2010 | McClain et al. |
| 2010/0069781 A1 | 3/2010 | Johansen et al. |
| 2010/0098659 A1 | 4/2010 | Watson et al. |
| 2010/0112041 A1 | 5/2010 | Ahmad et al. |
| 2012/0010245 A1 | 1/2012 | Masini-Eteve |
| 2012/0149761 A1 | 6/2012 | Quay |
| 2012/0164075 A1 | 6/2012 | Ahmad et al. |
| 2012/0301541 A1 | 11/2012 | Haronsky et al. |
| 2013/0046171 A1 | 2/2013 | Johansen et al. |
| 2013/0177590 A1 | 7/2013 | Combs et al. |
| 2013/0197087 A1 | 8/2013 | Schlotzer et al. |
| 2014/0088059 A1 | 3/2014 | Perumal et al. |
| 2014/0193334 A1 | 7/2014 | Bierbach et al. |
| 2014/0199391 A1 | 7/2014 | Birbara |
| 2015/0080339 A1 | 3/2015 | Wang et al. |
| 2015/0132388 A1 | 5/2015 | Angi et al. |
| 2015/0141391 A1 | 5/2015 | Chinnaiyan et al. |
| 2015/0250802 A1 | 9/2015 | Labrie et al. |
| 2016/0045502 A1 | 2/2016 | Brown |
| 2016/0346230 A1 | 12/2016 | Ahmad et al. |
| 2016/0375234 A1 | 12/2016 | Quay |
| 2017/0145515 A1 | 5/2017 | Chen et al. |
| 2017/0304232 A1 | 10/2017 | Khan et al. |
| 2018/0049999 A1 | 2/2018 | Quay |
| 2018/0200206 A1 | 7/2018 | Quay |
| 2019/0269697 A1 | 9/2019 | Labrie |
| 2020/0207704 A1 | 7/2020 | Quay et al. |
| 2023/0365490 A1 | 11/2023 | Quay et al. |

FOREIGN PATENT DOCUMENTS

| | | | |
|---|---|---|---|
| CN | 105579044 A | 5/2016 | |
| CN | 104230723 B | 8/2016 | |
| EP | 1731142 A1 | 12/2006 | |
| EP | 2101731 A2 | 9/2009 | |
| EP | 2350111 A1 | 8/2011 | |
| EP | 2508174 A1 * | 10/2012 | ........... A61K 31/198 |
| EP | 1709062 B9 | 2/2013 | |
| EP | 3202420 A1 | 8/2017 | |
| EP | 3202420 B1 | 3/2020 | |
| WO | WO-0064416 A3 | 3/2001 | |
| WO | WO-0174366 A1 | 10/2001 | |
| WO | 03039531 A1 | 5/2003 | |
| WO | WO-2008066783 A2 * | 6/2008 | ........... A61K 31/522 |
| WO | WO-2008070463 A2 | 6/2008 | |
| WO | WO-2008070463 A9 | 9/2008 | |
| WO | WO-2009032699 A1 | 3/2009 | |
| WO | WO-2009069140 A1 | 6/2009 | |
| WO | WO-2009120999 A2 | 10/2009 | |
| WO | WO-2009120999 A3 | 12/2009 | |
| WO | WO-2010066810 A1 | 6/2010 | |
| WO | WO-2010135703 A2 | 11/2010 | |
| WO | 2011007353 A1 | 1/2011 | |
| WO | WO-2011072244 A1 | 6/2011 | |
| WO | WO-2012050263 A1 | 4/2012 | |
| WO | WO-2012089677 A1 | 7/2012 | |
| WO | 2012162492 A1 | 11/2012 | |
| WO | WO-2013050280 A1 | 4/2013 | |
| WO | WO-2013134230 A1 | 9/2013 | |
| WO | WO-2014134165 A1 | 9/2014 | |
| WO | WO-2014141292 A2 | 9/2014 | |
| WO | WO-2014060640 A8 | 5/2015 | |
| WO | WO-2015106094 A1 | 7/2015 | |
| WO | WO-2015138340 A1 | 9/2015 | |
| WO | WO-2015187727 A2 | 12/2015 | |
| WO | WO-2016168021 A1 | 10/2016 | |
| WO | 2016187122 A1 | 11/2016 | |
| WO | WO-2017011623 A1 | 1/2017 | |
| WO | WO-2017070651 A1 | 4/2017 | |
| WO | WO-2017080770 A1 | 5/2017 | |
| WO | WO-2019051368 A1 | 3/2019 | |
| WO | WO-2019051370 A1 | 3/2019 | |
| WO | WO-2019051416 A1 * | 3/2019 | ........... A61K 31/138 |

OTHER PUBLICATIONS

Ahmad A., et al., "Endoxifen, A New Treatment Option for Mania: A Double-Blind, Active-Controlled Trial Demonstrates the Antimanic Efficacy of Endoxifen," Clinical and Translational Science, vol. 9 (5), Oct. 2016, pp. 252-259.

Ahmad A., et al., "Endoxifen for Breast Cancer: Multiple Dose, Dose Escalation Study Characterizing Pharmacokinetics and Safety in Metastatic Breast Cancer Patients," Journal of Clinical Oncology, vol. 30 (15), May 20, 2012, Abstarct 3089, 3 pages.

Ahmad A., et al., "Orally Administered Endoxifen is a New Therapeutic Agent for Breast Cancer," Breast Cancer Research Treatment, vol. 122 (2), Jul. 2010, pp. 579-584.

Aydiner, et al., "Meta-Analysis of Trials Comparing Anastrozole and Tamoxifen for Adjuvant Treatment of Oostmenopausal Women with Early Breast Cancer," Trials, vol. 9 (47), Jul. 29, 2008, pp. 1-9.

Bao, et al., "The Clinical Pharmacology of Anastrozole," European Oncology and Hematology, vol. 7 (2), 2011, pp. 106-108.

Bath, et al., "An Improved Sysnthesis of Raloxifene Hydrochoride: A Selective Estrogen Receptor Modulator," Heteroletters, vol. 4 (4), 2014, pp. 515-518.

Berg, et al., "Breat Imaging Reporting Data System: Inter-and Intraobserver Variablitiy in Feature Analysis and Final Assessment," 2000, pp. 1769-1777.

Bernhard H., et al., "Adoptive Transfer of Autologous, HER2-Specific, Cytotoxic T Lymphocytes for the Treatment of HER2-Overexpressing Breast Cancer," Cancer Immunology, Immunotherapy, 2008, vol. 57, pp. 271-280.

Chang M., "Tamoxifen Resistance in Breast Cancer," Biomolecules Therapeutics, May 2012, vol. 20 (3), pp. 256-267.

Clinical Trials Government, Identifier No. NCT01273168, "Endoxifen in Adults With Hormone Receptor Positive Solid Tumors," Jan. 10, 2011, 10 pages.

Clinical Trials Government, Identifier No. NCT02311933, "Tamoxifen Citrate or Z-Endoxifen Hydrochloride in Treating Patients With Locally Advanced or Metastatic, Estrogen Receptor-Positive, HER2-Negative Breast Cancer," Dec. 9, 2014, 13 pages.

Davison, et al., "In Vitro Effects on MCF-7 Breast Cancer Cells of Signal Transduction Inhibitor/Tamoxifen/ Eicosapentaenoic Acid Combinations and their Simultaneous Delivery Across Skin," Pharmaceutical Research, vol. 25, 2008, pp. 2516-2525.

Dowsett, et al., "The Effect of Anastrozole on the Pharmacokinetics of Tamoxifen in Post-Menopausal Women with Early Breast Cancer," British Journal of Cancer, vol. 79 (2), 1999, pp. 311-315.

Fasching P.A., et al., "Ki67, Chemotherapy Response and Prognosis in Breast Cancer Patients receiving Neoadjuvant Treatment," BMC Cancer, vol. 11, Article 486, 2011, 13 pages.

(56) References Cited

OTHER PUBLICATIONS

Fauq A.H., et al., "A Convenient Synthesis of (Z)-4-Hydroxy-N-Desmethyltamoxifen (Endoxifen)," Bioorganic and Medicinal Chemistry Letters, vol. 20 (10), 2010, pp. 3036-3038.

Forbes, et al., "Anastrozole Versus Tamoxifen for the Prevention of Locoregional and Contralateral Breast Cancer in Postmenopausal Women with Locally Excised Ductal Carcinoma in Situ (IBIS-II DCIS): A Double-Blind," Randomised Controlled trial Lancet, vol. 387, 2016, pp. 866-873.

Gauthier S., et al., "New Highly Stereoselective Synthesis of (Z)-4-Hydroxytamoxifen and (Z)-4-Hydroxytoremifene via McMurry Reaction," The Journal of Organic Chemistry, vol. 61(11), May 31, 1996, pp. 3890-3893.

Gelmon, et al., "Targeting Triple-Negative Breast Cancer: Optimizing Therapeutic Outcomes," Annals of Oncology, vol. 23 (9), Sep. 2012, pp. 2223-2234.

Goetz M.P., et al., "A First-in-Human Phase I Study of the Tamoxifen (TAM) Metabolite, Z-Endoxifen Hydrochloride (Z-Endx) in Women with Aromatase Inhibitor (AI) Refractory Metastatic Breast Cancer (MBC) (NCT01327781)," San Antonio Breast Conference, Dec. 2013, PD3-4, 4 pages.

Goetz M.P., et al., "Abstract PD2-03: Final Results of a First-in-Human Phase I Study of the Tamoxifen (TAM) Metabolite, Z-Endoxifen Hydrochloride (Z-Endx) in Women with Aromatase Inhibitor (AI) Refractory Metastatic Breast Cancer (MBC) (NCT01327781)," San Antonio breast cancer symposium, Dec. 8-12, 2015, 5 pages.

Goetz M.P., et al., "Final Results of a First in Human Phase I Study of the Tamoxifen (TAM) Metabolite, Endoxifen Hydrochloride in Women with Aromatase Inhibitor (AI) Refractory Metastatic Breast Cancer (MBC) (NCT01327781)," San Antonio Breast Conference, 2015, PD203, 1 page.

Goetz M.P., et al., "First-in-Human Phase I Study of the Tamoxifen Metabolite Z-Endoxifen in Women With Endocrine-Refractory Metastatic Breast Cancer," DOI: https://ascopubs.org/doi/10.1200/JCO.2017.73.3246, vol. 35, No. 30, Oct. 20, 2017, 16 pages.

Hawse J.R., et al., "Endoxifen's Molecular Mechanisms of Action are Concentration Dependent and Different than that of other Anti-Estrogens," PLOS one, vol. 8 (1), Jan. 2013, e54613, 18 pages.

Hershman, et al., "Early Discontinuation and Non-adherence to Adjuvant Hormonal Therapy in a Cohort of 8, 769 early Stage Breast Cancer Patients," Journal of Clinical Oncology, vol. 26(27), Sep. 20, 2010.

Ikeda H., et al., "Combination Treatment with Fulvestrant and various Cytotoxic Agents (Doxorubicin, Paclitaxel, Docetaxel, Vinorelbine, and 5-Fluorouracil) has a Synergistic Effect in Estrogen Receptor-Positive Breast Cancer," Cancer Science, vol. 102 (11), Nov. 2011, pp. 2038-2042, 5 p.

Ingle, et al., "Variation in Anastrozole Metabolism and Pharmacodynamics in Women with Early Breast Cancer," Cancer Research, vol. 70 (8), Apr. 15, 2010, pp. 3278-3286.

International Search Report and Written Opinion for International Application No. PCT/US2020/040757, mailed Oct. 9, 2020, 11 pages.

Jansen, et al., "High miR-26a and Low CDC2 Levels Associate with Decreased EZH2 Expression and with Favorable Putcome on Tamoxifen in Metastatic Breast Cancer," Breast Cancer ResearchTreatment, vol. 133, 2012, pp. 937-947.

Johnson M.D., et al., "Pharmacological Characterization of 4-Hydroxy-N-Desmethyl Tamoxifen, A Novel Active Metabolite of Tamoxifen," Breast Cancer Research and Treatment, vol. 85, 2004, pp. 151-159.

Johnson R.E., et al., "Gynecomastia—Evaluation and Current Treatment Options," Therapeutics and Clinical Risk Management, vol. 7, 2011, pp. 145-148.

Kamdem, et al., "In Vitro and in Vivo Oxidative Metabolism and Glucuronidation of Anastrozole," British Journal of Clinical Pharmacology, vol. 70 (6), 2010, pp. 854-869.

Karlsson H., et al., "CAR T-Cell Therapy: The Role of Physical Barriers and Immunosuppression in Lymphoma," Gene Ther, Aug. 2015, vol. 26(8), https://pubmed.ncbi.nlm.nih.gov/26230974/, pp. 498-505.

Kaur, et al., "Design, Synthesis and Evaluation of Ospemifene Analogs as Anti-Breast Cancer Agents," European Journal of Medicinal Chemistry, vol. 86, Oct. 30, 2014, pp. 211-218.

Kebamo., et al., "The Role of Biotransformation in Drug Discovery and Development," Journal of Drug Metabolism and Toxicology, vol. 6 (5), 2015, pp. 1-13.

Lancet, "Aromatase Inhibitors Versus Tamoxifen in Early Breast Cancer: Patient-Level Meta-Analysis of the Randomised Trials," vol. 386, 2015, pp. 1341-1352.

Lari, et al., "Biological Markers in DCIS and Risk of Breast Recurrence: A Systematic Review," Journal of Cancer, vol. 2, 2011, pp. 232-261.

Lee O., et al., "In Vitro Human Skin Permeation of Endoxifen: Potential for Local Transdermal Therapy for Primary Prevention and Carcinoma in Situ of the Breast," Breast Cancer: Targets and Therapy, vol. 3, 2011, pp. 61-70.

Lee O., et al., "Local Transdermal Therapy to the Breast for Breast Cancer Prevention and DCIS Therapy: Preclinical and Clinical Evaluation," Cancer Chemother Pharmacol, vol. 76(6), Dec. 2015, pp. 1235-1246.

Lehmann, "Identification of Human Triple-Negative Breast Cancer Subtypes and Preclinical Models for Selection of Targeted Therapies," Journal of Clinical Invest, vol. 121 (7), 2011, pp. 2750-2767.

Lemaine, et al., "Gynecomastia in Adolescent Males," Seminars Plastic Surgery, vol. 27 (1), Feb. 2013, pp. 56-61.

Li L., et al., "Prognostic Values of Ki-67 in Neoadjuvant Setting for Breast Cancer: A Systematic Review and Meta-Analysis," Future Oncology, vol. 13(11), May 2017, pp. 1021-1034.

Liby, et al., "The Combination of the Rexinoid, LG100268, and a Selective Estrogen Receptor Modulator, Either Arzoxifene or A colbifene, Synergizes in the Prevent and Treatment of Mammary Tumors in an Estrogen Receptor-Negative Model of Breast Cancer," Clinical Cancer Research, vol. 12 (19), Oct. 2006, pp. 5902-5909.

Mah, et al., "A Miniaturized Flow-through Cell to Evaluate Skin Permeation of Endoxifen," International Journal of pharmaceutics, vol. 441, 2013, pp. 433-440.

Mahoney M.E., et al., "Intraductal Therapy of Ductal Carcinoma In Situ: A Presurgery Study," Clinical Breast Cancer, Aug. 2013, 13(4), pp. 280-286.

Mansel R., et al., "A Phase II Trial of Afimoxifene (4-hydroxyTamoxifen gel) for Cyclical Mastalgia in Premenopausal Women," Breast Cancer Research Treatment, Dec. 2007, vol. 106 (3), pp. 389-397.

Maximov P.Y., et al., "Structure-Function Relationships of Estrogenic Triphenylethylenes Related to Endoxifen and 4-Hydroxytamoxifen," Journal of Medicinal Chemistry, Apr. 22, 2010, vol. 53 (8), pp. 3273-3283.

Melnikow J., et al., "Preferences of Women Evaluating Risks of Tamoxifen (POWER) study of preferences for Tamoxifen for Breast Cancer Risk Reduction," Cancer, vol. 103 (10), May 15, 2005, pp. 1996-2005.

Memorial Sloan Kettering: "T-Cell Therapy for Advanced Breast Cancer," 2016, pp. 1-8.

Miller, et al., "Stereospecific Synthesis of (Z)-Tamoxifen via Carbometallation of Alkynylsilanes," The Journal of Organic Chemistry, vol. 50 (12), 1985, pp. 2121-2123.

Ogawa K., et al., "Synthesis and Antiestrogenic Activity of the Compounds Related to the Metabolites of (Z)-4-[1-[4-[2-(Dimethylamino)ethoxy]phenyl]- 2-(4-isopropylphenyl)-1-butenyl]phenyl monophosphate (TAT-59)," Chemical and Pharmaceutical Bulletin, Apr. 1991, vol. 39(4), pp. 911-916.

Partridge, et al., "Adherence to Initial Adjuvant Anastrozole Therapy among Women with Early Stage Breast Cancer," Journal Clinical Oncology, Feb. 1, 2008, vol. 26 (4).

Partridge, et al., "Nonadherence to Adjuvant Tamoxifen Therapy in Women with Primary Breast Cancer," Journal of Clinical Oneology, Feb. 15, 2003, vol. 21.

Robertson, et al., "Fulvestrant: Pharmacokinetics and Pharmacology," British Journal of Cancer, 2004, vol. 90, pp. S7-S10.

Robertson, et al., "Pharmacokinetic Profile of Intramuscular Fulvestrant in Advanced Breast Cancer," Clinical Pharmacokinetics, 2004, vol. 43 (8), pp. 529-538.

Rouanet P., et al., "Neoadjuvant Percutaneous 4-Hydroxytamoxifen Decreases Breast Tumoral Cell Proliferation: A Prospective Con-

(56) References Cited

OTHER PUBLICATIONS trolled Randomized Study Comparing Three Doses of 4-hydroxytamoxifen Gel to Oral Tamoxifen," Journal of Clinical Oncology, May 1, 2005, vol. 23(13), pp. 2980-2987.
Sano, et al., "Short-step Synthesis of Droloxifene via the Three-Component Coupling Reaction among Aromatic Aldehyde, Cinnamyltrimethylsilane, and 13-Chlorophenetole," Tetrahedron Letters, Mar. 6, 2006, vol. 47 (10), pp. 1631-1635.
Stearns, et al. Active tamoxifen metabolite plasma concentrations after coadministration of tamoxifen and the selective serotonin reuptake inhibitor paroxetine. J Natl Cancer Inst. Dec. 3, 2003;95(23):1758-64.
Umareddy, et al., "Improved Process for Centchroman, A Selective Estrogen Receptor Modulator (SERM)," Journal of Chemical and Pharmaceutical Research, 2015, vol. 7 (7), pp. 736-741.
Umareddy, et al., "Total Synthesis of Lasofoxifene and Nafoxidine," An International Journal for Rapid Communication of Synthetic Organic Chemistry, 2016, vol. 46 (4), pp. 309-313.
Vergote, et al., "Fulvestrant is an Effective and Well-Tolerated Endocrine Therapy for Postmenopausal Women with Advanced Breast Cancer," Results from Clinical Trials, British Journal of Cancer, 90 (Suppl), 2004, pp. S11-S14.
Welsh J., "Induction of Apoptosis in Breast Cancer Cells in Response to Vitamin D and Antiestrogens," Biochemistry and Cell Biology, 1994, vol. 72 (11-12), pp. 537-545.
Wu X., et al., "The Tamoxifen Metabolite, Endoxifen, is a Potent Antiestrogen that Targets Estrogen Receptor Alpha for Degradation in Breast Cancer Cells," Cancer Research, Mar. 1, 2009, vol. 69(5), , pp. 1722-1727.
Yan Yaodong., "Design and Development of Sustained-Release and Controlled-Release Formulations," Chinese Medicine Science and Technology Publishing House, Jun. 30, 2006 (Jun. 30, 2006), pp. 421-428.
Yang Y., et al., "Dendron-Based Micelles for Topical Delivery of Endoxifen: A Potential Chemo-Preventive Medicine for Breast Cancer," Advanced Functional Materials, 2014, vol. 24, pp. 2442-2449.
Yao, et al., "Synthesis and Reactivity of Potential Toxic Metabolites of Tamoxifen Analogues: Droloxifene and Toremifene a-Quinones," Chemical Research in Toxicology, 2001, vol. 14 (12), pp. 1643-1653.
Yoneya, et al., "Thiochroman Derivative CH4986399, A New Nonsteroidal Estrogen Receptor Down-regulator, Is effective in Breast Cancer Models," Anticancer Research, 2010, vol. 30, pp. 873-878.
International Search Report and Written Opinion for International Application No. PCT/US2018/050272, dated Jan. 3, 2019, 12 pages.
Journal of Pharmaceutical Science and Technology, Japan, 2006, vol. 66, No. 6, pp. 435-439.(No English Translation available. Document showing a well-known technique).
Search Report and Written Opinion for Singapore Patent Application No. SG11202002105W mailed Apr. 21, 2021, 8 pages.
Ackerman A.B., et al., "Contrary View: The Breast is not an Organ Per Se, but a Distinctive Region of Skin and Subcutaneous Tissue," The American Journal of Dermatopathology, Apr. 2007, vol. 29 (2), pp. 211-218.
Anonymous, "History of Changes for Study: NCT02547961," Sep. 10, 2015, XP055669980, retrieved from the URL: https://clinicaltrials.gov/ct2/history/NCT02547961?V_1=View#StudyPageTop, on Feb. 19, 2020, 4 pages.
Bhatnagar P., et al., "Tumor Lysing Genetically Engineered T Cells Loaded with Multi-Modal Imaging Agents," Scientific Reports, vol. 4, No. 4502, DOI: 10.1038/srep04502, published on Mar. 28, 2014, 21 pages.
Extended European Search Report for EP Application EP17857260.8, dated Mar. 24, 2020, 16 pages.
International Search Report and Written Opinion for International Application No. PCT/US2018/050193, mailed Jan. 4, 2019, 9 pages.

Manni, et al., "Combination of Antiestrogens and Omega-3 Fatty Acids for Breast Cancer Prevention," Biomed Research International, Jan. 1, 2015, 10 pages.
Oken M.M., et al., "Toxicity and Response Criteria of the Eastern Cooperative Oncology Group," American Journal of Clinical Oncology, Dec. 1982, vol. 5(6), pp. 649-655.
Stearns et al., Preclinical and Clinical Evaluation of Intraductally Administered Agents in Early Breast Cancer, Science Translational Medicine, 3(106): 106ra108 (9 pages).
Sun M., et al., "Construction and Evaluation of a Novel Humanized HER2-Specific Chimeric Receptor," Breast Cancer Research, 2014, vol. 16:R61, 10 pages.
Wu, et al., "Single Cell MicroRNA Analysis using Microftuidic Ftow Cytometry," PLOS One, 2013, vol. 8 (1), e55044.
Zhang B., et al., "The Safety Parameters of the Study on Intraductal Cytotoxic Agent Delivery to the Breast Before Mastectomy," http://dx.doi.org/10.3978/j.issn.1000-9604.2014.10.06 , Sep. 9, 2014, Chinese Journal of Cancer Research, vol. 26(5), pp. 579-587.
Zhao Y., et al., "A Herceptin-Based Chimeric Antigen Receptor with Modified Signaling Domains Leads to Enhanced Survival of Transduced T Lymphocytes and Antitumor Activity," The Journal of Immunology, https://www.researchgate.net/publication/38024914 , Nov. 2009, vol. 183(9), pp. 5563-5574.
Dickschen K., et al., "Physiologically Based Pharmacokinetic Modeling of Tamoxifen and its Metabolites in Women of Different CYP2D6 Phenotypes Provides New Insight into the Tamoxifen Mass Balance," Frontiers in Pharmacology, vol. 3 (92), May 2012, 15 pages, www.frontiersin.org.
Donneyong M.M., et al., "Risk of Mortality with Concomitant use of Tamoxifen and Selective Serotonin Reuptake Inhibitors: Multi-Database Cohort Study," BMJ, Sep. 30, 2016, vol. 354 (i5014), 20 pages.
Extended European Search Report for European Application No. EP18853361.6, dated May 28, 2021, 5 pages.
Forefront., "Endoxifen Shows Promise As Breast Cancer Treatment", Mayo Clinic Cancer Center's Online Magazine, vol. 3, Issue 1, 2014, 3 pages.
Galeana P.C., et al., "Ki67 Changes Identify Worse Outcomes in Residual Breast Cancer Tumors After Neoadjuvant Chemotherapy," The Oncologist, vol. 23 (6), Jun. 2018, pp. 670-678.
Henderson S.L., et al., "Profound Reduction in Tamoxifen Active Metabolite Endoxifen in a Breast Cancer Patient Treated with Rifampin Prior to Initiation of an Anti-TNF a Biologic for Ulcerative Colitis: a Case Report," BMC cancer, vol. 16 (304), May 11, 2016, 6 pages.
Jordan V.C., "New Insights into the Metabolism of Tamoxifen and its Role in the Treatment and Prevention of Breast Cancer," Steroids, vol. 72 (13), Nov. 2007, pp. 829-842.
Lazzeroni M., et al., "Oral Low Dose and Topical Tamoxifen for Breast Cancer Prevention: Modern Approaches for an Old Drug," Breast Cancer Research, vol. 14(214), 2012, 11 pages.
Love, Susan M., et al. "A Feasibility Study of the Intraductal Administration of Chemotherapy." Cancer Prevention Research, vol. 6, No. 1, Jan. 2013, pp. 51-58.
SOLTAMOX Oral Solution, Rx Only. Savient Pharmaceuticals, Inc. 27 pages. (Aug. 25, 2005).
European Application No. 20834248.5 Extended Search Report dated Jun. 29, 2023.
Ali et al., Endoxifen is a new potent inhibitor of PKC: A potential therapeutic agent for bipolar disorder. Bioorganic & Medicinal Chemistry Letters 20(8): 2665-2667 (2010).
Elkins P., et al., "Characterization of the Isomeric Configuration and Impurities of (Z)-endoxifen by 2D NMR, High Resolution LC-MS, and Quantitative HPLC Analysis," Journal of Pharmaceutical and Biomedical Analysis, Jan. 2014; vol. 88 pp. 174-179.
Lim Y.C., et al., "Endoxifen (4-Hydroxy-N-Desmethyl-Tamoxifen) has Anti-Estrogenic Effects in Breast Cancer Cells with Potency Similar to 4-Hydroxy-Tamoxifen," Cancer Chemother Pharmacol, 2005, vol. 55, pp. 471-478.
Saravanan M. et al., "The Effect of Tablet Formulation and Hardness on in Vitro Release of Cephalexin from Eudragit L100 Based Extended Release Tablets," Biol. Pharm. Bull., Apr. 2002, vol. 25, No. 4, pp. 541-545.

(56) References Cited

OTHER PUBLICATIONS

Zheng et al., Elimination of antiestrogenic effects of active tamoxifen metabolites by glucuronidation. Drug Metab Dispos. 35(10): 1942-1948 (2007).
"Hardness of Tablet Chart," The 2nd paragraph under the section Bending Test, Aug. 5, 2023, 26 pages.
Jina Pharmaceuticals Inc., "Improved Pharmaceutical Composition of Endoxifen & Preparation Thereof," 2015, 46 pages.
Ku et al., "Performance qualification of a new hypromellose capsule: Part I. Comparative evaluation of physical, mechanical and processability quality attributes of Vcaps Plus, Quali-V and gelatin capsules." International Journal of Pharmaceutics 386: 30-41 (2010).

* cited by examiner

SUSTAINED RELEASE COMPOSITIONS OF ENDOXIFEN

CROSS-REFERENCE

The present application is a U.S. National Phase Application under 35 U.S.C. § 371 of International Application No. PCT/US2020/040757, entitled "SUSTAINED RELEASE COMPOSITIONS OF ENDOXIFEN", filed on Jul. 2, 2020, which claims the benefit of U.S. Provisional Application No. 62/870,656, entitled "SUSTAINED RELEASE COMPOSITIONS OF ENDOXIFEN", filed on Jul. 3, 2019, U.S. Provisional Application No. 62/989,342, entitled "SUSTAINED RELEASE COMPOSITIONS OF ENDOXIFEN", filed on Mar. 13, 2020, and U.S. Provisional Application No. 63/021,549, entitled "SUSTAINED RELEASE COMPOSITIONS OF ENDOXIFEN", filed on May 7, 2020, each of which applications are herein incorporated by reference in their entirety entireties for all purposes.

BACKGROUND OF THE INVENTION

Breast cancer is by far the most common form of cancer in women, and it is the second leading cause of cancer death in humans. In 2019, an estimated 268,600 new cases of invasive breast cancer are expected to be diagnosed in women in the U.S., along with 62,930 new cases of non-invasive (in situ) breast cancer. About 2,670 new cases of invasive breast cancer are expected to be diagnosed in men in 2019. Tamoxifen, a selective estrogen receptor modulator, is used for the treatment of women with endocrine responsive breast cancer, e.g., hormone dependent or hormone-sensitive breast cancer.

Adjuvant therapy, primarily via oral delivery of tamoxifen, is known to have severe or bothersome side effects such as vasomotor symptoms, for example hot flashes (reported frequency as high as 78% per drug dosing days (Mortimer et al. Breast Cancer Res Treat. 2008 April; 108(3): 421-426)) and serious side effects such as clotting problems (e.g., strokes, deep vein thrombosis), and reproductive tract (gynecologic) cancers. As a result, patient compliance remains a problem with tamoxifen therapy. Even though patients have been prescribed selective serotonin-reuptake inhibitors (SSRI) antidepressants such as paroxetine for the treatment of hot flashes, such SSRI are known to inhibit cytochrome P450 (CYP) enzymes (for example, CYP2D6 and CYP3A4) important for metabolism of many drugs, including tamoxifen. For example, paroxetine co-administration with tamoxifen is known to decrease the plasma concentration of 4-hydroxy-N-desmethyl-Tamoxifen (endoxifen), the active metabolite of tamoxifen. Further, the majority of the individuals on adjuvant tamoxifen therapy do not respond to the drug, and 30-50% of the patients subsequently die of their disease.

Therefore, several alternatives to tamoxifen are being developed for the treatment of breast cancer, which include tamoxifen's active metabolites, afimoxifene (see, U.S. Pat. Nos. 7,485,623; 7,507,769; 7,704,516; 7,786,172; 7,968, 532; and 8,048,927), endoxifen (see, U.S. Pat. Nos. 9,333, 190; 9,220,680; 9,090,640; and 9,200,045; U.S. Publication Nos. 2009/0291134, US20100112041, 20180049999, WO2019051416 (A1) and WO2019051370 (A1) Atossa Genetics), and their derivatives (see, U.S. Pat. No. 8,063, 249; U.S. Publication Nos. 2015/0080339 and 2014/ 0193334). It is widely accepted that (Z)-endoxifen is the main active metabolite of tamoxifen responsible for the clinical efficacy of tamoxifen. Endoxifen is primarily generated via CYP2D6 mediated hydroxylation and CYP3A4-mediated N-demethylation of tamoxifen. Any drug that can be a substrate of CYP3A4 or CYP2D6, especially CYP2D6 (e.g., SSRIs), can decrease the level of endoxifen and thus reduce the therapeutic benefits of tamoxifen. Administering endoxifen directly to such subjects circumnavigates the effects of such drug interactions.

While hydrochloride and citrate salts of endoxifen (See, e.g., Fauq et al., Bioorganic & Medicinal Chemistry Letters. 20 (2010) 3036-3038; Stearns et al., J. Natl. Cancer Inst. Vol 95, No. 23, 2003; US Publication Nos. 2009/0291134 and 2010/0112041; Clinical Trials Gov. Identifier Nos. NCT01273168 and NCT02311933; Goetz et al., 2015, San Antonio Cancer Symposium; Ahmad et al., Clinical Pharmacology & Therapeutics. 88(6) 814-817, 2010; and J Clin. Oncol. 30, 2012 (suppl; abstr 3089); Ahmad et al. Breast Cancer Research and Treatment 2010, 122, 579-584) are known in the art and currently under evaluation for metastatic cancer, there remains unmet medical need for new compositions and methods for the treatment and/or prevention of hormone dependent breast and reproductive tract (gynecologic) disorders and other disorders that are susceptible or responsive to endoxifen.

A strong need exists for methods to treat and to prevent breast diseases without significant adverse systemic side effects in men and women, particularly in the tamoxifen-refractory patients and in premenopausal population of women. A strong need also exists for formulations that provide blood levels of endoxifen that avoid rapid release or delivery of endoxifen in a subject that may be associated with side effects or tolerance issues for the patients. Further, a strong need also exists to ensure that a full amount of the (Z)-endoxifen dose is available to the patient, by ensuring the drug passes through the stomach without degradation in its acidic environment. In particular, there is a need for breast cancer treatments and preventatives that have reduced interactive effect with other medications or their metabolism.

SUMMARY OF THE INVENTION

Endoxifen free base and endoxifen salts of prior publications and patent and patent applications have been developed for treatment of subjects with breast cancers. U.S. Pat. No. 9,333,190 describes enteric-coated tablets and enteric-coated capsules made with endoxifen citrate. Patent publications WO2019051416 (A1) and WO2019051370 (A1) describe methods of making (Z)-endoxifen and compositions using (Z)-endoxifen. WO2019051416 (A1) describes an enteric (delayed release) API-in-capsule comprising (Z)-endoxifen free base, crystalline forms/polymorphs and salts thereof, and WO2019051370 (A1) describes topical compositions comprising (Z)-endoxifen free base and salts thereof. None of these describe the matrix tablet-type sustained release preparations relating to (Z)-endoxifen, or polymorphs or salts thereof wherein the active drug (Z)-endoxifen is released over a prolonged period of time, for example over 4 to 24 hours or from at least 2 hours to at least 72 hours.

The present disclosure provides novel sustained release compositions comprising Z-endoxifen, and polymorphs and salts thereof, and methods of making them. Non-limiting exemplary sustained release compositions in the form of sustained release tablets as well as enteric coated delayed release tablets and capsules are provided in the present disclosure. Sustained release compositions of the present disclosure provide certain advantages: novel sustained release (Z)-endoxifen compositions can be prepared by the methods disclosed herein and such sustained release compositions are stable, even at low doses. Since the sustained release compositions release (Z)-endoxifen or a polymorph or a salt thereof in slow and sustained manner, the maximum drug concentration ($C_{max}$) can be controlled in subject; high blood concentration and/or accumulation in a subject can be avoided or controlled, reducing the possibility of systemic and/or local side effects and toxicity. Subjects can be administered sustained release compositions of the present disclosure in lower doses or as necessary to reduce the side effects and ensure patient compliance. Further, the enteric coating of the sustained release compositions of the present disclosure provides surprisingly greater protection to (Z)-endoxifen in preventing or reducing the interconversion of active (Z)-endoxifen form to its inactive form, (E)-endoxifen, in the stomach resulting in greater amounts of (Z)-endoxifen release in the intestines. The unexpected advantages of suppressing this interconversion results in greater overall delivery of (Z)-endoxifen, and also aids in providing a slower, consistent release of the therapeutic agent. Targeting the small intestines, for example, the duodenum and colon, using enteric coated delayed release compositions increases the bioavailability of the drug in a subject, potentially increasing efficacy of the drug, and increases the potential of the compositions to withstanding the "food effect" (e.g., decreases susceptibility to physical stimulation by eating). The enteric coated delayed release tablets and capsules of the present disclosure are protected from the acidic environment of the stomach and release Z-endoxifen, and polymorphs and salts thereof in the small and large intestines, for example at least 2 hours post ingestion of the dose.

In various aspects, the present disclosure provides a sustained release composition comprising a therapeutic agent and a sustained release agent, wherein the therapeutic agent is (Z)-endoxifen free base, a polymorph of (Z)-endoxifen, a salt of (Z)-endoxifen, or a combination thereof, and wherein the therapeutic agent has at least two percentage dissolution parameters selected from: a percentage dissolution of less than 20% at 2 hours; a percentage dissolution of less than 40% at 7 hours; and a percentage dissolution of at least 30% at 12 hours, as measured at 37° C. in simulated gastric fluid at pH 1.2 from hours 0 to 2 and in simulated intestinal fluid at pH 6.8 after 2 hours.

In some aspects, the therapeutic agent has at least three of the percentage dissolution parameters. In some aspects, the therapeutic agent has percentage dissolution of less than 35% at 3 hours. In some aspects, the therapeutic agent has percentage dissolution ranging from 35% to 55% at 12 hours. In some aspects, the therapeutic agent has percentage dissolution of at least 50% at 24 hours. In some aspects, the therapeutic agent has percentage dissolution ranging from 65% to 85% at 24 hours. In some aspects, the sustained release agent is selected from the group consisting of a cellulosic ether, a gum, an acrylic resin, or a combination thereof.

In some aspects, the sustained release agent is a hydroxyalkyl cellulose, a hydroxyethyl cellulose, a hydroxypropyl cellulose, a hydroxypropylmethyl cellulose, or a combination thereof. In some aspects, the sustained release agent is hypromellose.

In various aspects, the present disclosure provides a sustained release composition comprising: a therapeutic agent, and a sustained release agent, wherein the therapeutic agent is (Z)-endoxifen free base, a polymorph of (Z)-endoxifen, a salt of (Z)-endoxifen, or a combination thereof, and wherein the sustained release agent is selected from the group consisting of hydroxyalkyl cellulose, hydroxyethyl cellulose, and hydroxypropyl cellulose.

In some aspects, the sustained release composition comprises at least 1% w/w, at least 10% w/w, at least 20% w/w, at least 25% w/w, at least 30% w/w, at least 35% w/w, or at least 40% w/w of the sustained release agent. In some aspects, the sustained release composition comprises from 1% to 99% w/w of the sustained release agent. In some aspects, the sustained release composition comprises from 5% to 90% w/w of the sustained release agent. In some aspects, the sustained release composition comprises from 5% to 70% w/w of the sustained release agent. In some aspects, the sustained release composition comprises from 10% to 40% w/w of the sustained release agent. In some aspects, the sustained release composition comprises from 15% to 40% w/w of the sustained release agent. In some aspects, the sustained release agent comprises from 0.25% to 10% w/w, from 0.5% to 8% w/w, or from 1% to 4% w/w of the therapeutic agent.

In some aspects, at least 90% w/w, at least 95% w/w, or at least 99% w/w of the therapeutic agent is Form I of (Z)-endoxifen, Form II of (Z)-endoxifen, Form III of (Z)-endoxifen, or a combination thereof.

In some aspects, the sustained release composition further comprises a binder, a lubricant, or a combination thereof. In some aspects, the binder is a monosaccharide, a disaccharide, a starch, a polyhedric alcohol, mannitol, xylitol, sorbitol, lactose, a polyethylene glycol, a gum, alginic acid, polyvinyl pyrrolidone, methyl cellulose, polyvinyl pyrrolidone, hydroxypropyl methyl cellulose, crystalline cellulose, microcrystalline cellulose, silicified microcrystalline cellulose, calcium carbonate, calcium phosphate, sodium carbonate, sodium phosphate, anhydrous dibasic calcium phosphate, talc, a dextrate, kaolin, mannitol, silicic acid, sorbitol, or a combination thereof. In some aspects, the binder is microcrystalline cellulose. In some aspects, the sustained release composition comprises from 1% to 99% w/w of the binder. In some aspects, the sustained release composition comprises from 1% to 99% w/w of the binder. In some aspects, the sustained release composition comprises from 30% to 97% w/w of the binder. In some aspects, the sustained release composition comprises from 40% to 75% w/w of the binder. In some aspects, the sustained release composition comprises from 50% to 75% w/w of the binder.

In some aspects, the lubricant is stearic acid, calcium stearate, magnesium stearate, zinc stearate, potassium stearate, hydrogenated vegetable oil, mineral oil, light mineral oil, glycerin, sorbitol, mannitol, a glycol, polyethylene glycol, sodium lauryl sulfate, magnesium lauryl sulfate, macrogol, talc, ethyl oleate, ethyl laureate, agar, waxes, or a combination thereof. In some aspects, the lubricant is magnesium stearate.

In some aspects, the sustained release composition further comprises an enteric coating enclosing a tablet comprising the therapeutic agent and the sustained release agent, wherein the enteric coating comprises: a delayed release agent; a plasticizer; an anti-tacking agent; or a combination thereof. In some aspects, the enteric coating is from 4% to 40% w/w of the sustained release composition. In some aspects, the enteric coating is from 5% to 30% w/w of the sustained release composition. In some aspects, the enteric coating is from 5% to 25% w/w of the sustained release composition. In some aspects, the enteric coating is from 5% to 20% w/w of the sustained release composition. In some aspects, the enteric coating is from 5% to 15% w/w of the sustained release composition.

In some aspects, the delayed release agent is present at from 0.1% to 30% w/w of the enteric coating. In some aspects, the delayed release agent is present at from 5% to 25% w/w of the enteric coating. In some aspects, the delayed release agent is present at from 8% to 14% w/w of the enteric coating. In some aspects, the delayed release agent is a polymethacrylate.

In some aspects, the sustained release composition further comprises a pharmaceutically acceptable excipient.

In various aspects, the present disclosure provides a sustained release composition comprising a tablet and an enteric coating enclosing the tablet, wherein the tablet comprises: a therapeutic agent; and a sustained release agent, and wherein the enteric coating comprises: a delayed release agent; a plasticizer; an anti-tacking agent; or a combination thereof, wherein the therapeutic agent is (Z)-endoxifen free base, a polymorph of (Z)-endoxifen, a salt of (Z)-endoxifen, or a combination thereof, wherein the sustained release agent is selected from the group consisting of hydroxyalkyl cellulose, hydroxyethyl cellulose, and hydroxypropyl cellulose.

In various aspects, the present disclosure provides a sustained release composition comprising a tablet and an enteric coating enclosing the tablet, wherein the tablet comprises a therapeutic agent and hypromellose, wherein the therapeutic agent comprises at least 90% (Z)-endoxifen, and wherein the enteric coating comprises a poly(meth)acrylate polymer and triethyl citrate.

In some aspects, the enteric coating further comprises talc. In some aspects, the tablet comprises at least 20% w/w hypromellose relative to the total tablet weight. In some aspects, the tablet comprises from 1% to 40% w/w therapeutic agent relative to the total tablet weight. In some aspects, the enteric coating comprises from 60% to 80% w/w poly(meth)acrylate polymer relative to the total enteric coating weight. In some aspects, the enteric coating comprises no more than 10% w/w triethyl citrate relative to the total enteric coating weight. In some aspects, the enteric coating comprises from 10% to 40% w/w talc relative to the total enteric coating weight.

In various aspects, the present disclosure provides a method of preparing a sustained release composition comprising: combining and mixing: a therapeutic agent selected from a (Z)-endoxifen free base, a polymorph of (Z)-endoxifen, a salt of (Z)-endoxifen, and a combination thereof; a sustained release agent; a binder; and a lubricant; and dry compressing the therapeutic agent, the at least one sustained release agent, the at least one binder, and the at least one lubricant to form a core tablet.

In some aspects, the method further comprises combining and mixing: at least one delayed release agent; at least one plasticizer; and at least one anti-tacking component or anti-adherent component, thereby forming a coating solution; and substantially coating the core tablet with the coating solution, thereby forming a functional coating.

In various aspects, the present disclosure provides a method of administering a sustained release composition comprising to a subject in need thereof, the method comprising orally administering the sustained release composition to the subject in need thereof, wherein the sustained release composition comprises a therapeutic agent and a sustained release agent, wherein the therapeutic agent is (Z)-endoxifen free base, a polymorph of (Z)-endoxifen, a salt of (Z)-endoxifen, or a combination thereof, and wherein the sustained release composition is formulated such less than 20% of the therapeutic agent dissolves 2 hours after administration and at least 30% of the therapeutic agent dissolves within 12 hours after administration.

In some aspects, the sustained release composition is formulated such less than 40% of the therapeutic agent dissolves 7 hours after administration.

In various aspects, the present disclosure provides a method of administering a sustained release composition comprising to a subject in need thereof, the method comprising orally administering the sustained release composition to the subject in need thereof, wherein the sustained release composition comprises a therapeutic agent and a sustained release agent, wherein the therapeutic agent is (Z)-endoxifen free base, a polymorph of (Z)-endoxifen, a salt of (Z)-endoxifen, or a combination thereof, and wherein the sustained release composition is formulated such less than 20% of the therapeutic agent dissolves in simulated gastric fluid after 2 hours and at least 30% of the therapeutic agent dissolves after 2 hours in simulated gastric fluid followed by 10 hours in simulated intestinal fluid.

In some aspects, the sustained release composition is formulated such less than 40% of the therapeutic agent dissolves after 2 hours in simulated gastric fluid followed by 5 hours in simulated intestinal.

In various aspects, the present disclosure provides a method of administering a sustained release composition comprising to a subject in need thereof, the method comprising orally administering the sustained release composition to the subject in need thereof, wherein the sustained release composition comprises a therapeutic agent and a sustained release agent, wherein the therapeutic agent is (Z)-endoxifen free base, a polymorph of (Z)-endoxifen, a salt of (Z)-endoxifen, or a combination thereof, and wherein the therapeutic agent exhibits a time to maximum observed concentration of at least 8 hours, at least 9 hours, at least 10 hours, at least 15 hours, at least 20 hours, or at least 24 hours in a serum of the subject.

In various aspects, the present disclosure provides a method of treating a subject in need thereof, wherein the subject has a disorder or is at risk of having the disorder, the method comprising administering to the subject the sustained release composition of the present disclosure.

In various aspects, the present disclosure provides a method of treating a subject in need thereof, wherein the subject has a disorder or is at risk of having the disorder, the method comprising administering to the subject a sustained release composition comprising: a therapeutic agent, and a sustained release agent, wherein the therapeutic agent is (Z)-endoxifen free base, a polymorph of (Z)-endoxifen, a salt of (Z)-endoxifen, or a combination thereof, and wherein the sustained release agent is selected from the group consisting of hydroxyalkyl cellulose, hydroxyethyl cellulose, and hydroxypropyl cellulose.

In some aspects, the disorder is a breast disorder. In some aspects, the breast disorder is a benign breast disorder, hyperplasia, atypia, atypical ductal hyperplasia, atypical lobular hyperplasia, increased breast density, gynecomastia, ductal carcinoma in situ, lobular carcinoma in situ, breast cancer, precocious puberty, or McCune-Albright Syndrome. In some aspects, the sustained release composition is administered orally. In some aspects, the therapeutic agent exhibits a time to maximum observed concentration of at least 8 hours, at least 9 hours, at least 10 hours, at least 15 hours, at least 20 hours, or at least 24 hours in a serum of the subject.

In some aspects, the sustained release composition is administered in combination with an additional therapeutic agent. In some aspects, the additional therapeutic agent is a selective serotonin-reuptake inhibitor. In some aspects, the selective serotonin-reuptake inhibitor is selected from the group consisting of: citalopram, escitalopram, fluoxetine, paroxetine, sertraline, and vilazodone.

In some aspects, the subject has a statistically significant alteration of a level of a biomarker in a tissue or fluid of the subject relative to a level of the biomarker in a normal subject. In some aspects, the biomarker is selected from the group consisting of: Ki-67, estrogen receptor, progesterone receptor, proliferating cell nuclear antigen, phosphor-histone H3, p16, p12, beta-galactosidase, terminal deoxynucleotidyl transferase dUTP nick end labeling, and an RNA sequence, or a combination thereof. In some aspects, the level of the biomarker in the tissue of the subject is reduced following administration of the sustained release composition. In some aspects, the level of the biomarker in the tissue of the subject is increased following administration of the sustained release composition. In some aspects, the tissue is a diseased tissue.

In some aspects, the sustained release composition is administered to the subject for from 14 days to 40 days, from 10 days to 50 days, from 10 days to 40 days, from 10 days to 35 days, from 10 days to 30 days, from 10 days to 25 days, from 12 days to 50 days, from 12 days to 40 days, from 12 days to 35 days, from 12 days to 30 days, from 12 days to 25 days, from 12 days to 45 days, from 12 days to 30 days, from 14 days to 30 days, from 14 days to 50 days, from 14 days to 40 days, from 14 days to 35 days, from 14 days to 30 days, from 14 days to 25 days, from 16 days to 50 days, from 16 days to 40 days, from 16 days to 35 days, from 16 days to 30 days, from 16 days to 25 days, from 18 days to 50 days, from 18 days to 40 days, from 18 days to 35 days, from 18 days to 30 days, from 18 days to 25 days. In some aspects, the sustained release composition is administered once per day, twice per day, every 2 days, every 3 days, every 4 days, every 5 days, every 6 days, or every 7 days. In some aspects, from 1 mg to 4 mg, from 2 mg to 4 mg, from 2 mg to 6 mg, from 2 mg to 8 mg, from 1 mg to 10 mg, from 1 mg to 12 mg, from 1 mg to 16 mg, from 2 mg to 10 mg, from 2 mg to 12 mg, from 2 mg to 16 mg, from 3 mg to 10 mg, from 3 mg to 12 mg, from 3 mg to 16 mg, from 4 mg to 10 mg, from 4 mg to 12 mg, or from 4 mg to 16 mg of the sustained release composition is administered to the subject per dose.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
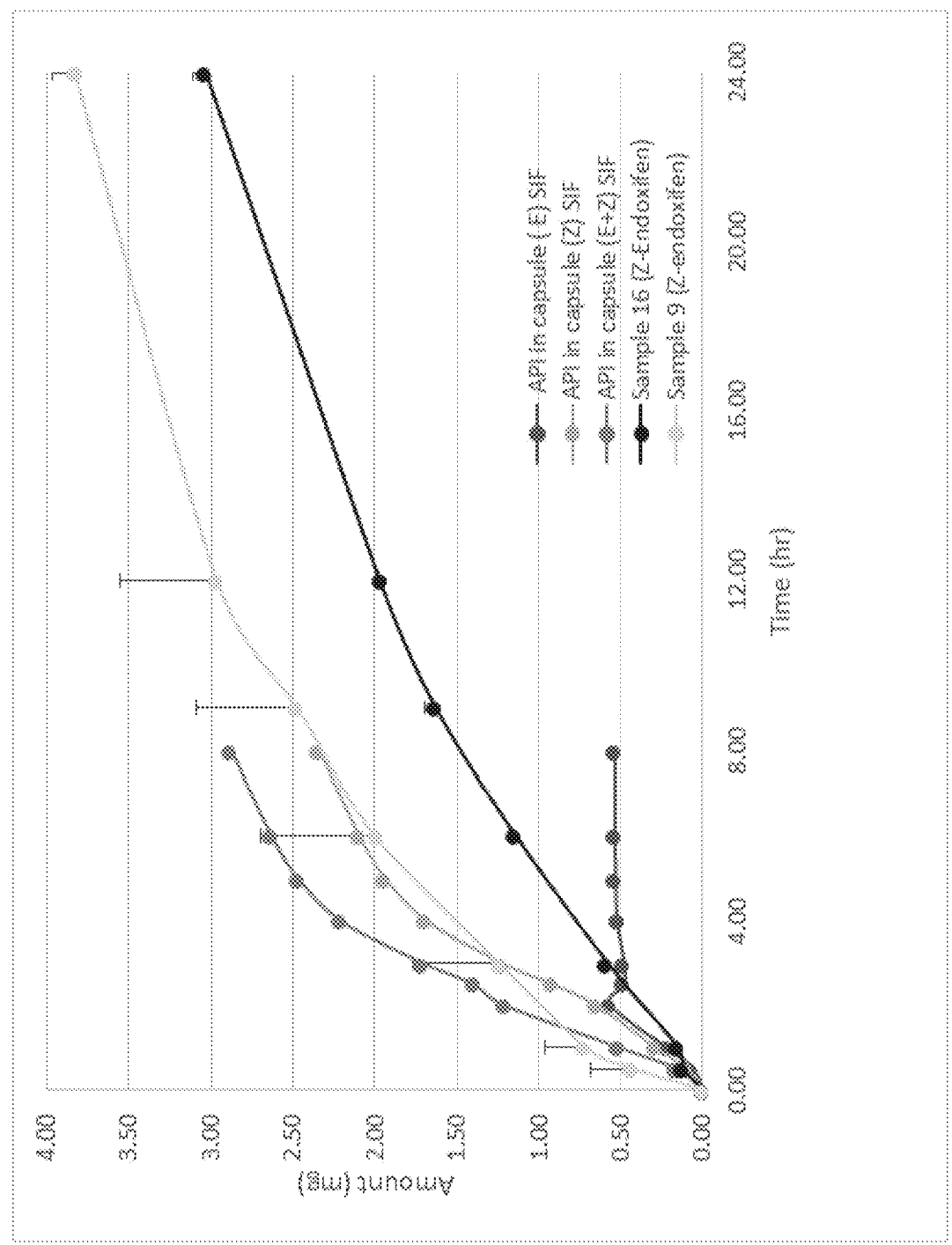
FIG. 1 shows percentage dissolution and release of (Z)-endoxifen from sustained release compositions in the form of a sustained release tablet (uncoated) containing 4 mg of (Z)-endoxifen free base in comparison to control (a 4 mg delayed release neat (Z)-endoxifen free base active pharmaceutical ingredient (API)-in-capsule), as measured according to United States Pharmacopeia (USP) I method. (Z)-endoxifen release upon dissolution of the compositions was measured using high performance liquid chromatography with ultraviolet detection (HPLC-UV).

Compounds are described using standard nomenclature. Unless otherwise defined, all technical and scientific terms used herein have the same meaning as is commonly understood by one of skill in the art to which this invention belongs.

As used herein, the terms "a," "an," and "the" include plural reference unless the context dictates otherwise.

As used herein, the terms "active pharmaceutical ingredient", "active ingredient", "API," "drug," "active," "actives" or "therapeutic agent" may be used interchangeably to refer to the pharmaceutically active compound(s) in a pharmaceutical composition. This is in contrast to other ingredients in the compositions, such as excipients, which are substantially or completely pharmaceutically inert. A suitable active pharmaceutical incredient (API) in accordance with the present disclosure is one where there is or likely may be patient compliance issues for treating a certain disease, condition, or disorder. The therapeutic agent as used herein includes the active compound and its salts, prodrugs, and metabolites. As used herein the term "drug" means a compound intended for use in diagnosis, cure, mitigation, treatment, and/or prevention of disease in man or other animals.

As used herein, "adjuvant therapy" refers to a therapy that follows a primary therapy and that is administered to subjects at risk of relapsing. Adjuvant systemic therapy in case of breast cancer or reproductive tract cancer, for example with tamoxifen, usually begins soon after primary therapy to delay recurrence, prolong survival or cure a subject.

As used herein, the term "tamoxifen" refers to (Z)-2-[4-(1,2-diphenyl-1-butenyl)phenoxy]-N,N-dimethyl-ethanamine. Tamoxifen can also refer to E-isomer or a combination of E-isomer and Z-isomer.

As used herein, the term "endoxifen" refers to 4-hydroxy-N-desmethyl-tamoxifen. It is a secondary active metabolite of tamoxifen.

As used herein and in the claims, the terms "comprising," "containing," and "including" are inclusive, open-ended and do not exclude additional unrecited elements, compositional components or method steps. Accordingly, the terms "comprising" and "including" encompass the more restrictive terms "consisting of" and "consisting essentially of."

As used herein, the term "Combination Therapy" refers to the use of an inventive composition described herein in combination with one or more of treatments. Treatment in Combination Therapy can be any treatment such as any prophylactic agent, additional therapeutic agent (example as chemotherapy and immunotherapy), radiotherapy, surgery, and the like. The combination can refer to inclusion of a therapeutic or prophylactic agent in a same composition as an inventive composition disclosed herein (for example, in the same capsule, tablet, caplet, etc.) or in separate compositions (for example, in 2 separate tablets). The separate compositions may be in a different dosage form or administered via different routes of administration. The use of the terms "Combination Therapy" and "in combination with" does not restrict the order in which an inventive composition described herein and prophylactic and/or therapeutic agent and/or treatment are administered to a subject in need thereof. Compositions of the present disclosure can be administered prior to (e.g., 1 minute (min), 5 min, 15 min, 30 min, 45 min, 1 hour (h), 2 h, 4 h, 6 h, 8 h, 10 h, 12 h, 24 h, 36 h, 48 h, 72 h, 96 h, 1 week (wk), 2 wk, 3 wk, 4 wk, 5 wk, 6 wk, 8 wk, 12 wk, 6 months (m), 9 m, or 1 year before), concomitant with, or subsequent to (e.g., 1 minute (min), 5 min, 15 min, 30 min, 45 min, 1 hour (h), 2 h, 4 h, 6 h, 8 h, 10 h, 12 h, 24 h, 36 h, 48 h, 72 h, 96 h, 1 week (wk), 2 wk, 3 wk, 4 wk, 5 wk, 6 wk, 8 wk, 12 wk, 6 months (m), 9 m, or 1 year after) administration of one or more prophylactic and/or therapeutic agents or treatment to a subject in thereof. Combination therapy as used herein can also refer to treatment of a subject having a single disease or multiple diseases or conditions, for example, prostate cancer in men and gynecomastia or breast cancer and breast density in women.

As used herein, the terms "test sample" means sample of blood obtained from a subject. It is to be understood that when blood sample is obtained from a subject, subject's blood as whole blood, plasma, and/or serum is used for determining the subject's endoxifen levels and/or other biomarkers that may be measured or tested. As used herein "plasma endoxifen" is used to refer to endoxifen levels in the subject's test sample whether the test is conducted on whole blood, plasma, and/or serum unless indicated expressly otherwise.

As used herein, the term "dosage form" means the form in which the compounds or compositions of the present disclosure are delivered to a patient.

As used herein, the term "pharmaceutically acceptable" or "pharmacologically acceptable" means materials, compositions, or vehicles that are compatible with other ingredients of the formulation and that they do not substantially produce adverse reactions, e.g., toxic, allergic, or immunological reactions, when administered to a subject. They may be approved by a regulatory agency, e.g., of the U.S. Federal or state government or listed in the U.S. pharmacopeia or other generally recognized pharmacopeia for use in animals, and more particularly in humans.

As used herein, the term "pharmaceutically acceptable carrier" or "carrier" means a pharmaceutically acceptable material, composition, or vehicle, such as a liquid or solid filler, diluent, excipient, solvent, or encapsulating material, involved in carrying or transporting one or more of the compounds of the present disclosure from one tissue, organ, or portion of the body or across the skin.

As used herein, the term "pharmaceutical composition" means a combination of the active agent (e.g., an active pharmaceutical compound or ingredient, API) with a carrier, inert or active (e.g., a phospholipid), making the compositions especially suitable for diagnostic, prophylactic, or therapeutic uses in vitro, in vivo, or ex vivo.

As used herein "primary therapy" refers to a first line of treatment upon initial diagnosis of an estrogen hormone dependent disorder or breast disorder or both in a subject. Exemplary primary therapies may involve surgery, a wide range of chemotherapies, and radiotherapy.

As used herein, the terms "subject," "patient," "participant" and "individual," may be used interchangeably herein and refer to a mammal such as a human. Mammals also include pet animals such as dogs, cats, laboratory animals, such as rats, mice, and farm animals such as cows and horses. Unless otherwise specified, a mammal may be of any gender or sex.

As used herein, the term "tamoxifen refractory" refers to subjects that have been dosed daily with tamoxifen for at least 2 days and have a level of plasma endoxifen of less than 30 nM (e.g., less than 20 nM, less than 25 nM, or less than 30 nM). As used herein, the term "tamoxifen resistance" refers to two classes of resistance: (a) de novo resistance, i.e., non-responsiveness to tamoxifen therapy from the beginning of the treatment, and (b) acquired resistance, i.e., non-responsiveness to tamoxifen therapy after initial responsiveness or tamoxifen-dependent growth/stimulated growth while continuing to express estrogen receptors (Minsun Chang. Biomol. Ther. 20(3), 256-267 (2012). The acquired resistance to tamoxifen may develop as early as 3 m to 1 year to as late as 5 to 10 years. As used herein the term "reference plasma endoxifen level" refers to a value of 30 nM.

As used herein, the term "Unit Dosage Form" refers to physically discrete units suitable for unitary dosages for subjects, each unit containing a predetermined quantity of active material calculated to produce the desired therapeutic effect, in association with a suitable pharmaceutical excipient.

Terms such as "include," "including," "contain," "containing," "has," or "having," and the like, mean "comprising."

Pharmacokinetic (PK) parameters used herein are defined and calculated as follows:

$C_{max}$: Maximum observed plasma/serum concentration obtained directly from the data.

$T_{max}$: Time to maximum observed concentration, taken directly from the data. If the maximum plasma/serum concentration occurs at more than one time point, the first is chosen.

$AUC_{0-tlast}$ or $AUC_{last}$: Area under the plasma/serum concentration versus time curve, calculated using the linear trapezoidal rule from time 0 to time t, where t is the time of last quantifiable concentration.

$\lambda z$: Terminal elimination rate constant obtained from the slope of the line, fitted by linear least squares regression through the terminal points of the logarithmic concentration-time profiles.

$AUC_{inf}$: Area under the plasma/serum concentration versus time curve from zero to infinity, calculated as $(AUC_{0-tlast}+Ct_{last}/\lambda z)$, where $Ct_{last}$ is the last quantifiable concentration.

$AUC_{tau}$: Area under the plasma/serum concentration versus time curve over the inter-dosing interval (tau), calculated using the linear trapezoidal rule.

$t_{1/2}$: Apparent terminal half-life, calculated as $(\ln(2)/\lambda z)$.

CL/F: Apparent total plasma/serum clearance of drug after oral administration, where F is the fraction of drug absorbed, calculated as $(Dose/AUC_{inf})$.

$CL/F_{ss}$: Apparent total plasma/serum clearance of drug after multiple oral administration, where F is the fraction of drug absorbed, calculated as $(Dose/AUC_{tau})$.

$V_z/F$: Apparent volume of distribution during terminal phase after oral administration, calculated as $(CL/F/\lambda z)$.

$C_{min}$: Minimum observed plasma/serum concentration over the inter-dose interval obtained directly from the data.

$C_{avg}$ or $C_{average}$: Average plasma/serum concentration at steady-state calculated as $(AUC_{tau}/tau)$.

AI: Accumulation index calculated as ($AUC_{tau}$ Day 39 dose/AUCs Day 1 dose).

The portion of $AUC_{inf}$ determined by extrapolation, % $AUC_{extrap}$, determined as $100\times(AUC_{inf}-AUC_{0-tlast})/AUC_{inf}$ The term "bioavailability," which has the meaning defined in 21 C.F.R. § 320.1(a), refers to the rate and extent to which an active ingredient or active moiety is absorbed from a drug product and becomes available at the site of action. For drug products that are not intended to be absorbed into the bloodstream, bioavailability may be assessed by measurements intended to reflect the rate and extent to which the active ingredient or active moiety becomes available at the site of action. For example, bioavailability can be measured as the amount of active ingredient in the blood (serum or plasma) as a function of time. Pharmacokinetic parameters such as AUC, $C_{max}$ or $T_{max}$ may be used to measure and assess bioavailability.

It is specifically understood that any numerical value cited herein includes all values from the lower value to the upper value, i.e., all possible combination of numerical values between the lowest value and the highest value enumerated are to be considered to be expressly stated in this application and the endpoint of all ranges are included within the range and independently combinable. For example, if a concentration range or beneficial range is stated as 1% to 50%, it is intended that values such as 2% to 40%, 10% to 30%, 1% to 3%, 1.5 to 2.5%, etc., are expressly enumerated in this specification. It is also to be understood that if a concentration or dose is stated as a specific value such as 1 mg or 10 mg or as "about 1 mg" or "about 10 mg", it is intended that it is intended to include 10% variation. As another example, a stated concentration of 20% or "about 20% is intended to include values±10%. Yet another example, if a ratio of 1:10 to 10:1 or "about 1:10 to about 10:1" is stated, then it is intended that ratios such as 1:9 to 9:1, from 1:8 to 8:1, from 1:7 to 7:1, from 1:6 to 6:1, from 1:5 to 5:1, from 1:4 to 4:1, from 1:3 to 3:1, from 1:2 to 2:1, from 1:1 to 2:1, 0.9:10.1 to 10.1 to 0.9, or from 2:5 to 3:5 etc. are specifically intended. There are only some examples of what is specifically intended. Unless specified otherwise, the values of the constituents or components of the compositions are expressed in weight percent of each ingredient or component in the core composition.

All compounds are understood to include all possible isotopes of atoms occurring in the compounds. Isotopes include those atoms having the same atomic number but different mass numbers. By way of example, and without limitation, isotopes of hydrogen include tritium and deuterium and isotopes of carbon include $^{11}C$, $^{13}C$ and $^{14}C$.

All methods described herein can be performed in a suitable order unless otherwise indicated or otherwise clearly contradicted by context. The use of any and all examples, or exemplary language (e.g., "such as" and "the like") is intended merely to illustrate the invention and does not pose a limitation on the scope of the invention unless otherwise claimed. No language in the specification should be construed as any indicating any non-claimed element as essential to practice of the invention as used herein.

As used herein, the terms "hormone dependent disorder" includes, without limitation, any disorder that is related to or is sensitive to a hormone such as estrogen, any disorder with estrogen-receptor positive (ER+) and/or progesterone-receptor positive (PR+) disorders, and any disorder that is susceptible or responsive to (Z)-endoxifen, or a polymorph or a salt thereof, including any hormone dependent reproductive tract disorder, breast disorders, endometriosis, uterine fibroids (also called leiomyomas), and hormone dependent mood disorder, etc. Reproductive tract disorders include endometrial, ovarian, cervical, uterus, vaginal, and vulvar, cancers. The terms "estrogen-related disorder" and "estrogen-receptor related disorder" may be used interchangeably to refer to the foregoing hormone dependent disorders. Examples of hormone dependent mood disorders include, but are not limited to, depression, mania, hypomania, bipolar disorders, and schizophrenic disorders. The hormone dependent disorders may be presented primarily or secondarily to an underlying disease, for example, prostate cancer or other disorders such as liver diseases. Hormone dependent disorders, for example, include McCune-Albright syndrome which is a disorder caused by a mutation in the GNAS gene affecting bones, skin, and several hormone-producing (endocrine) tissues, often resulting in abnormal scar-like (fibrous) tissue in their bones, a condition called polyostotic fibrous dysplasia, hyperthyroidism in individuals carrying such mutations, and in girls often resulting in precocious puberty.

As used herein, "breast disorder" means any aberration or a constellation of aberrations in the breast. Such aberration may be proliferative, non-proliferative, benign or malignant. Breast disorders include benign lesions of the breast (e.g., hyperplasia), increased breast density, gynecomastia, mastalgia, McCune-Albright syndrome, and breast cancer. Benign breast lesions include, but are not limited to, hyperplasia, atypia, ductal hyperplasia, lobular hyperplasia, atypical ductal hyperplasia (ADH), and atypical lobular hyperplasia (ALH). While not cancerous, ADH and ALH may be indicative of a predisposition for breast cancer.

Breast density is a breast disorder identified by visual techniques such as mammography ("mammographic breast density" or "MBD") or magnetic resonance imaging ("MRI"), X-ray, and reflects increased fibroglandular tissue within the breast, e.g., overgrowth of stromal and epithelial cells in the breast. Breast density is classified as Class A (previously Class I), B (previously Class II), C (previously Class III) or D (previously Class IV), based on the degree of amount or volume of dense tissue or severity of the density (Wolfe J N. AJR Am J Roentgenol 1976; 126:1130-1137). Whitehead et al., using data from the 1970s, showed that a masking effect of density existed but that it operated in addition to differences in the risk of breast cancer related to the classification of breast patterns described by Wolfe (Whitehead J, et al. Cancer 1985; 56:1280-1286). It is thus considered an independent risk factor for breast cancer. At least 35 states in USA require physicians to inform subjects if they have dense breast(s). There is currently no approved treatment for dense breasts, although subjects are reminded to make healthy lifestyle choices and undergo regular mammograms and other imaging monitor changes in breast.

Gynecomastia is a common male breast condition reflecting increased hyperplasia of the breast tissue, including epithelial hyperplasia, with prevalence of asymptomatic gynecomastia is 60% to 90% in neonates, 50% to 60% in adolescents, and up to 70% in men aged 50 to 69 years (Therapeutics and Clinical Risk Management 2011:7, 145-148). Newborn gynecomastia usually resolves itself within 4 weeks of birth and at least half of adolescent males experience gynecomastia with typical onset of 13 to 14 years of age (Tanner stage 3 or 4). Gynecomastia has been proposed to be a risk factor for male breast cancer.

Further, gynecomastia often presents itself secondarily to an underlying disorder such as prostate cancer, cirrhosis and liver disease, male hypogonadism, hyperthyroidism, renal failure and in patients undergoing hemodialysis, Type I diabetes mellitus, etc. Further, medications, such as anti-androgen medications or certain anti-psychotics, themselves have been reported to cause up to 25% of cases of gynecomastia and can be categorized by their hormone-like action. For example, the most common side effects attributed to bicalutamide, a nonsteroidal antiandrogen used for treatment of prostate cancer, are gynecomastia and breast pain.

As used herein, "breast cancer" means any malignant tumor of breast cells. Breast cancer may be at any stage of breast cancer, including stages of a pre-cancer, an early stage cancer, a non-metastatic cancer, a pre-metastatic cancer, a locally advanced cancer, and a metastatic cancer. There are several types of breast cancer. Exemplary breast cancers include, but are not limited to, ductal carcinoma in situ (DCIS), lobular carcinoma in situ (LCIS), invasive (or infiltrating) lobular carcinoma (ILC), invasive (or infiltrating) ductal carcinoma (IDC), microinvasive breast carcinoma (MIC), inflammatory breast cancer, ER-positive (ER+) breast cancer, ER-negative (ER−) breast cancer, HER2+ breast cancer, triple negative breast cancer (TNBC), BRCA1+ breast cancer, BRCA2+ breast cancer, adenoid cystic (adenocystic) carcinoma, low-grade adenosquamatous carcinoma, medullary carcinoma, mucinous (or colloid) carcinoma, papillary carcinoma, tubular carcinoma, metaplastic carcinoma, or micropapillary carcinoma. A single breast cancer tumor can be a combination of these types or be a mixture of invasive and in situ cancer.

Sustained Release Compositions

The present disclosure relates to novel sustained release compositions of (Z)-endoxifen, and polymorphs and salts thereof, as a therapeutic agent. The sustained release compositions of the present disclosure provide controlled release of the therapeutic agent or drug over a longer period of time (e.g., at least 2 hours to about 72 hours, at least 4 hours to 24 hours, at least 6 hours to 48 hours etc.). After about 2 hours post administration or ingestion of a dose, the sustained release compositions of the present disclosure provide prolonged release in the intestines after the passage of the compositions from the stomach to allow for uptake of the therapeutic agent ((Z)-endoxifen or a polymorph or a salt thereof) from the intestines and/or colon into the blood stream in a subject. The rate of release of (Z)-endoxifen, or a polymorph or a salt thereof, from the sustained release compositions (for example enteric-coated delayed release tablet) is slower than that observed for the reference product (the Capsule) which has been described in WO2019051416A1 (Methods for making and using endoxifen). The sustained release compositions provide a controlled and prolonged exposure of the subject to the therapeutic agent over a time period from at least about 2 hours to about 270 hours per dose after administration. Thus, by reducing the frequency of dosing and/or reducing the rate of uptake of the therapeutic agent into blood stream, the present disclosure provides the potential for improved or enhanced tolerance to the drug by the patient and for improved patient convenience and compliance. The slow and prolonged (or sustained) release and uptake into the blood stream of (Z)-endoxifen, or a polymorph or a salt thereof, also has the potential to provide reduced local and/or systemic side effects and toxicity and reduced drug accumulation as compared with other dosage forms such as the reference product, and/or reduced total amount of drug for treatment, because the patient may be exposed to lower peak concentration of drug over time. Targeting the intestines (for example, duodenum and jejunum) and colon, by delaying the release of the drug, to protect from the acidic environment of the stomach also increase the potential for improved bioavailability and ability to withstand "food effect" as well as increased efficacy.

The present disclosure provides sustained release compositions comprising (Z)-endoxifen, or a polymorph or a salt thereof, and a sustained release delivery system. The sustained release delivery system includes (i) at least one sustained release (SR) or release rate controlling agent ("sustained release agent" or "SR-agent" used interchangeably herein), (ii) at least one binder, and (iii) at least one lubricant.

In one aspect, the present disclosure provides sustained release compositions comprising stable (Z)-endoxifen free base, and polymorphs and salts thereof. In some embodiments, the sustained release compositions comprising (Z)-endoxifen free base or a polymorph or a salt thereof further comprise (E)-endoxifen. In some embodiments, the sustained release composition comprises endoxifen predominantly as (Z)-endoxifen free base.

In some embodiments, the sustained release compositions of the present disclosure are in the form of solid dosage forms such as tablets, mini-tablets, beads, microbeads, granules, spheres particles, multi-particulates, and the like. The present disclosure provides that the sustained release compositions of the present disclosure can be enteric coated for delayed release targeting the intestines and colon. Accordingly, in some embodiments, the sustained release compositions are in the form of enteric coated delayed release tablets, enteric coated delayed release tablet-in-tablets, enteric coated delayed release tablet-in-capsules, beads-in-capsules, spheres-in capsules, and the like.

The (Z)-endoxifen or a polymorph or a salt thereof may be dispersed in the sustained release compositions homogeneously.

In certain embodiments, sustained release compositions may comprise (Z)-endoxifen as at least 0.1%, at least 0.2%, at least 0.3%, at least 0.4%, at least 0.5%, at least 0.6%, at least 0.7%, at least 0.8%, at least 0.9%, at least 1%, at least 5%, at least 10%, at least 20%, at least 25%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.99%, and 100% of (Z)-endoxifen free base w/w of total endoxifen in the sustained release composition. In at least one sustained release composition, the sustained release composition comprises ≥90% of (Z)-endoxifen free base w/w of the total endoxifen in the sustained release composition. In another embodiment, the sustained release composition comprises ≥95% of (Z)-endoxifen free base w/w of the total endoxifen in the composition. In yet other embodiments, the sustained release compositions comprise ≥96%, ≥97%, ≥98%, ≥99%, ≥99.5%, or ≥99.9% of (Z)-endoxifen free base w/w of the total endoxifen in the sustained release composition.

In other embodiments, sustained release compositions comprising (Z)-endoxifen comprise about 0.01% to about 40%, about 0.01% to about 20%, about 0.05% to about 15%, and about 0.1% to about 10% of (Z)-endoxifen w/w of the sustained release composition. In at least one embodiment, the sustained release compositions comprising (Z)-endoxifen comprise 0.01% to 40% of (Z)-endoxifen w/w of the sustained release composition. In various other embodiments, the sustained release compositions comprising (Z)-endoxifen comprise about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, and about 20% of (Z)-endoxifen w/w of the sustained release composition. In some embodiments, the (Z)-endoxifen contained in sustained release compositions is substantially pure. Such sustained release compositions may contain less than 5%, less than 4%, less than 3%, less than 2.5% less than 2%, less than 1%, less than 0.5%, or less than 0.1% (E)-endoxifen. Such sustained release compositions may contain less than 5% less than 4%, less than 3% less than 2%, or less than 1% other impurities.

In some embodiments, the sustained release compositions of the present disclosure further comprise (E)-endoxifen. In some embodiments, the endoxifen in the sustained release composition has a ratio of (E)-endoxifen to (Z)-endoxifen (E/Z-ratio) of about 1:999, about 5:995, about 1:99; about 5:95; about 10:90, about 15:85; about 20:80, about 25:75; about 30:70; about 40:70, about 45:55; about 50:50; about 55:45; about 60:40; about 65:45; or about 70:30. In other embodiments, sustained release compositions comprise endoxifen having E/Z-ratio ranging from about 10:90 to about 70:30. In still other embodiments, sustained release compositions comprise endoxifen having E/Z-ratio ranging from about 45:55 to about 55:45.

Unless specifically referred to by the prefix (Z), (E) or (E/Z), endoxifen used generally without a prefix is used herein to include to any or all endoxifen isoforms. A mixture of (E)-endoxifen and (Z)-endoxifen, can be represented by Formula (III):

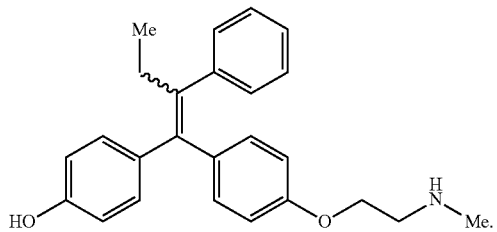

Formula (III)

In an aspect, the present disclosure provides that the sustained release compositions of the present disclosure specifically include, in some embodiments, polymorphic crystalline forms of (Z)-endoxifen, such as Form I, Form II, or Form III, as described in Applicant's patent publication WO2019051416 (A1) (incorporated herein by reference).

In certain aspects, the present disclosure provides crystalline forms of endoxifen, including crystalline forms of (Z)-endoxifen free base and crystalline forms of mixtures of (E)-endoxifen and (Z)-endoxifen. The present disclosure further provides pharmaceutical compositions of endoxifen comprising the crystalline forms described herein. A crystalline form of endoxifen may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product or active ingredient. Such variations may affect the preparation or formulation of pharmaceutical compositions in different dosage or delivery forms, such as solid oral dosage forms including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of endoxifen may provide advantages such as: improving the manufacturing process of an active agent or the stability or storability of a drug product form of the compound or an active ingredient, and/or having suitable bioavailability and/or stability as an active agent.

The use of certain solvents and fractional crystallization methods has been found to produce different polymorphic forms of endoxifen, including any one or more of polymorphic Forms I, II and III, which may exhibit one or more favorable characteristics described above. In some embodiments, a polymorphic form (e.g., Form I, Form II, or Form III) may affect one or more properties of a composition comprising endoxifen. For example, a polymorphic form (e.g., Form I, Form II, or Form III) of a therapeutic agent (e.g., endoxifen) may affect one or more of the dissolution rate, the solubility, the absorption rate, the $C_{max}$, the AUC, the $T_{max}$, or the $t_{1/2}$, of the therapeutic agent in a composition of the present disclosure. In some embodiments, the polymorphic form of endoxifen may confer one or more properties that favorably contribute to manufacturability of a compostions of the present disclosure (e.g., a sustained release composition comprising endoxifen). In some embodiments, the polymorphic form of endoxifen may confer improved stability to a composition of the present disclosure. The processes for the preparation of the polymorphs described herein, and characterization of these polymorphs are described in greater detail below.

Formula III, Form I

Figure 7:
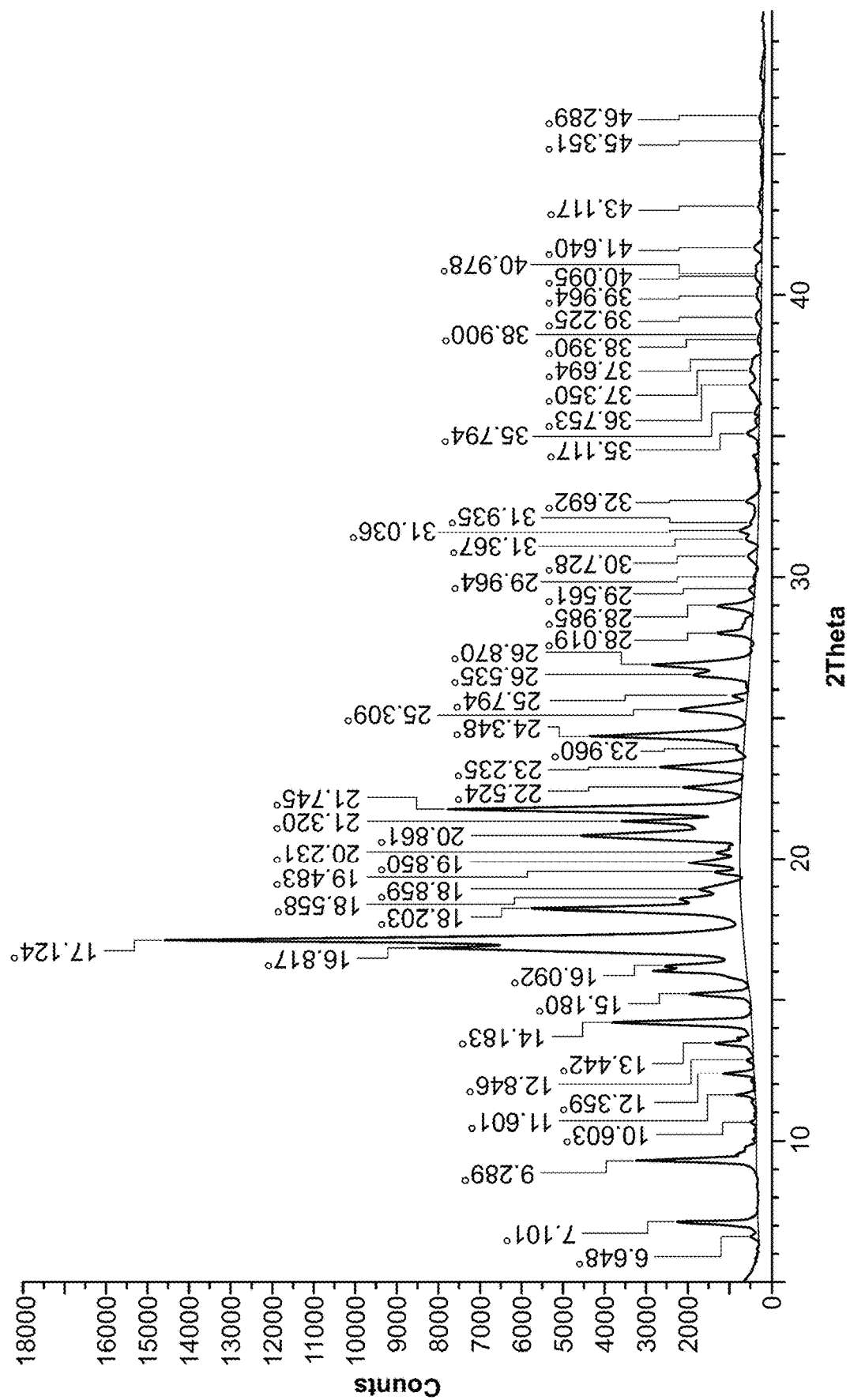
FIG. 7 is an X-ray powder diffraction (XRPD) pattern obtained from a sample of Form I of the compound of Formula (III).
Figure 8:
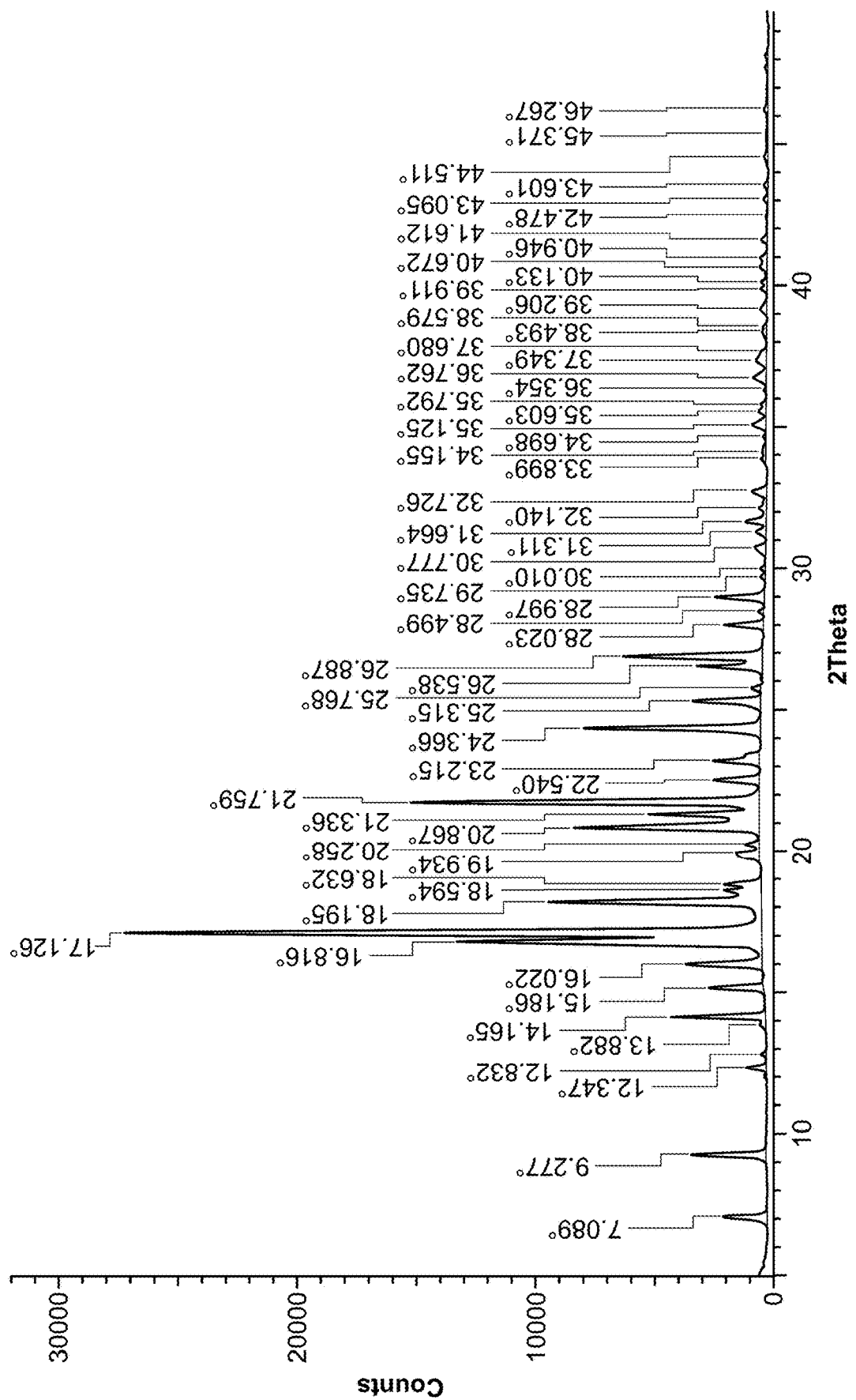
FIG. 8 is an XRPD pattern obtained from a sample of Form I of the compound of Formula (III).

In certain aspects, the present disclosure provides polymorphic Form I of a compound of Formula (III), wherein at least 90% by weight of the compound of Formula (III) in the composition is the (Z)-isomer (i.e., (Z)-endoxifen). In some embodiments, polymorphic Form I exhibits an x-ray powder diffraction (XRPD) pattern substantially as shown in FIG. 7 or FIG. 8. In some embodiments, polymorphic Form I has an XRPD pattern comprising at least two, at least three, at least four, at least five, or at least six of the major peaks as the XRPD pattern substantially as shown in FIG. 7 or FIG. 8.

The term "substantially as shown in" when referring, for example, to an XRPD pattern, includes a pattern that is not necessarily identical to those depicted herein, but that falls within the limits of experimental error or deviations when considered by one of ordinary skill in the art. The relative intensities of XRPD peaks can vary, depending upon the particle size, the sample preparation technique, the sample mounting procedure and the particular instrument employed. Moreover, instrument variation and other factors can affect the two theta (2θ) values. Accordingly, when a specified two theta angle is provided, it is to be understood that the specified two theta angle can vary by the specified value±0.5°, such as ±0.4°, ±0.3°, ±0.2°, or ±0.1°. As used herein, "major peak" refers to an XRPD peak with a relative intensity greater than 30%, such as greater than 35%. Relative intensity is calculated as a ratio of the peak intensity of the peak of interest versus the peak intensity of the largest peak in the XRPD pattern.

In certain embodiments, polymorphic Form I is characterized by an x-ray powder diffraction pattern comprising major peaks at 16.8±0.3°, 17.1±0.3° and 21.8±0.3° two theta. In some embodiments, polymorphic Form I is characterized by an x-ray powder diffraction pattern comprising peaks at 16.0±0.3°, 18.8±0.3° and 26.5±0.3° two theta. In some embodiments, polymorphic Form I is characterized by an x-ray powder diffraction pattern comprising major peaks at 16.8±0.3°, 17.1±0.3° and 21.8±0.3° two theta, and at least one peak selected from 16.0±0.3°, 18.8±0.3° and 26.5±0.3° two theta. In some embodiments, polymorphic Form I is characterized by an x-ray powder diffraction pattern comprising peaks at 12.3±0.3°, 28.0±0.3° and 29.0±0.3° two theta. In some embodiments, polymorphic Form I is characterized by an x-ray powder diffraction pattern comprising major peaks at 16.8±0.3°, 17.1±0.3° and 21.8±0.3° two theta, and at least one peak selected from 12.3±0.3°, 28.0±0.3° and 29.0±0.3° two theta. In some embodiments, polymorphic Form I is characterized by an x-ray powder diffraction pattern comprising major peaks at 16.8±0.3°, 17.1±0.3° and 21.8±0.3° two theta, and at least one peak selected from 12.3±0.3°, 16.0±0.3°, 18.8±0.3°, 26.5±0.3°, 28.0±0.3° and 29.0±0.3° two theta. In some embodiments, polymorphic Form I is characterized by an x-ray powder diffraction pattern comprising major peaks at 16.8±0.3°, 17.1±0.3° and 21.8±0.3° two theta, and peaks at 12.3±0.3°, 16.0±0.3°, 18.8±0.3°, 26.5±0.3°, 28.0±0.3° and 29.0±0.3° two theta.

In certain embodiments, the present disclosure provides a composition comprising polymorphic Form I. Greater than 90%, 95% or 99% by weight of the compound of Formula (III) in the composition may be polymorphic Form I. In some embodiments, the composition comprises 0.01 mg to 200 mg of polymorphic Form I. In some embodiments, the composition comprises about 1 mg, 2 mg, 4 mg, 6 mg, 10 mg or 20 mg of polymorphic Form I.

Formula III, Form II

Figure 9:
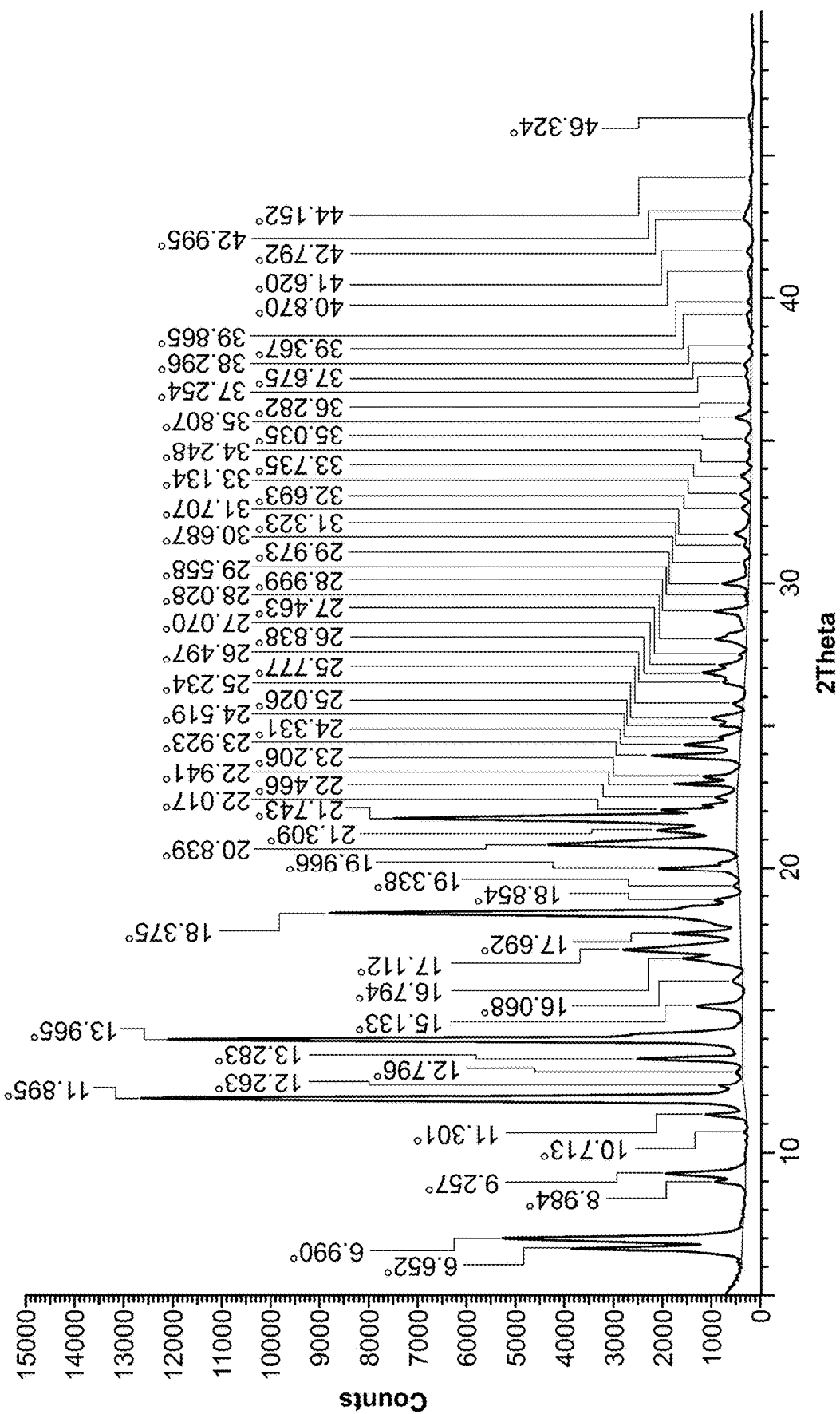
FIG. 9 is an XRPD pattern obtained from a sample of Form II of the compound of Formula (III).
Figure 10:
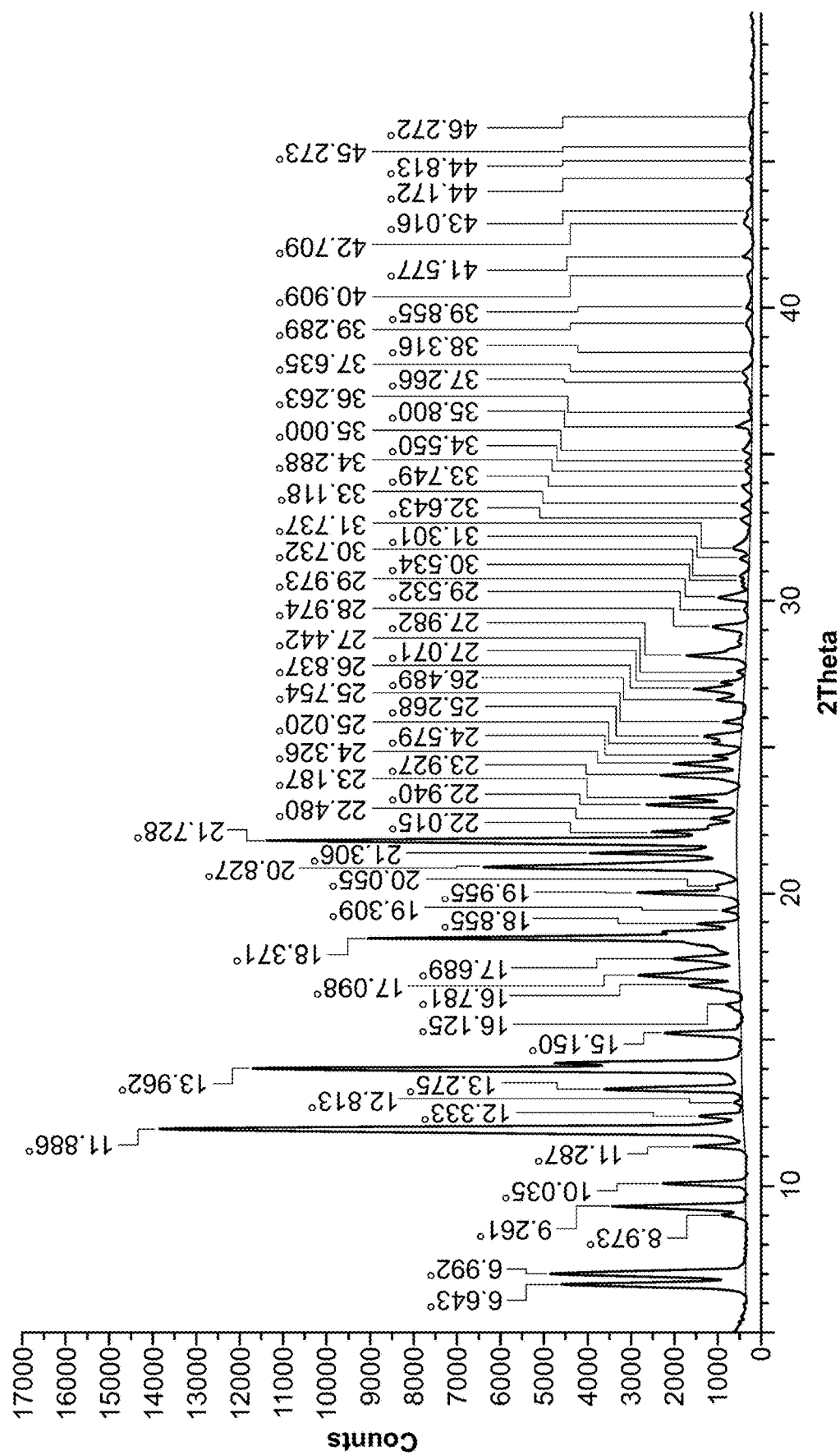
FIG. 10 is an XRPD pattern obtained from a sample of Form II of the compound of Formula (III).

In certain aspects, the present disclosure provides polymorphic Form II of a compound of Formula (III), wherein the composition comprises the (E)-isomer and the (Z)-isomer of the compound of Formula (III) (i.e., (E)-endoxifen and (Z)-endoxifen) in an E/Z ratio between 0.9 and 1.3, such as about 1.1. In some embodiments, polymorphic Form II exhibits an x-ray powder diffraction (XRPD) pattern substantially as shown in FIG. 9 or FIG. 10. In some embodiments, polymorphic Form II has an XRPD pattern comprising at least two, at least three, at least four, at least five, or at least six of the major peaks as the XRPD pattern substantially as shown in FIG. 9 or FIG. 10.

In certain embodiments, polymorphic Form II is characterized by an x-ray powder diffraction pattern comprising major peaks at 7.0±0.3°, 11.9±0.3°, 14.0±0.3° and 18.4±0.3° two theta. In some embodiments, polymorphic Form II is characterized by an x-ray powder diffraction pattern comprising a peak at 22.0±0.3° two theta. In some embodiments, polymorphic Form II is characterized by an x-ray powder diffraction pattern comprising major peaks at 7.0±0.3°, 11.9±0.3°, 14.0±0.3° and 18.4±0.3° two theta and a peak at 22.0±0.3° two theta. In some embodiments, polymorphic Form II is characterized by an x-ray powder diffraction pattern comprising at least one peak selected from 6.6±0.3°, 13.3±0.3° and 20.0±0.3° two theta. In some embodiments, polymorphic Form II is characterized by an x-ray powder diffraction pattern comprising major peaks at 7.0±0.3°, 11.9±0.3°, 14.0±0.3° and 18.4±0.3° two theta, and at least one peak selected from 6.6±0.3°, 13.3±0.3° and 20.0±0.3° two theta. In some embodiments, polymorphic Form II is characterized by an x-ray powder diffraction pattern comprising major peaks at 7.0±0.3°, 11.9±0.3°, 14.0±0.3° and 18.4±0.3° two theta, and at least one peak selected from 6.6±0.3°, 13.3±0.3°, 20.0±0.3° and 22.0±0.3° two theta. In some embodiments, polymorphic Form II is characterized by an x-ray powder diffraction pattern comprising major peaks at 7.0±0.3°, 11.9±0.3°, 14.0±0.3° and 18.4±0.3° two theta, and peaks at 6.6±0.3°, 13.3±0.3°, 20.0±0.3° and 22.0±0.3° two theta.

In certain embodiments, the present disclosure provides a composition comprising polymorphic Form II. Greater than 90%, 95% or 99% by weight of the compound of Formula (III) in the composition may be polymorphic Form II. In some embodiments, the composition comprises 0.01 mg to 200 mg of polymorphic Form II. In some embodiments, the composition comprises about 1 mg, 2 mg, 4 mg, 6 mg, 10 mg or 20 mg of polymorphic Form II.

Formula III, Form III

Figure 11:
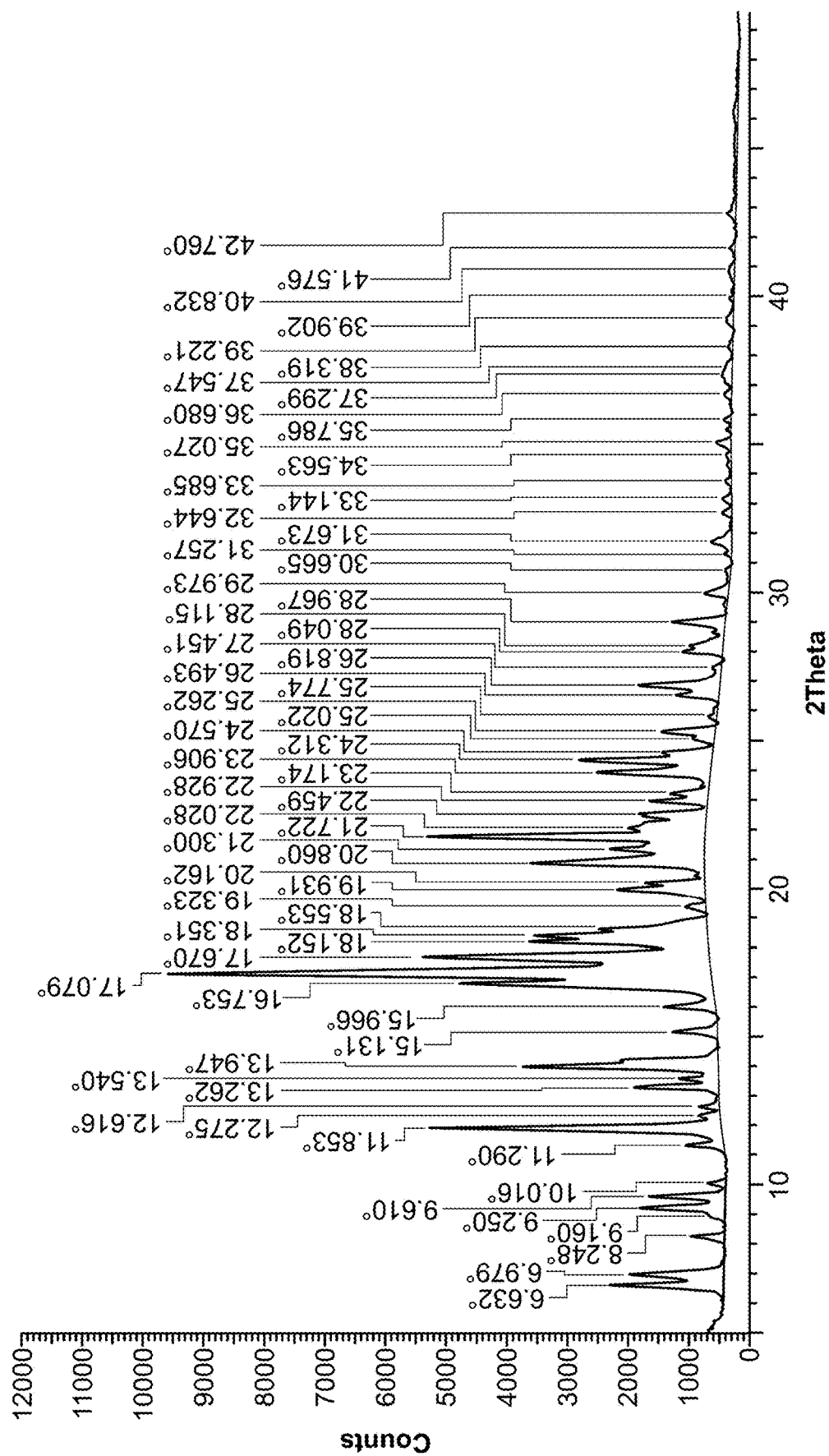
FIG. 11 is an XRPD pattern obtained from a sample of Form III of the compound of Formula (III).
Figure 12:
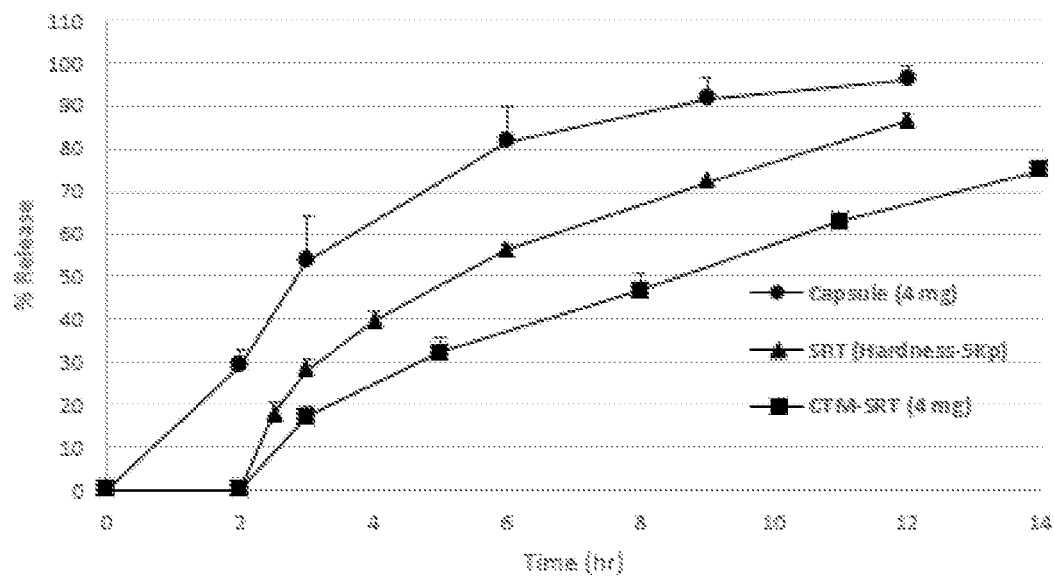
FIG. 12 shows the percentage dissolution and release of Z-endoxifen from a 4 mg exemplary sustained release compositions in the form of enteric coated delayed release tablet containing 4 mg of (Z)-endoxifen free base of hardness 5 Kp (SRT 5 Kp), CTM-SRT (used in Example 8), and the reference product/control (a 4 mg delayed release (Z)-endoxifen API-in-capsule) as measured according to USP II (paddle apparatus II) method in simulated intestinal fluid. (Z)-endoxifen release upon dissolution of the compositions was measured using HPLC-UV.
Figure 13:
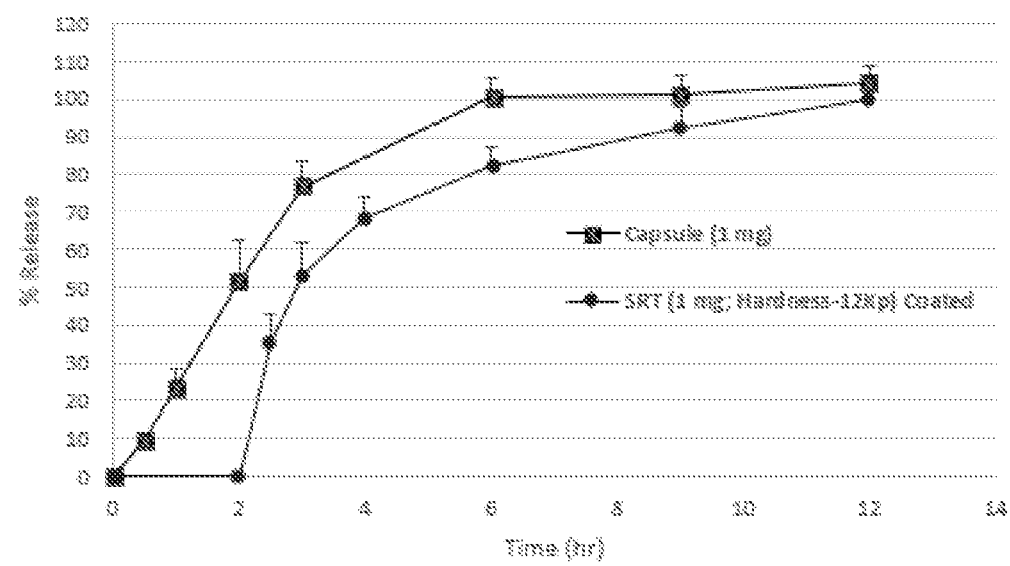
FIG. 13 shows the percentage dissolution and release of Z-endoxifen from exemplary sustained release compositions in the form of enteric coated delayed release tablet of hardness 12 Kp containing 1 mg of (Z)-endoxifen free base and the reference product (a 4 mg delayed release (Z)-endoxifen API-in-capsule) as measured according to USP II (paddle apparatus II) method in simulated intestinal fluid. (Z)-endoxifen release upon dissolution of the compositions was measured using HPLC-UV.
Figure 14:
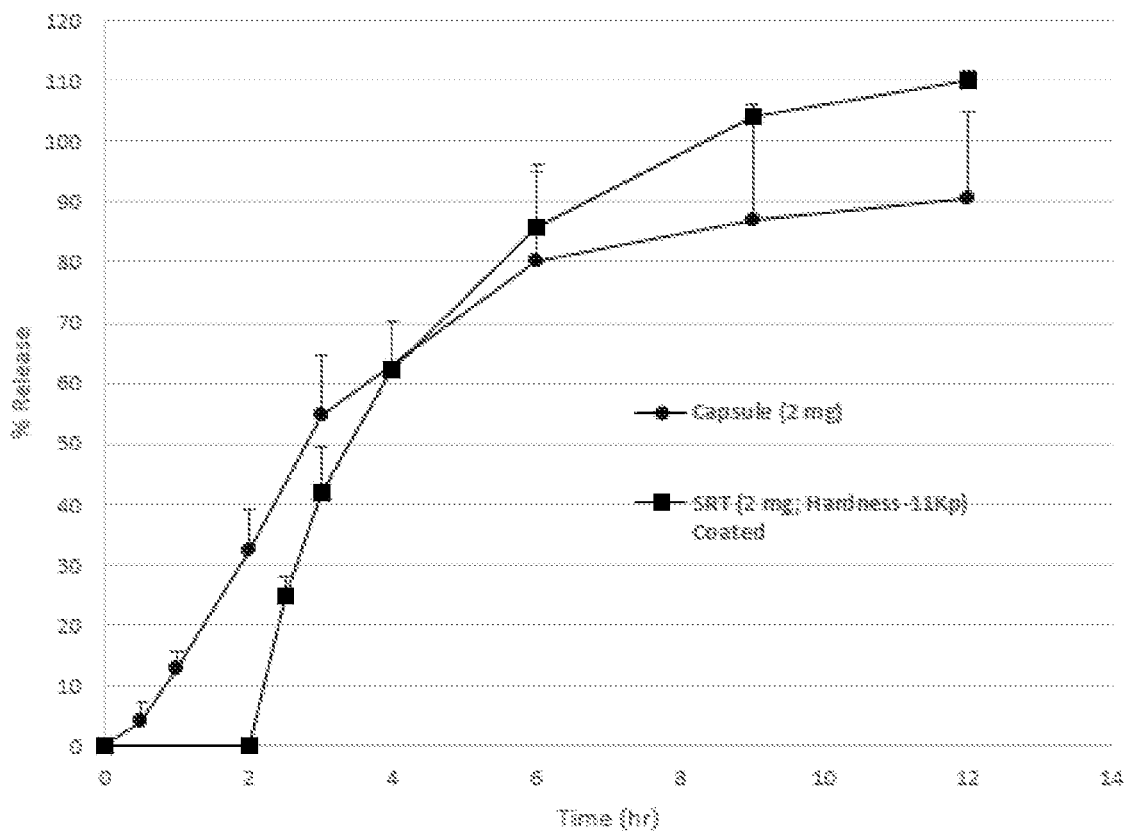
FIG. 14 shows the percentage dissolution and release of Z-endoxifen from exemplary sustained release compositions in the form of enteric coated delayed release tablet of hardness containing 2 mg of (Z)-endoxifen free base of hardness 11 Kp and reference product (a 4 mg delayed release (Z)-endoxifen API-in-capsule) as measured according to USP II (paddle apparatus II) method in simulated intestinal fluid. (Z)-endoxifen release upon dissolution of the compositions was measured using HPLC-UV.

In certain aspects, the present disclosure provides polymorphic Form III of a compound of Formula (III), wherein the composition comprises the (E)-isomer and the (Z)-isomer of the compound of Formula (III) (i.e., (E)-endoxifen and (Z)-endoxifen) in an E/Z ratio between 0.9 and 1.3, such as about 1.1. In some embodiments, polymorphic Form III exhibits an x-ray powder diffraction (XRPD) pattern substantially as shown in FIG. 11. In some embodiments, polymorphic Form III has an XRPD pattern comprising at least two, at least three, at least four, at least five, or at least six of the major peaks as the XRPD pattern substantially as shown in FIG. 11.

In certain embodiments, polymorphic Form III is characterized by an x-ray powder diffraction pattern comprising major peaks at 11.9±0.3°, 13.9±0.3°, 17.1±0.3° and 17.7±0.3° two theta. In some embodiments, polymorphic Form III is characterized by an x-ray powder diffraction pattern comprising a peak at 25.3±0.3° two theta. In some embodiments, polymorphic Form III is characterized by an x-ray powder diffraction pattern comprising major peaks at 11.9±0.3°, 13.9±0.3°, 17.1±0.3° and 17.7±0.3° two theta and a peak at 25.3±0.3° two theta. In some embodiments, polymorphic Form III is characterized by an x-ray powder diffraction pattern comprising at least one peak selected from 18.2±0.3°, 22.5±0.3° and 26.8±0.3° two theta. In some embodiments, polymorphic Form III is characterized by an x-ray powder diffraction pattern comprising major peaks at 11.9±0.3°, 13.9±0.3°, 17.1±0.3° and 17.7±0.3° two theta, and at least one peak selected from 18.2±0.3°, 22.5±0.3° and 26.8±0.3° two theta. In some embodiments, polymorphic Form III is characterized by an x-ray powder diffraction pattern comprising major peaks at 11.9±0.3°, 13.9±0.3°, 17.1±0.3° and 17.7±0.3° two theta, and at least one peak selected from 18.2±0.3°, 22.5±0.3°, 25.3±0.3° and 26.8±0.3° two theta. In some embodiments, polymorphic Form III is characterized by an x-ray powder diffraction pattern comprising major peaks at 11.9±0.3°, 13.9±0.3°, 17.1±0.3° and 17.7±0.3° two theta, and peaks at 18.2±0.3°, 22.5±0.3°, 25.3±0.3° and 26.8±0.3° two theta.

In certain embodiments, the present disclosure provides a composition comprising polymorphic Form III. Greater than 90%, 95% or 99% by weight of the compound of Formula (III) in the composition may be polymorphic Form III. In some embodiments, the composition comprises 0.01 mg to 200 mg of polymorphic Form III. In some embodiments, the composition comprises about 1 mg, 2 mg, 4 mg, 6 mg, 10 mg or 20 mg of polymorphic Form III.

The terms "crystalline form", "polymorph" and "Form" may be used interchangeably herein, and are meant to include all crystalline and amorphous forms of the compound, including, for example, polymorphs, pseudopolymorphs, salts, solvates, hydrates, unsolvated polymorphs (including anhydrates), conformational polymorphs, and amorphous forms, as well as mixtures thereof, unless a particular crystalline or amorphous form is referred to. Compound of the present disclosure include crystalline and amorphous forms of those compounds, including, for example, polymorphs, pseudopolymorphs, salts, solvates, hydrates, unsolvated polymorphs (including anhydrates), conformational polymorphs, and amorphous forms of the compounds, as well as mixtures thereof.

In some embodiments, the sustained release composition comprises (Z)-endoxifen predominantly as polymorph Form I. In some embodiments, the sustained release composition comprises (Z)-endoxifen predominantly as polymorph Form II. In some embodiments, the sustained release composition comprises (Z)-endoxifen predominantly as polymorph Form III. In certain embodiments, the (Z)-endoxifen can be any combination of Forms I, II and III.

In certain embodiments, a sustained release composition comprises (Z)-endoxifen as at least 0.1%, at least 0.2%, at least 0.3%, at least 0.4%, at least 0.5%, at least 1%, at least 5%, at least 10%, at least 20%, at least 25%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.99%, or 100% of a single polymorphic Form of endoxifen, such as Form I, Form II, or Form III, w/w of total endoxifen in the sustained release composition. For example, a sustained release composition may comprise (Z)-endoxifen as Form I as at least 0.1%, at least 0.2%, at least 0.3%, at least 0.4%, at least 0.5%, at least 1%, at least 5%, at least 10%, at least 20%, at least 25%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.99%, or 100% w/w of the total endoxifen in the sustained release composition. In another example, a sustained release composition may comprise (Z)-endoxifen as Form II as at least 0.1%, at least 0.2%, at least 0.3%, at least 0.4%, at least 0.5%, at least 1%, at least 5%, at least 10%, at least 20%, at least 25%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.99%, or 100% w/w of the total endoxifen in the sustained release composition. In another example, a sustained release composition may comprise (Z)-endoxifen as Form III as at least 0.1%, at least 0.2%, at least 0.3%, at least 0.4%, at least 0.5%, at least 1%, at least 5%, at least 10%, at least 20%, at least 25%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.99%, or 100% w/w of the total endoxifen in the sustained release composition.

In at least one sustained release composition, the composition comprises ≥90% of a single polymorphic Form of endoxifen, such as Form I, Form II, or Form III w/w of the total endoxifen in the sustained release composition. For example, a sustained release composition comprises ≥90% of Form I of endoxifen w/w of the total endoxifen in the sustained release composition. In another example, a sustained release composition comprises ≥90% of Form II of endoxifen w/w of the total endoxifen in the sustained release composition. In another example, a sustained release composition comprises ≥90% of Form III of endoxifen w/w of the total endoxifen in the sustained release composition. In another embodiment, the sustained release composition comprises ≥95% of a single polymorphic Form of endoxifen, such as Form I, Form II, or Form III, w/w of the total endoxifen in the sustained release composition. In yet another embodiment, the sustained release composition comprises ≥96%, ≥97%, ≥98%, ≥99%, or ≥99.5% of a single polymorphic Form of endoxifen, such as Form I, Form II, or Form III, w/w of the total endoxifen in the sustained release composition. For example, the sustained release composition comprises ≥96%, ≥97%, ≥98%, ≥99%, or ≥99.5% of Form I of endoxifen w/w of the total endoxifen in the sustained release composition. In another example, the sustained release composition comprises ≥96%, ≥97%, ≥98%, ≥99%, or ≥99.5% of Form II of endoxifen w/w of the total endoxifen in the sustained release composition. In another example, the sustained release composition comprises ≥96%, ≥97%, ≥98%, ≥99%, or ≥99.5% of Form III of endoxifen w/w of the total endoxifen in the sustained release composition. When a particular percentage by weight of endoxifen is a single polymorphic form, the remainder of endoxifen in the sustained release composition is some combination of amorphous endoxifen and/or one or more polymorphic forms of endoxifen excluding the single polymorphic form. When the polymorphic endoxifen is defined as one particular form of endoxifen, the remainder is made up of amorphous endoxifen and/or one or more polymorphic forms other than the particular form specified. Examples of single polymorphic forms include Forms I, II and III of endoxifen, as well as descriptions of a single polymorphic form characterized by one or more properties as described in Applicant's patent publication WO2019051416 (A1).

In other embodiments, a sustained release composition comprising (Z)-endoxifen comprises about 0.01% to about 20%, about 0.05% to about 15%, or about 0.1% to about 10% of a single polymorphic Form of endoxifen, such as Form I, Form II, or Form III, w/w of the sustained release composition. In at least one embodiment, the sustained release composition comprising (Z)-endoxifen comprises about 0.01% to about 20% of a single polymorphic Form of endoxifen, such as Form I, Form II, or Form III, w/w of the composition. In various other embodiments, the sustained release composition comprising endoxifen comprises about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 10%, or about 20% of a single polymorphic Form of endoxifen, such as Form I, Form II, or Form III, w/w of the sustained release composition. In an aspect, a sustained release composition comprising a single polymorphic Form of (Z)-endoxifen, such as Form I, Form II, or Form III, further comprises a second polymorphic Form of endoxifen.

In an aspect, a sustained release composition comprising a polymorphic Form of (Z)-endoxifen in amounts ranging from about 0.1 mg to about 200 mg in a unit dose. In various embodiments, the sustained release compositions comprise 0.1 mg, 0.5 mg, 1 mg, 2 mg, 3 mg, 4 mg, 5 mg, 6 mg, 7 mg, 8 mg, 9 mg, 10 mg, 20 mg and 40 mg of a polymorphic Form of (Z)-endoxifen such as Form I, Form II, or Form III, or a combination thereof. For example, a sustained release composition may comprise 0.1 mg, 0.5 mg, 1 mg, 2 mg, 3 mg, 4 mg, 5 mg, 6 mg, 7 mg, 8 mg, 9 mg, 10 mg, 20 mg and 40 mg of Form I of (Z)-endoxifen. In another example, a sustained release composition may comprise 0.1 mg, 0.5 mg, 1 mg, 2 mg, 3 mg, 4 mg, 5 mg, 6 mg, 7 mg, 8 mg, 9 mg, 10 mg, 20 mg and 40 mg of Form II of (Z)-endoxifen. In another example, a sustained release composition may comprise 0.1 mg, 0.5 mg, 1 mg, 2 mg, 3 mg, 4 mg, 5 mg, 6 mg, 7 mg, 8 mg, 9 mg, 10 mg, 20 mg and 40 mg of Form III of (Z)-endoxifen. In some embodiments, a sustained release composition may comprise from 0.1 mg to 1 mg, from 0.1 mg to 2 mg, from 0.1 mg to 3 mg, from 0.1 mg to 4 mg, from 0.1 mg to 5 mg, from 1 mg to 2 mg, from 1 mg to 3 mg, from 1 mg to 4 mg, from 1 mg to 5 mg, from 1 mg to 6 mg, from 1 mg to 7 mg, from 1 mg to 8 mg, from 1 mg to 9 mg, from 1 mg to 10 mg, from 5 mg to 6 mg, from 5 mg to 7 mg, from 5 mg to 8 mg, from 5 mg to 9 mg, from 5 mg to 10 mg, from 5 mg to 15 mg, from 5 mg to 20 mg, from 5 mg to 40 mg, from 10 mg to 15 mg, from 10 mg to 20 mg, or from 10 mg to 40 mg a polymorphic Form of (Z)-endoxifen such as Form I, Form II, or Form III, or a combination thereof.

Examples of salts of (Z)-endoxifen suitable for the sustained release compositions of the present disclosure include pharmacologically acceptable salts such as salts with inorganic acids, salts with organic acids, salts with amino acids and the like. Examples of (Z)-endoxifen salts with inorganic acids include salts with hydrochloric acid, hydrobromic acid, nitric acid, sulfuric acid, phosphoric acid and the like. In some embodiments, the present disclosure provides (Z)-endoxifen salts with inorganic acids selected from the group consisting of hydrochloric acid, hydrobromic acid, nitric acid, sulfuric acid, phosphoric acid and the like.

Examples of salts with organic acids include salts with formic acid, acetic acid, trifluoroacetic acid, fumaric acid, oxalic acid, tartaric acid, maleic acid, methanesulfonic acid, benzenesulfonic acid, p-toluenesulfonic acid, and the like.

Examples of the salts with acidic amino acids include salts with aspartic acid, glutamic acid, citric acid, and the like. In some embodiments, the present disclosure provides (Z)-endoxifen salts with aspartic acid, citric acid, or glutamic acid.

Examples of anion salts of (Z)-endoxifen include arecoline, besylate, bicarbonate, bitartarate, butylbromide, citrate, camysylate, gluconate, glutamate, glycollylarsanilate, hexylresorcinate, hydrabamine, hydrobromide, hydrochloride, hydroxynapthanoate, isethionate, malate, mandelate, mesylate, methylbromide, methylbromide, methylnitrate, methyl sulfate, mucate, napsylate, nitrate, pamaoate (Embonate), pantothenate, phosphate/diphosphate, polygalacuronate, salicylate, stearate, sulfate, tannate, Teoclate, and triethiodide.

Examples of cation salts of (Z)-endoxifen selected from the group consisting of benzathine, clemizole, chloroprocaine, choline, diethylamine, diethanolamine, ethylenediamine, meglumine, piperazine, procaine, aluminum, barium, bismuth, lithium, magnesium, potassium, and zinc, and the like.

In some embodiments, the present disclosure provides that embodiments include salts made with acids that are not pharmaceutically acceptable.

The present disclosure provides that in some embodiments the sustained release compositions comprises salts of (Z)-endoxifen selected from the group consisting of acetate, arecoline, benzathine, benzoic, besylate, benzosulfonate, bicarbonate, bitartarate, butylbromide, citrate, camysylate, clemizole, chloroprocaine, choline, diethylamine, diethanolamine, ethylenediamine, formate, fumarate, glucolate, gluconate, glutamate, glycollylarsanilate, hexylresorcinate, hydrabamine, hydrobromide, hydrochloride, hydroxynapthanoate, isethionate, malate, maleate, mandelate, meglumine, mesylate, methylbromide, methylbromide, methylnitrate, methylsulfate, methanesulfonate, mucate, napsylate, nitric, nitrate, oxalate, pamaoate (Embonate), pantothenate, perchloric, phosphate, diphosphate, piperazine, procaine, polygalacuronate, p-toluenesulfonate, salicylate, stearate, succinate, sulfate, sulfonate, sulfuric, tannate, tartarate, teoclate, triethiodide, trifluoroacetate, aluminum, barium, bismuth, lithium, magnesium, potassium, and zinc aluminum, barium, bismuth, lithium, magnesium, potassium, and zinc, or any combination thereof.

In some embodiments, the present disclosure provides sustained release compositions comprising pharmaceutically acceptable salts of (Z)-endoxifen. Provided herein in certain embodiments are sustained release compositions comprising 1%, 5%, 10%, 20%, 25%, 30%, 40%, 50%, 60%, 70%, 80%, 90%, 95%, 96%, 97%, 98%, 99%, 99.5%, 99.9%, 99.99% or 100% of (Z)-endoxifen salt w/w of total endoxifen. In some embodiments, a sustained release composition comprises ≥90%, ≥95%, ≥96%, ≥97%, ≥98%, ≥99%, ≥99.5%, ≥99.9%, ≥99.99%, or 100% of (Z)-endoxifen salt w/w of total endoxifen. Provided herein in certain embodiments are sustained release compositions comprising 1%, 5%, 10%, 20%, 25%, 30%, 40%, 50%, 60%, 70%, 80%, 90%, 95%, 96%, 97%, 98%, 99%, 99.5%, 99.9%, 99.99% or 100% of (Z)-endoxifen salt w/w of the composition. In some embodiments, a sustained release composition comprises from 1% to 50%, from 5% to 50%, from 10% to 50%, from 15% to 50%, from 20% to 50%, from 25% to 50%, from 30% to 50%, from 35% to 50%, from 40% to 50%, from 45% to 50%, from 20% to 80%, from 25% to 80%, from 30% to 80%, from 35% to 80%, from 40% to 80%, from 45% to 80%, from 50% to 80%, from 55% to 80%, from 60% to 80%, from 65% to 80%, from 70% to 80%, from 50% to 90%, from 55% to 90%, from 60% to 90%, from 65% to 90%, from 70% to 90%, from 75% to 90%, or from 80% to 90% of (Z)-endoxifen salt w/w of the composition.

In some embodiments, the salt is (Z)-endoxifen gluconate. Endoxifen gluconate can be selected from the group consisting of (Z)-endoxifen D-gluconate, (Z)-endoxifen L-gluconate, or a combination thereof.

In some embodiments, a sustained release composition comprising endoxifen gluconate is comprised of 10% to 100% of (Z)-endoxifen D-gluconate on a w/w basis of total endoxifen gluconate in the sustained release composition. In some embodiments, a sustained release composition comprising (Z)-endoxifen gluconate is comprised of 10% to 100% of (Z)-endoxifen L-gluconate on a w/w basis of total endoxifen in the sustained release composition.

In other embodiments, a sustained release composition comprising endoxifen gluconate is comprised of 10%, 20%, 30%, 40%, 50%, 60%, 65%, 70%, 75%, 80%, 85%, 90%, 91%, 92%, 93%, 94%, 95%, 96%, 97%, 98%, 99%, 99.5%, 99.75%, 99.99% and 100% of (Z)-endoxifen D-gluconate or (Z)-endoxifen L-gluconate with respect to total endoxifen gluconate. In some embodiments, the sustained release compositions comprise at least 80%, at least 85%, at least 90%, at least 91%, at least 92%, at least 93%, at least 94%, at least 95%, at least 96%, at least 97%, at least 98%, at least 99%, at least 99.5%, and at least 99.99% of (Z)-endoxifen D-gluconate, (Z)-endoxifen L-gluconate or a combination thereof.

Provided herein in some embodiments are sustained release compositions comprising (Z)-endoxifen D-gluconate and (E)-endoxifen D-gluconate. (Z)-endoxifen D-gluconate and (E)-endoxifen D-gluconate may be present in the sustained release compositions at ratios ranging from 10:90 to 99:1 w/w respectively. In some embodiments, the ratio of (Z)-endoxifen D-gluconate to (E)-endoxifen D-gluconate is (w/w) 10:90 to 99:1 (e.g., 45:55, 50:50, 60:40, 70:30, 80:20, 90:10; 91:9; 92:8; 93:7; 94:8; 95:5, 96:4, 97:3, 98:2, 99:1, 99.5:0.5, or 99.99:0.01) respectively. In certain embodiments, the ratio of (Z)-endoxifen D-gluconate to (E)-endoxifen D-gluconate (w/w) is 90:10; 91:9; 92:8; 93:7; 94:8; 95:5, 96:4, 97:3, 98:2, and 99:1; 99.5:0.5; or 99.99:0.01 respectively. One of skill in the art will recognize that other combinations of endoxifen gluconate isomers are encompassed in the present disclosure.

In some embodiments, sustained release composition comprising endoxifen gluconate comprise 0.01%, 0.05%, 0.01%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% and 20% (Z)-endoxifen D-gluconate (w/w) of the sustained release composition. In some embodiments, sustained release compositions comprising endoxifen gluconate comprise 0.01%, 0.05%, 0.01%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% and 20% (Z)-endoxifen L-gluconate (w/w) of the sustained release composition.

While the content of (Z)-endoxifen or a polymorph or a salt thereof in the sustained release compositions of the present disclosure varies depending on the dosage form of the sustained-release composition, target disease, severity of disease, and the like, it is an amount generally corresponding or equivalent to from about 0.01 mg to about 200 mg of (Z)-endoxifen. One of skill in the art will recognize that when sustained release compositions include salts of (Z)-endoxifen, the endoxifen salt will be in an equivalent amount on the basis of (Z)-endoxifen to be released.

In some embodiments, (Z)-endoxifen or a polymorph or a salt thereof is present in the sustained release compositions of the present disclosure in an amount ranging from about 0.01 mg to about 200 mg; from about 0.1 mg to about 150 mg, from about 0.5 mg to about 100 mg; from about 0.5 mg to about 40 mg; from about 0.5 mg to about 20 mg, from about 1 mg to about 10 mg, or from about 20 mg to about 100 mg per unit dose. In some embodiments, (Z)-endoxifen or a polymorph or a salt thereof is present in the sustained release compositions of the present disclosure in an amount ranging from about 0.1 mg to about 40 mg or from about 0.5 mg to about 20 mg per unit dose. In some embodiments, the (Z)-endoxifen or a polymorph or a salt thereof is present in the sustained release compositions of the present disclosure in an amount about 0.1 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, or about 40 mg per unit dose.

(Z)-endoxifen and polymorphs and salts thereof may be diluted with a diluent generally used in the medical field, food field, and the like.

One of skill will recognize that the amounts of (Z)-endoxifen polymorphs and salts will be present in the sustained release compositions in amount equivalent, on a molar basis, to the pharmacologically active (Z)-endoxifen free form.

In an aspect, the present disclosure provides that the sustained release compositions of the present disclosure show a sustained release of the drug (Z)-endoxifen, or a polymorph or a salt thereof, from the sustained release composition over a period of about 2 hours to about 72 hours. In some embodiments, the sustained release compositions of the present disclosure show a sustained release of the drug (Z)-endoxifen, or a polymorph or a salt thereof, from the sustained release composition over a period of about 4 hours to about 24 hours or more. In some embodiments, the sustained release compositions of the present disclosure release (Z)-endoxifen, or a polymorph or a salt thereof, in a sustained manner over a period of at least 2 hours, at least 3 hours at least 4 hours, at least 5 hours, at least 6 hours, at least 7 hours, at least 8 hours, at least 9 hours, at least 10 hours, at least 12 hours, at least 14 hours, at least 16 hours, at least 18 hours, at least 24 hours, at least 48 hours, and at least 72 hours. In some embodiments, the sustained release (Z)-endoxifen or a polymorph or a salt thereof is released over a period of from 6 hours to 48 hours. In some embodiments, the (Z)-endoxifen or a polymorph or a salt thereof is released from the sustained release compositions after about 2 hours pose dose for a period ranging from about 2 hours to about 72 hours. In some embodiments, after about 2 hours post dose the (Z)-endoxifen or a polymorph or a salt thereof is released from the sustained release compositions for about 2 hours, about 3 hours, about 4 hours, about 5 hours, about 6 hours, about 7 hours, about 8 hours, about 9 hours, about 10 hours, about 11 hours, about 12 hours about 13 hours, about 14 hours, about 15 hours, about 16 hours, about 17 hours, about 18 hours, about 19 hours, about 20 hours, about 21 hours, about 22 hours, about 23 hours and about 24 hours. In some embodiments, the rate of release of the therapeutic agent ((Z)-endoxifen or a polymorph or a salt thereof) is slower and more sustained or prolonged than that of a reference product, the enteric resistant delayed release (Z)-endoxifen capsule ("Capsule" or "Control" as used interchangeably herein) as shown herein this disclosure.

In dissolution tests of certain sustained release compositions of the present disclosure conducted according to USP I Method, the sustained release compositions show percentage dissolution ranging from about 0% to 35% at 3 hours, from about 35% to about 55% at 12 hours, and from about 65% to 85% at 24 hours in a dissolution test according to the 75 RPM USP I method and using pH 1.2 at 37° C. for 2 hours in simulated gastric fluid and pH 6.8 at 37° C. for 24 hours in simulated intestinal fluid as a test medium.

A method for measuring a dissolution of a composition (e.g., a sustained release composition) may comprise measuring the dissolution in an acid phase (e.g., simulated gastric fluid) followed by a buffer phase (e.g., simulated intestinal fluid). The acid phase may comprise placing 750 mL of 0.1 N hydrochloric acid in the vessel, and assembling the apparatus (e.g., the paddle apparatus or the basket apparatus). The medium may be allowed to equilibrate to a temperature of 37±0.5°. One dosage unit may be placed in the apparatus, the vessel covered, and the apparatus operated at the specified rate. After 2 hours of operation in 0.1 N hydrochloric acid, an aliquot of the fluid may be withdrawn. Then the method may proceed immediately as directed under the buffer stage. An analysis of the aliquot may be performed using a suitable assay method. While operating the apparatus at a specified rate, 250 mL of 0.20 M tribasic sodium phosphate that has been equilibrated to 37±0.5° may be added to the fluid in the vessel. The fluid may be adjusted, if necessary, with 2N hydrochloric acid or 2 N sodium hydroxide to a pH of 6.8±0.05. The apparatus may continue to be operated for 45 minutes, or for the specified time. At the end of the time period, an aliquot of fluid may be withdrawn, and an analysis of the aliquot may be performed using a suitable assay method.

In some embodiments, the percentage dissolution is measured by the 75 rpm USP paddle method in simulated gastric fluid at pH 1.2 and at 37° C. from hours 0-2, and in simulated intestinal fluid at pH 6.8 and at 37° C. after hour 2. The percentage dissolution refers to the percentage of the composition that has dissolved, by weight percent. The percentage dissolution refers to the weight percent dissolution of (Z)-endoxifen, or the polymorph or salt thereof, during the dissolution study. As a non-limiting example, if a tablet comprises 4 mg of (Z)-endoxifen, and during the dissolution study at a time point of 3 hours, 1 mg of the (Z)-endoxifen is dissolved into the solution, then the percentage dissolution at 3 hours is 25%. The percentage dissolution can be determined by, for example, high pressure liquid chromatography.

In some embodiments, the sustained release composition has a percentage dissolution ranging from about 5% to about 35%, from about 10% to about 15%, from about 20% to about 25%, from about 30% to about 35%, from about 5% to about 30%, from about 5% to about 25%, from about 5% to about 20%, from about 5% to about 15%, from about 5% to about 10%, from about 10% to about 15%, from about 15% to about 20%, from about 20% to about 25%, from about 25% to about 30%, or from about 30% to about 35% at 3 hours, measured by the 75 rpm USP paddle method in simulated gastric fluid at pH 1.2 and at 37° C. from hours 0-2, and in simulated intestinal fluid at pH 6.8 and at 37° C. after hour 2.

In some embodiments, the sustained release composition has a percentage dissolution at 2 hours of no more than about 5%, no more than about 10%, no more than about 15%, no more than about 20%, no more than about 25%, no more than about 30%, no more than about 35%, no more than about 40%, no more than about 45%, or no more than about 50%, measured by the 75 rpm USP paddle method in simulated gastric fluid at pH 1.2 and at 37° C. from hours 0-2, and in simulated intestinal fluid at pH 6.8 and at 37° C. after hour 2. In some embodiments, the sustained release composition has a percentage dissolution of not more than (NMT) about 30%, NMT about 25%, NMT about 20%, NMT about 15%, NMT about 10%, or NMT about 5% at 3 hours.

In some embodiments, the sustained release composition has a percentage dissolution of (Z)-endoxifen or a polymorph or a salt thereof at 2 hours of less than about 5% and at 3 hours ranging from about 5% to about 80%, from about 10% to about 75%, from about 20% to about 70%, from about 30% to about 65%, from about 5% to about 75%, from about 5% to about 70%, from about 5% to about 60%, from about 5% to about 65%, from about 5% to about 60%, from about 10% to about 55%, from about 5% to about 50%, from about 30% to about 80%, from about 25% to about 75%, from about 35% to about 80%, or not less than about 70%, as measured by the 75 rpm USP paddle method in simulated gastric fluid at pH 1.2 and at 37° C. from hours 0-2, and in simulated intestinal fluid at pH 6.8 and at 37° C. after hour 2.

In some embodiments, the sustained release composition has a percentage dissolution of (Z)-endoxifen or a polymorph or a salt thereof at 7 hours of less than about 10%, less than about 15%, less than about 20%, less than about 25%, less than about 30%, less than about 31%, less than about 32%, less than about 33%, less than about 34%, less than about 35%, less than about 36%, less than about 37%, less than about 38%, less than about 39%, less than about 40%, as measured by the 75 rpm USP paddle method in simulated gastric fluid at pH 1.2 and at 37° C. from hours 0-2, and in simulated intestinal fluid at pH 6.8 and at 37° C. after hour 2.

In some embodiments, the sustained release composition has a percentage dissolution of (Z)-endoxifen or a polymorph or a salt thereof at 2 hours of less than about 5% and at 6 hours ranging from about 70% to about 99%, from about 75% to about 95%, from about 85% to about 95%, from about 90% to about 95%, from about 75% to about 90%, from about 85% to about 90%, from about 75% to about 85%, from about 80% to about 99%, from about 85% to about 99%, from about 90% to about 99%, from about 95% to about 99% or not less than about 95%, as measured by the 75 rpm USP paddle method in simulated gastric fluid at pH 1.2 and at 37° C. from hours 0-2, and in simulated intestinal fluid at pH 6.8 and at 37° C. after hour 2.

In some embodiments, the sustained release composition has a percentage dissolution of (Z)-endoxifen or a polymorph or a salt thereof at 2 hours of less than about 5% and at 6 hours of not less (NLT) than about 20%, about 25%, about 30%, about 35%, or about 40%.

In some embodiments, the sustained release composition has a percentage dissolution of (Z)-endoxifen or a polymorph or a salt thereof at 2 hours of less than about 5% and at 9 hours of NLT about 40%, about 45%, about 50%, about 55%, or about 60%.

In some embodiments, the sustained release composition has a percentage dissolution ranging from about 35% to about 55%, from about 40% to about 55%, from about 45% to about 55%, from about 50% to about 55%, from about 35% to about 50%, from about 35% to about 45%, from about 35% to about 40%, from about 35% to about 40%, from about 40% to about 45%, from about 45% to about 50%, or from about 50% to about 55% at 12 hours, measured by the 75 rpm USP paddle method in simulated gastric fluid at pH 1.2 and at 37° C. from hours 0-2, and in simulated intestinal fluid at pH 6.8 and at 37° C. after hour 2.

In some embodiments, the sustained release composition has a percentage dissolution of (Z)-endoxifen or a polymorph or a salt thereof of less than 20% at 2 hours, and a percentage dissolution of at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% at 12 hours, measured by the 75 rpm USP paddle method in simulated gastric fluid at pH 1.2 and at 37° C. from hours 0-2, and in simulated intestinal fluid at pH 6.8 and at 37° C. after hour 2.

In some embodiments, the sustained release composition has a percentage dissolution of (Z)-endoxifen or a polymorph or a salt thereof of less than 20% at 2 hours, and a percentage dissolution of at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% at 24 hours, measured by the 75 rpm USP paddle method in simulated gastric fluid at pH 1.2 and at 37° C. from hours 0-2, and in simulated intestinal fluid at pH 6.8 and at 37° C. after hour 2.

In some embodiments, the sustained release composition has a percentage dissolution of (Z)-endoxifen or a polymorph or a salt thereof at 2 hours of less than about 5% and at 12 hours ranging from about 70% to about 99%, from about 75% to about 95%, from about 85% to about 95%, from about 90% to about 95%, from about 75% to about 90%, from about 85% to about 90%, from about 75% to about 85%, from about 80% to about 99%, from about 85% to about 99%, from about 90% to about 99%, from about 95% to about 99% or about 100%, measured by the 75 rpm USP paddle method in simulated gastric fluid at pH 1.2 and at 37° C. from hours 0-2, and in simulated intestinal fluid at pH 6.8 and at 37° C. after hour 2.

In some embodiments, the sustained release composition has a percentage dissolution of (Z)-endoxifen or a polymorph or a salt thereof at 2 hours of less than about 5% and at 14 hours ranging from about 55% to about 90%, from about 60% to about 85%, from about 70% to about 80%, measured by the 75 rpm USP paddle method in simulated gastric fluid at pH 1.2 and at 37° C. from hours 0-2, and in simulated intestinal fluid at pH 6.8 and at 37° C. after hour 2. In some embodiments, the sustained release composition has a percentage dissolution of (Z)-endoxifen or a polymorph or a salt thereof at 2 hours of less than about 5% and at 14 hours of NLT about 70%, about 75%, about 80%, about 85%, or about 90%.

In some embodiments, the sustained release composition has a percentage dissolution ranging from about 65% to about 85%, from about 70% to about 85%, from about 75% to about 85%, from about 80% to about 85%, from about 65% to about 80%, from about 65% to about 75%, from about 65% to about 70%, from about 65% to about 70%, from about 70% to about 75%, from about 75% to about 80%, or from about 80% to about 85%, at 24 hours, measured by the 75 rpm USP paddle method in simulated gastric fluid at pH 1.2 and at 37° C. from hours 0-2, and in simulated intestinal fluid at pH 6.8 and at 37° C. after hour 2.

In some embodiments, the sustained release composition has a percentage dissolution of (Z)-endoxifen or a polymorph or a salt thereof at 2 hours of less than about 5% and at 72 hours ranging from about 55% to about 100%, from about 60% to about 99%, from about 75% to about 90%, from about 80% to about 85%, from about 55% to about 99%, from about 65% to about 99%, from about 70% to about 99%, from about 75% to about 99%, from about 80% to about 99%, from about 90% to about 99%, from about 80% to about 95%, or from about 75% to about 95%, as measured by the 75 rpm USP paddle method in simulated gastric fluid at pH 1.2 and at 37° C. from hours 0-2, and in simulated intestinal fluid at pH 6.8 and at 37° C. after hour 2.

In dissolution tests of certain sustained release compositions of the present disclosure conducted according to USP II Paddle Method, the sustained release compositions show percentage dissolution ranging from about 0% to 35% at 3 hours, from about 35% to about 55% at 12 hours, and from about 65% to 85% at 24 hours in a dissolution test according to the 75 RPM USP paddle method and using pH1.2 at 37° C. for 2 hours in simulated gastric fluid and pH 6.8 at 37° C. for 24 hours in simulated intestinal fluid as a test medium.

In some embodiments, sustained release compositions of the present disclosure show a percentage dissolution of (Z)-endoxifen, or a polymorph or a salt thereof about 0% to 30% at 3 hours, about 40% to about 50% at 12 hours and about 70% to 80% at 24 hours in a dissolution test according to the 75 rpm USP paddle method and using pH 1.2 at 37° C. for 2 hours in simulated gastric fluid and pH 6.8 at 37° C. for 24 hours in simulated intestinal fluid.

In some embodiments, sustained release compositions of the present disclosure show a percentage dissolution of (Z)-endoxifen, or a polymorph or a salt thereof NMT 30% at 3 hours, NMT 50% at 12 hours and NLT 80% at 24 hours in a dissolution test according to the 75 rpm USP paddle method and using pH 1.2 at 37° C. for 2 hours in simulated gastric fluid and pH 6.8 at 37° C. for 24 hours in simulated intestinal fluid.

In some embodiments, the sustained release compositions show percentage dissolution of (Z)-endoxifen, or a polymorph or a salt thereof of not more than (NMT) about 5% at 2 hours, not less than (NLT) 70% at 3 hours, NLT 90% at 6 hours, and about 100% at 12 hours in a dissolution test according to the 75 RPM USP II method and using pH 1.2 at 37° C. for 2 hours in simulated gastric fluid and pH 6.8 at 37° C. for 24 hours in simulated intestinal fluid In some embodiments, the sustained release compositions show percentage dissolution of (Z)-endoxifen, or a polymorph or a salt thereof of NMT about 5% at 2 hours, NLT about 10% at 3 hours, NLT about 30% at 6 hours, NLT about 50% at 9 hours, and about 80% at 14 hours in a dissolution test according to the 75 RPM USP II method and using pH1.2 at 37° C. for 2 hours in simulated gastric fluid and pH 6.8 at 37° C. for 24 hours in simulated intestinal fluid.

In some embodiments, sustained release compositions of the present disclosure show a percentage dissolution of (Z)-endoxifen, or a polymorph or a salt thereof at least 10%, at least 20%, at least 30%, or at least 40% after 24 hours in a dissolution test according to the 75 rpm USP paddle method and using pH 1.2 at 37° C. for 2 hours in simulated gastric fluid and pH 6.8 at 37° C. for 24 hours in simulated intestinal fluid.

With such particular dissolution property, sustained release compositions for use in the treatment of disorders such as estrogen hormone dependent disorders, including breast disorders such as breast cancers, increase breast density, gynecomastia, etc., and mood disorders can be prepared and used.

In an aspect, the sustained release compositions of the present disclosure are formulated or prepared as solid dosage forms including, but not limited to, tablets, mini-tablets, caplets, beads, microbeads, spheres, pellets, microspheres, granules, pills, tablet-in-tablet, tablets-in-capsule, granules in capsules, and the like. The sustained release compositions of the present disclosure in the form of solid dosage form provide slow and controlled release of the drug, the active ingredient (Z)-endoxifen or a polymorph or a salt thereof over a surprisingly longer period of time than that observed with other compositions containing (Z)-endoxifen (e.g., at least about 4 hours to about 24 hours, at least about 2 hours to about 72 hours). In at least one embodiment, the sustained release composition in the form of a solid dosage form is a tablet.

Such sustained release compositions may be coated or uncoated.

In an aspect, the present disclosure provides that the solid dosage forms of the present disclosure are capable of being delivered orally.

In an aspect, the present disclosure provides that the active ingredient ((Z)-endoxifen or a polymorph or a salt thereof) is dispersed in a sustained release delivery system. (Z)-endoxifen or a salt or polymorph thereof may be evenly or homogeneously dispersed. The sustained release delivery system includes but is not limited to, at least one controlled release agent such as a sustained release agent that controls the release rate of the drug (Z)-endoxifen or a salt or polymorph thereof, at least one binder, and at least one lubricant.

In some embodiments, the sustained release delivery system is present in the sustained release compositions of the present disclosure in an amount ranging from about 60% to about 99.99%.

In some embodiments, the sustained release delivery system is present in the sustained release compositions of the present disclosure in an amount ranging from about 10 mg to about 499.5 mg; from about 25 mg to about 450 mg; from about 50 to about 400 mg, or from about 100 mg to about 300 mg. In at least one embodiment, the sustained release delivery system is present in the sustained release compositions in an amount from about 50 mg to about 199.5 mg. In another embodiment, the sustained release delivery system is present in the sustained release compositions in an amount of about 30 mg, about 40 mg, about 50 mg, about 60 mg, about 70 mg, about 80 mg, about 90 mg, about 95 mg, or about 100 mg. In still another embodiment, the sustained release delivery system is present in the sustained release compositions in an amount of about 110 mg, about 120 mg, about 125 mg, about 130 mg, about 140 mg, about 145 mg, about 150 mg, about 160 mg, about 170 mg, about 180 mg, about 190 mg, about 195 mg, about 200 mg, about 210 mg, about 225 mg, about mg, about 300 mg, about 400 mg, about 450 mg, about 460 mg, about 470 mg, about 480 mg, about 490 mg, about 495 mg or about 499.5 mg. In some embodiments, the sustained release delivery system is present in the sustained release compositions in an amount from about 50 mg to 99.5 mg. In at least one embodiment, the sustained release delivery system is present in the sustained release compositions in an amount of about 90 mg, about 91 mg, about 92 mg, about 93 mg, about 94 mg, about 95 mg, about 96 mg, about 97 mg, about 98 mg, about 99 mg, or about 99.5 mg.

In some embodiments, the sustained release compositions of the present disclosure, the ratio of (Z)-endoxifen or a polymorph or a salt thereof to the sustained release delivery system is generally about 4:1 to about 0.1:100. In some embodiments, the ratio of (Z)-endoxifen or a polymorph or a salt thereof to the sustained release delivery system is 2.5:1 to about 1:20.

Sustained release agent present in a sustained release composition of the present disclosure may be any sustained release agent known in the art to slow the release of a hydrophobic drug such as (Z)-endoxifen or a polymorph or a salt thereof.

Examples of sustained release agents include cellulosic ethers, gums, acrylic resins such as polymers and copolymers of acrylic acid, methacrylic acid, methyl acrylate, methyl methylacrylate, and combinations thereof, polyvinyl pyrrolidine, and protein-derived compounds. Examples of cellulosic ethers include hydroxyalkyl celluloses, hydroxyethyl celluloses, hydroxypropyl celluloses, hydroxypropylmethyl celluloses (HPMC or hypromellose, for example Nos. 2208, 2906, 2910), carboxyalkyl celluloses, and carboxymethyl celluloses. In some embodiments, the at least one sustained release agent is a pH sustained release agent such as acid insoluble polymers which become increasingly soluble and permeable above pH 5.0 but remaining impermeable below pH 5.0. Such controlled release polymers target upper small intestines and/or colon. Non-limiting examples of acid-insoluble polymers include cellulose acetate phthalate, cellulose acetate butyrate, hydroxypropyl methyl cellulose phthalate, algenic acid salts such as sodium or potassium alginate, shellac, pectin, acrylic acid-methylacrylic acid copolymers, including those available commercially from Evonik or Rohm ((Eudragit® sustained release polymers Eudragit® RL (high permeability), Eudragit® RS (low permeability) and Eudragit® NM 30D (low permeability)—alone or in any combination thereof to achieve the desired permeability for sustained release. The viscosity of sustained release agents may be any viscosity suitable for sustained release of (Z)-endoxifen or a polymorph or a salt thereof. In certain embodiments, the viscosity of the at least sustained release agent ranges from about 1000 mPa·s to about 150,000 mPa·s. In some embodiments, the sustained release delivery system includes one or more SR/release rate controlling agents with viscosity ranging from about 1000 mPa·s to about 10,000 mPa·s, from about 10,000 mPa·s to about 70,000 mPa·s, from about 70,000 mPa·s to about 150,000 mPa·s. or a combination thereof. In some embodiments, the present disclosure provides that the sustained release delivery system includes two or more sustained release agents. Each sustained release agent may have the same viscosity or a differing viscosity, for example one sustained release agent may have a viscosity ranging from about 1000 mPa·s to about 10,000 mPa·s, while other sustained release agent may have a viscosity of about 10,000 mPa·s to about 70,000 mPa·s or about 70,000 mPa·s to about 150,000 mPa·s.

In some embodiments, the sustained release agent is HPMC/hypromellose (e.g., Nos. 2208, 2906, 2910). Hypromellose to be used in the present disclosure has a weight molecular average of about 20,000-500,000. In some embodiments, hypromellose has a molecular weight average of generally 20,000-250,000. Hypromellose is commercially available from Dow Chemicals under the trade name Methocell™, for example, Methocel™ K100 (average molecular weight 26,000, 2% viscosity; 75,000-140,000 mPa·s); Methocell™ K15M (average molecular weight 120,000, 2% viscosity; 15,000 cP, 13275-24,780 mPa·s); Methocell™ K4M (average molecular weight 86,000, 2% viscosity; 4,000 cP, 75,000-140,000 mPa·s). Hypromellose of one grade may be used alone or in combination with another grade.

When a sustained release composition showing release of (Z)-endoxifen or a polymorph or a salt thereof in a sustained manner for at least 2 hours, at least 3 hours, at least 4 hours, at least 5 hours, at least 6 hours, at least 7 hours, at least 8 hours, at least 9 hours, at least 10 hours, at least 12 hours, at least 14 hours, at least 16, at least 18 hours, at least 24 hours, at least 48 hours, and at least 72 hours is obtained, in some embodiments the sustained release agent, such as Hypromellose, has an average molecular weight generally ranging from 15,000 to 140,000 Daltons. In at least one embodiment, the average molecular weight of about 15,000 Daltons.

The amount of sustained release agent in the composition may be any amount effective to delay the release of the therapeutic agent (Z)-endoxifen, or a polymorph or a salt thereof, for about 2 hours post-dose to protect the therapeutic agent from the acidic environment of the stomach and allow passage of the therapeutic agent through the stomach into the intestines and prolong such release for a period of about 2 hours to about 72 hours. The amount of sustained release agent in the composition may be any amount effective to provide a slower rate of release of the therapeutic agent (Z)-endoxifen, or a polymorph or a salt thereof as compared with the reference product. In some embodiments, the amount of sustained release agent in the composition may be any amount effective to delay the release of the therapeutic agent (Z)-endoxifen, or a polymorph or a salt thereof, for at least about 1 hour, at least about 1.1 hours, at least about 1.2 hours, at least about 1.3 hours, at least about 1.4 hours, at least about 1.5 hours, at least about 1.6 hours, at least about 1.7 hours, at least about 1.8 hours, at least about 1.9 hours, at least about 2 hours, at least about 2.1 hours, at least about 2.2 hours, at least about 2.3 hours, at least about 2.4 hours, or at least about 2.5 hours post-dose, as compared with the reference product.

When a sustained release composition shows percentage dissolution ranging from about 0% to 35% at 3 hours, from about 35% to about 55% at 12 hours, and from about 65% to 85% at 24 hours in a dissolution test according to the 75 RPM USP paddle method and using pH 1.2 at 37° C. for 2 hours in simulated gastric fluid and pH 6.8 at 37° C. for 24 hours in simulated intestinal fluid as a test medium, at least one sustained release agent, such as Hypromellose (HPMC), may generally be present in a sustained release composition of the present disclosure in amounts from about 0.1% to about 99%, from about 0.1% to about 90%, from about 5% to about 90%, from about 5% to about 80%, from about 5% to about 70%, and from about 5% to about 60% w/w of the sustained release composition. In some embodiments, the sustained release agent (e.g., a gum, an acrylic resin, methacrylic acid, methyl acrylate, methyl methylacrylate, polyvinyl pyrrolidine, a protein-derived compound, a hydroxyalkyl cellulose, a hydroxyethyl cellulose, a hydroxypropyl cellulose, a hydroxypropylmethyl celluloses, a carboxyalkyl cellulose, or, a carboxymethyl cellulose) may be present in an amount of from about 10% to about 40%, from about 10% to about 50%, from about 10% to about 60%, from about 20% to about 40%, from about 20% to about 50%, from about 20% to about 60%. In some embodiments, the sustained release agent may be present in an amount of at least about 10%, at least about 20%, at least about 30%, or at least about 40%. Such sustained release compositions of the present disclosure as disclosed herein release (Z)-endoxifen or polymorphs or salts thereof in a sustained manner for at least 2 hours, at least 3 hours, at least 4 hours, at least 5 hours, at least 6 hours, at least 7 hours, at least 8 hours, at least 9 hours, at least 10 hours, at least 12 hours, at least 14 hours, at least 16 hours, at least 18 hours, at least 24 hours, at least 48 hours, and at least 72 hours. See Example 1-Example 8 and FIG. 1-FIG. 6 and FIG. 12-FIG. 17. In some embodiments, the therapeutic agent in the sustained release composition is released over a period of from 6 hours to 48 hours. In some embodiments, the therapeutic agent (e.g., (Z)-endoxifen or a polymorph or a salt thereof) is released over a period of from 2 hours to 72 hours as tested by USP II method and using pH1.2 at 37° C. for 2 hours in simulated gastric fluid and pH 6.8 at 37° C. for 24 hours in simulated intestinal fluid.

As non-limiting examples, the ratio of (Z)-endoxifen or a polymorph or a salt thereof to sustained release agent ranges from about 1:20 to about 20:1, from about 1:10 to about 10:1, from about 1:5 to about 2:5 to prepare sustained release compositions of the present disclosure. To prepare sustained release tablets containing about 0.1 mg to about 200 mg (Z)-endoxifen or a salt thereof, drug to sustained release agent will range from about 20:1 to about 1:20. In some embodiments drug to sustained release agent in sustained release tablets containing about 0.1 mg to about 200 mg (Z)-endoxifen or a salt thereof will range from about 10:1 to about 1:10. In certain embodiments, the ratio of the therapeutic drug (Z)-endoxifen or a polymorph or a salt thereof to the sustained release agent is about 1:5. One of skill will recognize that the rate of release of (Z)-endoxifen or a polymorph or a salt thereof may be adjusted for sustained release as desired by varying the viscosity grade of the sustained release compositions of the present disclosure and the amount of sustained release agent as disclosed herein.

Binder present in a sustained release composition of the present disclosure may be any binder known in the art that can hold the components or the ingredients in the sustained release compositions of the present disclosure together. Binders suitable for use in the sustained release compositions provided herein include, but are not limited to, monosaccharides (such as sucrose, dextrose, fructose), disaccharides, starches such as corn starch, potato starch, or starches such as starch paste, pregelatinized starch, and starch 1500, polyhedric alcohols, mannitol, xylitol, sorbitol, lactose, polyethylene glycols such as PEG 6000, natural and synthetic gums such as acacia, sodium alginate, alginic acid, other alginates, tragacanth, guar gum, cellulose (e.g., powdered cellulose and pregelatinized starch) and its derivatives (e.g., ethyl cellulose, cellulose acetate, methyl cellulose, carboxymethyl cellulose calcium, sodium carboxymethyl cellulose), polyvinyl pyrrolidone, methyl cellulose, polyvinyl pyrrolidone, hydroxypropyl methyl cellulose (e.g., Nos. 2208, 2906, 2910), crystalline cellulose, microcrystalline cellulose (MCC), silicified microcrystalline cellulose, calcium carbonate and salts thereof, calcium phosphate, precipitated calcium phosphate, sodium carbonate, sodium phosphate, anhydrous dibasic calcium phosphate, talc, dextrates, kaolin, mannitol, silicic acid, sorbitol and combinations or mixtures thereof. Suitable forms of crystalline and microcrystalline cellulose include, but are not limited to, the materials commercially sold as AVICEL® PH 101, AVICEL PH 103 AVICEL® RC 581, AVICEL® PH 105 (available from FMC Corporation, American Viscose Division, Avicel Sales, Marcus Hook, Pa.), Pharmacel 101. Anhydrous or low moisture excipients are preferable. Suitable anhydrous or low moisture excipients or additives include microcrystalline cellulose commercially available as AVICEL® PH 101, AVICEL® PH 103, Pharmacel 101. In at least one embodiment, the binder is microcrystalline cellulose (such as AVICEL® PH 101) or silicified microcrystalline cellulose.

The sustained release compositions of the present disclosure typically may comprise at least one binder in amounts ranging from about 1% to about 99%, from about 5% to about 95%, from about 10% to about 90%, from about 15% to about 85%, from about 20% to about 80%, or from about 20% to about 85% on a w/w basis relative to the weight of the sustained release composition. In certain embodiments, the sustained release compositions of the present disclosure typically comprise microcrystalline cellulose in amounts ranging from about 1% to about 99%, from about 5% to about 95%, from about 10% to about 90%, from about 15% to about 85%, from about 20% to about 80%, or from about 20% to about 85% on a w/w basis relative to the weight of the sustained release composition.

Exemplary lubricants that can be used in the sustained release compositions provided herein include, but are not limited to, stearic acid, calcium stearate, magnesium stearate, zinc stearate, potassium stearate, hydrogenated vegetable oil (e.g., peanut oil, cottonseed oil, sunflower oil, sesame oil, olive oil, corn oil, and soybean oil), mineral oil, light mineral oil, glycerin, sorbitol, mannitol, glycols, polyethylene glycol, sodium lauryl sulfate, magnesium lauryl sulfate, macrogol, talc, ethyl oleate, ethyl laureate, agar, waxes, and combinations thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), Q7-9120 (Dow Corning), and combinations thereof. In some embodiments, the lubricant is magnesium stearate. Magnesium stearate reduces the friction between the die wall and tablet mix during the compression and ejection of the tablets. It helps prevent adhesion of tablets to the punches and dies. Magnesium stearate also aids in the flow of the powder in the hopper and into the die. It has a particle size range of 450-550 microns and a density range of 1.00-1.80 g/mL It is stable and does not polymerize within the tableting mix. One lubricant, magnesium stearate, may also be employed in the formulation.

Typically, a sustained release composition of the present disclosure may include at least one lubricant in an amount ranging from about 0.01% to about 5%, from about 0.2% to about 2%, or from about 0.5% to about 1.5% on a w/w basis relative to the weight of the sustained release composition.

In certain embodiments, a sustained release composition of the present disclosure includes magnesium stearate in an amount ranging from about 0.01% to about 5%, from about 0.2% to about 2%, or from about 0.5% to about 1.5% on a w/w basis relative to the weight of the sustained release composition.

Certain exemplary embodiments of sustained release compositions of the present disclosure include, but are not limited to, the following embodiments.

In some embodiments, at least one sustained release agent (e.g., HPMC, cellulose acetate phthalate, cellulose acetate butyrate, hydroxypropyl methyl cellulose phthalate, sodium alginate, potassium alginate, shellac, pectin, or acrylic acid-methylacrylic acid copolymers) is present in a sustained release composition in an amount ranging from about 0.1% to about 99%; at least one binder is present in a sustained release composition in an amount ranging from about 1% to about 99%; the at least one lubricant is present in the sustained release delivery system in an amount ranging from about 0.01% to about 5% wherein the percentages are on a w/w basis relative to the weight of the sustained release composition.

In some embodiments, at least one sustained release agent is present in a sustained release composition in an amount ranging from about 0.1% to about 90%; at least one binder is present in a sustained release composition in an amount ranging from about 1% to about 99%; the at least one lubricant is present in the sustained release delivery system in an amount ranging from about 0.01% to about 5% wherein the percentages are on a w/w basis relative to the weight of the sustained release composition.

In at least one embodiment, the sustained release composition includes the at least one sustained release agent in an amount ranging from about 5% to 60%; the at least one binder in an amount ranging from about 10% to about 90%, and the at least one lubricant in an amount ranging from about 0.01% to about 5% wherein the percentages are on a w/w basis relative to the weight of the sustained release composition.

In some embodiments, at least one sustained release agent is present in a sustained release composition in an amount ranging from about 0.1% to about 10%; at least one binder is present in a sustained release composition in an amount ranging from about 80% to about 99%; the at least one lubricant is present in the sustained release delivery system in an amount ranging from about 0.02% to about 2% wherein the percentages are on a w/w basis relative to the weight of the sustained release composition.

In at least one embodiment, the sustained release composition includes the at least one sustained release agent in an amount ranging from about 10% to 45%; the at least one binder in an amount ranging from about 50% to about 80%, the at least one lubricant in amounts ranging from about 0.02% to about 2% wherein the percentages are on a w/w basis relative to the weight of the sustained release composition.

In certain embodiments, the at least one sustained release agent is present in the sustained release composition in an amount of about 8%, about 9%, about 10%, about 12%, about 15%, about 18%, about 20%, about 22% about 25%, about 30%, about 35%, about 40%, about 45%, about 50% about 55%, about 60%; the at least one binder is present in the sustained release composition in an amount of about 30%, about 35%, about 40%, about 45%, about 50% about 55%, about 60%, about 65%, about 70%, about 75%, or about 80%; and the at least one lubricant of about 0.02%, about 0.05%, about 0.1%, about 1.2%, about 1.3%, about 1.4%, about 1.5%, about 1.6%, about 1.7%, about 1.8%, about 1.9% or about 2%, wherein the percentages are on a w/w basis relative to the weight of the sustained release composition.

In certain embodiments, the at least one sustained release agent is present in the sustained release composition in an amount of about 15%, about 16%, about 17%, about 18%, about 19%, about 20%, about 21%, about 22%, about 23%, about 24%, or about 25%; at least one binder is present in the sustained release composition in an amount of about 29%, about 25%, about 30%, about 35%, about 39%, about 40%, about 45%, about 49%, about 50%, about 55%, about 60%, about 64%, about 69%, about 70%, about 71%, about 72%, about 73%, about 74%, about 75%, about 76%, about 77%, about 78%, about 79% or about 80%; and at least one lubricant is present in the sustained release composition in an amount of about 0.8%, about 0.9%, about 1%, about 1.2%, about 1.3%, about 1.4%, or about 1.5%, in each case on a w/w basis relative to the weight of the sustained release composition.

In at least one embodiment, the at least one sustained release agent is present in the sustained release composition in an amount of about 10%, about 20%, or about 40; at least one binder is present in the sustained release composition in an amount of about 55%, about 75%, about 80%, about 85% or about 87%; and at least one lubricant is present in the sustained release composition in an amount of about 0.9% to about 1.1%. The percentages are on a w/w basis relative to the weight of the sustained release composition.

In certain embodiments, the sustained release compositions of the present disclosure include additional sustained release agents, binders, lubricants or any combination thereof.

The compositions of the present disclosure and the sustained release delivery systems may further include a pharmaceutically acceptable excipient. The pharmaceutically acceptable excipient may be any additive conventionally used in the technical field of preparation such as fillers, stabilizers, glidants, surfactants, light shielding agents, sweeteners, colorants, flavorants, anti-oxidants, preservatives, reducing agent, chelating agent and the like. The pharmaceutically acceptable excipients are used in an amount conventionally used in the technical field of preparation. In addition, two or more kinds of these additives may be mixed at an appropriate ratio and used.

Examples of fillers suitable for use in the sustained release compositions of the present disclosure include, but are not limited to, talc, calcium carbonate (e.g., granules or powder), sugars such as dextrose, sucrose, lactose, a salt such as calcium carbonate, calcium phosphate, sodium carbonate, sodium phosphate, starches, microcrystalline cellulose, powdered cellulose, cellulosic bases such as methyl cellulose, carboxymethyl cellulose, dextrates, kaolin, mannitol, silicic acid, sorbitol, starch, pregelatinized starch, and mixtures thereof.

Examples of stabilizers include sodium ascorbate tocopherol, tertrasodium edetate, cyclodextrins, nicotinic acid amide, alkaline earth metal salts (e.g., calcium carbonate, calcium hydroxide, magnesium carbonate, magnesium silicate magnesium aluminate) and butylhydroxyanisole.

Examples of glidants include, but are not limited to, colloidal silicone dioxide, cellulose, calcium phosphate, di or tri-basic and the like.

Examples of surfactants include sodium lauryl sulfate, polysorbate 80, and the like.

Examples of light shielding agents include titanium oxide. Light shielding agents are desirable for light sensitive active ingredients such as (Z)-endoxifen, and polymorphs and salts thereof.

Examples of anti-oxidants include butylhydroxytoluene (BHT), butylhydrozyanysole (BHA), tocopherol, tocopherol esters (e.g. tocopherol acetate), ascorbic acid or alkali or alkaline earth metal salt thereof, lycopene and beta-carotene.

Examples of reducing agents include cystine and cysteine.

Examples of chelating agents include EDTA or alkali metal or alkaline earth metal salt thereof.

Examples of colorants include food colors such as Food Color Yellow No. 5, US Food color No. 6, Swedish orange, Food color Blue No. 2, Food color Red No. 2 and the like, food lake colors, yellow ferric oxide, (yellow ferric oxide pigment), red ferric oxide (red ferric oxide pigment), black ferric oxide (black ferric oxide pigment), riboflavin, riboflavin organic acid ester, riboflavin phosphate or alkali metal or alkaline metal earth metal slats thereof, phenolphthalein, titanium oxide, lycopene, and beta-carotene.

Examples of sweeteners include aspartame, acesulfame potassium, thaumatin, saccharin sodium and dipotassium glycyrrhizinate.

Examples of flavorants include menthol, peppermint oil, lemon oil, vanillin, and strawberry.

The shape of the sustained release compositions in the form of solid dosage forms, such as a tablet, is not particularly limited, and may be any shape suitable for administration, for example, for oral administration, such as spherical, oval, ellipsoidal, pear, cylindrical, cubic, regular and/or irregular shaped. The tablet may have one of a variety of different shapes. For example, the tablet may be shaped as a polyhedron, such as a cube, pyramid, prism, or the like; or may have the geometry of a space figure with some non-flat faces, such as a cone, truncated cone, cylinder, sphere, torus, or the like. In certain embodiments, a tablet has one or more major faces. For example, the tablet surface typically has opposing upper and lower faces formed by contact with the upper and lower punch faces in the compression machine. In such embodiments the tablet surface typically further includes a "belly-band" located between the upper and lower faces, and formed by contact with the die walls in the compression machine.

In an aspect, the present disclosure provides that the sustained release compositions in the form of sustained release tablets have a tablet weight of about 60 to about 500 mg. In some embodiments, sustained release compositions in the form of sustained release tablets have a tablet weight of about 90 to about 110 mg. The sustained release compositions in the form of sustained release tablets have a tablet thickness of about 2.75 to about 3.75 mm. In some embodiments, the sustained release composition in the form of sustained release tablets have a tablet thickness of about 3 to about 3.5 mm.

The hardness of the tablets of the present invention may vary, depending on a variety of factors, including, for example, the relative amounts and specific types of ingredients used, the tableting equipment employed, and the selected processing parameters. The compaction and pressure used to prepare the tablets can influence the release profile of the therapeutic agent (Z)-endoxifen or a polymorph or a salt thereof into the subject. The compaction and pressure used to prepare the tablets of the present invention may vary depending upon their surface area and the amount and particle size of the therapeutic agent (Z)-endoxifen, or a polymorph or a salt thereof, sustained release agents, binders, lubricants, and other excipients included in the tablet. The degree of hydration and solvation of the components in the composition will also be important in determining the hardness of the tablets. In some embodiments, the sustained release composition in the form of sustained release tablets have a tablet hardness of about 4 Kilopond (Kp) to about 16 Kp. In some embodiments, the sustained release composition in the form of sustained release tablets about 10 to about 16 Kp. In some embodiments, the sustained release composition in the form of sustained release tablets have a tablet hardness of about 4 Kp, about 4.5 Kp, about 5 Kp, about 5.5 Kp, about 6 Kp, about 6.5 Kp, about 7 Kp, about 7.5 Kp, about 8 Kp, about 8.5 Kp, about 9 Kp, about 9.5 Kp, about 10 Kp, about 10.5 Kp, about 11 Kp, about 11.5 Kp, about 12 Kp, about 12.5 Kp, about 13 Kp, about 13.5 Kp, about 14 Kp, about 14.5 Kp, about 15 Kp, about 15.5 Kp and about 16 Kp. In some embodiments, the sustained release composition in the form of sustained release tablets have a tablet hardness of about 13 Kp. In at least one embodiment, the sustained release composition in the form of sustained release tablets have a tablet hardness of 5 Kp.

The friability of the sustained release tablets is typically not more than (NMT) 1.0%. In some embodiments, the sustained release compositions in the form of sustained release tablets include a light shielding agent such as titanium oxide. The sustained release compositions in the form of sustained release tablets can be of any color known in the art, for example Food Color Yellow No. 5, US Food color No. 6, Swedish orange, Food color Blue No. 2, Food color Red No. 2 and the like, food lake colors, yellow ferric oxide, (yellow ferric oxide pigment), red ferric oxide (red ferric oxide pigment), black ferric oxide (black ferric oxide pigment), riboflavin, riboflavin organic acid ester, riboflavin phosphate or alkali metal or alkaline metal earth metal slats thereof, phenolphthalein, titanium oxide, lycopene, and beta-carotene. In some embodiments, the sustained release compositions in the form of sustained release tablets are white or off-white in color.

The sustained release compositions, such as the sustained release tablets described herein, may be coated or uncoated.

In another aspect, the present disclosure provides that the sustained release compositions of the present disclosure are used to prepare enteric coated delayed release solid dosage forms such as enteric coated delayed release tablets. An advantageous aspect of such enteric coated compositions is that these sustained release compositions, including enteric coated delayed release tablets, are formulated to minimize the release of (Z)-endoxifen or a polymorph or a salt thereof in stomach to avoid destruction of (Z)-endoxifen or a polymorph or a salt thereof, and to target the release of the active ingredient (Z)-endoxifen or a polymorph or a salt thereof into the small intestine or colon or both. Targeting the intestines and colon increases the bioavailability of the (Z)-endoxifen or a polymorph or salt thereof. In some embodiments, the sustained release compositions of the present disclosure deliver (Z)-endoxifen or a polymorph or a salt thereof into duodenum or jejunum.

One of skill in the art will recognize that the sustained release compositions of the present disclosure function as sustained release compositions in themselves (See Example 5 and Table 6 and Table 7), and they can also serve as "cores" (e.g., core tablets) used in the preparation of enteric coated dosage forms (such as enteric coated delayed release tablets or enteric coated delayed release capsules) that provide delayed release of the (Z)-endoxifen or a polymorph or a salt thereof targeting small intestines or colon or both.

Accordingly, in some embodiments the sustained release compositions of the present disclosure in a solid dosage form (for example, as a tablet) forms a "core" composition (e.g., core tablet) for the preparation of an enteric coated delayed release composition. Such sustained release compositions allow for the protection of the acid sensitive active ingredient (Z)-endoxifen or a polymorph or a salt thereof from the acidic environment of the stomach and dissolve at pH higher than 5.5, generally in the intestines, for example in duodenum, jejunum and/or ileum of the small intestine and/or in colon. The enteric coating protects the interconversion of active (Z)-endoxifen to (E)-endoxifen in the stomach and the drug (Z)-endoxifen is released thereafter, for example after 2 hours post dose, 3 hours post dose, 4 hours post dose, 5 hours post dose, 6 hours post dose, 7 hours post dose, 8 hours post dose, etc., in the intestines at a slower rate. The surprisingly reduced interconversion of the (Z)-endoxifen based on the formulations disclosed herein provide unexpected benefits in the administration of (Z)-endoxifen, or a polymorph or a salt thereof.

As a non-limiting example, the present disclosure provides sustained release compositions of the present disclosure in the form of solid dosage forms such as enteric coated delayed release tablets. A sustained release composition in the form of a tablet as described above serve as core (referred to as "core", "core tablet" or "tablet core" hereinafter and used interchangeably) that is substantially covered by at least one layer of a functional coating. In other words, an enteric coated delayed release tablet of the present disclosure has a core which includes (i) (Z)-endoxifen or a salt or polymorph thereof, (ii) at least one sustained-release agent, and (iii) at least one lubricant, and the core is substantially covered with at least one layer of a functional coating.

In some embodiments, the functional coating comprises at least one controlled release agent, such as a delayed release agent targeting the intestines (e.g., duodenum) or colon or both. The present disclosure provides that the functional coating may further comprise additional excipients such as plasticizers, anti-tacking agents, and the like. The addition of a delayed release agent to the functional coating provided surprisingly advantageous results, resulting in a substantial decrease in conversion of (Z)-endoxifen to (E)-endoxifen. The surprising advantage of coating the compositions (e.g., the tablets) with a coating comprising a delayed release agent evidences that such coatings can facilitate delivery of (Z)-endoxifen more efficiently. Furthermore, it was surprisingly found that the coatings comprising a delayed releasing agent provided for a more consistent, slower release.

In certain embodiments, the functional coating of the present disclosure comprises at least one controlled release agent such as a delayed release agent, at least one plasticizer, and at least one anti-tacking agent/anti-adherent. In some embodiments, the enteric coated delayed release tablet may be coated with at least two coatings wherein at least one coating is a functional coating comprising a delayed release agent, at least one plasticizer, and at least one anti-tacking agent/anti-adherent.

Accordingly, in some embodiments the sustained release compositions comprising (Z)-endoxifen or a polymorph or a salt thereof of the present disclosure comprise a core (e.g., a core tablet) that is substantially coated with at least one layer of a functional coating with a coating solution. The coating solution comprises at least one controlled release agent, such as a delayed release agent, at least one plasticizer, and at least one anti-tacking agent/anti-adherent. One of skill in the art will recognize that the core tablets disclosed herein can be enclosed in tablets, caplets or capsules and the like, and further coated with coating solutions disclosed herein to prepare other solid dosage forms such as tablet-in-tablets, tablet-in caplets, tablet-in-capsules and the like. In such cases, the sustained release compositions such as tablet-in-tablets, tablet-in caplets, tablet-in-capsules and the like will be substantially coated with at least one layer of functional coating as described herein. Coated tablets included inside other coated tablets, caplets and capsules can thus provide release of (Z)-endoxifen or a polymorph or a salt thereof in pulses.

One of skill in the art will also recognize that, like the core tablets described herein, the other solid dosage forms of sustained release compositions such as mini-tablets, spheres, beads, granules, pellets, pills and the like, can also be used as cores for the preparation of enteric coated delayed release tablets, caplets, and capsules. Examples of such sustained release compositions include, but are not limited to, sustained release enteric tablets, enteric mini-tablets, enteric caplets, enteric beads, enteric spheres, enteric granules, enteric pellets, enteric pills, enteric tablet-in-tablet, enteric tablets-in-capsule, and the like and are used for delayed release of (Z)-endoxifen or a polymorph or a salt thereof into the small intestines or colon or both. Commercially available delayed release capsules such as those available from Capsugel (e.g., VCaps® Plus enteric capsules), can be used to prepared enteric coated delayed release capsules and are encompassed in the present disclosure. In some embodiments, the enteric delayed release capsules can be non-animal based capsules, such as a hypromellose capsule (for example, commercially available self-gelling Vcaps, VCaps Plus, VCaps enteric, other enteric capsules made using Xcellodose, ENCODE colonic delivery technology, and EnTrinsicTM drug delivery technology from Capsugel). Other technologies known in the art and available commercially (for example, Qualicaps, USA, Nutrascience, USA, etc.) for the formulating enteric forms of oral solid dosage forms can also be utilized.

The present disclosure provides that functional coating of a core can be performed with a coating solution which includes, but is not limited to, at least one controlled release agent, such as a delayed release agent. In some embodiments, the functional coating solution can comprise plasticizers, anti-tacking agents, and the like. In some embodiments, functional coating of a core can be performed with a coating solution which includes, but is not limited to, at least one controlled release agent, such as a delayed release agent at least one plasticizer, and at least one anti-tacking agent/anti-adherent. The coating solutions provided herein can be applied as films, such as thin films, on a range of solid dosage forms including particles, beads, spheres, granules, pellets, tablets, mini-tablets, pills, multiparticulates and capsules (with hard and soft shells) encapsulating the core (for example, immediate release capsules) to prepare the enteric coated delayed release solid dosage forms using the sustained release compositions described herein.

Where a sustained release composition, such as an enteric coated delayed release tablet, shows percentage dissolution ranging from about 0% to about 35% at 3 hours, from about 35% to about 55% at 12 hours, and from about 65% to about 85% at 24 hours in a dissolution test according to the 75 RPM USP paddle method and using pH 1.2 at 37° C. for 2 hours in simulated gastric fluid and pH 6.8 at 37° C. for 24 hours in simulated intestinal fluid as a test medium, the at least one layer of functional coating provides from about 1% to about 60%, from about 2% to about 40%, from about 5% to about 30%, and from about 6% to about 20% weight gain of over the weight of the core (e.g., core tablet).

Where a sustained release composition, such as an enteric coated delayed release tablet, shows percentage dissolution of NMT about 5% at 2 hours, NLT about 60% at 3 hours, NLT about 95% at 6 hours and about 100% at 12 hours in a dissolution test according to the 75 RPM USP paddle method and using pH 1.2 at 37° C. for 2 hours in simulated gastric fluid and pH 6.8 at 37° C. for 24 hours in simulated intestinal fluid as a test medium, the at least one layer of functional coating provides from about 1% to about 60%, from about 2% to about 40%, from about 5% to about 30%, and from about 6% to about 20% weight gain of over the weight of the core (e.g., core tablet).

Where a sustained release composition, such as an enteric coated delayed release tablet, shows percentage dissolution NMT about 10% at 3 hours, NLT about 30% at 6 hours, NLT about 50% at 9 hours, and NLT about 80% at 14 hours in a dissolution test according to the 75 RPM USP paddle method and using pH 1.2 at 37° C. for 2 hours in simulated gastric fluid and pH 6.8 at 37° C. for 24 hours in simulated intestinal fluid as a test medium, the at least one layer of functional coating provides from about 1% to about 60%, from about 2% to about 40%, from about 5% to about 30%, and from about 6% to about 20% weight gain of over the weight of the core (e.g., core tablet).

Tablet weight will also vary in accordance with, among other things, the dosage of the therapeutic agent (Z)-endoxifen, or a polymorph or a salt thereof, the type and amount of sustained release agent used, and the presence, types and amounts of additional materials. For dosages of the therapeutic agent from about 0.5 mg to about 200 mg; tablet weights can range from about 10 mg to about 2000 mg per tablet. In some embodiments, the tablet weight ranges from 50 mg to 500 mg. In some embodiments, the enteric coated delayed release tablet has a tablet weight ranging from about 101 mg to 160 mg, from 90 mg to 110 mg, or from about 105 mg to about 120 mg. For time delay or delayed-release pharmaceutical preparations of sustained release composition of the present disclosure in the form of oral dosage forms, and acid-insoluble polymers (e.g., polymethacrylates) can be used as delayed release agent in the coating solution.

For enteric coated delayed-release preparations, cellulosic polymers such as glyceryl monostearate, glyceryl distearate, hydroxypropyl cellulose, hydoxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT® (Evoniks, Rohm Pharma; Westerstadt, Germany), including methacrylic acid-ethyl acrylate copolymer (1:1) (EUDRAGIT® L30D-55) and L100-55 (soluble at pH 5.5 and above). EUDRAGIT® 1,100D (soluble at pH 6.0 and above), EUDRAGIT® S (soluble at pH 7.0 and above, as a result of a higher degree of esterification), and EUDRAGIT® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylase and guar gum; zein and shellac.

In certain embodiments, the delayed release agent is a pH-sensitive polymer such as a polymethacrylate. In some embodiments, the delayed release agent is methacrylic acid-ethyl acrylate copolymer (1:1) USP-NF (EUDRAGIT® L30D-55). In some embodiments, the delayed release agent is methacrylic acid-ethyl acrylate copolymer (1:2).

The present disclosure also provides that combinations or mixtures of different delayed release agents may be used in a single layer of functional coating. In some embodiments, multilayer (e.g., two or more layers) coatings using different delayed release agents or polymers may also be applied to the core.

When a sustained release composition in the form of an enteric coated delayed release dosage form (such as an enteric coated delayed release tablet) releases (Z)-endoxifen or polymorphs salts thereof in a sustained manner for at least 2 hours, at least 3 hours, at least 4 hours, at least 5 hours, at least 6 hours, at least 7 hours, at least 8 hours, at least 9 hours, at least 10 hours, at least 12 hours, at least 14 hours, at least 16 hours, at least 18 hours, at least 24 hours, at least 48 hours, or at least 72 hours is obtained, the delayed release agent, such as methacrylic acid-ethyl acrylate copolymer (1:1) USP-NF (EUDRAGIT® L30D-55 is present in the at least one layer of a functional coating in an amount ranging from about 0.1% to about 35%, from about 5% to about 35%, or from about 8% to about 20% w/w of the weight of the core (e.g., core tablet).

When a sustained release composition of the present disclosure, such as a delayed release tablet, shows percentage dissolution ranging from about 0% to 35% at 3 hours, from about 35% to about 55% at 12 hours, and from about 65% to 85% at 24 hours in a dissolution test according to the 75 RPM USP paddle method and using pH 1.2 at 37° C. for 2 hours in simulated gastric fluid and pH 6.8 at 37° C. for 24 hours in simulated intestinal fluid as a test medium, the delayed release agent is present in the at least one layer of coating in amounts ranging from about 0.1% to about 30%, from about 5% to about 25%, or from about 8% to about 14% w/w of the weight of the core tablet. In some embodiments, the delayed release agent is present in the at least one layer of coating in amounts ranging from about 0.1% to about 20% on a w/w basis relative to the weight of the core tablet.

When a sustained release composition of the present disclosure, such as a delayed release tablet, shows percentage dissolution of NMT about 5% at 2 hours, NLT about 70% at 3 hours, NLT about 95% and about 100% at 12 hours in a dissolution test according to the 75 RPM USP paddle method and using pH 1.2 at 37° C. for 2 hours in simulated gastric fluid and pH 6.8 at 37° C. for 24 hours in simulated intestinal fluid as a test medium, the delayed release agent is present in the at least one layer of coating in amounts ranging from about 0.1% to about 30%, from about 5% to about 25%, or from about 8% to about 14% w/w of the weight of the core tablet. In some embodiments, the delayed release agent is present in the at least one layer of coating in amounts ranging from about 0.1% to about 20% on a w/w basis relative to the weight of the core tablet.

Such a release of (Z)-endoxifen or polymorphs salts thereof from the sustained release composition of the present disclosure is generally initiated in the intestines about 2 hours post-dose.

At least one plasticizer is added to control the softness or pliability of the sustained release compositions prepared as solid dosage forms, such as an enteric coated delayed release tablet or a shell of a capsule or a caplet, and thus, may improve the mechanical properties of the pH-sensitive materials of the coatings on the solid dosage forms.

Suitable plasticizers, include petroleum oils (for e.g., a paraffinic process oil, a naphthenic process oil, and an aromatic process oil), squalene, squalane, plant oils, (e.g., olive oil, camelia oil, castor oil, tall oil, and a peanut oil), mineral oils, silicon oils, dibasic or phthalic acid esters, (e.g., dibutyl phthalate, diethyl phthalate, and dimethyl phthalate, and dioctyl phthalate), liquid rubbers (e.g., polybutene and a liquid isoprene rubber), liquid fatty acid esters (e.g., isopropyl myristate ISM), hexyl laurate, diethyl sebacate, and diisopropyl sebacate, citric acid esters such as triethyl citrate, tributyl citrate, acetyl tributyl citrate, and acetyl triethyl citrate, triacetin, propylene glycol, diethylene glycol, polyethylene glycols, polypropylene glycol, other polyethylene oxide sorbitan esters, phthalates, sorbitol, glycol salicylate, crotaminton, glycerin, PLASACRYL™ T20, or mixtures thereof.

In some embodiments, the at least one plasticizer in the functional coating is triethyl citrate. In some embodiments, the at least one plasticizer (e.g., citric acid esters such as triethyl citrate) is present in amounts ranging from about 0.01% to about 5%, from about 0.1% to about 4%, from about 0.2% to about 2%, or from about 0.5% to about 1.5% w/w of the weight a core tablet.

The present disclosure provides that at least one layer of functional coating includes at least one anti-tacking/anti-adherent agent. Anti-tacking agent/anti-adherent is included in the coating solution for coating to prevent sticking of the tablets to punch faces and prevent sticking to machine dosators, tamping pins, etc. Exemplary anti-tacking agent include talc, glyceryl monostearate, colloidal silicon dioxide, kaolin, or any combination thereof.

The addition of talc as an anti-tacking agent to the functional coating provided surprisingly advantageous results, resulting in a substantial decrease in conversion of (Z)-endoxifen to (E)-endoxifen. The surprising advantage of coating the compositions (e.g., the tablets) with a coating comprising talc evidences that such coatings can facilitate delivery of (Z)-endoxifen more efficiently. Furthermore, it was surprisingly found that the coatings comprising a delayed releasing agent provided for a more consistent, slower release.

The sustained release compositions (e.g., enteric coated delayed release tablets) include at least one anti-tacking agent present in amounts ranging from about 0.1% to about 10% of w/w, from 1% to about 8%, or from about 2% to about 6% w/w of core.

Exemplary enteric coated delayed release tablets are provided herein and in Example 2 and Example 3.

An exemplary sustained release composition in the form of an enteric coated delayed release tablet comprises a core tablet, wherein the core tablet comprises: about 0.01% to about 40% or about 0.5 mg to about 200 mg of (Z)-endoxifen or a polymorph or a salt thereof, hypromellose, microcrystalline cellulose, and magnesium stearate; the core tablet being substantially enclosed in at least one layer of a functional coating, wherein the at least one layer of functional coating comprises methacrylic acid-ethyl acrylate copolymer (ranging from 2:1 to 1:2), triethylcitrate, and talc.

An exemplary sustained release composition in the form of an enteric coated delayed release tablet, comprises a core tablet wherein the core tablet comprises: (i) about 0.01% to about 40% (Z)-endoxifen or a polymorph or a salt thereof, (ii) about 0.1% to about 99% hypromellose; (iii) about 1% to about 99% microcrystalline cellulose; and (iv) about 0.01% to about 5% magnesium stearate; the core tablet being substantially enclosed in at least one layer of functional coating; wherein the at least one layer of functional coating comprises: (i) about 5% to about 40% methacrylic acid-ethyl acrylate copolymer (1:1) (polymethacrylate Methacrylic Acid Copolymer Dispersion, 30% solids); wherein the at least one layer of functional coating contributes to about 2% to about 20% weight gain over the average core tablet weight. The amounts are expressed in terms of percentage by weight based on the weight of the core tablet. In some embodiments, the foregoing sustained release composition has a drug ((Z)-endoxifen or a polymorph or a salt thereof) to sustained release agent ratio of 1:5.

An exemplary sustained release composition in the form of an enteric coated delayed release tablet, comprises a core tablet wherein the core tablet comprises: (i) about 0.01% to about 40% (Z)-endoxifen or a polymorph or a salt thereof, (ii) about 5% to about 60% hypromellose; (iii) about 10% to about 90% microcrystalline cellulose; and (iv) about 0.01% to about 5% magnesium stearate; the core tablet being substantially enclosed in at least one layer of functional coating; wherein the at least one layer of functional coating comprises: (i) about 5% to about 40% methacrylic acid-ethyl acrylate copolymer (1:1) (polymethacrylate Methacrylic Acid Copolymer Dispersion, 30% solids); wherein the at least one layer of functional coating contributes to about 2% to about 20% weight gain over the average core tablet weight. The amounts are expressed in terms of percentage by weight based on the weight of the core tablet.

An exemplary sustained release composition in the form of an enteric coated delayed release tablet, comprises a core tablet wherein the core tablet comprises: (i) about 0.01% to about 40% (Z)-endoxifen or a polymorph or a salt thereof, (ii) about 5% to about 60% hypromellose; (iii) about 10% to about 90% microcrystalline cellulose; and (iv) about 0.01% to about 5% magnesium stearate; the core tablet being substantially enclosed in at least one layer of functional coating; wherein the at least one layer of functional coating comprises: (i) about 0.1% to about 20% methacrylic acid-ethyl acrylate copolymer (1:1) (polymethacrylate Methacrylic Acid Copolymer Dispersion, 30% solids), (ii) about 0.01% to about 5% triethyl citrate, and (iii) about 1% to about 10% talc; wherein the at least one layer of functional coating contributes to about 2% to about 20% weight gain over the average core tablet weight. The amounts are expressed in terms of percentage by weight based on the weight of the core tablet.

An exemplary sustained release composition in the form of an enteric coated delayed release tablet comprises a core tablet, wherein the core tablet comprises: (i) 0.5 mg, 1 mg, 2 mg, 4 mg, 5 mg, 6 mg, 8 mg, 10 mg, 20 mg or 40 mgs of (Z)-endoxifen or a polymorph or a salt thereof, (ii) about 0.1% to about 99% or about 5% to about 60% hypromellose; (iii) about 1% to about 99% or about 10% to about 90% microcrystalline cellulose; and (iv) about 0.01% to about 5% magnesium stearate; the core tablet being substantially enclosed in at least one layer of a functional coating; wherein the at least one layer of the functional coating comprises: (a) about 0.1% to about 20% methacrylic acid-ethyl acrylate copolymer (1:1) (polymethacrylate Methacrylic Acid Copolymer Dispersion, 30% solids), (b) about 0.01% to about 5% triethyl citrate, and (c) about 1% to about 10% talc; wherein the at least one layer of functional coating contributes to about 2% to about 20% weight gain over the average core tablet weight. The amounts of all components from (ii) to (iv) and from (a) to (c) are expressed in terms of percentage by weight based on the weight of the core tablet. Such an enteric coated delayed release tablet (i) provides a sustained release of (Z)-endoxifen or a polymorph or a salt thereof over a time period of at least 2 hours, at least 3 hours, at least 4 hours, at least 6 hours, at least 7 hours, at least 8 hours, at least 9 hours, at least 10 hours, at least 12 hours, at least 14 hours, at least 16 hours, at least 18 hours, at least 24 hours, at least 48 hours, or at least 72 hours in a dissolution test according to the 75 RPM USP paddle method and using pH 1.2 at 37° C. for 2 hours in simulated gastric fluid and pH 6.8 at 37° C. for 24 hours in simulated intestinal fluid as a test medium.

In some embodiments, such an enteric coated delayed release tablet shows a percentage dissolution of about 0% to about 30% at 3 hours, about 30% to about 50% at 12 hours, and about 65% to about 85% after 12 hours in a dissolution test according to the 75 RPM USP paddle method and using pH 1.2 at 37° C. for 2 hours in simulated gastric fluid and pH 6.8 at 37° C. for 24 hours in simulated intestinal fluid as a test medium.

In some embodiments, such an enteric coated delayed release tablet shows in a dissolution test according to the 75 RPM USP paddle method and using pH 1.2 at 37° C. for 2 hours in simulated gastric fluid and pH 6.8 at 37° C. for 24 hours in simulated intestinal fluid as a test medium a percentage dissolution: (i) ranging from about 0% to 35% at 3 hours, from about 35% to about 55% at 12 hours, and from about 65% to 85% at 24 hours, (ii) of NMT 30% at 3 hours, NMT 50% at 12 hours, and NLT 80% at 24 hours; or (iii) of at least 20% to 30% after 24 hours.

In some embodiments, such an enteric coated delayed release tablet shows in a dissolution test according to the 75 RPM USP paddle method and using pH 1.2 at 37° C. for 2 hours in simulated gastric fluid and pH 6.8 at 37° C. for 24 hours in simulated intestinal fluid as a test medium a percentage dissolution of NMT about 5% at 2 hours, NLT about 70% at 3 hours, NLT about 95% at 6 hours and about 100% at 12 hours.

In some embodiments, such an enteric coated delayed release tablet shows in a dissolution test according to the 75 RPM USP paddle method and using pH 1.2 at 37° C. for 2 hours in simulated gastric fluid and pH 6.8 at 37° C. for 24 hours in simulated intestinal fluid as a test medium a percentage dissolution of NMT about 5% at 2 hours, NMT about 10% at 3 hours, NLT about 30% at 6 hours, NLT about 50% at 9 hours, and NLT about 80% at 14 hours.

In some embodiments, such an enteric coated delayed release tablet shows in a dissolution test according to the 75 RPM USP paddle method and using pH 1.2 at 37° C. for 2 hours in simulated gastric fluid and pH 6.8 at 37° C. for 24 hours in simulated intestinal fluid as a test medium a percentage dissolution of NMT about 10% at 3 hours, NLT about 30% at 6 hours, NLT about 50% at 9 hours, and NLT about 80% at 14 hours.

Functional coatings of sustained release compositions of the present disclosure, including the enteric coated delayed release tablets, may further include a pharmaceutically acceptable excipient. Pharmaceutically acceptable excipient may be any additive conventionally used in the technical field of preparation such as fillers, stabilizers, glidants, surfactants, light shielding agents, sweeteners, colorants, flavorants, anti-oxidants, preservatives, reducing agent, chelating agent and the like described herein. The pharmaceutically acceptable excipients are used in an amount conventionally used in the technical field of preparation. In addition, two or more kinds of these pharmaceutically acceptable excipients may be mixed at an appropriate ratio and used. In an aspect, the present disclosure provides that the sustained release compositions upon release of the therapeutic agent (Z)-endoxifen or a polymorph or a salt thereof provide a sustained exposure of the subject to the therapeutic agent upon oral administration from about 2 hours to about 270 hours per dose. In some embodiments, the sustained release compositions provide a sustained exposure of the subject to the released therapeutic agent (Z)-endoxifen or a polymorph or a salt thereof for at least 2 hours, at least 4 hours, at least 6 hours, at least 8 hours, at least 10 hours, at least 12 hours, at least 14 hours, at least 18 hours, at least 20 hours, at least 24 hours, at least 36 hours, at least 48 hours, at least 72 hours, at least 96 hours, at least 120 hours, at least 160 hours, at least 180 hours, at least 200 hours, at least 220 hours, at least 250 hours and at least 270 hours.

Pharmacokinetic Characteristics

In an aspect, sustained release compositions of the present disclosure comprising therapeutic agent (Z)-endoxifen or a polymorph or a salt thereof can provide enhanced pharmacokinetics as compared to the reference product, the Capsule in a subject upon oral administration.

Provided herein are exemplary pharmacokinetic parameters of a single dose of sustained release tablets in the form of enteric coated delayed release tablets of the present disclosure. While the PK parameters disclosed herein are generally mean plasma parameters, the present disclosure provides that the PK parameters for serum are typically 1.1 to 1. fold higher than the plasma PK parameters. As non-limiting example, for certain embodiments, a single oral dose of a sustained release composition (for example in the form of an enteric coated delayed release tablet) ingested by a subject can provide or is capable of achieving a mean plasma $AUC_{last}$ (hr*ng/mL) of at least about 40%, at least about 45%, at least about 50%, at least about 55%, at least about 60%, at least about 70%, at least about 75%, at least about 80%, at least about 85%, and at least about 90% of the $AUC_{last}$ of an equivalent single oral dose of the Capsule. In certain embodiments, a single dose of enteric coated delayed release tablet of the present disclosure, orally ingested by a subject in a fasting state, can provide or is capable of achieving a mean plasma $AUC_{last}$ of at least 70% of the mean plasma $AUC_{last}$ of an equivalent single oral dose of the Capsule in a fasting state.

Similarly, in certain embodiments, a single oral dose of a sustained release composition (for example in the form of an enterically coated delayed release tablet) ingested by a subject can provide or is capable of achieving a mean plasma $C_{max}$ (ng/mL) of at least about 30%, at least about 35%, at least about 40%, at least about 45%, at least about 50%, at least about 55%, at least about 60%, at least about 65%, at least about 70% at least about 75% at least about 80% at least about 85%, and at least about 90% of the $C_{max}$ of an equivalent single oral dose of the Capsule. In certain embodiments, a single dose of orally ingested enterically coated delayed release tablet of hardness of the present disclosure can provide or is capable of achieving a mean plasma $C_{max}$ (ng/mL) of at least about 45% of the $C_{max}$ of an orally ingested equivalent single dose of the Capsule.

The present disclosure provides that a single oral dose of sustained release compositions such as the enteric coated delayed release tablets of the present disclosure ingested by a subject can provide or is capable of achieving a mean plasma $T_{max}$ (hr) greater than the mean plasma $T_{max}$ (hr) of an equivalent single oral dose of the reference product, Capsule. As a non-limiting example, the mean plasma $T_{max}$ (hr) of a single oral dose of an enterically coated delayed release tablet ingested by a subject in fasting state is greater than the mean plasma $T_{max}$ (hr) of an equivalent single oral dose of Capsule. Similarly, in certain embodiments, a single oral dose of the sustained release compositions of the present disclosure, for example in the form of enteric coated delayed release tablets, can have a mean plasma $T_{max}$ (hr) that is at least 0.1, at least 0.5, at least 1, at least 1.5, at least 2, at least 2.5, at least about 3, at least about 3.5, at least about 4, at least about 4.5, at least 5, at least about 5.5, at least about 6, at least about 6.5, at least about 7, at least about 7.5, at least about 8, at least about 8.5, at least 9 time, at least 9.5 and at least 10 times greater than that of an equivalent single oral dose of the reference product, the Capsule. Thus, the sustained release compositions of the present disclosure reach their mean plasma $C_{max}$ considerably later than the reference product, the Capsule (See Table 15). Mean plasma concentrations over time following a single dose of a sustained release composition and the reference product, the Capsule, is provided in Table 14. In certain embodiments, the sustained release compositions of the present disclosure in the form of enteric coated delayed release tablet of hardness can have a mean plasma $T_{max}$ (hr) that is at least about 6 to about 10 time greater than the reference product, the Capsule.

In some embodiments, a sustained release composition of the present disclosure (e.g., an enteric coated delayed release tablet) may produce a mean $T_{max}$ of a therapeutic agent (e.g., (Z)-endoxifen) of at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 26 hours, at least about 28 hours, at least about 30 hours, at least about 32 hours, at least about 34 hours, at least about 36 hours, at least about 38 hours, at least about 40 hours, at least about 42 hours, at least about 44 hours, at least about 46 hours, at least about 48 hours, at least about 50 hours, at least about 55 hours, at least about 60 hours, at least about 65 hours, at least about 70 hours, at least about 75 hours, or at least about 80 hours in a plasma or a serum of a subject orally administered the sustained composition. In some embodiments, a sustained release composition may produce a mean $T_{max}$ of the therapeutic agent of from 4 hours to 80 hours, from 5 hours to 80 hours, from 6 hours to 80 hours, from 7 hours to 80 hours, from 8 hours to 80 hours, from 9 hours to 80 hours, from 10 hours to 80 hours, from 15 hours to 80 hours, from 24 hours to 80 hours, from 36 hours to 80 hours, from 48 hours to 80 hours, from 4 hours to 70 hours, from 5 hours to 70 hours, from 6 hours to 70 hours, from 7 hours to 70 hours, from 8 hours to 70 hours, from 9 hours to 70 hours, from 10 hours to 70 hours, from 15 hours to 70 hours, from 24 hours to 70 hours, from 36 hours to 70 hours, from 48 hours to 70 hours, from 4 hours to 60 hours, from 5 hours to 60 hours, from 6 hours to 60 hours, from 7 hours to 60 hours, from 8 hours to 60 hours, from 9 hours to 60 hours, from 10 hours to 60 hours, from 15 hours to 60 hours, from 24 hours to 60 hours, from 36 hours to 60 hours, from 48 hours to 60 hours, from 4 hours to 55 hours, from 5 hours to 55 hours, from 6 hours to 55 hours, from 7 hours to 55 hours, from 8 hours to 55 hours, from 9 hours to 55 hours, from 10 hours to 55 hours, from 15 hours to 55 hours, from 24 hours to 55 hours, from 36 hours to 55 hours, or from 48 hours to 55 hours in a plasma or a serum of a subject orally administered the sustained composition.

Further, the higher $T_{max}$ and the drug release profile of the sustained release compositions such as enteric coated delayed release tablets above as compared to the Capsule suggest that the rate of release and the rate of absorption or rate of uptake (as used interchangeably in the present disclosure) of the therapeutic agent ((Z)-endoxifen or a polymorph or a salt thereof) into the blood of a subject from an orally administered sustained release composition is also slower as compared with the rate of release and the rate of absorption of the therapeutic agent from the Capsule.

In certain embodiments, the present disclosure provides that the sustained release compositions, for example, in the form of sustained release tablets such as enterically coated delayed release tablets, are capable of achieving one or more of the pharmacokinetic parameters and mean plasma concentration as disclosed in Table 14, Table 15 and Table 17 following oral administration of a single dose of the sustained release composition to a subject. In some embodiments, the median $T_{max}$ of sustained release compositions of the present disclosure after a single dose is about 65 to 75 hr. In at least one embodiment, the median $T_{max}$ of sustained release compositions of the present disclosure after single dose administration is about 73 hours.

Provided herein are exemplary pharmacokinetic parameters of multiple doses (for example, 14 once daily dose) of sustained release tablets in the form of enteric coated delayed release tablets of the present disclosure.

As non-limiting example, for certain embodiments, the sustained release compositions (for example, in the form of sustained release tablets such as enterically coated delayed release tablets) can provide or is capable of achieving a mean plasma $AUC_{last}$ (hr*ng/mL) of at least about 40%, at least about 45%, at least about 50%, at least about 55%, at least about 60%, at least about 70%, at least about 75%, at least about 80%, at least about 85%, and at least about 90% of the $AUC_{last}$ of the Capsule when the sustained release compositions and the Capsule are orally dosed with multiple equivalent doses (as non-limiting example, for 14 days 1 mg once daily) to subjects. In certain embodiments, a sustained release composition in the form of an enteric coated delayed release tablet of hardness of the present disclosure can provide or is capable of achieving a mean plasma $AUC_{last}$ of at least 60% of the mean plasma $AUC_{last}$ of the Capsule when the sustained release composition and the Capsule are orally dosed in multiple equivalent doses (for example, for 14 days 4 mg once daily) to subjects in a fasting state.

As non-limiting example, for certain embodiments, the sustained release compositions (for example, in the form of sustained release tablets such as enterically coated delayed release tablets) can provide or is capable of achieving a mean plasma $AUC_{tau}$ (hr*ng/mL) of at least about 40%, at least about 45%, at least about 50%, at least about 55%, at least about 60%, at least about 70%, at least about 75%, and at least about 80%, at least about 85%, and at least about 90% of the $AUC_{tau}$ of the Capsule when the sustained release compositions and the Capsule are orally dosed with multiple equivalent doses (as non-limiting example, for 14 days 1 mg once daily) to subjects. In certain embodiments, the sustained release compositions of the present disclosure in the form of enteric coated delayed release tablets of the present disclosure can provide or are capable of achieving a mean plasma $AUC_{tau}$ (hr*ng/mL) of at least about 50% of the $AUC_{tau}$ of the Capsule when the sustained release compositions and the Capsule are orally dosed with multiple equivalent doses (as non-limiting example, for 14 days 4 mg once daily) to subjects in a fasting state.

Similarly, in certain embodiments, the sustained release compositions of the present disclosure (for example, in the form of sustained release tablets such as enteric coated delayed release tablets) can provide or is capable of achieving a mean plasma $C_{max}$ (ng/mL) of at least about 30%, at least about 35%, at least about 40%, at least about 45%, at least about 50%, at least about 55%, at least about 60%, at least about 65%, at least about 70% at least about 75% at least about 80% at least about 85%, and at least about 90% of the $C_{max}$ of the Capsule when the sustained release compositions and Capsule are orally dosed with multiple equivalent doses (as non-limiting example, for 14 days 1 mg once daily) to subjects. In certain embodiments, the sustained release compositions of the present disclosure, for example, in the form of enteric coated delayed release tablets of the present disclosure, can provide or are capable of achieving a mean plasma $C_{max}$ (ng/mL) of at least about 45% of the $C_{max}$ of the Capsule when the sustained release compositions and Capsule are orally dosed with multiple equivalent doses (as non-limiting example, for 14 days 4 mg once daily) to subjects in a fasting state.

Similarly, in certain embodiments, the sustained release compositions of the present disclosure (for example in the form of sustained release tablets such as enteric coated delayed release tablets) can provide or are capable of achieving a mean plasma $C_{min}$ (ng/mL) of at least about 40%, at least about 45%, at least about 50%, at least about 55%, and at least about 60% of the $C_{min}$ of the dose of Capsule when the sustained release compositions and Capsule are orally dosed with multiple equivalent doses (as non-limiting example, for 14 days 1 mg once daily) to subjects.

In certain embodiments, the sustained release compositions of the present disclosure in the form of enteric coated delayed release tablets of the present disclosure can provide or are capable of achieving a mean plasma $C_{min}$ (ng/mL) of at least 45% of the $C_{min}$ of the Capsule when the sustained release compositions and Capsule are orally dosed with multiple equivalent doses (as non-limiting example, for 14 days 4 mg once daily) to subjects in a fasting state.

The present disclosure provides that sustained release compositions of the present disclosure, (for example, the sustained release tablets such as enterically coated delayed release tablets) can provide or are capable of achieving a mean plasma $C_{average}$ (ng/mL) that is substantially the same or less than the mean plasma $C_{average}$ (ng/mL) of a reference product, the Capsule, when the sustained release compositions and Capsule are orally dosed with multiple equivalent doses (as non-limiting example, for 14 days 1 mg once daily) to subjects. As a non-limiting example, the mean plasma $C_{average}$ (ng/mL) of a sustained release tablet in the form of an enteric coated delayed release tablet is less than the mean plasma $C_{average}$ (ng/mL) of the reference product, Capsule, when the sustained release compositions and Capsule are orally dosed with multiple equivalent doses (as non-limiting example, for 14 days 4 mg once daily) to subjects in a fasting state (See Table 16). In certain embodiments, the sustained release compositions of the present disclosure can provide or are capable of achieving a mean plasma $C_{average}$ (ng/mL) of at least about 40%, at least about 45%, at least about 50%, at least about 55%, and at least about 60% of the $C_{average}$ of the Capsule when the sustained release compositions and Capsule are orally dosed with multiple equivalent doses (as non-limiting example, for 14 days 1 mg once daily) to subjects. In certain embodiments, the sustained release compositions of the present disclosure in the form of enteric coated delayed release tablets of present disclosure can provide or are capable of achieving a mean plasma $C_{average}$ (ng/mL) of at least 45% of the $C_{average}$ of the Capsule when the sustained release compositions and Capsule are orally dosed with multiple doses (as non-limiting example, for 14 days 4 mg once daily) to subjects in a fasting state.

Mean time to reach steady state levels of (Z)-endoxifen or a polymorph or a salt thereof upon multiple doses of a sustained release composition of the present disclosure is about 14 days. At steady state, the sustained release compositions of the present disclosure show less fluctuation over the inter-dosing interval compared with reference product, the Capsule.

A composition of the present disclosure (e.g., a composition comprising (Z)-endoxifen) may produce an average concentration steady state (Css) of endoxifen within a subject. In some embodiments, the composition may produce an average concentration steady state (Css) of from 1 ng/mL to 10 ng/mL, from 5 ng/mL to 15 ng/mL, from 10 ng/mL to 20 ng/mL, from 15 ng/mL to 25 ng/mL, from 20 ng/mL to 30 ng/mL, from 25 ng/mL to 35 ng/mL, from 30 ng/mL to 40 ng/mL, from 35 ng/mL to 45 ng/mL, from 40 ng/mL to 50 ng/mL, from 45 ng/mL to 60 ng/mL, from 50 ng/mL to 70 ng/mL, from 60 ng/mL to 80 ng/mL, from 70 ng/mL to 90 ng/mL, from 80 ng/mL to 100 ng/mL, from 90 ng/mL to 110 ng/mL, from 100 ng/mL to 120 ng/mL, from 110 ng/mL to 130 ng/mL, from 120 ng/mL to 140 ng/mL, or from 130 ng/mL to 150 ng/mL in a subject. In some embodiments, the composition may produce an average concentration steady state (Css) in a subject of from 1 ng/mL to 10 ng/mL, from 5 ng/mL to 15 ng/mL, from 10 ng/mL to 20 ng/mL, from 15 ng/mL to 25 ng/mL, from 20 ng/mL to 30 ng/mL, from 25 ng/mL to 35 ng/mL, or from 30 ng/mL to 40 ng/mL per milligram of endoxifen administered to the subject.

In certain embodiments, the present disclosure provides that the sustained release compositions, for example, in the form of a sustained release tablet such as enteric coated delayed release tablets, are capable of achieving one or more of the pharmacokinetic parameters shown in Table 16 or Table 17 following oral administration of multiple doses to a subject or at steady state. In other embodiments, the median $T_{max}$ of sustained release compositions of the present disclosure after multiple doses or at steady state range from 3 to 5 hours. In at least one embodiment, the median $T_{max}$ of the sustained release compositions of the present disclosure after multiple doses or at steady state is 4 hours.

The present disclosure provides that in some embodiments, the relative bioavailability of the therapeutic agent from the sustained release compositions of the present disclosure such as the enteric coated delayed release tablets when dosed orally in a single and/or multi dose ranges from about at least 40% to about at least 90% as compared to equivalent, single or multiple dose(s) of the reference product, the Capsule orally administered to subjects. In certain embodiments, a single and/or multiple dose(s) of orally ingested enterically coated delayed release tablet of the present disclosure in a subject can provide or are capable of achieving relative bioavailability of at least about 60% to at least about 90% as compared to equivalent single or multiple oral doses of the Capsule. The sustained release compositions in the form of enteric coated delayed release tablets having bioavailability of the therapeutic agent with improved pharmacokinetic parameters (such as longer plasma and serum $T_{max}$ and low fluctuation of the therapeutic agent ((Z)-endoxifen or a polymorph or a salt thereof) as disclosed herein and lower frequency and/or intensity of vasomotor side effects (See Example 8) may be desirable for longer term use for breast disorders, for example for the treatment and prevention breast disorders, for example, treatment and prevention of breast cancers, the prevention of increased breast density, reduction of breast density and unmasking of breast cancer by reducing breast density, and for continued use and compliance by the subjects.

Thus, the present disclosure provides that the therapeutic agent ((Z)-endoxifen or a polymorph or a salt thereof) is absorbed and systemically available in a controlled sustained manner after 2 hours. The present disclosure also provides that the sustained release compositions display dose proportionality in peak drug concentrations in plasma and serum and AUC cures such as $AUC_{inf}$ over the dose range 0.1 mg to 8 mg.

In an aspect, the present disclosure provides that the sustained release compositions of the present disclosure and their pharmacokinetics advantageously cause fewer side effects such as vasomotor symptoms (hot flashes, night sweats, sensation of "feeling hot", sleep disturbances, and the like) as compared with tamoxifen. The present disclosure provides that less than 50%, less than 45% less than 40%, less than 35%, less than 30%, and less than 25% of the subjects orally administered with the sustained release compositions of the present disclosure experience side effects such as vasomotor symptoms such as hot flashes, night sweats, sensation of feeling, hot, sleep disturbances and the like whereas 78% of subjects taking tamoxifen reportedly experienced hot flashes (Mortimer et al. Breast Cancer Res Treat. 2008 April; 108(3): 421-426). In some embodiments, less than 50% of subjects ingesting sustained release tablets experience vasomotor symptoms such as hot flashes, night sweats and the like. In some embodiments, less than 30% of subjects ingesting sustained release tablets experience vasomotor symptoms such as hot flashes, night sweats, and the like. In certain embodiments, sustained release compositions of the present disclosure administered orally cause such vasomotor symptoms in a subject at a frequency of less than about 25%, less than about 20%, less than about 15%, less than about 10%, less than about 9%, less than about 8%, less than about 7%, less than about 6%, less than about 5%, less than about 4%, less than about 3%, less than about 2%, and less than about 1% days of drug dosing-days. In at least one embodiment, oral administration of sustained release compositions of the present disclosure result in such vasomotor symptoms experienced by a subject at a frequency of less than about 25% day of the drug dosing days.

In another aspect, the present disclosure provides that the sustained release compositions of the present disclosure provide a subject a more prolonged controlled exposure to (Z)-endoxifen, or a polymorph or a salt thereof. In some embodiments, the subjects are exposed to the therapeutic agent (Z)-endoxifen, or a polymorph or a salt thereof after release of the therapeutic agent from the sustained release compositions for a period ranging from about 2 hours to about 270 hours per dose.

In another aspect, the present disclosure relates to methods of making sustained release compositions of the present disclosure. Preparation of solid dosage forms of the sustained release compositions of the present disclosure may be performed by dry compression, dry granulation or wet granulation. To reduce the potential for the interconversion of the (Z)-endoxifen to inactive (E)-endoxifen isomer in solution phase, direct dry compression or dry granulation is preferred.

In one embodiment of the invention, the (Z)-endoxifen, or a polymorph or a salt thereof and the sustained release agent are mixed with a binder, which is also defined herein as the tablet matrix. In one embodiment, the binder has an average particle size of about 10 μm to about 500 μm, such as between 25 μm and 150 μm. Particles in this size range are particularly useful for direct compression processes. In one embodiment, the components are blended together, for example as dry powders, and fed into the die cavity of an apparatus that applies pressure to form a tablet. Any suitable compacting apparatus may be used, including, but not limited to, conventional unitary or rotary tablet press. In one embodiment, the tablet may be formed by compaction using a rotary tablet press (e.g., such as those commercially available from Fette America Inc., Rockaway, N.J., or Manesty Machines LTD, Liverpool, UK). In general, a metered volume of the blended mixture is filled into a die cavity (where the blended mixture is either gravity fed or mechanically fed from a feeder) of the rotary tablet press, and the cavity rotates as part of a "die table" from the filling position to a compaction position. At the compaction position, the blended mixture is compacted between an upper and a lower punch, then the resulting tablet is pushed from the die cavity by the lower punch and then guided to an injection chute by a stationary "take-off" bar.

In one embodiment, the tablet may be a directly compressed tablet core made from a powder that is substantially free of water-soluble polymeric binders and hydrated polymers. As used herein, what is meant by "substantially free" is less than 5 percent, such as less than 1 percent, such as less than 0.1 percent, such as completely free (e.g., 0 percent). This composition is advantageous for minimizing processing and material costs and providing for optimal physical and chemical stability of the tablet.

Example 1 provides further details on the methods for making sustained release tablets (cores) comprising (Z)-endoxifen free base. Non-limiting, exemplary tablet cores comprising 4% (4 mg) (Z)-endoxifen free base produced by the disclosed method are provided in Table 2. Characteristics of certain exemplary sustained release tablets (core tablets) produced by such methods is provided in Table 3.

As non-limiting examples, sustained release tablets comprising 0.5 mg, 1 mg, 2 mg, 3 mg, 4 mg, 5 mg, 6 mg, 7 mg, 8 mg, 9 mg, 10 mg, 20 mg, and 40 mg (Z)-endoxifen tablets as provided in Table 1 and Table 5, may be prepared using the methods disclosed herein. One of skill in the art will recognize that additional sustained release tablets comprising 0.5 mg to 200 mg sustained release solid dosage forms (cores) may be prepared based on the present disclosure.

TABLE 1

Exemplary sustained release tablets (cores)

Core Tablet Formulation-Components and functionality

| API (Z)-EDX (mg) | Sustained release Agent Hypromellose (K15M) (mg) | Binder Microcrystalline cellulose (MCC, mg) | Lubricant Mg Stearate (mg) | Total Formulation Weight (mg) |
| --- | --- | --- | --- | --- |
| 0.5 | 2-5 | 93.5-96.5 | 1 | 100 |
| 1 | 4-10 | 88-94 | 1 | 100 |
| 2 | 8-20 | 77-89 | 1 | 100 |
| 5 | 20-50 | 44-74 | 1 | 100 |
| 5 | 20-50 | 143-173 | 2 | 200 |
| 6 | 24-60 | 33-69 | 1 | 100 |
| 6 | 24-60 | 132-168 | 2 | 200 |
| 8 | 40-80 | 71 | 1 | 100 |
| 8 | 40-80 | 110-150 | 2 | 200 |

TABLE 1-continued

Exemplary sustained release tablets (cores)

| Hypromellose (K100M) (mg) | MCC (mg) | Mg Stearate (mg) | | |
|---|---|---|---|---|
| 10 | 20-100 | 88-168 | 2 | 200 |
| 20 | 20-120 | 58-158 | 2 | 200 |
| 40 | 40-100 | 58-118 | 2 | 200 |

| Hypromellose K4M (mg) | MCC (mg) | Mg Stearate (mg) | | |
|---|---|---|---|---|
| 20 | 20-100 | 78-158 | 2 | 200 |
| 40 | 20-80 | 78-138 | 2 | 200 |

In at least one embodiment, provided herein is a method of preparing a sustained release composition in the form of an enteric coated delayed release tablet for sustained release of (Z)-endoxifen or a polymorph or a salt thereof comprising the steps of preparing an solid dosage form such as a tablet wherein the preparation of the solid dosage form such as core tablet comprises the steps of:
   a. Combining (i) (Z)-endoxifen or a polymorph or a salt thereof, (ii) at least one sustained release agent (such as hypromellose), (iii) at least one binder (such as microcrystalline cellulose), and (iv) at least one lubricant (such as magnesium stearate) to provide a component mixture;
   b. Blending the component mixture of step (a) such that (Z)-endoxifen or a polymorph or a salt thereof is homogeneously dispersed within the component mixture to provide a blended mixture; and
   c. Dry compressing the blended mixture to form a solid dosage form such as a tablet (e.g., a core tablet).

In some embodiments, the method comprises the steps of (a) combining and blending (i) (Z)-endoxifen or a polymorph or a salt thereof, (ii) at least one sustained release agent (such as hypromellose), and (iii) at least one binder (such as microcrystalline cellulose) to form a component mixture; (b) adding at least one lubricant such as magnesium stearate to the component mixture, and further blending to provide a blended mixture; and (c) dry compressing the blended mixture to form an solid dosage form such as a tablet (e.g., a core tablet).

In certain embodiments, the sustained release compositions that are in the form of solid dosage forms are substantially enclosed in at least one layer of functional coating by a coating a functional coating solution on the solid dosage forms, wherein the coating solutions is prepared by combining at least one controlled release agent such as a delayed release agent (as a non-limiting example, a poly(methacrylate) polymer such as methacrylic acid-ethyl acrylate copolymer (1:1) (polymethacrylate Methacrylic Acid Copolymer Dispersion, 30% solids) with a diluent or solvent to form a coating solution.

In certain embodiments, the ratio of (Z)-endoxifen, or a polymorph or a salt thereof to the sustained release agent ranges from 1:10 to 10:1. In some embodiments, the ratio of (Z)-endoxifen, or a polymorph or a salt thereof to the sustained release agent ranges from 2:6 to 6:2. In certain embodiments, the ratio of (Z)-endoxifen, or a polymorph or a salt thereof to the sustained release agent is 1:5.

In certain embodiments, the sustained release compositions that are in the form of solid dosage forms are substantially enclosed in at least one layer of functional coating by a coating a functional coating solution on the solid dosage forms, wherein the coating solutions is prepared by combining at least one controlled release agent such as a delayed release agent (as a non-limiting example, a poly(methacrylate) polymer such as methacrylic acid-ethyl acrylate copolymer (1:1) (polymethacrylate Methacrylic Acid Copolymer Dispersion, 30% solids), at least one plasticizer (such as triethyl citrate) and at least one anti-tacking/anti-adherent (such as talc) to form a coating solution.

In at least one embodiment, provided herein is a method of preparing an enteric coated delayed release tablet for sustained release of (Z)-endoxifen or a salt or a polymorph thereof comprising the steps of:
   a. preparing a solid dosage form such as a tablet wherein the preparation of the solid dosage form such as core tablet comprises the steps of: (1) combining (i) (Z)-endoxifen or a polymorph or a salt thereof, (ii) at least one rate release controller (such as hypromellose), (iii) at least one binder (such as microcrystalline cellulose), and (iv) at least one lubricant (such as magnesium stearate) to provide a combined mixture; (2) blending the combined mixture of step (a) such that (Z)-endoxifen or a polymorph or a salt thereof is homogeneously dispersed within the combined mixture; and (3) dry compressing the combined mixture to provide a core tablet; and
   b. combining at least one controlled delayed release agent (as a non-limiting example, a poly(methacrylate) polymer such as methacrylic acid-ethyl acrylate copolymer (1:1) (polymethacrylate Methacrylic Acid Copolymer Dispersion, 30% solids), at least one plasticizer (such as triethyl citrate) and at least one anti-tacking/anti-adherent (such as talc) to form a coating solution; and
   c. substantially coating the core tablet of step (a) with the coating solution to form at least one layer of functional coating.

Example 2 and Example 3 provide further details on methods for preparation of enteric coated delayed release tablets using the cores prepared in Example 1 and disclosed in Table 1 and Table 2. Coating solution used to prepare at least one layer of functional coating is provided in Table 4. Similarly, enteric coated delayed release tablets comprising 0.5 mg to 200 mg of (Z)-endoxifen, or a polymorph or a salt there of can be prepared.

One of skill in the art will further recognize that sustained release compositions disclosed herein may comprise one or more of the excipients known in the art and disclosed herein in any combination appropriate for a desired formulation or preparation. Additional excipients may generally be found in Remington's The Science and Practice of Pharmacy, Meade Publishing Co., United States Pharmacopeia/National Formulary, and the Handbook of Pharmaceutical Excipients, 3rd edition, Edited by A. H. Kibbe, Published by: American Pharmaceutical Association, Washington D.C., ISBN: 0-917330-96-X, or Handbook of Pharmaceutical Excipients (4th edition), Edited by Raymond C Rowe—Publisher: Science and Practice. One of skill in the art will be able to select suitable excipients necessary for the preparation of the formulations and appropriate dosage forms compatible with the route of administration based on his or her skill and knowledge in the art and the disclosures made herein. In all cases, the ultimate dosage form should not exceed the standards of microbial purity and quality and stable under the conditions of manufacture and storage.

The methods and compositions disclosed herein are industrially scalable and meet the standards required for administering such sustained release compositions to a subject. Uniformity of dosage units will meet the criteria of USP <905>.

For formulations of the tablets disclosed herein, as the water activity (Aw) is less than 0.75, testing Total Aerobic Plate Count (TAC) and USP indicator organism is not necessary. The publication, "Microbial Bioburden on Oral Solid Dosage Form," by Jose E. Martinez, Pharmaceutical Technology, February 2002, pages 58 to 70, is hereby incorporated by reference in its entirety.

Furthermore, since formulations of the compositions disclosed herein also have water activity of less than 0.75, then no detailed microbial testing of that should be done. TAC is an estimation of the total viable aerobic microbes present in a sample of raw material, in-process material, or finished product. Samples are analyzed in accordance with the most current USP 42 <61>, "Microbiological Examination of Nonsterile Products: Microbial Enumeration Tests."

Acceptable TAC for oral solid dosage forms are established for the formulation of the inventive compositions in terms of alert and action levels, which could be $10^3$ cfu g/mL, and $1\times10^4$ cfu g/mL respectively. A TAC that is $2\times10^4$ cfu g/mL is considered unacceptable. Acceptable combined yeast and mold count (TYMC) is NMT $10^2$ CFU/g. Absence of E. coli in 1 g (per USP <1111>) is considered acceptable.

The present disclosure provides that the sustained release compositions of the present disclosure are stable at ambient temperature for at least 1 month, at least 3 months, at least 6 months, at least 9 months, at least 12 months, at least 18 months, at least 2 years, at least 3 years, at least 4 years and at least 5 years. The present disclosure also provides that the (Z)-endoxifen, and polymorphs and salts thereof in the sustained release compositions of the present disclosure are stable at ambient temperature for at least 1 month, at least 3 months, at least 6 months, at least 9 months, at least 12 months, at least 18 months, at least 2 years, at least 3 years, at least 4 years and at least 5 years. In at least one embodiment, the sustained release compositions in the form of sustained release tablets and enteric coated delayed release tablets are stable at ambient temperature at least 1 year. In at least one embodiment, the (Z)-endoxifen or a polymorph or a salt thereof in the sustained release compositions in the form of sustained release tablets and enteric coated delayed release tablets is stable at ambient temperature at least 1 year. The present disclosure provides that the sustained release compositions of the present disclosure are stable at 25° C./60% RH (relative humidity) and at 40° C./75% RH (relative humidity) for at least 1 month, at least 3 months, at least 6 months, at least 9 months, at least 12 months, at least 18 months, at least 2 years, at least 3 years, at least 4 years and at least 5 years. The present disclosure also provides that the (Z)-endoxifen, and polymorphs and salts thereof in the sustained release compositions of the present disclosure are stable at 25° C./60% RH and at 40° C./75% RH for at least 1 month, at least 3 months, at least 6 months, at least 9 months, at least 12 months, at least 18 months, at least 2 years, at least 3 years, at least 4 years, and at least 5 years.

The sustained release compositions comprising (Z)-endoxifen and polymorphs and salts thereof disclosed herein, may be used in the manufacture of medicaments for use in the treatment of a subject in need thereof.

In an aspect the present disclosure provides that, regardless of the mechanism of action or any other theory, subjects having or at risk of having disorders that are susceptible to (Z)-endoxifen and polymorphs and salts thereof can be treated by sustained release compositions of the present disclosure. In some embodiments, the disorder is a hormone dependent disorder. In some embodiments, the disorder is a mental or mood disorder such as depression, mania, hypomania, or bipolar disorder. Such mental or mood disorders may be with or without psychotic features. Such a mental or mood disorder may be hormone-independent or hormone dependent.

The sustained release compositions of the present disclosure may be used by orally administering to a subject in need thereof. In certain embodiments, the subjects are orally administered a sustained release composition of the present disclosure in the form of a sustained release tablet. In other embodiments, the subjects are orally administered a sustained release composition of the present disclosure in the form of an enteric coated delayed release tablet as disclosed herein.

The sustained release compositions of the present disclosure may be used as a primary therapy, as a part of a neoadjuvant therapy (to primary therapy), or as part of adjuvant therapy regimen, where the intention is to ameliorate or cure a subject having or at risk of having a disorder such as a hormone dependent disorder or mental or mood disorder. In some embodiments, the sustained release compositions may be used during a "window of opportunity" wherein newly diagnosed patients with such disorders receive the compositions from time of diagnosis up to the day of surgery. As a non-limiting example, newly-diagnosed patients with ER+ and HER2 negative (HER2−) stage 1 or 2 invasive breast cancer, requiring mastectomy or lumpectomy can receive the sustained release compositions of the present disclosure for at least 14 days from the time of diagnosis up to the day of surgery. In some embodiments, a window of opportunity may be after a patient is diagnosed with a cancer and before the patient has surgery to remove the cancer. A treatment may be administered in the window of opportunity between diagnosis and surgery even if the patient never undergoes surgery. For example, a composition of the present disclosure may be administered to a patient following a cancer diagnosis but before the patient is predicted, scheduled, or recommended to undergo surgery to remove the cancer. In some embodiments, a window of opportunity may begin when a breast condition (e.g., cancer, a lesion, or a dense breast) is identified in a mammogram. Administration of the composition may expand the window of opportunity by delaying the surgery or reducing or eliminating a need surgery, thereby expanding the window of opportunity. In some embodiment, administration of a composition comprising endoxifen may extend a window of opportunity following a cancer diagnosis. The extended window of opportunity may provide more time to obtain imaging studies, tumor specimens, and blood samples.

In some embodiments, a window of opportunity (e.g., a window between a cancer diagnosis and a surgery to remove the cancer) may be extended by at least 5 days, at least 10 days, at least 15 days, at least 20 days, at least 25 days, at least 30 days, at least 60 days, at least 90 days, at least 120 days, at least 1 month, at least 2 months, at least 3 month, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 1 year, at least 1.2 years, at least 1.4 years, at least 1.6 years, at least 1.8 years, at least 2 years, at least 2.5 years, at least 3 years, at least 3.5 years, at least 4 years, at least 4.5 years, or at least 5 years. In some embodiments, a window of opportunity may be extended indefinitely following administration of a composition of the present disclosure (e.g., a composition comprising endoxifen).

In certain embodiments, the disorder is a breast disorder. In some embodiments, the disorder is hormone dependent breast disorder. In other embodiments, the disorder is hormone dependent reproductive tract disorder. In still other embodiments, the subject has both a hormone dependent breast disorder and a hormone dependent reproductive tract disorder. In some embodiments, the hormone dependent disorder is a benign breast disorder, hyperplasia, atypia, atypical ductal hyperplasia, atypical lobular hyperplasia, increased breast density, gynecomastia, DCIS, LCIS, breast cancer, endometrial cancer, ovarian cancer, uterine cancer, cervical cancer, vaginal cancer or vulvar cancer.

In some embodiments, the breast disorder is increased breast density. For example, the breast disorder is a BI-RAD class B (formerly Class II), class C (formerly class III) or class D (formerly class IV) breast density. Administration of a sustained release composition of the present disclosure to a subject having increased breast density (class B, C or D) reduces the amount or severity of breast density observed in the subject. The sustained release composition induced reduction of breast density in the subject is advantageous in that it not only reduces independent risk factor for breast cancer that increased breast density poses, but also unmasks previously undetectable breast disorder such as breast cancer. Thus, in some embodiments, subjects having their breast cancers masked by increased breast density can be treated by sustained release compositions of the present disclosure, thereby reducing breast density in a subject and unmasking breast cancer.

In some embodiments, the hormone dependent breast disorder or hormone dependent reproductive tract disorder is precocious puberty. In other embodiments, the hormone dependent breast disorder or hormone dependent reproductive tract disorder is McCune-Albright Syndrome.

In some embodiments, the breast disorder is gynecomastia. In some embodiments, gynecomastia is presented secondarily to an underlying disease or as a result of certain medication use (such as exogenous estrogens, anti-androgens such as Bicalutamide, flutamide, finasteride, dutasteride), anti-hypertensives such as spironolactone, 5 alpha-reductase inhibitors, anti-retrovirals such as Protease inhibitors (e.g., saquinavir, indinavir, nelfinavir, ritonavir, lopinavir), reverse transcriptase inhibitors (stavudine, zidovudine, lamivudine), and gastrointestinal drugs such as H2 histamine receptor blockers (e.g., cimetidine). Accordingly, in some embodiments the subject also has underlying disease selected from the group consisting of prostate cancer, cirrhosis and liver disease, male hypogonadism, hyperthyroidism, renal failure and in patients undergoing hemodialysis, or type I diabetes mellitus. In certain embodiments, the subject has prostate cancer as the underlying disease, wherein the subject has or is at risk of having gynecomastia. Administration of a sustained release composition of the present disclosure to a subject having or at risk of having gynecomastia reduces gynecomastia or risk of developing gynecomastia. The sustained release composition induced reduction of gynecomastia can result in decrease at least one symptom of the disorder, such as breast swelling (breast tissue volume), discomfort or pain. Such sustained release composition may also improve a subject's physical and mental health, including depression.

In certain embodiments, the breast cancer is DCIS, LCIS, ILC, IDC, MIC, inflammatory breast cancer, ER-positive (ER+) breast cancer, HER2+ breast cancer, BRCA1+ breast cancer, BRCA2+ breast cancer, adenoid cystic (adenocystic) carcinoma, low-grade adenosquamatous carcinoma, medullary carcinoma, mucinous (or colloid) carcinoma, papillary carcinoma, tubular carcinoma, metaplastic carcinoma, or micropapillary carcinoma. In at least one embodiment, a single breast cancer tumor may be a combination of the foregoing or be a mixture of invasive and in situ cancer.

The present disclosure contemplates the use of the sustained release compositions disclosed herein at various stages in tumor development and progression, including the treatment of advanced and/or aggressive neoplasms, e.g., overt disease in a subject that is not amenable to cure by local modalities of treatment such as surgery or radiotherapy, metastatic disease, or locally advanced disease. Accordingly, in some embodiments the breast cancer is a pre-cancer, an early stage cancer, a non-metastatic cancer, a pre-metastatic cancer, or a locally advanced cancer. In at least one embodiment, the breast disorder is metastatic cancer. In some embodiments, the subject further has prostate cancer.

Administration of a sustained release composition of the present disclosure may reduce the development of any of the hormone dependent disorders. In subject having breast cancer, administration, for example, orally, of a sustained release composition of the present disclosure to a subject having breast cancer may reduce or ameliorate the disease symptoms, reduce disease burden, reduce cancer growth rate, reduce tumor volume or size, reduce or prevent neovascularization of the tumor, tumor escape and metastasis, reduce a biomarker of the disease, such as, BRCA-1, BRCA-2, ER, PR, Her2, uPA, PAI, Tf, p53, Ki-67, cytokeratins, cancer tumor antigens, and other biomarkers measured by Mammaprint, OncotypeDx, PAM50, EndoxPredict, MammoStrat, and other diagnostic and predictive tests known in the art. For example, administration of a composition of the present disclosure (e.g., a composition comprising (Z)-endoxifen) may reduce a level of a Ki-67 biomarker in a tumor by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% following administration of endoxifen as compared to the level prior to administering endoxifen. In some embodiments, a level of a biomarker (e.g., BRCA-1, BRCA-2, ER, PR, Her2, uPA, PAI, Tf, p53, Ki-67, cytokeratins, or cancer tumor antigens) may be measured in a tissue collected from a subject (e.g., a breast tissue, a cancerous tissue, a non-cancerous tissue, or a biopsy tissue). In some embodiments, a level of a biomarker may be measured in a fluid collected from a subject (e.g., blood, plasma, intraductal fluid, breast milk, urine, or saliva). In some embodiments, a level of a biomarker in a tissue or a fluid collected from a subject following treatment with endoxifen may be compared to a level of the biomarker in a tissue or a fluid collected from a subject prior to administering endoxifen. In some embodiments, a level of a biomarker in a tissue or a fluid collected from a subject following treatment with endoxifen may be compared to an average or expected value for a level of the biomarker in a similar tissue or fluid from a normal subject (e.g., a non-diseased individual). In some embodiments, a level of a biomarker in a tissue or a fluid collected from a subject prior to administering endoxifen may be compared to an average or expected value for a level of the biomarker in a similar tissue or fluid from a non-diseased individual. In some embodiments, the average or expected value for a level of the biomarker may be from a database of biomarker levels.

Administration of a sustained release composition of the present disclosure to a subject having a breast disorder such as breast cancer or increased breast density may experience less side effects such as vasomotor effects, for example, hot flashes, night sweats, headaches, dry mouth and the like as compared with anti-cancer drug such as tamoxifen or immediate release versions of endoxifen. Tamoxifen, while efficacious for breast cancer or breast density reduction, causes vasomotor symptoms with frequency that can be over 25 times per day, as often as every day, and as intense as mild, moderate or severe. As many 78% of subject taking tamoxifen endure hot flashes (Mortimer et al.). The number of events of hot flashes times the severity of each event (using a scale of 1 for mild, 2 for moderate, and 3 for severe) is used to derive a score for tolerance ("tolerance score"). For example, a woman with hot flash events on 2 days with 5 mild and 2 severe events would have a score of 1 times 5 plus 2 times 3 for a total of 11. Higher this number, lower the tolerance to the drug. As a result, while tamoxifen can prevent over 50% of breast cancer, less than 5% of the women who could benefit from tamoxifen or endoxifen actually take the drug due to low tolerance resulting in low compliance with the treatment regimen. This represents a huge unmet medical need for drugs with improved tolerance. For some time, SSRIs were administered to the women administered with tamoxifen to reduce the vasomotor symptoms, but the SSRI reduced the symptoms by merely depressing the formation of the active metabolite of tamoxifen, namely, endoxifen necessary to treatment and/or recurrence of breast cancer.

In an aspect, the present disclosure provides that as compared with subjects orally administered with tamoxifen, the Capsule, subjects orally administered with a sustained release (Z)-endoxifen composition of the present disclosure, such as a sustained release tablet, experience lower the frequency (for example, fewer days or fewer events) of vasomotor symptoms such as hot flashes, night sweats, cold sweats, sensation of feeling hot etc., over the period of drug dosing days. In another aspect, the present disclosure provides that the fewer subjects administered with such sustained release compositions experience vasomotor symptoms as compared to those administered with tamoxifen. In another aspect, the present disclosure provides that the vasomotor symptoms experienced by the subjects orally administered with sustained release compositions are of milder intensity than the that experienced by subjects administered with tamoxifen.

The present disclosure provides that the lower i.e., improved, tolerance scores for subjects taking sustained release compositions is observed as compared with the tolerance scores for those taking tamoxifen.

Based on the in vitro release profiles of the sustained release compositions disclosed herein and the pharmacokinetic profiles disclosed herein, subjects ingesting the sustained release tablets, for example, those in the form of enteric coated delayed release tablets, absorb the therapeutic agent (Z)-endoxifen, and polymorphs and slats thereof into their blood at a slow rate. Without wishing to be bound by any mechanism of action or any other theory, the present disclosure provides that improved tolerance score and/or reduction in vasomotor symptoms experienced by subjects ingesting sustained release compositions of the present disclosure (for example, in the form of sustained release tablets) is attributable to the novel sustained release compositions and the desirable pharmacokinetic profiles of the enteric coating delayed release tablets.

Provided herein are methods of treating a subject having a disorder by orally administering a sustained release composition of the present disclosure, wherein the composition is capable of achieving one or more pharmacokinetic parameter disclosed in Table 14-Table 17.

The present disclosure provides that the subjects orally administered a sustained release composition of the present disclosure experience vasomotor effects (such as hot flashes, night sweats, or a sensation of feeling hot) at a frequency of less than 25%, less than 20%, less than 15% less than 10%, and less than 5% of drug-dosing days. In certain embodiments, subjects orally administered a sustained release composition of the present disclosure experience vasomotor effects at a frequency of less than 25% of drug dosing days. In at least one embodiment, subjects orally administered a sustained release composition of the present disclosure experience vasomotor effects at a frequency of less than 5% of drug dosing days. Accordingly, provided herein are methods of treating a subject having a disorder by orally administering a sustained release composition of the present disclosure, wherein the subject upon ingesting the sustained release composition experiences vasomotor effects (such as hot flashes, night sweats, or a sensation of feeling hot) at a frequency of less than 25% of drug dosing days. For example, if the subject has been administered a sustained release composition of the present disclosure for 100 days once daily, then the subject will experience a vasomotor symptom (for example, hot flashes) on 25 days of the days the subject ingested the composition.

The percentage of subjects administered or ingesting sustained release (Z)-endoxifen tablet experiencing vasomotor symptoms (hot flashes, sensation of feeding hot, and night sweats, etc.), (about 25%) is also lower compared with reported percentage of subjects administered with tamoxifen experiencing hot flashes (about 78%) It will be easily understood by one of skill in the art that improved tolerance of sustained release compositions (such as the sustained release (Z)-endoxifen tablets of the present disclosure) due to reduced or fewer vasomotor symptoms advantageously promotes greater compliance with the treatment regimen in subject having a disorder, such as a breast disorder.

Administration of a sustained release composition of the present disclosure to a subject at risk of having breast cancer or breast cancer recurrence may prevent the development or recurrence of breast cancer, for example it might delay (or extend) the time to recurrence. Thus, the sustained release compositions may be used for prophylaxis and for treatment. Current choice for therapeutics for such breast cancer disorders remains tamoxifen, despite serious adverse effects, poor patient compliance and resistance to the drug due to low plasma endoxifen levels seen subjects. Such subjects may have low endoxifen levels upon dosing with tamoxifen for any number of reasons, such as having CYP gene mutations, for example, in CYP2D6, CYP3A4, or CYP2C9, making them unable to metabolize tamoxifen to its active metabolite, endoxifen, or low or dysfunctional estrogen receptor preventing (or decreasing) sufficient tamoxifen uptake, for other reasons yet to be identified. Reported therapeutic levels of plasma tamoxifen in subjects dosed with 20 mg of oral tamoxifen is ≥30 nM ((Lyon et al. Genet Med. 2012 December; 14(12):990-1000). Notwithstanding the mechanism underlying the low plasma endoxifen in a subject, the sustained release compositions of the present disclosure are useful for any condition wherein a subject has low endoxifen or the subject has or is at a risk of having hormone dependent disorder. Therefore, the compositions of the present disclosure can be particularly important in the treatment of tamoxifen-resistant, hormone dependent disorders including hormone dependent breast disorders or hormone dependent reproductive tract disorders.

Provided herein in certain embodiments are patient populations for whom the pharmaceutical compositions are particularly useful. The sustained release compositions of the present disclosure are also particularly important in the treatment of tamoxifen-refractory subjects with hormone dependent disorders, including hormone dependent breast disorders and hormone dependent reproductive tract disorders. Accordingly, in some embodiments, the sustained release compositions disclosed herein are useful for the treatment of tamoxifen refractory or tamoxifen resistant subjects having or at risk of having hormone dependent disorders. In some embodiments, sustained release compositions comprising an endoxifen salt, such as (Z)-endoxifen gluconate, (Z)-endoxifen citrate or (Z)-endoxifen hydrochloride administered to such subject at the doses disclosed herein, will be advantageous. In some embodiments, the sustained release compositions are administered orally to the subjects.

Further, Donneyong et al. have shown that drug interactions between tamoxifen and selective serotonin reuptake inhibitors (SSRI) drugs like fluoxetine (Prozac) and paroxetine (Paxil) exist and are detrimental to breast cancer subjects (Donneyong et al. BMJ 2016; 354:i5014). The SSRI drugs SSRI's are antidepressants that reduce or stop liver metabolism of tamoxifen to endoxifen in subjects on SSRI drugs. Thus, provided herein in certain embodiments are patient populations being treated or to be treated with SSRI drugs (drugs such as citalopram (Celexa), escitalopram (Lexapro), fluoxetine (Prozac), paroxetine (Paxil, Pexeva), sertraline (Zoloft), vilazodone (Viibryd) and the like) that would be benefitted by treatment with compositions of the present disclosure.

Sustained release compositions disclosed herein are also suitable for the treatment of subjects having or at risk of having disorders such as mental or mood disorders such as depression, mania, hypomania, bipolar, and schizophrenic disorders, whether or not the subject is being treated with SSRI drugs. Such mental disorder may be with or without psychotic features. Studies have shown that female reproductive events and hormonal treatments may impact the course of bipolar disorders and schizophrenic disorders in women (Gogos A, Sbisa A M, Sun J, Gibbons A, Udawela M, Dean B. A Role for Estrogen in Schizophrenia: Clinical and Preclinical Findings. Int J Endocrinol. 2015; 2015: 615356. doi: 10.1155/2015/615356. Epub 2015 Sep. 27. PubMed PMID: 26491441; PubMed Central PMCID: PMC4600562). Further, studies have shown that the risk of postpartum mental disorders among primiparous mothers is increased for several months after childbirth (Munk-Olsen, T et al. JAMA. 2006 Dec. 6; 296(21):2582-9). In particular, childbirth is known to be associated with onset of affective episodes in women with bipolar disorder (Meinhard N. et al. Nord J Psychiatry. 2014 February; 68(2):81-7). Preliminary studies by Ahmad et al. and other suggest that tamoxifen and its metabolite endoxifen may have anti-manic activity. Accordingly, the present disclosure provides that a sustained release composition of the present disclosure may be administered orally to a subject having a mental or mood disorder such as such as depression, mania, hypomania, bipolar disorder, or schizophrenic disorders. Sustained release compositions disclosed herein administered orally maintain the subject's plasma endoxifen at steady state levels greater than 30 nM, for example, at levels ranging from 30 nM to 80 nM or at levels ranging from 30 nM to 300 nM. In some embodiments, the plasma steady state endoxifen levels are maintained at >40 nM.

Maintenance of such a plasma endoxifen at steady state levels greater than 30 nM is advantageous in that the likelihood of recurrence (relapse) of hormone dependent disorders, particularly breast cancer, at plasma endoxifen levels lower than 30 nM is reduced. It is particularly advantageous for subjects that are poor-metabolizers of tamoxifen (with plasma endoxifen levels lower than 16 nM), intermediate metabolizers of tamoxifen (with plasma endoxifen levels lower than 27 nM) to be dosed with a composition disclosed herein. It also advantageous for subjects having a mental or mood disorder (such as depression, mania, hypomania, bipolar, and schizophrenic disorders), and for subject being treated or to be treated with antidepressant drugs such as SSRI drugs such as citalopram (Celexa), escitalopram (Lexapro), fluoxetine (Prozac), paroxetine (Paxil, Pexeva), sertraline (Zoloft), vilazodone (Viibryd) and the like, for example, a subject having or likely to have a mental or mood disorder such as depression.

While ≥30 nM plasma endoxifen is desirable for treatment and prevention of hormone dependent disorders such as breast cancer in subjects having or at risk of having such disorders, under certain instances lower plasma (Z)-endoxifen levels in subjects may be desirable, for example for the treatment, prevention of development and progression of dense breasts (i.e., breast density). While dense breasts (i.e., increased or high breast density) is a common breast disorder and, in the U.S. alone, 40-50 percent of women ages 40-74 have dense breasts (which is in itself an independent risk factor for breast cancer in addition to masking the presence and preventing the detection of existing breast tumors and cancer), and while there are laws in in about 34 states in the U.S. requiring doctors to provide subjects a written letter notifying them of their high breast density status, there is no approved drug for the treatment or prevention (of development or progression) of breast density. In one aspect, the present disclosure provides that sustained release compositions of the present disclosure may be administered to subjects having dense breasts (BIRADs classes B-D) in an amount effective to reduce breast density. In another aspect, the sustained release compositions may be administered to prevent the development of high breast density or to prevent the progression of density to a higher class of breast density. In another aspect, the present disclosure provides that sustained release compositions of the present disclosure may be administered to subjects at risk of having breast density-masked breast cancer, thereby reducing breast density and unmasking breast cancer. Accordingly, provided herein is a method for reducing breast density in a subject, the method comprising the steps of (a) determining whether the subject has increased breast density by: (i) performing or having performed mammography on the subject's breasts; (ii) quantifying or having quantified dense tissue volume in subject's breasts to classify the subject's breast density into one of class A, class B, class C or class D, wherein if the subject has a class C or class D dense breast, the subject is determined to have increased breast density and at risk of having breast cancer; and (b). orally administering an amount of a sustained release composition of the present disclosure to the subject, thereby reducing breast density in the subject. In some embodiments, the administration of the sustained release composition unmasks the presence of breast cancer in the subject.

The amount administered by any amount effective to reduce breast density and/or to unmask breast cancer. In some embodiments, such amounts may be any amount that maintains subjects' plasma (Z)-endoxifen levels ranging from 2 nM to 300 nM for the treatment and prevention of increased breast density or progression of dense breasts to higher classes of breast density. In some embodiments, plasma levels of (Z)-endoxifen or a polymorph or a salt thereof in subjects orally administered a sustained release composition of the present disclosure may be maintained at ranges from 2 nM to 25 nM, from 10 nM to 30 nM, from 5 to 15 nM, or from 10 nM to 20 nM. In some embodiments, the plasma levels of (Z)-endoxifen or a polymorph or a salt thereof upon oral administration of sustained release compositions to subjects may be maintained at ranges from ≥30 nM to 300 nM. Orally administered composition to such subjects can reduce, prevent the development of or arrest the progression of breast density to higher class of breast density, unmask underlying breast cancer, and/or reduce the independent risk of developing breast cancer. In some embodiments, the sustained release composition administered to the subject is an enteric coated delayed release tablet capable of achieving one or more parameters of any one or more of Table 14, Table 15, Table 16, and Table 17.

In certain embodiments, subjects' response to the treatment may be monitored. For example, changes in breast density or tumor size (if any detectable) may be determined by performing or having performed mammography on the subjects' breasts and comparing the breast density and/or tumor size in the subjects' breasts before and after treatment. Accordingly, the methods of treatment further comprise the steps of performing or having performed mammography on the subject's breasts, and determine or having determined if the subject's breast density or breast tumor size show a decrease, an increase or no change in comparison with the subject's breast density or breast tumor size quantified prior to initiation of treatment with the sustained release compositions. An attending health professional may adjust the treatment regimen based on the changes observed. As a non-limiting example, the health professional may administer a higher dose of the sustained release composition if the density or tumor size has increased, or lower the dose if the subject's breast density or tumor size has decreased. In some embodiments, the health professional may initiate treatment to maintain a lower plasma level of (Z)-endoxifen in the subject. In another aspect, provided herein are methods of treating a subject having or at risk of having a disorder that is susceptible to (Z)-endoxifen, wherein the subject experiences vasomotor symptoms at a frequency of ≥50% of subject's drug dosing days upon being administered with tamoxifen. Such subjects may benefit from oral administration of a sustained release composition of the present disclosure, for example by experiencing reduced frequency of vasomotor symptoms at less than 50% of the subject's drug dosing days. For example, if a subject is dosed once daily for 14 days with a sustained release composition, the subject may experience vasomotor symptoms on fewer than 7 days (i.e., on 6 days or fewer) the subject is dosed with the drug. In some embodiments, the frequency of vasomotor symptoms experienced by the subjects ingesting a sustained release composition of the present disclosure may be reduced to less than 25% of the subject's drug dosing days. Accordingly, provided herein is the method of treating a subject having or at risk of having a disease susceptible to (Z)-endoxifen, wherein the subject experiences vasomotor symptoms at a frequency of greater than 50% of subject's drug dosing days upon ingesting tamoxifen, comprising administering a sustained release composition of the present disclosure thereby reducing the frequency of subject experiencing vasomotor symptoms to less than 50% of the subject's drug dosing days. In some embodiments, the subjects ingesting a sustained release composition of the present disclosure may experience vasomotor symptoms at a frequency of less than 25% of the drug dosing days. In some embodiments, the sustained release compositions of the present disclosure ingested by the subject is capable of achieving one or more parameters of any one or more of Table 14, Table 15, Table 16, and Table 17. In some embodiments, the subject's individual pharmacokinetic parameters for the (Z)-endoxifen or a polymorph or a salt thereof released from the sustained release composition may be monitored to determine one or more of the pharmacokinetic parameters such the rate of absorption, $T_{max}$, bioavailability of the therapeutic agent (Z)-endoxifen or a polymorph or a salt thereof from the sustained release composition in the subject. An attending health professional may prescribe a sustained release composition having a drug release profile that is tailored to the subject by determining the pharmacokinetic parameters of the drug in the subject and using rate of absorption, bioavailability, $T_{max}$ of the drug to determine the optimum sustained release composition suitable for administering to the subject.

In another aspect, provided herein are methods of treating a subject having or at risk of having a breast disorder, the method comprising the steps of (a) orally administering to a subject a sustained release composition of the present disclosure; (b) obtaining or having obtained a biological sample such as whole blood, plasma, and/or serum from the subject; (c) measuring or having measured (Z)-endoxifen in the subject's whole blood, plasma, and/or serum over a period of time, for example, at least 6 hr, at least 12 hr, at least 24 hr, at least 48 hr, at least 72 hr, at least 120 hours, at least 7 days, or at least 14 days; and (d) if the subject experiences vasomotor symptoms at a frequency of greater than 50% of dosing days, then orally administering a different sustained release composition of the present disclosure to the subject, wherein the sustained release composition is capable of achieving one or more parameters of any one or more of Table 14, Table 15, Table 16, and Table 17.

Whether a subject is tamoxifen-refractory may be determined by dosing a subject with an initial dosage of tamoxifen and determining the subject's plasma endoxifen steady state level. Plasma endoxifen steady state levels in a subject dosed with tamoxifen serves as a biomarker for the tamoxifen-refractory subjects. The plasma endoxifen levels (acute and/or steady state) may be determined by obtaining from the subject a test sample, which may be blood sample, collected from the subject after dosing the subject with tamoxifen. Plasma or serum may be obtained from blood samples for testing the biomarker endoxifen levels. The initial dosage may comprise administering tamoxifen daily for at least 1 day, 2 days, 3 days, 15 days, 1 week, 2 weeks, 4 weeks, 1 month, 2 months, 3 months, 4 months, 5 months, or 6 months. The subject may also be administered with a first composition comprising tamoxifen daily for at least 1 day, 2 days, 3 days, 15 days, 1 week, 2 weeks, 4 weeks, 1 month, 2 months, 3 months, 4 months, 5 months, 6 months, 1 year, 2 years, 3 years, 4 years, 5 years or 10 years.

A subject's plasma endoxifen steady state level may be determined by measuring endoxifen in a test sample. The subject's plasma endoxifen steady state levels are compared to a reference plasma endoxifen level. For the purposes of the present disclosure, the reference plasma level is 30 nM. If the subject's plasma endoxifen level is determined to be lower than 30 nM, then the subject is defined as tamoxifen-refractory. Such a tamoxifen-refractory subject who has or who may be at risk of having a hormone dependent disorder is treated by administering to the subject a sustained release composition comprising (Z)-endoxifen or a polymorph or a salt thereof disclosed herein. In some embodiments, the sustained release composition administered orally to such a subject comprises (Z)-endoxifen free base. In some embodiments, the sustained release composition administered orally to such a subject comprises a polymorphic form, such as Form I, Form II or Form III of endoxifen. In other embodiments, the sustained release composition administered orally to such a subject comprises endoxifen gluconate selected from the group consisting of (Z)-endoxifen D-gluconate, (Z)-endoxifen L-gluconate, (E)-endoxifen D-gluconate, (E)-endoxifen L-gluconate, or a combination thereof. In other embodiments, the sustained release composition comprising (Z)-endoxifen salt is (Z)-endoxifen hydrochloride or (Z)-endoxifen citrate. The present disclosure also contemplates that a subject's plasma endoxifen levels are determined or monitored periodically or as necessary. If required, a subject who has been administered an initial dosage of tamoxifen may have his or her plasma endoxifen steady state levels adjusted by administering orally a sustained release composition comprising (Z)-endoxifen, or a polymorph or a salt thereof on an ongoing basis based on the test results.

In some embodiments, the subject's tamoxifen-refractory status may be determined by determining the subject's tamoxifen-metabolites profile which is compared with a reference tamoxifen-metabolite profile as seen in control or normal subjects. Subjects with low plasma endoxifen levels in subject's tamoxifen-metabolite profile as compared to the reference tamoxifen-metabolite profile are administered a sustained release composition comprising (Z)-endoxifen or a polymorph or a salt thereof. Such compositions may comprise synthetically prepared endoxifen.

The plasma endoxifen may be measured by any of method known in the art. The levels of plasma endoxifen in test sample may be determined based on subject's genes, DNA, RNA, protein, tamoxifen-metabolite profile or a combination thereof. The tamoxifen-metabolites profile can include at least tamoxifen, 4-OHT, N-desmethyltamoxifen, and/or endoxifen. In some embodiments, the level of plasma endoxifen and/or tamoxifen-metabolite profile in the test sample is measured by High Performance Liquid Chromatography (HPLC), High Performance Liquid Chromatography Mass spectrometry (HPLC-MS), Gas Chromatography Mass Spectrometry (GC-MS), Liquid Chromatography Mass spectrometry (LC-MS), Liquid Chromatography Tandem Mass spectrometry (LC-MS/MS), immunohistochemistry (IHC), polymerase chain reaction (PCR), quantitative PCR (qPCR), and the like. In some embodiments, the tamoxifen-metabolites profile is predicted based on the subject's genetic composition. In some embodiments, the subject's CYP genotype includes, without limitation, analysis of CYP2D6, CYP3A4, CYP2C9 genes. In some embodiments, subject's estrogen receptor levels may be analyzed. In other embodiments, the determination of plasma endoxifen may be performed by a third party laboratory.

Accordingly, provided herein are methods of maintaining in a subject in need thereof a plasma endoxifen a level greater than 30 nM by administering orally to the subject a sustained release composition comprising (Z)-endoxifen or a polymorph or a salt thereof. In some embodiments, the subject's plasma endoxifen level is maintained at a steady state level greater than 30 nM. In some embodiments, the subject's plasma endoxifen levels are maintained at a steady state level ranging from 30 nM to 5000 nM (for example, from 40 nM to 4000 nM, from 50 nM to 3000 nM, from 60 nM to 2000 nM, from 30 nM to 300 nM, or from 30 nm to 80 nM). In some embodiments, the subject's plasma endoxifen levels are maintained at a steady state level >40 nM.

In another aspect, the subjects may have their test samples tested for their biomarker profile that may be indicative or monitoring a hormone dependent disorder. Such biomarkers are known in the art and include, by way of non-limiting examples, biomarkers such as CYP2D6, BRCA-1, BRCA-2, ER, PR, Her2, uPA, PAI, Tf, p53, Ki-67, cytokeratins, cancer tumor antigens, and other biomarkers measured by Mammaprint, OncotypeDx, PAM50, EndoxPredict, MammoStrat, and other diagnostic and predictive tests. A subject with biomarker profile indicating that the subject has or is at risk of having a hormone dependent disorder can be administered orally a sustained release composition disclosed herein. In one aspect, the present disclosure provides a method of treating a subject having or at risk of having a hormone dependent disorder, comprising determining a subject's tamoxifen-refractory or tamoxifen-resistant status and administering to the subject a sustained release composition described herein.

A level of a biomarker may be measured in a subject. For example, a level of one or more of Ki-67, estrogen receptor, progesterone receptor, proliferating cell nuclear antigen, phosphor-histone H3, p16, p12, beta-galactosidase, terminal deoxynucleotidyl transferase dUTP nick end labeling, an RNA sequence, or a combination thereof may be measured in a subject. In some embodiments, a level may be measured before administering a composition of the present disclosure. In some embodiments, a level may be measured after administering a composition of the present disclosure. A level of a biomarker following administration of a composition may be compared to a level of the biomarker prior to administration of the composition. The level of the biomarker may be measured by any method known in the art. For example, a level of a biomarker may be measured by immunohistochemistry, fluorescence in situ hybridization (FISH), Western plot, quantitative PCR, quantitative PCR with reverse transcription, mass spectrometry, or chromatography.

In some aspects, provided herein are methods of treating a tamoxifen-refractory or tamoxifen-resistant subject, the method comprising oral administration to the subject a sustained release composition comprising (Z)-endoxifen, or a polymorph or a salt thereof.

In some embodiments disclosed herein are methods of treating a tamoxifen-refractory subject having or at risk for having a hormone dependent disorder, the method comprising administration to the subject an sustained release composition comprising (Z)-endoxifen, or a polymorph or a salt thereof, wherein the subject has plasma endoxifen level of less than 30 nM, less than 25 nM, less than 20 nM, less than 15 nM, less than 10 nM, less than 5 nM or less than 1 nM. In certain embodiments, the sustained release composition comprising (Z)-endoxifen salt is (Z)-endoxifen gluconate, (Z)-endoxifen hydrochloride, or (Z)-endoxifen citrate. In other embodiments, a sustained release solid dosage form comprising at least 90% (Z)-endoxifen or a salt thereof is orally administered. In other embodiments, a sustained release solid dosage form comprising at least 90% of polymorph Form I, Form II, or Form III of endoxifen is orally administered.

Also provided herein are methods of treating a tamoxifen-refractory or a tamoxifen-resistant subject, the method comprising: (a) determining or having determined plasma endoxifen level in a test sample obtained from the subject; (b) comparing or having compared or having determined the level of plasma endoxifen in the test sample with a reference plasma endoxifen level; (c) determining or having determined a reduced level of plasma endoxifen in the test sample as compared to the reference plasma endoxifen level; and (d) administering a sustained release composition comprising (Z)-endoxifen or a polymorph or a salt thereof to the subject. The oral administration of a sustained release composition comprising (Z)-endoxifen or a polymorph or a salt thereof maintains the levels of plasma endoxifen in the subject at steady state levels greater than 30 nM. In some embodiments, the levels of plasma endoxifen in the subject are maintained at steady state levels ranging from 30 nM to about 300 nM. Provided herein are methods of treating a subject having or at risk of having a hormone dependent disorder, the method comprising: (a) administering to the subject a first composition comprising tamoxifen; (b) determining or having determined the level of plasma endoxifen in a test sample obtained from the subject; (c) determining or having determined reduced level of plasma endoxifen in test sample as compared to a reference level of plasma endoxifen; and (d) orally administering a sustained release composition disclosed herein to the subject. The subject may be administered with the first composition comprising tamoxifen daily for at least 1 day, 2 days, 3 days, 15 days, 1 week, 2 weeks, 4 weeks, 1 month, 2 months, 3 months, 4 months, 5 months, 6 months, 1 year, 2 years, 3 years, 4 years, 5 years or 10 years. In some embodiments, oral administration of the sustained release composition comprising (Z)-endoxifen or a polymorph or a salt thereof maintains the subject's plasma endoxifen at levels greater than 30 nM. In other embodiments, oral administration of the sustained release composition comprising (Z)-endoxifen or a polymorph or a salt thereof maintains the subject's plasma endoxifen at levels ranging from 30 nM to 5000 nM (e.g., from 40 nM to 4000 nM, from 50 nM to 3000 nM, from 60 nM to 2000 nM, from 30 nM to 300 nM, or from 30 nM to 80 nM). In some embodiments, the subject is orally administered sustained release composition comprising (Z)-endoxifen D-gluconate, (Z)-endoxifen L-gluconate, (E)-endoxifen D-gluconate, (E)-endoxifen L-gluconate, or a combination thereof. In other embodiments, sustained release composition comprising (Z)-endoxifen salt is (Z)-endoxifen hydrochloride or (Z)-endoxifen citrate. In some embodiments, the subject is orally administered a sustained release composition comprising polymorph Form I, Form II or Form III of endoxifen disclosed herein.

Provided herein are methods of treating a subject having or at risk of having a hormone dependent disorder, a mood disorder or any disorder susceptible to (Z)-endoxifen or a polymorph or a salt thereof, the method comprising: (a) dosing the subject with a first composition comprising tamoxifen; (b) determining or having determined the subject's tamoxifen-metabolites profile in a test sample obtained from the subject; (c) determining a reduced level of subject's plasma endoxifen based on the subject's tamoxifen-metabolites profile to compared to a level of reference plasma endoxifen in a reference tamoxifen-metabolites profile; and (d) administering orally a sustained release composition comprising (Z)-endoxifen or a polymorph or a salt thereof to the subject. In certain embodiments, the sustained release composition comprising (Z)-endoxifen is (Z)-endoxifen gluconate, (Z)-endoxifen hydrochloride, or (Z)-endoxifen citrate. In some embodiments, the sustained release composition comprises polymorph Form I, Form II, or Form III of endoxifen.

Provided herein are methods for adjusting plasma endoxifen levels in a subject being treated for hormone dependent disorder who has one or more CYP2D6 or CYP3A4 mutations or has been previously administered with initial dosage of tamoxifen, and who has a plasma endoxifen level less than reference plasma endoxifen level, the method comprising: (a) measuring the subject's plasma endoxifen level after initial dosage of tamoxifen; (b) comparing the subject's plasma endoxifen levels to the reference plasma endoxifen level; (c) orally administering a sustained release composition comprising (Z)-endoxifen or a polymorph or a salt thereof to the subject to maintain the subject's plasma endoxifen level at levels greater than 30 nM. In some embodiments, the oral administration of the sustained release composition comprising (Z)-endoxifen or a polymorph or a salt thereof maintains the subject's plasma endoxifen at levels ranging from 30 nM to 5000 nM (e.g., from 40 nM to 4000 nM, from 50 nM to 3000 nM, from 60 nM to 2000 nM, from 30 nM to 300 nM, or from 30 nM to 80 nM). In some embodiments, the subject's plasma endoxifen level is maintained at a steady state level. The subject may be administered with initial dosage of tamoxifen daily for at least 1 day, 2 days, 3 days, 15 days, 1 week, 2 weeks, 4 weeks, 1 month, 2 months, 3 months, 4 months, 5 months, or 6 months.

In an aspect, the present disclosure contemplates a method of treating a subject having or at risk of having a hormone dependent disorder, the method comprising resection of breast tissue of the subject or administering radiotherapy to the subject and orally administering a sustained release composition comprising (Z)-endoxifen or a polymorph or a salt thereof disclosed herein. In another aspect, the present disclosure contemplates a method of treating a subject having or at risk of having a hormone dependent disorder, the method comprising orally administering a sustained release composition disclosed herein prior to resection of breast tissue of the subject or administering radiotherapy to the subject.

Dosage to be administered to a subject will be usually in a unit dosage form. Examples of ranges for endoxifen in each dosage unit form are from 0.01 mg to 200 mg. Dosage shall generally be an effective amount and equivalent, on a molar basis, of the pharmacologically active (Z)-endoxifen free form produced by a dosage formulation upon metabolic release of the active free drug to achieve its desired pharmacological and physiological effects. In some embodiments, the sustained release compositions comprising (Z)-endoxifen or a polymorph or a salt thereof are orally administered to the subject at a dose of 0.01 mg to 200.0 mg. In other embodiments, the sustained release compositions comprising (Z)-endoxifen or a polymorph or a salt thereof are orally administered to the subject at a dose of 1 mg to 200.0 mg. In some embodiments, the sustained release compositions comprising (Z)-endoxifen or a polymorph or a salt thereof are orally administered to the subject at a dose of 0.01 mg, 0.05 mg, 0.1 mg, 0.25 mg, 0.5 mg, 0.75 mg, 1.0 mg, 1.5 mg, 2 mg, 3 mg, 4 mg, 5 mg, 6 mg, 8 mg, 10 mg, 20 mg, 40 mg, 50 mg, 100 mg or 200 mg per unit dose. In certain embodiments, the sustained release compositions comprising at least 90% (Z)-endoxifen (w/w) of endoxifen are orally administered at a dose of 0.5 mg 1 mg, 2 mg, 3 mg, 4 mg, 5 mg, 6 mg, 8 mg, 10 mg, 20 mg, 40 mg, 50, 100 mg or 200 mg per unit dose. In some embodiments, the sustained release compositions comprising endoxifen gluconate are orally administered at a dose ranging from 0.01 to 20 mg. In some embodiments, a sustained release composition comprising (Z)-endoxifen D-gluconate is orally administered at 0.5 mg, 1 mg, 2 mg 4 mg, 6 mg, 8 mg, 10 mg, 20 mg, 40 mg, 50 mg, 100 mg, and 200 mg per unit dose. In some embodiments, a sustained release composition comprising 1 mg of (Z)-endoxifen D-gluconate is orally administered. In other embodiments, a sustained release composition comprising 1 mg of (Z)-endoxifen L-gluconate is orally administered. In yet other embodiments, a sustained release composition comprising 2 mg of (Z)-endoxifen D-gluconate and (E)-endoxifen D-gluconate is orally administered. In certain embodiments, a sustained release composition comprising at least 90% of a polymorph, such as polymorph Form I, Form II or Form III, of endoxifen (w/w) is orally administered at a dose of 0.5 mg, 1 mg, 2 mg, 3 mg, 4 mg, 5 mg, 6 mg, 8 mg, 10 mg, 20 mg, 40 mg, 50 mg, 100 mg or 200 mg per unit dose. In some embodiments, a sustained release composition comprising a polymorphic form, such as Form I, Form II or Form III, of endoxifen is orally administered at a dose ranging from 0.01 to 20 mg.

A composition comprising endoxifen may be administered to a subject at a dose of from 0.5 mg to 2 mg, from 1 mg to 3 mg, from 2 mg to 4 mg, from 3 mg to 5 mg, from 4 mg to 5 mg, from 5 mg to 8 mg, from 5 mg to 10 mg, from 8 mg to 12 mg, from 10 mg to 14 mg, from 12 mg to 15 mg, from 14 mg to 16 mg, from 15 mg to 18 mg, from 16 mg to 20 mg, from 18 mg to 25 mg, from 20 mg to 30 mg, from 25 mg to 40 mg, from 30 mg to 50 mg, from 40 mg to 60 mg, from 50 mg to 70 mg, from 60 mg to 80 mg, from 70 mg to 90 mg, from 80 mg to 100 mg, from 90 mg to 125 mg, from 100 mg to 150 mg, from 125 mg to 175 mg, or from 150 mg to 200 mg of endoxifen per day. A composition comprising endoxifen may be administered to a subject for from 1 to 14, from 7 to 14, from 7 to 21, from 7 to 28, from 7 to 35, from 7 to 40, from 7 to 42, from 7 to 49, from 7 to 50, from 14 to 21, from 14 to 28, from 14 to 35, from 14 to 40, from 14 to 42, from 14 to 49, from 14 to 50, from 21 to 28, from 21 to 35, from 21 to 40, from 21 to 42, from 21 to 49, from 21 to 50, from 40 to 50, from 40 to 60, from 40 to 70, from 40 to 80, or from 40 to 90, from 40 to 100 days. In some embodiments, a composition comprising endoxifen may be administered to a subject once, twice, or three times per day. In some embodiments, a composition comprising endoxifen may be administered to a subject every 1, 2, 3, 4, 5, 6, 7, 8, 9, or 10 days.

Breast cancer growth rate studies have shown, using mammographic screening of subjects with breast cancer, that the breast cancer growth rate in the 25th percentiles of women ages 50 to 59 indicate an unmet need for exposure of the subject to quick acting therapeutics (Weeden-Fekjaer et al. Breast Cancer Research200810:R41). Increased bioavailability and absorption in a sustained manner of the anti-cancer therapeutics such as (Z)-endoxifen that can further reduce the cancer growth rate, tumor volume or size, disease burden etc., is highly desirable.

In one aspect, the present disclosure provides a method of treating a subject having or at risk of having a hormone dependent disorder, the method comprising orally administering a sustained release composition comprising (Z)-endoxifen or a polymorph or a salt thereof, wherein the sustained release composition comprising (Z)-endoxifen or a polymorph or a salt thereof shows a sustained release of the drug (Z)-endoxifen or a polymorph or a salt thereof from the sustained release composition over a period of about 4 hours to about 24 hours or more in a subject. In some embodiments, the sustained release compositions of the present disclosure release (Z)-endoxifen or a polymorph or a salt thereof in a sustained manner over a period of about 2 hours to about 72 hours. In some embodiments, the sustained release compositions of the present disclosure release (Z)-endoxifen or a polymorph or a salt thereof in a sustained manner over a period of at least 2 hours, at least 3 hours, at least 4 hours, at least 5 hours, at least 6 hours, at least 7 hours, at least 8 hours, at least 9 hours, at least 10 hours, at least 12 hours, at least 14 hours, at least 16 hours, at least 18 hours at least 24, at least 48 hours, and at least 72 hours. The present disclosure provides that in these methods, the (Z)-endoxifen or a polymorph or a salt thereof are released in the intestines about 2 hours post dose (e.g., ingestion by the subjects)

In one aspect, the present disclosure provides a method of treating a subject having or at risk of having a hormone dependent disorder, the method comprising orally administering a sustained release composition comprising (Z)-endoxifen or a polymorph or a salt thereof, wherein the sustained release composition comprising (Z)-endoxifen or a polymorph or a salt thereof shows a percentage dissolution of about 0% to 30% at 3 hours, about 30% to about 50% at 12 hours, and about 65% to about 85% after 12 hours in a dissolution test using a test sample (such as subject's blood, serum, plasma and the like) from the subject according to the 75 rpm USP II Paddle Method using pH 1.2 at 37° C. for 2 hours in simulated gastric fluid and pH 6.8 at 37° C. for 24 hours in simulated intestinal fluid. In some embodiments, the sustained release compositions show in a dissolution test of conducted according to USP II Paddle Method, a percentage dissolution:

a. ranging from about 0% to about 35% at 3 hours, from about 35% to about 55% at 12 hours, and from about 65% to about 85% at 24 hours;

b. about 0% to about 30% at 3 hours, about 40% to about 50% at 12 hours and about 70% to about 80% at 24 hours;

c. of NMT about 30% at 3 hours, NMT about 50% at 12 hours and NLT about 80% at 24 hours;

d. of NMT about 5% at 2 hours, NMT about 10% at 3 hours, NLT about 30% at 6 hours, NLT 50% at 9 hours, and NLT about 80% at 14 hours;

e. of NMT about 5% at 2 hours, NLT about 60% at 3 hours, NLT about 90% at 6 hours and about 100% at 12 hours; or f. of at least 10%, at least 20%, at least 30% or at least 40% after 24 hours.

In some embodiments, the sustained release composition comprises a therapeutic agent, wherein: the therapeutic agent is (Z)-endoxifen free base, a polymorph of (Z)-endoxifen, a salt of (Z)-endoxifen, or a combination thereof; and the therapeutic agent has at least one percentage dissolution parameters selected from: a percentage dissolution ranging from about 0% to about 35% at 3 hours; a percentage dissolution ranging from about 35% to about 55% at 12 hours; or a percentage dissolution ranging from about 65% to about 85% at 24 hours, wherein the percentage dissolution is measured by the 75 rpm USP paddle method in simulated gastric fluid at pH 1.2 and at 37° C. from hours 0-2, and in simulated intestinal fluid at pH 6.8 and at 37° C. after hour 2. In some embodiments, the composition comprises at least two of the percentage dissolution parameters. In some embodiments, the composition comprises all three of the percentage dissolution parameters.

In some embodiments, the sustained release compositions in the form of sustained release tablets or an enteric coated delayed release tablets show in a dissolution test of conducted according to USP II Paddle Method, a percentage dissolution:

a. ranging from about 0% to about 35% at 3 hours, from about 35% to about 55% at 12 hours, and from about 65% to about 85% at 24 hours;

b. about 0% to about 30% at 3 hours, about 40% to about 50% at 12 hours and about 70% to about 80% at 24 hours;

c. of NMT 30% at 3 hours, NMT about 50% at 12 hours and NLT about 80% at 24 hours;
d. of NMT about 5% at 2 hours, NMT about 10% at 3 hours, NLT about 30% at 6 hours, NLT about 50% at 9 hours, and NLT about 80% at 14 hours;
e. of NMT about 5% at 2 hours, NLT about 60% at 3 hours, NLT about 90% at 6 hours and about 100% at 12 hours; or
f. of at least 10%, at least 20%, at least 30% or at least 40% after 24 hours.

A healthcare professional, such as an attending physician, may adjust the dosing regimen based on the pharmacokinetic profile of the sustained release composition in the subject.

In still another aspect, the present disclosure provides a method of treating a subject in need thereof comprising administering orally a sustained release composition comprising (Z)-endoxifen or a polymorph or a salt thereof once per day, twice per day, every 2 days, every 3 days, every 4 days, every 5 days, every 6 days, or every 7 days, twice a week, or weekly.

In one aspect, the sustained release compositions of the present disclosure can be used alone or in a combination therapy. For example, sustained compositions disclosed herein may be used in combination with one or more "additional therapeutic agents" as part of primary therapy, neoadjuvant therapy, or an adjuvant therapy. For example, a composition comprising endoxifen may be administered as a neoadjuvant therapy to reduce tumor cell proliferation. It is an aspect of the present disclosure that the sustained release compositions of the present disclosure can be used in combination with other therapies such as surgery and radiation as neoadjuvant or adjuvant therapy. In some embodiments, a composition of the present disclosure may be administered as a neoadjuvant therapy to reduce tumor size or tumor cell activity prior to performing surgery. In some embodiments, a treatment method comprising other therapies may be modified based on an outcome of the neoadjuvant therapy (e.g., comprising endoxifen). In some embodiments, an adjuvant therapy may be reduced or eliminated following a favorable outcome from treatment with a composition of the present disclosure (e.g., comprising endoxifen). For example, a patient awaiting surgery for cancer (e.g., breast cancer) may no longer require the surgery following treatment with a composition comprising endoxifen. In some embodiments, a composition (e.g., a composition comprising endoxifen) may be used as an adjunct to mammography. For example, a patient may be treated with an orally administered endoxifen composition following or concurrent with a mammogram identifying a breast disorder or a potential breast disorder (e.g., a BIRADS 3, BIRADS 4, BIRADS 5, or BIRADS 6 classification, or a BIRADS B, BIRADS C, or BIRADS D classification). In some embodiments, a mammogram may be performed subsequent to or concurrent with endoxifen treatment to monitor a state of a breast disorder or a potential breast disorder.

Combinations of the sustained release compositions may act to improve the efficacy of the additional therapeutic agents, and therefore can be used to improve standard cancer therapies. For example, when a subject has prostate cancer and is on bicalutamide or enzalutamide therapy for the treatment of prostate cancer, the subject is likely to develop gynecomastia a result of the therapy. The compositions disclosed herein can be administered as a combination therapy to the subject having prostate cancer in order to prevent and/or treat gynecomastia. As another example, a subject with ER+/Her2+ positive breast cancer would be on a combination therapy with trastuzumab or other oncology drugs such as anti-neoplastics or immunotherapy, and a sustained release composition disclosed herein can be used to treat such a subject with ER+/Her2+ positive breast cancer. Accordingly, in some embodiments, the compositions further comprise as additional therapeutic agents bicalutamide, enzalutamide or anticancer drugs such as trastuzumab, atezolizumab (Tecentriq), alpelisib (Piqray), olaparib (Lynparza), talazoparib (Talzenna), ribociclib (Kisqali), neratinib (Nerlynx), antineoplastics such as capecitabine (Xeloda), carboplatin (Paraplatin), cisplatin (Platinol), cyclophosphamide (Neosar), docetaxel (Docefrez, Taxotere), doxorubicin (Adriamycin), pegylated liposomal doxorubicin (Doxil), epirubicin (Ellence), fluorouracil (5-FU, Adrucil), gemcitabine (Gemzar), methotrexate (multiple brand names), paclitaxel (Taxol), protein-bound paclitaxel (nab-paclitaxel or Abraxane), vinorelbine (Navelbine), eribulin (Halaven), ixabepilone (Ixempra), immune checkpoint inhibitors (such as inhibitors of PD1, PD-L1 and CTLA4), and ATP-cassette binding protein inhibitors.

In another aspect, a sustained release composition disclosed herein may comprise therapeutic agents that increase bioavailability of (Z)-endoxifen in a subject. P-glycoprotein (P-gp, ABCB1) is a highly efficient drug efflux pump expressed in brain, liver, and small intestine, but also in cancer cells, that affects pharmacokinetics and confers therapy resistance for many anticancer drugs. Accordingly, in some embodiments, the compositions further comprise inhibitors of ATP-binding cassette (ABC family) transporters, such as inhibitors of breast cancer resistance protein (BCRP protein) and P-gp. Several inhibitors of BCRP protein and P-Gp are known in the art. For example, inhibitors of BCRP protein include cyclosporine, omeprazole, pantoprazole, saquinavir, and tacrolimus.

Non-limiting examples of P-gp inhibitors include first generation inhibitors such as Verapamil, cyclosporin A, reserpine, quinidine, yohimbine, tamoxifen and toremifene, second generation inhibitors such as Dexverapamil, dexniguldipine, valspodar (PSC 833), and Dofequidar fumarate (MS-209), third generation P-gp inhibitors such as Cyclopropyldibenzosuberane zosuquidar (LY335979), laniquidar (R101933), mitotane (NSC-38721), biricodar (VX-710), elacridar (GF120918/GG918), ONT-093, tariquidar (XR9576), and HM30181 and anti-P-gp monoclonal antibodies such as MRK-16).

The present disclosure additionally provides for therapeutic kits containing one or more of the sustained release compositions disclosed herein for use in the treatment of a subject having or at risk of having a hormone dependent disorder. The kits of the present disclosure may include a sustained release composition disclosed herein, a sealed container for housing the composition, and instructions for use of the sustained release composition. In an aspect, the kits of the present disclosure can include a second or additional therapeutic agent. Such a second or additional therapeutic agent may be bicalutamide, enzalutamide or an anticancer drug such as trastuzumab, antineoplastics such as capecitabine (Xeloda), carboplatin (Paraplatin), cisplatin (Platinol), cyclophosphamide (Neosar), docetaxel (Docefrez, Taxotere), doxorubicin (Adriamycin), pegylated liposomal doxorubicin (Doxil), epirubicin (Ellence), fluorouracil (5-FU, Adrucil), gemcitabine (Gemzar), methotrexate (multiple brand names), paclitaxel (Taxol), protein-bound paclitaxel (Abraxane), vinorelbine (Navelbine), eribulin (Halaven), ixabepilone (Ixempra), immune checkpoint inhibitors (such as inhibitors of PD1, PD-L1 and CTLA4), and ATP-binding cassette (ABC transporter) inhibitors such as P-gp inhibitors.

In still another aspect, the present disclosure relates to a kit for treating a subject having or at risk of having an estrogen dependent disorder, in a subject in need thereof comprising: (a) a sustained release compositions disclosed herein; and (b) a sealed container for housing the sustained release composition; and c) instructions for use of the sustained release composition.

In still another aspect, the present disclosure relates to a kit for treating a subject having or at risk of having an estrogen dependent disorder, in a subject in need thereof comprising: (a) a sustained release compositions disclosed herein; and (b) a sealed container for housing the sustained release composition; and c) instructions for use of the sustained release composition, wherein the kit comprises a second or additional therapeutic agent selected from the group consisting of bicalutamide, enzalutamide and anticancer drugs such as trastuzumab, atezolizumab (Tecentriq), alpelisib (Piqray), olaparib (Lynparza), talazoparib (Talzenna), ribociclib (Kisqali), neratinib (Nerlynx), antineoplastics such as capecitabine (Xeloda), carboplatin (Paraplatin), cisplatin (Platinol), cyclophosphamide (Neosar), docetaxel (Docefrez, Taxotere), doxorubicin (Adriamycin), PEGylated liposomal doxorubicin (Doxil), epirubicin (Ellence), fluorouracil (5-FU, Adrucil), gemcitabine (Gemzar), methotrexate (multiple brand names), paclitaxel (Taxol), protein-bound paclitaxel (Abraxane), vinorelbine (Navelbine), eribulin (Halaven), ixabepilone (Ixempra), checkpoint inhibitors such as inhibitors of PD1, PD-L1, CTLA4, and ATP-cassette binding protein transport inhibitors.

In still another aspect, the present disclosure relates to a method of administering a composition prepared in accordance with any of the processes described herein to a subject in need thereof in accordance with instructions for use comprised in a kit comprising the composition.

Advantageous aspects of the sustained release compositions comprising a sustained release composition comprising (Z)-endoxifen or a salt or polymorph thereof with the desirable pharmacokinetic parameters as disclosed in the present disclosure will be obvious to one of skill in the art in that the sustained release compositions disclosed herein maintain therapeutic concentrations over prolonged periods, their use is likely to avoid the high blood concentrations as desired, reduce the side-effects such as vasomotor symptoms (e.g., hot flashes), and/or toxicity by slowing drug release and allowing slower and steady absorption over prolonged periods, avoiding or minimizing troughs in bloods levels between once daily doses, minimize drug accumulations generally observed with chronic dosing, minimize use of total drug, minimize local and systemic side effects, improve tolerability and the patient compliance, improve bioavailability of (Z)-endoxifen and treatment efficacy.

Numbered Embodiments

The following embodiments recite non-limiting permutations of combinations of features disclosed herein. Other permutations of combinations of features are also contemplated. In particular, each of these numbered embodiments is contemplated as depending from or relating to every previous or subsequent numbered embodiment, independent of their order as listed. 1. A sustained release composition comprising a therapeutic agent, wherein: the therapeutic agent is (Z)-endoxifen free base, a polymorph of (Z)-endoxifen, a salt of (Z)-endoxifen, or a combination thereof; and the therapeutic agent has at least two percentage dissolution parameters selected from: a percentage dissolution of no more than 35% at 3 hours; a percentage dissolution ranging from 35% to 55% at 12 hours; or a percentage dissolution ranging from 65% to 85% at 24 hours, as measured by the 75 rpm USP paddle method in simulated gastric fluid at pH 1.2 and at 37° C. from hours 0 to 2, and in simulated intestinal fluid at pH 6.8 and at 37° C. after hour 2. 2. The sustained release composition of embodiment 1, wherein the therapeutic agent has at least three of the percentage dissolution parameters. 3. The sustained release composition of any one of embodiments 1-2, comprising from 0.01 mg to 200 mg of the therapeutic agent. 4. The sustained release composition of any one of embodiments 1-3, comprising 0.5 mg, 1 mg, 2 mg, 3 mg, 4 mg, 5 mg, 6 mg, 8 mg, 10 mg, 20 mg, or 40 mg of the therapeutic agent. 5. The sustained release composition of any one of embodiments 1-4, wherein the therapeutic agent is (Z)-endoxifen free base. 6. The sustained release composition of any one of embodiments 1-5, wherein greater than 90% by weight, greater than 95% by weight, or greater than 99% by weight of the therapeutic agent is Form I of (Z)-endoxifen, Form II of (Z)-endoxifen, Form III of (Z)-endoxifen, or a combination thereof 7. The sustained release composition of any one of embodiments 1-6, further comprising at least one sustained release agent, at least one binder, and at least one lubricant. 8. A sustained release composition comprising: a therapeutic agent selected from the group consisting of a (Z)-endoxifen free base, a polymorph of (Z)-endoxifen, a salt of (Z)-endoxifen, and a combination thereof; at least one sustained release agent; at least one binder; and at least one lubricant. 9. The sustained release composition of any one of embodiments 1-8, wherein the sustained release composition comprises 0.5 mg, 1 mg, 2 mg, 4 mg, 5 mg, 6 mg, 10 mg, 20 mg or 40 mg of any of Form I of (Z)-endoxifen, Form II of (Z)-endoxifen, Form III of (Z)-endoxifen, or a combination thereof. 10. The sustained release composition of any one of embodiments 1-9, wherein the salt of (Z)-endoxifen is selected from the group consisting of an acetate, an arecoline, a benzathine, a benzoic, a besylate, a benzosulfonate, a bicarbonate, a bitartarate, a butylbromide, a citrate, a camysylate, a clemizole, a chloroprocaine, a choline, a diethylamine, a diethanolamine, an ethylenediamine, a formate, a fumarate, a glucolate, a gluconate, a glutamate, a glycollylarsanilate, a hexylresorcinate, a hydrabamine, a hydrobromide, a hydrochloride, a hydroxynapthanoate, an isethionate, a malate, a maleate, a mandelate, a meglumine, a mesylate, a methylbromide, a methylbromide, a methylnitrate, a methylsulfate, a methanesulfonate, a mucate, a napsylate, a nitric, a nitrate, an oxalate, a pamaoate a pantothenate, a perchloric, a phosphate, a diphosphate, a piperazine, a procaine, a polygalacuronate, a p-toluenesulfonate, a salicylate, a stearate, a succinate, a sulfate, a sulfonate, a sulfuric, a tannate, a tartarate, a teoclate, a triethiodide, a trifluoroacetate, an aluminum, a barium, a bismuth, a lithium, a magnesium, a potassium, a zinc, and any combination thereof 11. The sustained release composition of any one of embodiments 7-10, wherein the at least one sustained release agent has a viscosity ranging from 1000 mPa·s to 150,000 mPa·s. 12. The sustained release composition of any one of embodiments 7-11, wherein the at least one sustained release agent has a viscosity ranging from 1000 mPa·s to 10,000 mPa·s, from 10,000 mPa·s to 70,000 mPa·s, from 70,000 mPa·s to 150,000 mPa·s, or any combination thereof at 25° C. 13. The sustained release composition of any one of embodiments 7-12, comprising from 0.1% to 99% w/w, from 1% to 95% w/w, from 5% to 90% w/w, from 5% to 80% w/w, from 5% to 70% w/w, or from 5% to 60% w/w of the at least one sustained release agent. 14. The sustained release composition of any one of embodiments 7-13, wherein the at least one sustained release agent is hypromellose. 15. The sustained release composition of any one of embodiments 7-14, comprising from 1% to 99% w/w, from 5% to 95% w/w, from 10% to 90% w/w, from 15% to 85% w/w, from 20% to 80% w/w, or from 20% to 85% w/w of the at least one binder. 16. The sustained release composition of any one of embodiments 7-15, wherein the at least one binder is microcrystalline cellulose. 17. The sustained release composition of any one of embodiments 7-16, comprising from 0.01% to 5% w/w, from 0.2% to 2% w/w, or from 0.5% to 1.5% w/w of the at least one lubricant. 18. The sustained release composition of any one of embodiments 7-17, wherein the at least one lubricant is magnesium stearate. 19. The sustained release composition of any one of embodiments 1-18, wherein the sustained release composition is a sustained release tablet or an enteric coated delayed release tablet. 20. The sustained release composition of embodiment 19, wherein the sustained release tablet is coated with a coating solution comprising at least one delayed release agent, and wherein the sustained release tablet serves as a core tablet substantially enclosed in at least one layer of the coating solution, thereby forming a functional coating to provide the enteric coated delayed release tablet. 21. The sustained release composition of embodiment 19, wherein the sustained release tablet is coated with a coating solution comprising: at least one delayed release agent; at least one plasticizer; and at least one anti-tacking agent, wherein the sustained release tablet serves as a core tablet substantially enclosed in at least one layer of the coating solution, thereby forming a functional coating to provide the enteric coated delayed release tablet. 22. The sustained release composition of any one of embodiments 20-21, wherein the at least one delayed release agent is present in the at least one layer of the functional coating in an amount from 0.1% to 30% w/w, from 5% to 25% w/w, or from 8% to 14% w/w of the functional coating. 23. The sustained release composition of any one of embodiments 20-21, wherein the delayed release agent is present in the at least one layer of the functional coating in an amount from 0.1% to 30% w/w, from 5% to 25% w/w, or from 8% to 14% w/w of the core tablet weight. 24. The sustained release composition of any one of embodiments 20-23, wherein the at least one delayed release agent is a poly(meth)acrylate. 25. The sustained release composition of any of embodiments 20-24, wherein the at least one delayed release agent comprises methacrylic acid and ethyl acrylate copolymer in a ratio of about 1:1 w/w. 26. The sustained release composition of any of embodiments 20-24, wherein the at least one delayed release agent comprises methacrylic acid and ethyl acrylate copolymer in a ratio from 2:1 to 1:2. 27. The sustained release composition of any of embodiments 21-26, wherein the at least one plasticizer is present in an amount from 0.01% to 5% w/w, from 0.1% to 4% w/w, from 0.2% to 2% w/w, or from 0.5% to 1.5% w/w of the core tablet weight. 28. The sustained release composition of any of embodiments 21-26, wherein the at least one plasticizer is present in an amount from 0.01% to 5% w/w, from 0.1% to 4% w/w, from 0.2% to 2% w/w, or from 0.5% to 1.5% w/w of the functional coating. 29. The sustained release composition of any of embodiments 21-28, wherein the at least one plasticizer is triethyl citrate. 30. The sustained release composition of any of embodiments 21-29, wherein the at least one anti-tacking agent is present in an amount from 0.1% to 10% w/w, from 1% to 8% w/w, or from 2% to 6% w/w of the core tablet weight. 31. The sustained release composition of any of embodiments 21-29, wherein the at least one anti-tacking agent is present in an amount from 0.1% to 10% w/w, from 1% to 8% w/w, or from 2% to 6% w/w of the functional coating. 32. The sustained release composition of any of embodiments 21-31, wherein the anti-tacking agent is talc. 33. The sustained release composition of any of embodiments 21-32, wherein the at least one layer of the functional coating provides from 1% to 60%, from 2% to 40%, from 5% to 30%, or from 6% to 20% weight gain over the core tablet weight. 34. The sustained release composition of any of embodiments 21-33, wherein the functional coating comprises from 1% to 60% w/w, from 2% to 40% w/w, from 5% to 30% w/w, or from 6% to 20% w/w of weight gain over the core tablet weight. 35. The sustained release composition of any of embodiments 21-34, wherein the core tablet has a weight from 60 mg to 500 mg. 36. The sustained release composition of any of embodiments 21-35, wherein the core tablet has a weight from 100 mg to 160 mg, from 90 mg to 110 mg, or from 100 mg to 120 mg. 37. The sustained release composition of any of embodiments 21-36, wherein the core tablet has a thickness from 2.75 mm to 3.75 mm. 38. The sustained release composition any of embodiments 21-37, wherein the core tablet has a thickness from 3 mm to 3.5 mm. 39. The sustained release composition any of embodiments 21-38, wherein the core tablet has a hardness from 4 Kp to 16 Kp or from 10 Kp to 16 Kp. 40. The sustained release composition any of embodiments 21-39, wherein the core tablet has a hardness of about 13 Kp. 41. A sustained release composition according to any of embodiments 1 to 40, in the form of an enteric coated delayed release tablet, comprising: a core tablet enclosed in at least one layer of a functional coating, wherein the core tablet comprises: from 0.01 mg to 200 mg of the therapeutic agent; from 0.1% to 99% w/w hypromellose; from 1% to 99% w/w microcrystalline cellulose; and from 0.01% to 5% w/w magnesium stearate; the functional coating, wherein the functional coating comprises: from 0.1% to 20% w/w methacrylic acid and ethyl acrylate copolymer having a ratio of about 1:1; from 0.01% to 5% w/w triethyl citrate; and from 1% to 10% w/w talc, wherein the at least one layer of the functional coating contributes from 2% to 20% weight gain over the average core tablet weight. 42. The sustained release composition of embodiment 41, wherein the core tablet comprises from 5% to 60% w/w hypromellose. 43. The sustained release composition of embodiment 41 or embodiment 42, wherein the core tablet comprises from 10% to 90% w/w microcrystalline cellulose. 44. The sustained release composition of any one of embodiments 41-43, wherein the sustained release composition comprises 0.5 mg, 1 mg, 2 mg, 4 mg, 5 mg, 6 mg, 8 mg, 10 mg, 20 mg, or 40 mg of the therapeutic agent. 45. The sustained release composition of any one of embodiments 41-43, wherein the sustained release composition comprises from 0.5 mg to 1 mg, from 1 mg to 2 mg, from 2 mg to 3 mg, from 3 mg to 4 mg, from 4 mg to 5 mg, from 5 mg to 6 mg, from 6 mg to 7 mg, from 7 mg to 8 mg, from 8 mg to 9 mg, from 9 mg to 10 mg, from 10 mg to 20 mg, or from 20 mg to 40 mg of the therapeutic agent. 46. The sustained release composition of any one of embodiments 41-45, wherein the sustained release composition provides a sustained release of the therapeutic agent over a time period of at least 2 hours, at least 3 hours, at least 4 hours, at least 5 hours, at least 6 hours, at least 7 hours, at least 8 hours, at least 9 hours, at least 10 hours, at least 12 hours, at least 14 hours, at least 16 hours, at least 18 hours, at least 24 hours, at least 48 hours, or at least 72 hours post dose. 47. The sustained release composition of any one of embodiments 41-46, wherein the sustained release composition provides a sustained release of the therapeutic agent over a time period from at least 3 hours to 72 hours or from at least 6 hours to 48 hours. 48. The sustained release composition of any one of embodiments 41-47, wherein the sustained release composition shows a percentage dissolution of no more than 30% at 3 hours, from 30% to 50% at 12 hours, and from 65% to 85% at 12 hours measured by the 75 rpm USP paddle method in simulated gastric fluid at pH 1.2 and at 37° C. from hours 0-2, and in simulated intestinal fluid at pH 6.8 and at 37° C. after hour 2. 49. The sustained release composition of any one of embodiments 41-48, wherein the sustained release composition has a percentage dissolution of: no more than 35% at 3 hours, from 35% to 55% at 12 hours, and from 65% to 85% at 24 hours; no more than 30% at 3 hours, no more than 50% at 12 hours, and no less than 80% at 24 hours; no more than 5% at 2 hours, no more than 10% at 3 hours, no less than 30% at 6 hours, no less than 50% at 9 hours and no less than 80% at 14 hours; of no more than 5% at 2 hours, no less than 60% at 3 hours, no less than 90% at 6 hours, and 100% at 12 hours; or at least 10%, at least 20%, at least 30% or at least 40% after 24 hours, measured by the 75 rpm USP paddle method in simulated gastric fluid at pH 1.2 and at 37° C. from hours 0-2, and in simulated intestinal fluid at pH 6.8 and at 37° C. after hour 2. 50. The sustained release composition of any one of embodiments 19-49, wherein the enteric coated delayed release tablet has a weight from 101 mg to 160 mg, or from 105 mg to 120 mg. 51. The sustained release composition of any one of embodiments 1-50, further comprising a pharmaceutically acceptable excipient. 52. The sustained release composition of any of embodiments 1-51, wherein the sustained release composition is stable at ambient temperature, 25° C./65% RH, or 40° C./75% RH for at least 1 month, at least 3 months, at least 6 months, at least 9 months, at least 12 months, at least 18 months, at least 2 years, at least 3 years, at least 4 years, or at least 5 years. 53. The sustained release composition of any one of embodiments 1-52, wherein the therapeutic agent in the sustained release composition is stable at ambient temperature, 25° C./65% RH, or 40° C./75% RH for at least 1 month, at least 3 months, at least 6 months, at least 9 months, at least 12 months, at least 18 months, at least 2 years, at least 3 years, at least 4 years, or at least 5 years. 54. The sustained release composition of any one of embodiments 19-53, having a total level of impurities less than 5% w/w of the weight of the enteric coated delayed release tablet or of the core tablet. 55. A sustained release composition disclosed in Table 1, Table 2, Table 5, Table 6, or Table 7. 56. A sustained release composition comprising a core tablet enclosed in at least one layer of a functional coating, wherein the core tablet comprises: from 0.01 mg to 200 mg of a therapeutic agent selected from the group consisting of (Z)-endoxifen free base, a polymorph of (Z)-endoxifen, and a salt of (Z)-endoxifen, or a combination thereof; from 0.1% to 99% w/w hypromellose; from 1% to 99% w/w microcrystalline cellulose; and from 0.01% to 5% w/w magnesium stearate. 57. The sustained release composition of embodiment 56, wherein the core tablet comprises from 5% to 60% w/w hypromellose. 58. The sustained release composition of embodiment 56 or embodiment 57, wherein the core tablet comprises from 10% to 90% w/w microcrystalline cellulose. 59. The sustained release composition of any one of embodiments 56-58, wherein the functional coating comprises: from 0.1% to 20% w/w methacrylic acid and ethyl acrylate copolymer having a ratio from 2:1 to 1:2; from 0.01% to 5% w/w triethyl citrate; and from 1% to 10% w/w talc. 60. The sustained release composition of embodiment 59, wherein the ratio of methacrylic acid and ethyl acrylate copolymer is about 1:1. 61. The sustained release composition of any one of embodiments 56-60, wherein the at least one layer of the functional coating contributes from 2% to 20% weight gain over the average core tablet weight. 62. The sustained release composition of any one of embodiments 1-61, wherein the sustained release composition has a percentage dissolution ranging from 5% to 35%, from 10% to 15%, from 20% to 25%, from 30% to 35%, from 5% to 30%, from 5% to 25%, from 5% to 20%, from 5% to 15%, from 5% to 10%, from 10% to 15%, from 15% to 20%, from 20% to 25%, from 25% to 30%, or from 30% to 35% at 3 hours, measured by the 75 rpm USP paddle method in simulated gastric fluid at pH 1.2 and at 37° C. from hours 0-2, and in simulated intestinal fluid at pH 6.8 and at 37° C. after hour 2. 63. The sustained release composition of any one of embodiments 1-62, wherein the sustained release composition has a percentage dissolution ranging from 35% to 55%, from 40% to 55%, from 45% to 55%, from 50% to 55%, from 35% to 50%, from 35% to 45%, from 35% to 40%, from 35% to 40%, from 40% to 45%, from 45% to 50%, or from 50% to 55% at 12 hours, measured by the 75 rpm USP paddle method in simulated gastric fluid at pH 1.2 and at 37° C. from hours 0-2, and in simulated intestinal fluid at pH 6.8 and at 37° C. after hour 2. 64. The sustained release composition of any one of embodiments 1-63, wherein the sustained release composition has a percentage dissolution ranging from 65% to 85%, from 70% to 85%, from 75% to 85%, from 80% to 85%, from 65% to 80%, from 65% to 75%, from 65% to 70%, from 65% to 70%, from 70% to 75%, from 75% to 80%, or from 80% to 85%, at 24 hours, measured by the 75 rpm USP paddle method in simulated gastric fluid at pH 1.2 and at 37° C. from hours 0-2, and in simulated intestinal fluid at pH 6.8 and at 37° C. after hour 2. 65. The sustained release composition of any one of embodiments 1-64, wherein the sustained release composition has a percentage dissolution of (Z)-endoxifen or a polymorph or a salt thereof at 2 hours of less than 5% and at 3 hours ranging from 5% to 80%, from 10% to 75%, from 20% to 70%, from 30% to 65%, from 5% to 75%, from 5% to 70%, from 5% to 60%, from 5% to 65%, from 5% to 60%, from 10% to 55%, from 5% to 50%, from 30% to 80%, from 25% to 75%, from 35% to 80%, or not less than 70%, measured by the 75 rpm USP paddle method in simulated gastric fluid at pH 1.2 and at 37° C. from hours 0-2, and in simulated intestinal fluid at pH 6.8 and at 37° C. after hour 2. 66. The sustained release composition of any one of embodiments 1-65, wherein the sustained release composition has a percentage dissolution of (Z)-endoxifen or a polymorph or a salt thereof at 2 hours of less than 5% and at 6 hours ranging from 70% to 99%, from 75% to 95%, from 85% to 95%, from 90% to 95%, from 75% to 90%, from 85% to 90%, from 75% to 85%, from 80% to 99%, from 85% to 99%, from 90% to 99%, from 95% to 99%, or not less than 95%, measured by the 75 rpm USP paddle method in simulated gastric fluid at pH 1.2 and at 37° C. from hours 0-2, and in simulated intestinal fluid at pH 6.8 and at 37° C. after hour 2. 67. The sustained release composition of any one of embodiments 1-66, wherein the sustained release composition has a percentage dissolution of (Z)-endoxifen or a polymorph or a salt thereof at 2 hours of less than 5% and at 12 hours ranging from 70% to 99%, from 75% to 95%, from 85% to 95%, from 90% to 95%, from 75% to 90%, from 85% to 90%, from 75% to 85%, from 80% to 99%, from 85% to 99%, from 90% to 99%, from 95% to 99%, or 100%, measured by the 75 rpm USP paddle method in simulated gastric fluid at pH 1.2 and at 37° C. from hours 0-2, and in simulated intestinal fluid at pH 6.8 and at 37° C. after hour 2. 68. The sustained release composition of any one of embodiments 1-67, wherein the sustained release composition has a percentage dissolution of (Z)-endoxifen or a polymorph or a salt thereof at 2 hours of less than 5% and at 72 hours ranging from 55% to 100%, from 60% to 99%, from 75% to 90%, from 80% to 85%, from 55% to 99%, from 65% to 99%, from 70% to 99%, from 75% to 99%, from 80% to 99%, from 90% to 99%, from 80% to 95%, or from 75% to 95%, as measured by the 75 rpm USP paddle method in simulated gastric fluid at pH 1.2 and at 37° C. from hours 0-2, and in simulated intestinal fluid at pH 6.8 and at 37° C. after hour 2. 69. The sustained release composition of any one of embodiments 1-68, wherein the sustained release composition has a percentage dissolution of NMT about 10% at 3 hours, NLT about 30% at 6 hours, NLT about 50% at 9 hours, and NLT about 80% at 14 hours, as measured by the 75 rpm USP paddle method in simulated gastric fluid at pH 1.2 and at 37° C. from hours 0-2, and in simulated intestinal fluid at pH 6.8 and at 37° C. after hour 2. 70. The sustained release compositions of any one of embodiments 1-69, wherein the wherein the sustained release composition has a percentage dissolution of NMT about 5% at 2 hours. 71. The sustained release composition of any one of embodiments 1-70, wherein the sustained release composition after oral administration provides a sustained exposure of the subject to the therapeutic agent over a time period from at least 3 hours to 270 hours per dose. 72. The sustained release composition of any of embodiments 1-71, wherein a single dose of the sustained release composition following oral administration to a subject is capable of achieving one or more pharmacokinetic parameters of Table 15. 73. The sustained release composition of any of embodiments 1-72, wherein the sustained release composition following oral administration of multiple doses to a subject or at steady state is capable of achieving one or more pharmacokinetic parameters of Table 16. 74. The sustained release composition of any of embodiments 1-73, wherein a single dose of the sustained release composition provides an oral bioavailability of at least 70 percent as measured by a decrease in AUC when compared to a reference product or wherein multiple doses of the sustained release composition provide an oral bioavailability of at least 40 percent as measured by a decrease in the AUC when compared to the reference product. 75. A sustained release composition comprising a core tablet substantially enclosed in at least one layer of a functional coating, wherein the core tablet comprises: a therapeutic agent selected from the group consisting of (Z)-endoxifen free base, a polymorph of (Z)-endoxifen, a salt of (Z)-endoxifen, and a combination thereof; at least one sustained release agent; at least one binder; and at least one lubricant; and wherein after oral administration of a single dose to a subject, the sustained release composition is capable of achieving one or more pharmacokinetic parameters of Table 15; wherein after oral administration of multiple doses to a subject or at steady state, the sustained release composition is capable of achieving one or more pharmacokinetic parameters of Table 16; wherein the sustained release composition after oral administration provides a sustained exposure of the subject to the therapeutic agent over a time period from at least 4 hours to 270 hours per dose; wherein a single dose of the sustained release composition provides an oral bioavailability of at least 70 percent as measured by a decrease in AUC when compared to a reference product; wherein multiple doses of the sustained release composition provide an oral bioavailability of at least 40 percent as measured by a decrease in the AUC when compared to the reference product; or wherein upon oral administration to a subject, the subject experiences vasomotor symptoms at a frequency of less than 25% of the drug dosing days. 76. The sustained release composition of any of embodiments 1-75, wherein the core tablet comprises: from 0.01 mg to 200 mg of (Z)-endoxifen free base as the therapeutic agent; from 0.1% to 99% w/w hypromellose as the at least one sustained release agent; from 1% to 99% w/w microcrystalline cellulose as the at least one binder; and from 0.01% to 5% w/w magnesium stearate as the at least one lubricant; wherein the functional coating comprises: from 0.1% to 20% w/w methacrylic acid and ethyl acrylate copolymer having a ratio from 2:1 to 1:2; from 0.01% to 5% w/w triethyl citrate; and from 1% to 10% w/w talc. 77. The sustained release composition of any of embodiments 1-76, wherein upon administration of the sustained release composition to a subject, the subject experiences vasomotor symptoms (such as hot flashes, night sweats, dry mouth, sensation of feeling heat, cold sweats and the like) at a frequency of less than 5% of drug dosing days. 78. A sustained release composition of any of embodiments 1-77, wherein the composition further comprises an additional therapeutic agent. 79. The sustained release composition of embodiment 78, wherein the additional therapeutic agent is selected from the group consisting of bicalutamide, enzalutamide or anticancer drugs such as trastuzumab, atezolizumab (Tecentriq), alpelisib (Piqray), olaparib (Lynparza), talazoparib (Talzenna), ribociclib (Kisqali), neratinib (Nerlynx), antineoplastics such as capecitabine (Xeloda), carboplatin (Paraplatin), cisplatin (Platinol), cyclophosphamide (Neosar), docetaxel (Docefrez, Taxotere), doxorubicin (Adriamycin), pegylated liposomal doxorubicin (Doxil), epirubicin (Ellence), fluorouracil (5-FU, Adrucil), gemcitabine (Gemzar), methotrexate (multiple brand names), paclitaxel (Taxol), protein-bound paclitaxel (nab-paclitaxel or Abraxane), vinorelbine (Navelbine), eribulin (Halaven), ixabepilone (Ixempra), immune checkpoint inhibitors (such as inhibitors of PD1, PD-L1 and CTLA4), and ATP-cassette binding protein inhibitors. 80. A method of preparing a sustained release composition in the form of an enteric coated delayed release tablet for sustained release of (Z)-endoxifen or a polymorph or a salt thereof comprising the steps of: (a) combining, blending, and dry compressing (Z)-endoxifen or a polymorph or a salt thereof, at least one sustained release agent, at least one binder, and at least one lubricant to form a core tablet; (b) combining at least one delayed release agent, at least one plasticizer and at least one anti-tacking/anti-adherent to form a coating solution; and (c) substantially coating the core tablet of step (a) with the coating solution of step (b) to form at least one layer of functional coating. 81. The method of embodiment 80, wherein the coating is performed by spraying the coating solutions on the core tablet. 82. A method of preparing a sustained release composition for release of a therapeutic agent comprising the steps of: combining and mixing: a therapeutic agent selected from a (Z)-endoxifen free base, a polymorph of (Z)-endoxifen, a salt of (Z)-endoxifen, and a combination thereof; at least one sustained release agent; at least one binder; and at least one lubricant; and dry compressing the therapeutic agent, the at least one sustained release agent, the at least one binder, and the at least one lubricant to form a core tablet. 83. The method of any one of embodiments 80-82, wherein the percentage of (E)-endoxifen in the sustained release composition is less than 5%, less than 4%, less than 3%, less than 2.5%, or less than 2% w/w of the average core tablet weight 84. The method of any one of embodiments 80-83, wherein the enteric coated delayed release tablet has a total level of impurities less than 5% w/w. 85. The method of any one of embodiments 80-84, wherein the core tablet has a total level of impurities less than 5% w/w. 86. The method of any one of embodiments 80-85, wherein the enteric coated delayed release tablet has: a total aerobic microbial count of no more than 103 cfu/g; a total combined yeast and mold count of no more than 102 CFU/g; and an *E. coli* level that is undetectable in 1 g, per USP <1111>. 87. The method of any one of embodiments 80-86, wherein the at least one sustained release agent is hypromellose. 88. The method of any one of embodiments 80-87, wherein the at least one binder is microcrystalline cellulose. 89. The method of any one of embodiments 80-88, wherein the at least one lubricant is magnesium stearate. 90. The method of any one of embodiments 81-89, further comprising: combining and mixing: at least one delayed release agent; at least one plasticizer; and at least one anti-tacking component or anti-adherent component, thereby forming a coating solution; and substantially coating the core tablet with the coating solution, thereby forming at least one layer of a functional coating. 91. The method of embodiment 90, wherein the at least one delayed release agent is a poly(methacrylate) polymer. 92. The method of any one of embodiments 90-91, wherein the at least one delayed release agent is methacrylic acid and ethyl acrylate copolymer having a ratio from 1:2 to 2:1. 93. The method of embodiment 92, wherein the ratio of the methacrylic acid and ethyl acrylate copolymer is about 1:1. 94. The method of any one of embodiments 90-93, wherein the at least one plasticizer is triethyl citrate. 95. The method of any one of embodiments 90-94, wherein the at least one anti-tacking component is talc. 96. A method of treating a disorder in a subject in need thereof comprising orally administering to the subject in need the sustained release composition of any one of embodiments 1-79. 97. A method of treating a subject having a disorder, or a subject at risk of having the disorder, comprising orally administering to the subject the sustained release composition of any one of embodiments 1-79. 98.

The method of any one of embodiments 96-97, wherein the sustained release composition is in the form of an enteric coated delayed release tablet or a sustained release tablet. 99. The method of any of embodiments 96-98, wherein the disorder is a hormone dependent disorder. 100. The method of embodiment 99, wherein the hormone dependent disorder is a breast disorder. 101. The method of any one of embodiments 96-100, wherein the disorder is a breast disorder. 102. The method of any one of embodiments 100-101, wherein the breast disorder is a benign breast disorder, hyperplasia, atypia, atypical ductal hyperplasia, atypical lobular hyperplasia, increased breast density, gynecomastia, DCIS, LCIS, breast cancer, precocious puberty, or McCune-Albright Syndrome. 103. The method of any one of embodiments of 96-99, wherein the disorder is depression, mania, hypomania, a bipolar disorder, or a schizophrenic disorder. 104. The method of any one of embodiments 96-103, wherein the subject is tamoxifen refractory or tamoxifen resistant. 105. The method of any one of embodiments 96-104, wherein the subject is or will be treated with an SSRI drug selected from the group consisting of citalopram, escitalopram, fluoxetine, paroxetine, sertraline, and vilazodone. 106. The method of any one of embodiments 96-105, wherein the subject is administered a sustained release composition of any of embodiments 1-79 in combination with an additional therapeutic agent or a treatment, and wherein the sustained release composition is administered orally. 107. The method of any one of embodiments 96-106, wherein the subject experiences fewer vasomotor effects selected from hot flashes, night sweats, a sensation of feeling hot, or a combination thereof upon ingestion of the sustained release composition as compared with ingestion of tamoxifen. 108. The method of any one of embodiments 96-107, wherein the subject experiences a vasomotor effect selected from hot flashes, night sweats, a sensation of feeling hot, or a combination thereof on fewer than 5% of drug dosing days. 109. The method of any one of embodiments 96-108, wherein the subject is exposed to the therapeutic agent for at least 180 days post administration of the dose as measured by level of (Z)-endoxifen in subject's whole blood, plasma, serum, or a combination thereof. 110. The method of any one of embodiments 96-109, wherein the sustained release composition is capable of achieving one or more of the pharmacokinetic parameters provided in Table 15 following administration of a single dose of the sustained release composition to the subject. 111. The method of any one of embodiments 96-110, wherein the sustained release composition is capable of achieving one or more of the pharmacokinetic parameters provided in Table 16 or Table 17, following administration of multiple doses of the sustained release composition to the subject or at steady state. 112. A method for treating a subject at risk of having breast cancer, the method comprising the steps of: a. determining whether the subject has increased breast density by: (i) performing or having performed mammography on the subject's breasts; (ii) quantifying or having quantified dense tissue volume in subject's breasts to classify the subject's breast density into one of class A, class B, class C or class D, wherein if the subject has a class C or class D dense breast, the subject is determined to have increased breast density and at risk of having breast cancer; and b. orally administering an amount of sustained release composition according to any of embodiments 1-79 to the subject. 113. A method for reducing breast density in a subject, the method comprising the steps of: a. determining whether the subject has increased breast density by: (i) performing or having performed mammography on the subject's breasts; (ii) quantifying or having quantified dense tissue volume in subject's breasts to classify the subject's breast density into one of class A, class B, class C or class D, wherein if the subject has a class B, class C or class D dense breast, the subject is determined to have increased breast density and at risk of having breast cancer; and b. orally administering an amount of a sustained release composition according to any of embodiments 1-79 to the subject, thereby reducing breast density in the subject. 114. The method of embodiment 113, wherein the administration of the sustained release composition unmasks the presence of breast cancer in the subject. 115. A method of treating a breast cancer in a subject in need thereof, the method comprising administering a sustained release composition comprising endoxifen to the subject and subsequently surgically removing a breast cancer tissue from the subject, thereby treating the breast cancer in the subject. 116. A non-surgical method of treating a breast cancer in a subject in need thereof, the method comprising administering a sustained release composition comprising endoxifen to the subject without surgically removing a breast cancer tissue from the subject, thereby treating the breast cancer in the subject. 117. The method of any one of embodiments 115-116, wherein the sustained release composition comprising endoxifen is the sustained release composition of any one of embodiments 1-75. 118. The method of any one of embodiments 115-117, wherein the breast cancer is an invasive breast cancer. 119. The method of any one of embodiments 115-118, wherein the breast cancer is metastatic breast cancer. 120. The method of any one of embodiments 115-119, wherein treating the breast cancer comprises reducing a level of Ki-67 in the subject. 121. The method of embodiment 120, wherein the level of Ki-67 in the subject is reduced by at least 25%, at least 30%, at least 40%, at least 50%, at least 60%, or at least 70% as compared to a level of Ki-67 in the subject prior to administering the sustained release composition. 122. The method of any one of embodiments 115-121, wherein the administering comprises oral administration. 123. The method of any one of embodiments 115-122, wherein sustained release composition is administered to the subject while the subject is awaiting surgery to remove a breast cancer tissue. 124. The method of any one of embodiments 115-123, wherein prior to administering the sustained release composition to the subject, the subject has a statistically significant alteration of a level of one or more biomarkers relative to a level of the biomarker in a normal subject, wherein the biomarker is selected from the group consisting of: Ki-67, estrogen receptor, progesterone receptor, proliferating cell nuclear antigen, phosphor-histone H3, p16, p12, beta-galactosidase, terminal deoxynucleotidyl transferase dUTP nick end labeling, and an RNA sequence, or a combination thereof 125. The method of any one of embodiments 115-124, wherein the subject has a statistically significant alteration of a level of one or more biomarkers relative to prior to administering endoxifen, wherein the biomarker is selected from the group consisting of: Ki-67, estrogen receptor, progesterone receptor, proliferating cell nuclear antigen, phosphor-histone H3, p16, p12, beta-galactosidase, terminal deoxynucleotidyl transferase dUTP nick end labeling, and an RNA sequence, or a combination thereof 126. The method of any one of embodiments 115-125, further comprising detecting in the subject a level of a biomarker selected from the group consisting of: Ki-67, estrogen receptor, progesterone receptor, proliferating cell nuclear antigen, phosphor-histone H3, p16, p12, beta-galactosidase, terminal deoxynucleotidyl transferase dUTP nick end labeling, and an RNA sequence, or a combination thereof. 127. The method of any one of embodiments 115-126, wherein the endoxifen comprises (Z)-endoxifen. 128. The method of any one of embodiments 96-127, wherein the sustained release composition is administered to the subject daily for from 14 days to 40 days, from 10 days to 50 days, from 10 days to 40 days, from 10 days to 35 days, from 10 days to 30 days, from 10 days to 25 days, from 12 days to 50 days, from 12 days to 40 days, from 12 days to 35 days, from 12 days to 30 days, from 12 days to 25 days, from 12 days to 45 days, from 12 days to 30 days, from 14 days to 30 days, from 14 days to 50 days, from 14 days to 40 days, from 14 days to 35 days, from 14 days to 30 days, from 14 days to 25 days, from 16 days to 50 days, from 16 days to 40 days, from 16 days to 35 days, from 16 days to 30 days, from 16 days to 25 days, from 18 days to 50 days, from 18 days to 40 days, from 18 days to 35 days, from 18 days to 30 days, from 18 days to 25 days. 129. The method of any one of embodiments 96-128, wherein from 1 mg to 4 mg, from 2 mg to 4 mg, from 2 mg to 6 mg, from 2 mg to 8 mg, from 1 mg to 10 mg, from 1 mg to 12 mg, from 1 mg to 16 mg, from 2 mg to 10 mg, from 2 mg to 12 mg, from 2 mg to 16 mg, from 3 mg to 10 mg, from 3 mg to 12 mg, from 3 mg to 16 mg, from 4 mg to 10 mg, from 4 mg to 12 mg, or from 4 mg to 16 mg of the sustained release composition is administered to the subject daily. 130. The method of any one of embodiments 115-129, wherein the breast cancer is positive for estrogen receptor and negative for human epidermal growth factor receptor 2. 131. A kit for the treatment of a disorder in a subject comprising the sustained release composition of any of embodiments 1-79 and instructions for use.

EXAMPLES

Example 1

Preparation of Sustained Release Tablets (Cores)

Tablets containing 4 mg of (Z)-endoxifen free base were prepared using the components and quantities that listed in the following table.

TABLE 2

Core Tablet Formulation-Components and functionality

| Sample No. | SustainedRelease agent-HPMC/Hypromellose 2208 (USP-NF) (gm) | | | Binder (gm) MCC | Lubricant (gm) Mg Stearate | Weight (gm) |
|---|---|---|---|---|---|---|
| | Methocell K4M | Methocell K15M | Methocell K100M | | | |
| 1 | 20 | 0 | 0 | 75 | 1 | 100 |
| 2 | 20 | 0 | 0 | 75 | 1 | 100 |
| 3 | 0 | 15 | 0 | 80 | 1 | 100 |
| 4 | 0 | 0 | 10 | 85 | 1 | 100 |
| 5 | 10 | 10 | 0 | 75 | 1 | 100 |
| 6 | 10 | 0 | 10 | 75 | 1 | 100 |
| 7 | 0 | 10 | 10 | 75 | 1 | 100 |
| 8 | 0 | 20 | 0 | 75 | 1 | 100 |
| 9 | 0 | 20 | 0 | 75 | 1 | 100 |
| 10 | 0 | 20 | 0 | 75 | 1 | 100 |
| 11 | 0 | 20 | 0 | 75 | 1 | 100 |
| 12 | 0 | 20 | 0 | 75 | 1 | 100 |
| 13 | 0 | 0 | 20 | 75 | 1 | 100 |
| 14 | 0 | 0 | 20 | 75 | 1 | 100 |
| 15 | 40 | 0 | 0 | 55 | 1 | 100 |
| 16 | 0 | 40 | 0 | 55 | 1 | 100 |
| 17 | 0 | 0 | 40 | 55 | 1 | 100 |
| 18 | 0 | 20 | 0 | 174 | 2 | 200 |

All examples provided in the Table 2 above were made with 4 g of (Z)-endoxifen as API.

Sieving and Mixing. The different components listed in Table 2 were passed through 60-80 mesh sieves. Required amounts of API ((Z)-endoxifen), the rate controlling sustained release agent (hypromellose 2208) of various viscosities ranging from 1,000 to 150,000 mPa·s at 2% in water at 20° C. (ex. Methocell™ K4M (~2.5K to 5K cP), K15M (~13K-25K cP), and K100M (~75K to 140K cP) available commercially from ColorCon) and microcrystalline cellulose PH101 (available commercially from DFE Pharma) as disclosed in the Table 2 were weighed and blended for approximately 10 minutes in a V-Blender. Next, the required amount of the lubricant, magnesium stearate (available from Sigma Aldrich) as disclosed above, was added to the blended mixtures and blended further for 2 more minutes.

Tableting. Tableting of the blended mixtures may be performed by direct compression, dry granulation or wet granulation. To reduce the potential for the interconversion of the active (Z)-endoxifen isomer to inactive (E)-endoxifen isomer specially in solution phase, directly compression method was used to prepare the tablets. The blended mixture was collected and directly dry compressed using a tablet press (Tableting Machine Manesty B3B-16 station rotary press) and punches (manufacturer Natoli (lower and upper) to form matrix tablets with sustained release agent. The obtained matrix tablets were tested for hardness and friability with a target hardness of 13 Kp, target friability of NMT 1.0%, content uniformity, and dissolution rates. Table 3 below provides exemplary tablet parameters.

TABLE 3

Tablet Parameters

| Sample No | Punch size | Pressure (ton) | Average core tablet weight (n = 3) | Tablet Hardness (N) | Tablet external diameter (mm) | Tablet Height (mm) |
|---|---|---|---|---|---|---|
| 1 | 6 | 3.2 | 108.44 ± 1.39 | 16.5 | 5.68 | 6.38 |
| 2 | 7 | 5 | 102.7 ± 0.57 | 140 | 6.41 | 4.19 |
| 3 | 7 | 5 | 102.79 ± 1.52 | 22 | 6.41 | 4.19 |
| 4 | 7 | 5 | 103.88 ± 2.55 | 45.3 | 6.41 | 4.19 |
| 5 | 7 | 5 | 104.98 ± 1.8 | 43 | 6.41 | 4.19 |
| 6 | 7 | 5 | 101.81 ± 0.76 | 51.6 | 6.41 | 4.19 |
| 7 | 7 | 5 | 103.44 ± 0.19 | 53.8 | 6.41 | 4.19 |
| 8 | 7 | 5 | 104.98 ± 0.76 | 47.6 | 6.41 | 4.19 |
| 9 | 7 | 5 | 100.0 ± 1.38 | 139 | 6.41 | 4.19 |
| 10 | 7 | 5 | 100 ± 1.38 | 130 | 6.41 | 4.19 |
| 11 | 7 | 5 | 105.2 ± 0.34 | 150 | 6.41 | 4.19 |
| 12 | 7 | 5 | 102.5 ± 1.13 | 80 | 6.41 | 4.19 |
| 13 | 7 | 5 | 99.94 ± 0.56 | 42.8 | 6.41 | 4.19 |
| 14 | 7 | 5 | 105.2 ± 0.34 | 153.3 | 6.41 | 4.19 |
| 15 | 7 | 5 | 101.83 ± 0.87 | 150 | 6.41 | 4.19 |
| 16 | 7 | 5 | 99.96 ± 0.32 | 143.3 | 6.41 | 4.19 |
| 17 | 7 | 5 | 98.76 ± 1.35 | 137 | 6.41 | 4.19 |
| 18 | 8 | 5 | 101.83 ± 0.87 | 130 | 8.14 | 4.54 |

Example 2

Preparation of Enteric Coated Delayed-Release Tablets

To prepare coating for delayed-release tablets made using the tablet cores from Example 1 above, an aqueous suspension for a functional coating #1 containing a controlled release agent that is a delayed release agent targeting the intestines was prepared as described below.

Coating Solution #1 was prepared using Eudragit L30-D55 (30% solids), an acid resistant poly(meth)acrylate polymer as a delayed release agent targeting release in intestines at above pH 5.5. Eudragit L30-D55 (30% solids) is available commercially from Evonik as a solution. The coating solution was filtered by passing through a 60-mesh screen sieve into another container and stirred continuously to avoid sedimentation. Spray coater pump was pre-run and atomizing air was initiated to achieve the following targeted parameters: inlet temp: 55° C.±10° C., outlet temperature 33° C.±° C., pan speed 20 rpm, pump speed 15%±5% and pattern air 15%±5% psi, atomizing air 15%±5% psi.

The core tablets (e.g., Samples 9) shown in Example 1 were loaded in coating pans and warmed to 38° C. Using the spray coater, the tablet cores were coated with the functional coating solution to achieve substantial enclosure of the tablet cores within the functional coating. A peristaltic pump was used to deliver the coating dispersion to the spray nozzle. A magnetic stirrer was used to continually mix the coating solution during the coating process to prevent sedimentation. The coating solution was stirred slowly to avoid the production of air bubbles. After the tablet bed reached the desired temperature, tablets were spray coated with the coating solution. At least one round of coating process was performed to obtain three targeted weight gains (1.5%, 6%, and 8%) over the weight of the tablet core.

The targeted coating efficiency was "No drug release detected in pH 1.2 for 2 hours" using a validated detection method which was measured in dissolution trials by methods disclosed in Example 5 using USP 1 paddle method (gastric simulated fluid with polysorbate PS80 at pH 1.2 for 2 hours+22 hours in simulated intestinal fluid at pH 6.8).

The functionally coated tablets obtained by this method were allowed to air dry in the tablet bed in the coating pan for initial drying time of 15±3 minutes at 35±2° C. Ten (10) tablets were collected and tested for actual weight gain by the tablets after initial round of coating. The coating process was continued to ensure the targeted weight gain was achieved and then allowed to dry with a final drying time of 10±5 minutes at 35±2° C. For example, the enteric coated delayed release tablets were coated until functional coating weight gains were 1.5% (n=3), 6% (n=3) and 8% (n=3) over the weight of the tablet cores.

Results show that tablets coated with 1.5% weight gain showed at least 60% (Z)-endoxifen release after 2 hours. Tablets coated with 6% and 8% weight gain showed no release before 2 hours and cumulative (Z)+(E)-endoxifen release of 58.81% and 58.56% respectively and cumulative (Z)-endoxifen release at 24 hours were approximately 30% for both sets of tablets.

Example 3

Preparation of Enteric Coated Delayed-Release Tablets

To prepare coating for delayed-release tablets made using the tablet cores from Example 1 above, an aqueous suspension for a functional coating was prepared using the components and the proportions indicated in the following Table 4.

TABLE 4

| Coating Solution # 2 | | |
| --- | --- | --- |
| Coating Component | Functionality | Weight taken (gm) |
| Poly(meth)acrylate polymers, (acid resistant), targeting release in intestines at above pH 5.5 (ex. Eudragit L30-D55 (30% solids)) | Delayed-Release Polymer | 29.77 |
| Triethyl citrate | Plasticizer | 0.89 |
| Talc | Anti-adherent/anti-tacking | 4.47 |
| Purified Water for injection USP | Solvent | 33.34 |

As a non-limiting example, a functional coating solution (a polymethacrylate polymer coating suspension) was prepared by adding water to the commercially available Eudragit L30 D 55 (methacrylic acid-ethyl acrylate copolymer (1:1)) in a container in the amounts shown in Table 4. Triethyl citrate and talc were added into the container and mixed well for about 60 minutes to form a uniform solution. The coating solution was then filtered by passing through a 60-mesh screen sieve into another container and stirred continuously to avoid sedimentation. Spray coater pump was pre-run and atomizing air was initiated to achieve the following targeted parameters: inlet temp: 55° C.±10° C., outlet temperature 33° C.±° C., pan speed 20 rpm, pump speed 15%±5% and pattern air 15%±5% psi, atomizing air 15%±5% psi.

The core tablets (e.g., Samples 9, 10, 11 and 12 of Table 2) obtained in Example 1 were loaded in coating pans and warmed to 38° C. Using the spray coater, the tablet cores were coated with the functional coating solution to achieve substantial enclosure of the tablet cores within the functional coating. A peristaltic pump was used to deliver the coating dispersion to the spray nozzle. A magnetic stirrer was used to continually mix the coating solution during the coating process to prevent sedimentation. The coating solution was stirred slowly to avoid the production of air bubbles. After the tablet bed reached the desired temperature, tablets were spray coated with the coating solution. At least one round of coating process was performed to obtain three targeted weight gains (6%, 8%, and 12.5%) over the weight of the tablet core.

The targeted coating efficiency was "No drug release detected in pH 1.2 for 2 hours" using a validated detection method which was measures in dissolution trials (Example 4).

The functionally coated tablets obtained by this method were allowed to air dry in the tablet bed in the coating pan for initial drying time of 15±3 minutes at 35±2° C. Ten (10) tablets were collected and tested for actual weight gain by the tablets after initial round of coating. The coating process was continued to ensure the targeted weight gain was achieved and then allowed to dry with a final drying time of 10±5 minutes at 35±2° C. For example, Sample 9 tablets were coated until functional coating weight gains were 6% (n=3), 8% (n=3), and 12.5% (n=10) over the weight of the tablet cores.

TABLE 5

| Components | | Amount/Tablet (mg) | | | | | | | |
| --- | --- | --- | --- | --- | --- | --- | --- | --- | --- |
| | Composition/Tablet No. | 1a | 1b | 2a | 2b | 3 | 4 | 5 | 6 |
| Core Tablet | (Z)-endoxifen (API) (mg) | 1 | | 2 | | 4 | 8 | 10 | 20 |
| | HPMC/hypromellose 2208 USP, NF-Methocell K4M (USP, NF) (SR Agent) | 0 | 0 | 0 | 0 | 0 | 0 | 0 | 20 |
| | HPMC/hypromellose 2208 USP, NF-Methocell K15M (USP, NF) (SR Agent) | 20 | 5 | 20 | 10 | 20 | 20 | 0 | 0 |

TABLE 5-continued

| Components | | Amount/Tablet (mg) | | | | | | | |
|---|---|---|---|---|---|---|---|---|---|
| | Composition/Tablet No. | 1a | 1b | 2a | 2b | 3 | 4 | 5 | 6 |
| | HPMC/hypromellose 2208 USP, NF-Methocell K100M (USP, NF) (SR Agent) | 0 | 0 | 0 | 0 | 0 | 0 | 20 | 0 |
| | MCC-Pharmacell 101 (USP, NF) (Binder) | 78 | 93 | 77 | 87 | 75 | 71 | 69 | 59 |
| | Magnesium Stearate-(Lubricant) | 1 | 1 | 1 | 1 | 1 | 1 | 1 | 1 |
| | Total Tablet Core Weight | 100 | 100 | 100 | 100 | 100 | 100 | 100 | 100 |
| Coating | | | | | | | | | |
| | Polymethacrylate polymer (Eudragit L30-D55, 30% solids) (USP, NF) (Delayed-Release Polymer) | 4.0 | 7.8 | 5.9 | 7.8 | 7.81 | 12 | 16 | 20 |
| | Triethylcitrate (USP, NF) (Plasticizer) | 0.5 | 0.78 | 0.6 | 0.78 | 0.78 | 0.91 | 1.2 | 1.5 |
| | Talc (USP, NF) (Anti-Adherent/Anti-Tacking Agent) | 0.6 | 3.9 | 2.1 | 3.9 | 3.91 | 6 | 8 | 10 |
| | Water (Diluent) | NA | NA | NA | NA | NA | NA | NA | NA |
| | Total Weight Coated Tablet | 105.1 | 112.48 | 108.6 | 112.48 | 112.50 | 118.91 | 125.2 | 131.5 |

Exemplary Coated Tablets 1b, 2b, and 3 shown in Table 5 were prepared and coated using above described methods. Coated Tablets 1b, 2b, and 3 of Table 5 had a coated tablet weight of about 112 mg with a weight gain of approximately 12.5% over the weight of the core tablet. Coated Tablets 1b, 2b, and 3 were obtained as white to off-white colored tablet without visible defects. Coated Tablets ranged in hardness from about 5 Kp to about 16 Kp.

The sample tablets (Coated Tablet 3) were stored in LDPE bags for bulk packaging (double bagged with silica gel sachet) which were then stored in HDPE dark (UV black) bottles for transport and stability testing. The drug release profile of these enteric coated tablets containing (Z)-endoxifen were tested in dissolution trials (Example 4).

Tablets prepared as disclosed above, for example, Coated Tablets No. 1b, 2b, and 3 of Table 5 have an off-white to white color without visible defects. The core tablet weight uniformity ranged from 90-110 mg (100±10%) with an average of 101.89 (n=50). Thickness ranged from 3.0 to 3.5 mm (3.25±7.5%) with an average of 3.23 mm (n=10). Blend uniformity was at least NMT 5% with an average of 4.08 (n=6). Friability was NMT 1.0%, and the tablet hardness ranged from 10-16 Kp. Additional core tablets of hardness ranging from 5 to 16 Kp were also prepared.

Coated tablet weight uniformity ranged from 106.8 to 118.2 mg (112±5%) with an average of 114.3 mg and costing efficiency of "no drug release detected in pH 1.2 for at least two hours" using a validated assay as indicated by absence of drug (Z)-endoxifen peak for at least 2 hrs after dosing. Virtually no drug release detected in acidic pH for at least 2 hours is predictive of protection of the drug in acidic environment in stomach and subsequent release of (Z)-endoxifen in the intestines.

Standards

Uniformity of dosage units meets the criteria of USP <905>.

Exemplary Coated Tablet No. 3 of Table 5 showed total aerobic microbial count (TAMC) in coated tablet 3 of <10 colony forming units (CFU)/g and a total combined yeast and mold count (TMMC) of <10 CFU/g. E. coli was absent per 1 g. Processes for making sustained release compositions in the form of sustained release tablets (cores) and enteric coated delayed release tablets are scalable. Coated Tablets 1-2 and 4-6 can be prepared as disclosed.

Example 4

In Vitro Dissolution of Uncoated Tablets—USP I

In vitro dissolution tests were carried out to study the (Z)-endoxifen release profile obtained with the uncoated and enteric coated (delayed release) tablets disclosed in Example 1 according to USP Procedure Drug Release General Chapter <711> Dissolution.

A. Phosphate Buffer. In vitro dissolution tests according to USP method 1 were carried for the test tablets Samples 1 to 17 containing 4 mg (Z)-endoxifen, per USP method in phosphate buffer phase 6.8 for six (6) to twenty five (25) hours at 37° C., 50 rpm to mimic the intestinal fluids (without enzymes or bile) and in certain experiments in the presence of polysorbate 80 (PS-80). (Z)-endoxifen and (E)-endoxifen release into the medium were measured at various time points to determine if the (Z)-endoxifen in the uncoated tablets sustained over a longer period.

Into a dissolution a 1000 mL of 0.05M phosphate buffer pH 6.8 was added while maintaining temperature of the bath at 37±0.5° C. Sample compositions in the form of tablets were prepared and added once the buffer media reached 37° C.±0.5. Samples aliquots (test media) were taken at various time points for testing for dissolution of the uncoated tablet (cores) and (Z)-endoxifen release. Equal amount of adjusted 6.8 pH buffer into the vessel were added to maintain sink conditions.

(Z)-endoxifen and (E)-endoxifen release from the uncoated tablets into the test media were analyzed by High Performance Liquid Chromatography (HPLC) with UV detector.

Instrument Parameters
    Instrument: Vankel VK 7000
    Type: Type II Paddle
    Temperature Program: 37° C.
    Bath volume: 1000 mL.
    Paddle Speed: 50 RPM
    Sample Volume: 3 mL [Replaced same amount after every sampling]

Sample Time Points: Various—typically 0, 0.5, 1, 2, 2.5, 3, 4, 6, 8, 9, 12, 14, 22, and 26 hours. Not all timepoints were studied for all sample compositions tested.

Analytical Equipment and parameters: High Performance Liquid Chromatography using Agilent 1100 liquid chromatograph equipped with an auto sampler and DAD detector. Column: Phenomenex 2.6 µm Phenyl Hexyl 100A 150 mm×4.6 µm. Flow rate 0.75 mL/min. Detection: UV@243 nm. Injection vol: 20 µL. Run time: 10 minutes. Mobile phase A: 10 mM ammonium formate with 0.03% formic acid on water. Mobile phase B: 10 mM ammonium formate in methanol. Diluent: methanol.

Table 6 below discloses the approximate time in hours of 10%, 20%, 50% and 70% percent cumulative dissolution and (Z)-endoxifen release from exemplary uncoated tablets samples (cores) in the test medium.

TABLE 6

| Sample No. (Uncoated Tablet) | 10% | 20% | 50% | 70% |
|---|---|---|---|---|
| % Drug Release/Dissolution in Phosphate Buffer, pH 6.8, 50 RPM 37° C. (n = 2) (USP I) | | | | |
| 1 | 0.5 | 2 | 4 | 7 |
| 3 | 0.25 | 0.5 | 2 | 5 |
| 4 | 0.25 | 0.5 | 2 | 5 |
| 5 | 0.5 | 2 | 4 | 7 |
| 2 | 3 | 6 | >12 | >12 |
| 9 | 1 | 3 | 10 | 19 |
| 10 | 1 | 3 | 9 | 19 |
| 11 | 1.5 | 3.5 | 9 | 15 |
| 14 | 1 | 3.5 | >12 | >12 |
| 15 | 3 | 6 | 14 | 25 |
| 16 | 4 | 8 | 15 | 20 |
| 17 | 6 | 12 | >25 | >25 |
| Control | 1.5 | 3 | 5 | >8 |
| % Drug Release/Cumulative Dissolution in Phosphate Buffer + 0.5% PS-80, pH 6.8, 50 RPM 37° C. (n = 2) (USP I) | | | | |
| 2 | 2.5 | 6 | 15 | 24 |
| 5 | 0.5 | 1 | 4 | 7 |
| 6 | <0.25 | 0.5 | 3 | 6 |
| 7 | <0.25 | 0.25 | 0.5 | 1 |
| 8 | 0.5 | 1 | 3 | 6 |
| 9 | 2 | 3 | 11 | 16 |
| 13 | 0.25 | 0.5 | 3 | 6 |
| 14 | 1 | 3 | 15 | 23 |
| 15 | 3 | 6 | 15 | 25 |
| 16 | 3.5 | 7 | 14 | 21 |
| 17 | 7 | 12 | 24 | >24 |

Results are representative of multiple separate experiments.

*Control: (Z)-endoxifen neat in with enteric resistant delayed release capsules prepared with DRcaps commercially available from Capsugel, USA ("Capsule", "reference product," "API-in-Capsule" or "DRCaps" used interchangeably herein).

Table 7 shows the approximate percentage dissolution and (Z)-endoxifen release from uncoated tablet (core) samples at 12 hours and 24 hours.

TABLE 7

| Sample No. | % (Z)-endoxifen release/ Cumulative Dissolution | |
|---|---|---|
| Uncoated Tablet (Core) | 12 hr | 24 hr |
| 2 | 39.17% | 89.00% |
|  |  | 63.11% |

TABLE 7-continued

| Sample No. | % (Z)-endoxifen release/ Cumulative Dissolution | |
|---|---|---|
| Uncoated Tablet (Core) | 12 hr | 24 hr |
| 5 | 94.74% | |
| 6 | 90.73% | |
| 8 | 93.76% | |
| 9 | 51.80% | 79.93% |
| 10 | ~58% | 78.31% |
| 11 | ~58% | 86.33% |
| 13 | 91.07% | |
| 14 | 41.66% | 77.87% |
| 15 | 38.10% | 73.07% |
| 16 | 38.80% | 74.06% |
| 17 | 19.73% | 49.53% |
| Control | 60% at 8 h | |

Results shown in Table 6 and Table 7 are representative of multiple separate experiments.

*Control: (Z)-endoxifen neat in enteric resistant delayed release capsules prepared with DRcaps commercially available from Capsugel, USA ("Capsule" "API-in-Capsule" "reference product" or "DRCaps"). A method for making the Capsule is described below.

In vitro dissolution test results disclosed in Table 6 and Table 7 show that uncoated tablets release (Z)-endoxifen into the test medium (phosphate buffer pH 6.8±PS-80 at 50 RPM at 37° C.) in a sustained manner over a prolonged period ranging from 4 to 24 hours, and in certain cases of certain samples over 24 hours functioning. Thus, the compositions of the present disclosure, and specifically those exemplified in Example 1 function as sustained release tablets in themselves, and are also suitable for use as core tablets.

Sample 7 immediately released its (Z)-endoxifen in the test medium functioning as immediate release (Z)-endoxifen tablet. It will be understood by one of skill in the art that the compositions Sample 7 when substantially coated with at least one layer of coating as disclosed in the present disclosure is a novel enteric coated delayed release tablet that is useful for treatment of subjects in need thereof.

FIG. 1 shows the amount of (Z)-endoxifen (% cumulative dissolution) released from uncoated sustained release tablets (cores) containing 4 mg of (Z)-endoxifen free base (Samples 9 and 16) of Table 6 as compared to a control (neat (Z)-endoxifen free base enclosed in an enteric resistant delayed release capsule prepared with the commercially available DRCaps from Capsugel, a Lonza Company, USA, referred herein interchangeably to as "Capsule" "DR-Capsule" "API-in-capsule" "API-in-DR-capsule" or "reference product")

Results show that the release of (Z)-endoxifen from uncoated tablets of the present disclosure is slower and more sustained than control (delayed release API-in-capsule). The control (delayed release API-in capsule) releases approximately 2.4 mg of (Z)-endoxifen and approximately 0.5 mg of (E)-endoxifen by 8 hours whereas the exemplary uncoated sustained release tablets Samples 9 and 16 of Table 6 release approximately 2.4 mg at by about 8 hours and about 16 hours respectively. (E)-endoxifen was undetectable at 24 hours.

B. Simulated Fluids. In vitro dissolution tests were carried out for the uncoated test tablets containing 4 mg (Z)-endoxifen, per USP method 1 (750 mL of simulated gastric fluid (SGF) acid phase for two hours with addition of 250 mL of simulated intestinal fluid without enzymes (buffer phase) to convert the pH from 1.2 to pH 6.8 and study extended for additional eight (8) to twenty two (22) hours. (Z)-endoxifen and (E)-endoxifen release into the medium were measured at various time points to determine if the (Z)-endoxifen in the uncoated tablets were sustained over a longer period.

(Z)-endoxifen and (E)-endoxifen release from the uncoated tablets into the test media were analyzed by High Performance Liquid Chromatography (HPLC) with UV detector.

Analytical Equipment and parameters: High Performance Liquid Chromatography using Agilent 1100 liquid chromatograph equipped with an auto sampler and DAD detector. Column: Phenomenex 2.6 µm Phenyl Hexyl 100A 150 mm×4.6 µm. Flow rate 0.75 mL/min. Detection: UV@243 nm. Injection vol: 20 µL. Run time: 10 minutes. Mobile phase A: 10 mM ammonium formate with 0.03% formic acid on water. Mobile phase B: 10 mM ammonium formate in methanol. Diluent: methanol.

Table 8 below discloses the approximate time in hours of 10%, 20%, 50% and 70% percent cumulative dissolution and (Z)-endoxifen release from exemplary uncoated tablets samples (cores) in the test medium.

TABLE 8

| Sample | 10% | 20% | 50% | 70% |
|---|---|---|---|---|
| % Dissolution of (Z)-endoxifen in Simulated Fluids (2 hr at 1.2 pH + 22 hr at pH 6.8) 50 RPM @ 37° C. (USP I) in hours | | | | |
| 14 | 4 | 22 | >25* | >25* |
| 15 | 8 | 24 | >24* | >24* |
| % Dissolution of (Z + E)-endoxifen in Simulated Fluids (2 hr at 1.2 pH + 22 hr at pH 6.8) 50 RPM @ 37° C. (USP I) | | | | |
| 14 | 1.5 | 5 | >25* | >25* |
| 15 | 2 | 6 | >24* | >24* |

*Results are extrapolated.

Example 5

In Vitro Dissolution Testing of Coated Tablets

In vitro dissolution tests were carried for the test tablets containing 4 mg (Z)-endoxifen coated with a functional enteric coating with targeted weight gains of 1.5%, 6%, and 8%, per USP method 1 (750 mL of simulated gastric fluid (SGF) acid phase for two hours with addition of 250 mL of simulated intestinal fluid without enzymes (buffer phase) to convert the pH from 1.2 to 6.8 and study extended for additional eight (8) to twenty two (22) hours. (Z)-endoxifen and (E)-endoxifen release into the medium were measured at various time points to determine if the (Z)-endoxifen in the enteric coated tablets were (1) delayed released, (2) sustained over a longer period, or (3) both.

(Z)-endoxifen and (E)-endoxifen release from the uncoated tablets into the test media were analyzed by High Performance Liquid Chromatography (HPLC) with UV detector.

Analytical Equipment and parameters: High Performance Liquid Chromatography using Agilent 1100 liquid chromatograph equipped with an auto sampler and DAD detector. Column: Phenomenex 2.6 µm Phenyl Hexyl 100A 150 mm×4.6 µm. Flow rate 0.75 mL/min. Detection: UV@243 nm. Injection vol: 20 µL. Run time: 10 minutes. Mobile phase A: 10 mM ammonium formate with 0.03% formic acid on water. Mobile phase B: 10 mM ammonium formate in methanol. Diluent: methanol.

Exemplary results shown in Table 9. discloses the approximate percent cumulative dissolution from exemplary uncoated delayed release tablets samples (cores) in the test medium.

TABLE 9

Drug Release Profile of Exemplary Enteric Coated Tablets

| Sample No. | % (Z)-endoxifen release/Cumulative Dissolution in SIF¶-USP I, 50 RPM 37° C. | | | | |
|---|---|---|---|---|---|
| (Coated Tablet) | pH 1.2 | | pH 6.8 | | |
| Time (h) | 1 | 2 | 3 | 12 | 24 |
| 9 + 1.5% coating (coating solution 1) | 20% | 25% | 30% | 52% | 60% |
| 9 + 6% coating | ND£ | ND | 8% | 54% | 68% |
| 9 + 8% coating | ND | ND | 8% | 55% | 72% |
| 11 Hardness 120N + 8% coating | ND | ND | 20% | 65% | 72.44% |
| 12 Hardness 80N + 8% coating | NT‡ | ND | 8% | 42% | 94.54% |

| | pH 1.2 | | | pH 6.8 | | |
|---|---|---|---|---|---|---|
| Time (h) | 2 | 2.5 | 3 | 6 | 9 | 12 | 24 |
| Control (Z)-EDX in DR-Capsule | 15% | 33% | 40% | 66% | 74% | 76% | 77% |
| Control (Z + E) Release | 29% | 46% | 54% | 82% | 92% | 96% | 99.99% |

¶SIF = Simulated Gastric fluid with PS-80 at pH 1.2 (2 hr) + Simulated Intestinal Fluid without enzymes or bile salts pH 6.8 (22 hr)
£ND = Not detected;
‡NT = Not tested Results shown in Table 9 suggest that the sustained release compositions in the form of enteric coated delayed release tablets of the present disclosure protect (Z)-endoxifen from the acidic environment as would be present in stomach delaying release and are capable of targeting release of (Z)-endoxifen into intestines in a mammal over an extended period of time, for example for at least 4 hours, for at least 5 hours, for at least 6 hours, for at least 7 hours for at least 8 hours, for at least 9 hours, for at least 10 hours, for at least 12 hours, at least 18 hours, and for at least 24 hours in a sustained manner. The enteric coated delayed release tablets of the present disclosure are also capable of releasing at least 20%, at least 30%, and at least 40% of the active drug after 24 hours. The results show that enteric coated delayed release tablets of the present disclosure have sustained release of (Z)-endoxifen.

Further, coatings on the sustained release tablets such as those disclosed in Example 1 were surprisingly advantageous in reducing the conversion of (Z)-endoxifen to (E)-endoxifen upon release into the SIF test medium as very little (E)-endoxifen (<3%) was detected in the validated assay for measuring endoxifen isoforms. A person of ordinary skill in the art would not have predicted that the present formulation of the sustained release compositions would reduce the conversion of (Z)-endoxifen to (E)-endoxifen in the SIF test medium.

Figure 2:
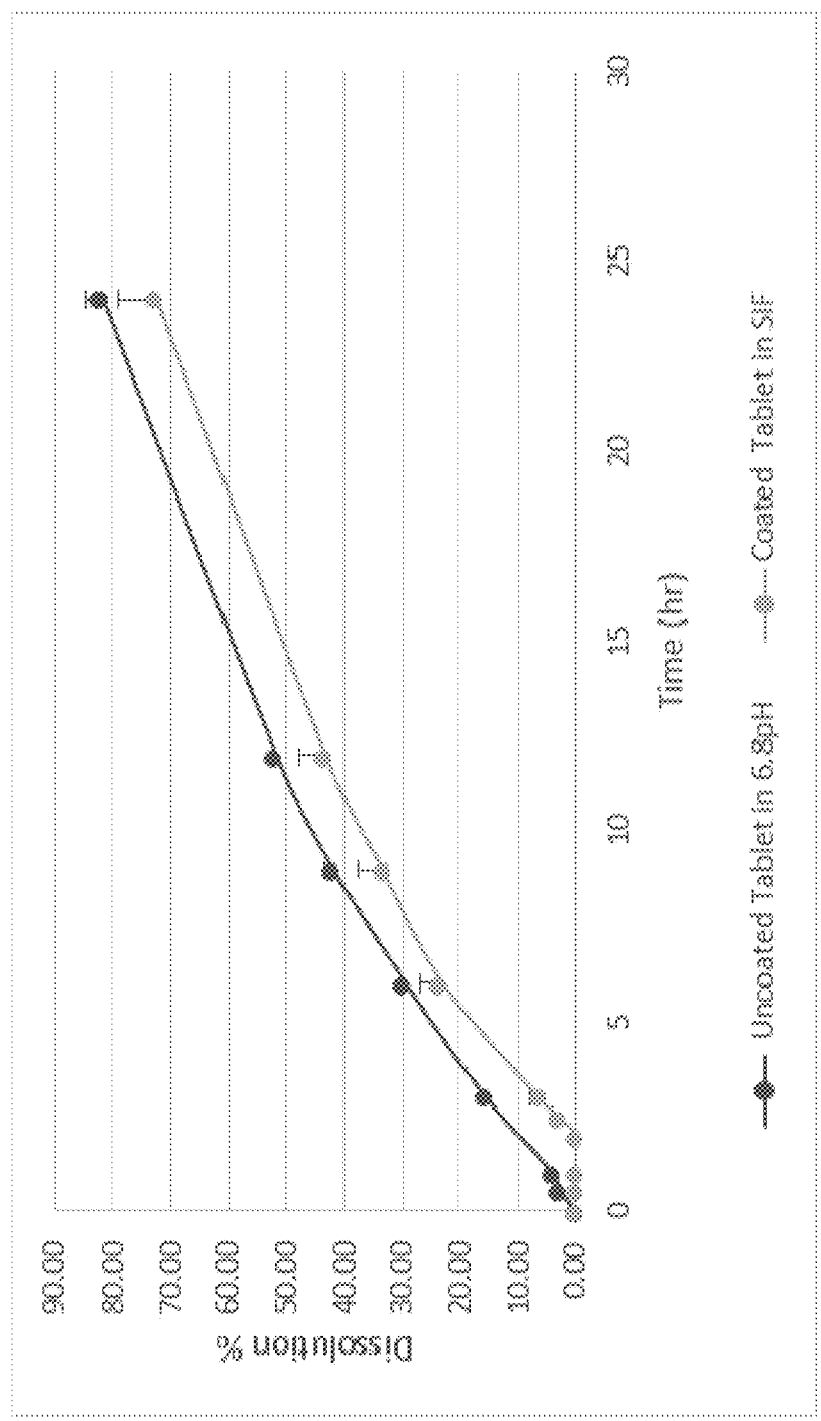
FIG. 2 shows percentage dissolution and release of (Z)-endoxifen from exemplary sustained release compositions in the form of a sustained release tablet (uncoated) and an enteric coated delayed release tablet containing 4 mg of (Z)-endoxifen free base, as measured according to USP I method. (Z)-endoxifen release upon dissolution of the compositions was measured using HPLC-UV.
Figure 3:
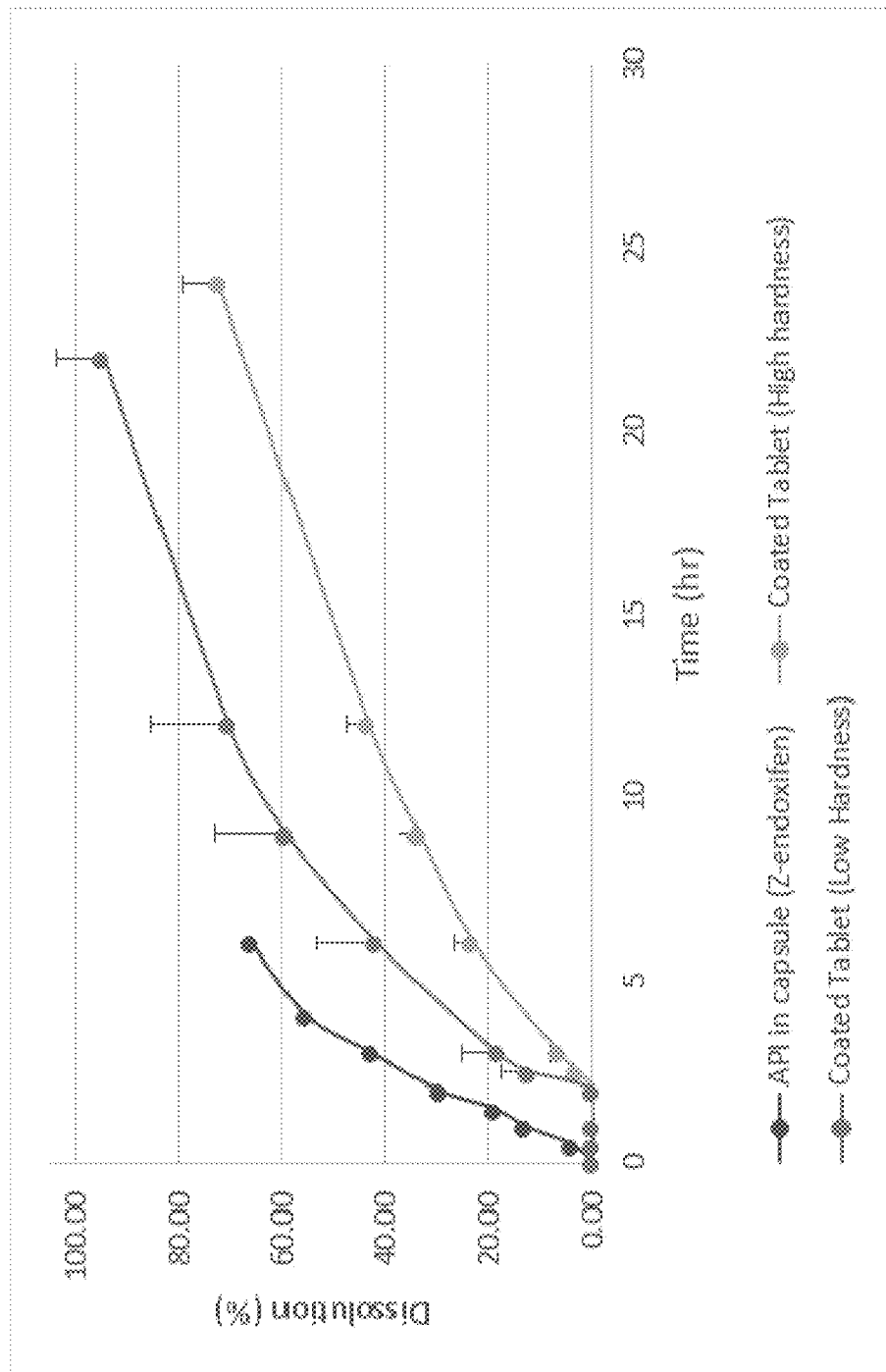
FIG. 3 shows percentage dissolution and release of (Z)-endoxifen from exemplary sustained release compositions in the form of enteric coated delayed release tablets of low hardness (80N) and high hardness (120N) containing 4 mg of (Z)-endoxifen free base, and control (a 4 mg delayed release (Z)-endoxifen API-in-capsule), as measured according to USP I method. (Z)-endoxifen release upon dissolution of the compositions was measured using HPLC-UV.

Dissolution of (Z)-endoxifen in simulated intestinal fluids (n=2) from spray coated Sample 9 tablets with a functional coating over the core tablet was compared with uncoated tablet and the results are shown in FIG. 2. The functional coating was performed with a coating solution containing 8% delayed reagent polymer and contributed to about a weight gain of approximately 12% weight gain over the core tablet. Results show that not only is the (Z)-endoxifen undetectable by validated assay suggesting no drug release occurs until after 2 hours, but also that rate of release of (Z)-endoxifen is slow and sustained over a period ranging from 2 hours to about 24 hours when the sustained release tablets (cores) are enteric coated with at least one layer of functional coating as described in Example 3. Further, at least 20% to at least 40% of the active (Z)-endoxifen in the coated tablets is available for release after 24 hours (FIG. 2 and Table 9). Comparison of exemplary coated tablets with low (Sample 12) and high hardness (Sample 11) was performed in simulated fluids (simulated gastric fluid at pH 1.2 for 2 hours+simulated intestinal fluid at pH 6.8 for 22 hours) and the results are shown in FIG. 3.

Figure 4:
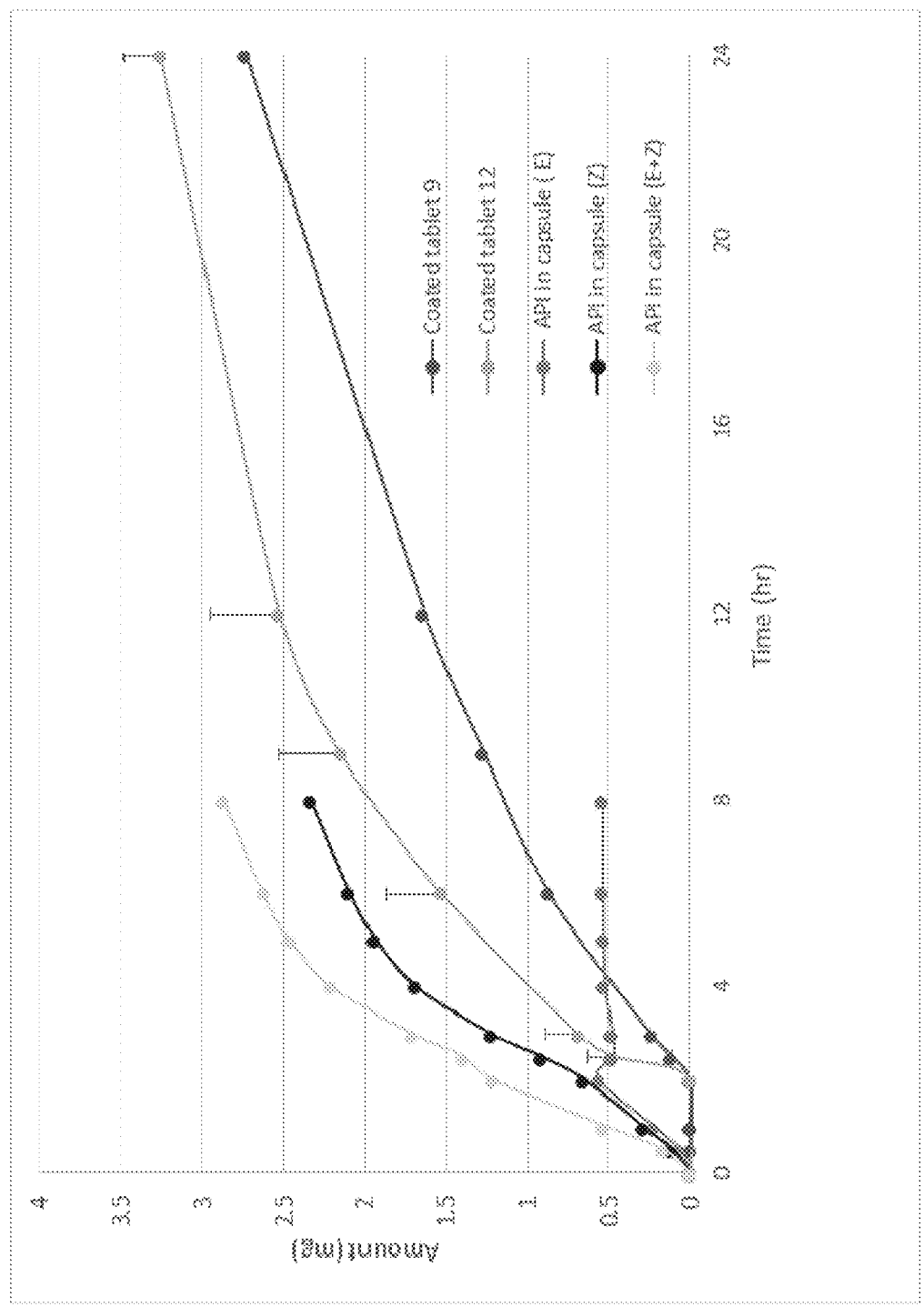
FIG. 4 shows dissolution and release of (Z)-endoxifen in mg from exemplary sustained release compositions in the form of enteric coated delayed release tablets of low hardness (80N) and high hardness (120N) containing 4 mg of (Z)-endoxifen free base and control API-in-capsule as measured according to USP I method in simulated intestinal fluid. (Z)-endoxifen release upon dissolution of the compositions was measured using HPLC-UV.

FIG. 4 shows the amount of (Z)-endoxifen in mg released from the sustained release compositions in the form of enteric coated delayed release tablets containing 4 mg of (Z)-endoxifen free base as compared to a control API-in-capsule containing neat (Z)-endoxifen free base). Results show that tablets of varying hardness can be used for the preparation of enteric coated delayed release tablets showing sustained release of (Z)-endoxifen, for example, core tablets 9 and 12 coated with a functional coating with coating solution No. 2 of Table 4. Results show that the release of (Z)-endoxifen from enteric coated delayed release tablets of the present disclosure is slower and more sustained compared to (Z)-endoxifen released from control API-in-capsule. API-in capsule release approximately 2.4 mg of (Z)-endoxifen by 8 hours whereas the enteric coated delayed release tablets release approximately 2.4 mg at by about 12 and about 240 hours respectively.

Thus, the enteric coated delayed release tablets of the present disclosure release (Z)-endoxifen into test media that simulates an environment as would be seen in stomach and the intestines in a mammal over an extended period of time in a sustained manner, for example, for at least 4 hours, for at least 5 hours for at least 6 hours, for at least 7 hours for at least 8 hours, for at least 9 hours, for at least 10 hours for at least 12 hours, at least 18 hours, and at least 24 hours.

TABLE 10

| | | Average % Cumulative Release | | |
|---|---|---|---|---|
| Time (hr) | pH | E-Endoxifen | Z-Endoxifen | (E + Z)-Endoxifen |
| 0 | 1.2 | 0.00 | 0.00 | 0.00 |
| 2 | 1.2 | 0.00 | 0.00 | 0.00 |
| 3 | 6.8 | 0.00 | 17.16 ± 2.45 | 17.16 ± 2.45 |
| 5 | 6.8 | 0.00 | 32.19 ± 3.43 | 32.19 ± 3.43 |
| 8 | 6.8 | 0.00 | 46.67 ± 3.88 | 46.67 ± 3.88 |
| 11 | 6.8 | 1.29 ± 1.18 | 61.77 ± 1.59 | 63.06 ± 1.23 |
| 14 | 6.8 | 2.73 ± 0.39 | 72.18 ± 1.82 | 74.91 ± 2.02 |
| 24 | 6.8 | 4.68 ± 0.62 | 99.65 ± 3.09 | 104.33 ± 3.39 |

Figure 5:
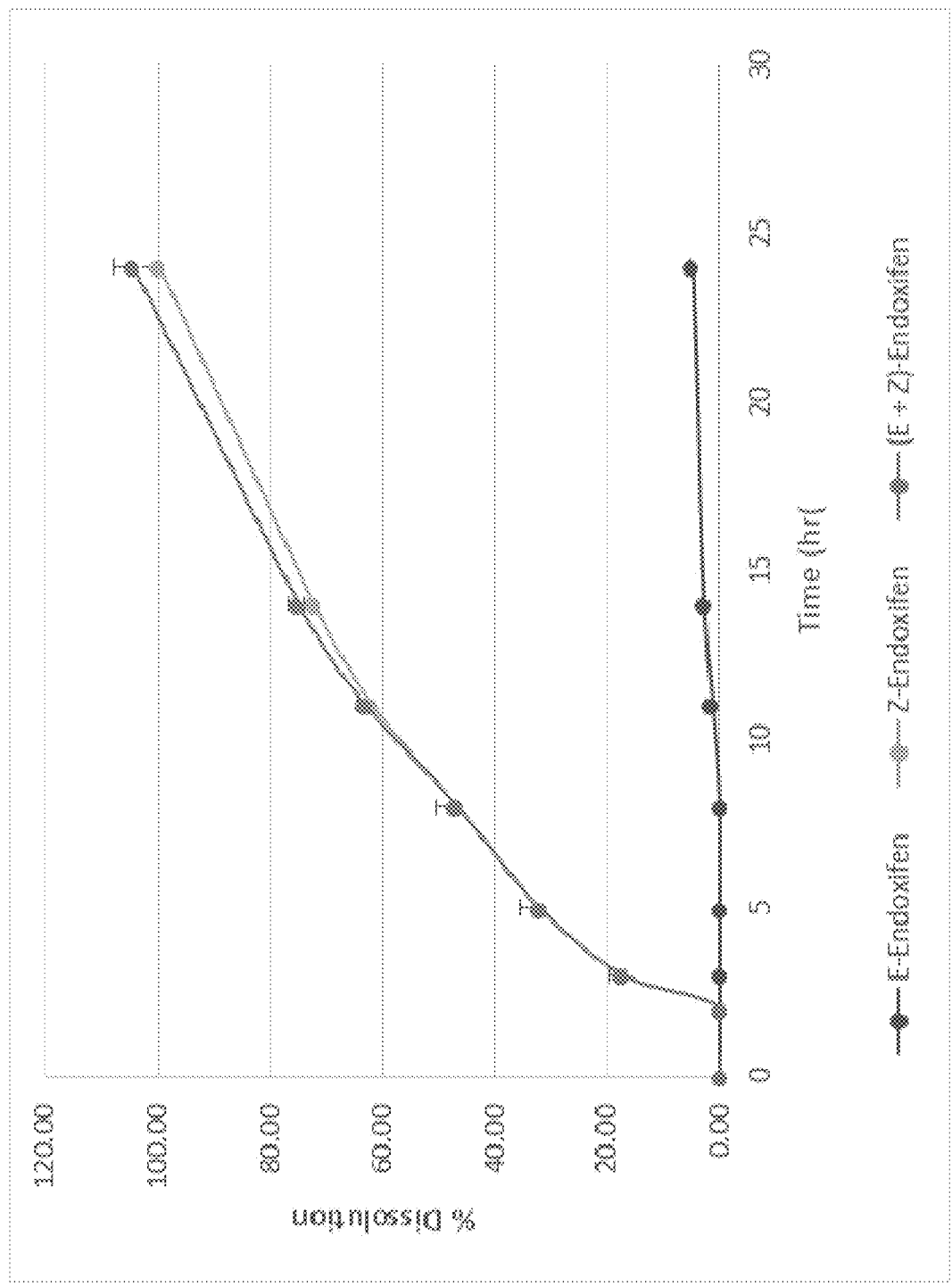
FIG. 5 shows Endoxifen isoforms release profiles from an exemplary sustained release composition in the form of enteric coated delayed release tablet containing 4 mg of (Z)-endoxifen free base, as measured according to USP II (paddle apparatus II) method in simulated intestinal fluid. Endoxifen isoforms ((Z) and (E)) release upon dissolution of the compositions was measured using HPLC-UV.

FIG. 5, and Table 10 show that an exemplary sustained release composition in the form of an enteric coated delayed release tablet protects (Z)-endoxifen from converting to its inactive form, the (E)-Endoxifen in the stomach and intestines such that most of the endoxifen that is released is released in the active form (Z)-endoxifen as measured using USP II method (SIF Medium: 1.2 pH for 2 hr and pH 6.8 pH for 22 hr).

Example 6

In Vitro Dissolution of Enteric Coated Delayed Release Tablets

In vitro dissolution tests were carried out with a series of enteric coated delayed release test tablets of the present disclosure using USP apparatus II (paddle) at paddle speed 50 RPM 37±0.5° C. For each test, 1000 mL of medium (0.05M phosphate buffer, pH 6.8) was added into a dissolution bath and maintained at 37±0.5° C. Test tablets were added to the media once the media reached 37±0.5° C. Samples were aliquoted at various time points to measure tablet dissolution and assay the levels of released endoxifen (Z) and (E) isoforms in the medium. Equal amount of adjusted pH6.8 buffer was added back into the vessel to maintain sink conditions.

Instrument Parameters
  Instrument: Vankel VK 7000
  Paddle type: Type II
  Temperature Program: 37° C.
  Bath volume: 1000 mL
  Paddle Speeds: 50, 75, 100 RPM
  Sample volume: 3 mL (replaced same amount after every sampling)
  Sample time points: Generally 0.5 hr, 1 hr, 2 hr, 2.5 hr, 3 hr, 6 hr, 9 hr, 12 hr, 22 hr and 24 hr
  Drug release (Z)- and (E)-endoxifen from the enteric coated delayed release tablets into the media were analyzed by High Performance Liquid Chromatography (HPLC) with UV detector.
  Analytical Equipment and parameters: High Performance Liquid Chromatography using Agilent 1100 liquid chromatograph equipped with an auto sampler and DAD detector. Column: Phenomenex 2.6 μm Phenyl Hexyl 100A 150 mm×4.6 μm. Flow rate 0.75 mL/min. Detection: UV@243 nm. Injection vol: 20 μL. Run time: 10 minutes. Mobile phase A: 10 mM ammonium formate with 0.03% formic acid on water. Mobile phase B: 10 mM ammonium formate in methanol. Diluent: methanol.

Figure 6:
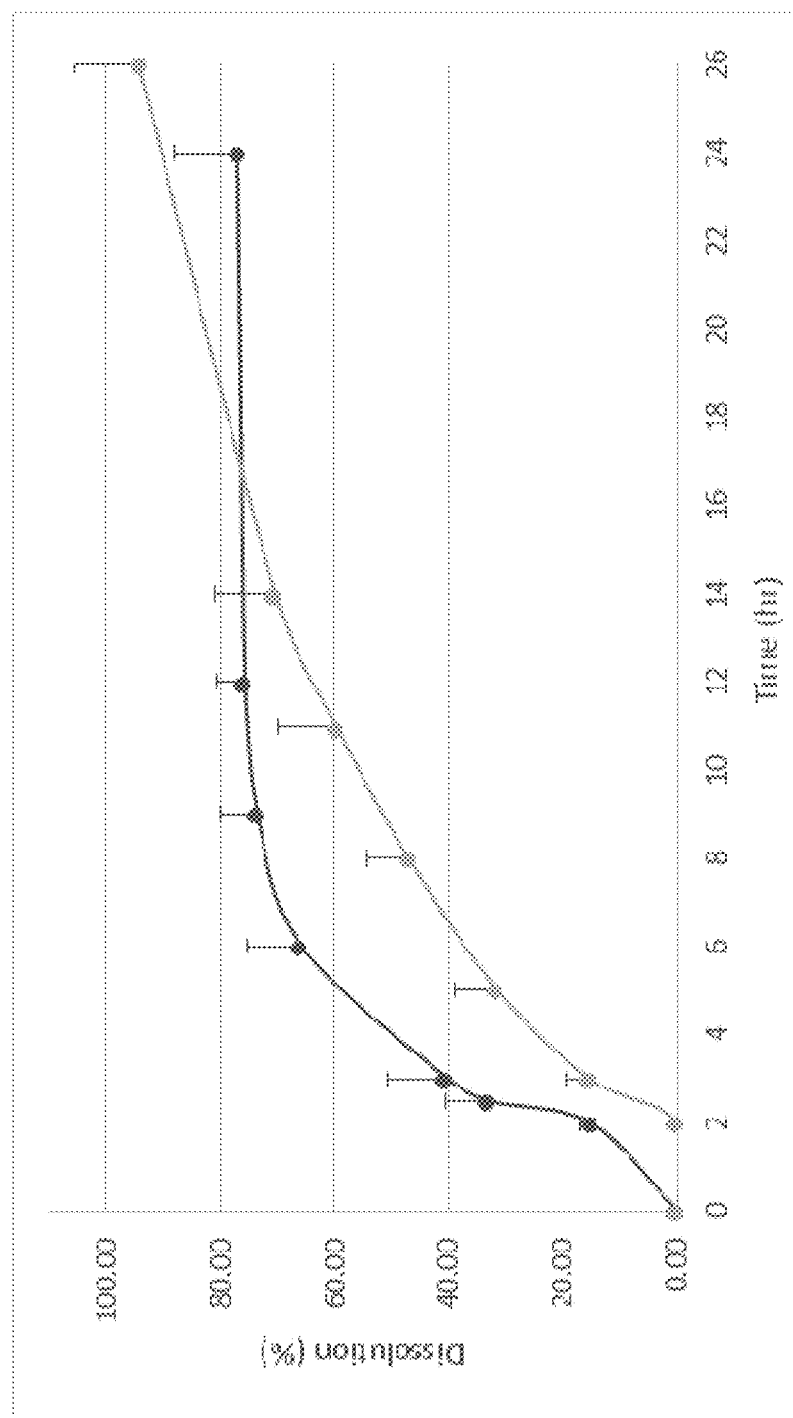
FIG. 6 shows percentage dissolution and release of Z-endoxifen from exemplary sustained release compositions in the form of enteric coated delayed release tablet containing 4 mg of (Z)-endoxifen free base and control (a 4 mg delayed release (Z)-endoxifen API-in-capsule) as measured according to USP II (paddle apparatus II) method in simulated intestinal fluid. (Z)-endoxifen release upon dissolution of the compositions was measured using HPLC-UV.

A dissolution profile of an exemplary sustained release composition in the form of an enteric coated delayed release tablet (prepared using the coating solution of Table 4 to functionally coat a core tablet (Sample 9)) is shown in FIG. 6.

Results show using the USP II (paddle) method at 75 RPM, in SIF medium at 1.2 pH (2 hours), 6.8 pH (22 hours) an exemplary sustained release composition in the form of an enteric coated delayed release tablet containing 4 mg of (Z)-endoxifen free base, having a hardness of 13 Kp releases (Z)-endoxifen as shown in FIG. 6. The enteric coated delayed release tablet shows a more sustained release of (Z)-endoxifen even when compared with a Control (delayed release formulation of neat 4 mg of (Z)-endoxifen free base in a delayed release capsule (DR-Cap or API-in-capsule)).

The percentage dissolution of (Z)-endoxifen at 3 hours, 8 hours, and 14 hours from the coated tablet was 15.5±3.92, 47.17±2.6, and 70.45±10.72. The amount of (E)-endoxifen was observed to be less than 1% suggesting that substantially all of the endoxifen released from the tablet was present as (Z)-endoxifen.

Results from another exemplary enteric coated delayed release tablet showed that percent (Z)-endoxifen released at 3 hours, 8 hours, 14 hours, and 26 hours from the coated tablet was 15.50±3.92%, 47.17±7.26% and 48% respectively as compared to approximately 40%, 72% and 7.45±10.72% 94.37+11.14 of (Z)-endoxifen release from the DR-capsule for the same time. (E)-endoxifen was undetectable in the test media for time points 0 to 11 hours and remained less than 3% until 26 hours.

Example 7

Forced Degradation Tests & Stability (Z)-endoxifen (reference product) and enteric coated delayed release tablets containing (Z)-endoxifen free base of the present disclosure and placebo were subjected to forced degradation conditions of acid, base, heat and oxidation by placing 25 mgs of sample into individual amber scintillation vials and prepared and tested for acid, base, heat and oxidative stress as described below.

TABLE 11

| Type | Conditions | Stressed Sample Preparation |
|---|---|---|
| Acid | 0.5N HCl for 27 hrs | 3 mL of O.5N HCl was added to each vial and reaction as allowed to proceed at room temperature for 27 hr. Next, 3 mL of 0.5N NaOH was added to the vial to neutralize the solution. The solution was diluted with methanol and (Z)-endoxifen was measured in the diluted solution by HPLC-UV |
| Base | 0.5N NaOH for 27 hrs | 3 mL of O.5N NaOH was added to each vial and reaction as allowed to proceed at room temperature for 27 hr. Next, 3 mL of 0.5N HCl was added to the vial to neutralize the solution. The solution was diluted with methanol and (Z)-endoxifen was measured in the diluted solution by HPLC-UV |
| Heat | 105° C. for 51 hrs | The vials were heated in an oven at 105° C. for 51 hrs. after 51 hrs, the vials were removed from the oven and cooled to room temperature. The methanol was used to transfer the sample to a volumetric flask and further dilute the sample and mixed well. (Z)-endoxifen was measured in the diluted solution by HPLC-UV |
| Oxidation | 50% $H_2O_2$ for 51 hrs | 3 mL of 50% $H_2O_2$ was added to the vials and the reaction was allowed to proceed at room temperature for 51 hrs. Next, 3 mL of distilled water was added into the vial to the solution. The solution diluted with methanol and mixed well. (Z)-endoxifen. |

TABLE 12

Chromatographic retention time

| Sample | Retention time | Tailing factor | Resolution |
|---|---|---|---|
| (Z)-endoxifen API | 15.117 | 1.88 | 1.04 |
| Tablet | 15.946 | 0.89 | 3.61 |
| Placebo | No peaks | No peaks | No peaks |

TABLE 13

Results-Forced Degradation and Stability

| Type | Conditions | (Z)-endoxifen API % degradation | Placebo % degradation | Tablet % degradation |
|---|---|---|---|---|
| Acid | 0.5N HCl for 27 hrs | No degradation | No degradation | 13.98% |
| Base | 0.5N NaOH for 27 hrs | 0.12% | No degradation | 64.35% |
| Heat | 105° C. for 51 hrs | No degradation | NA | NA* |
| Oxidation | 50% H2O2 for 51 hrs | 74.04% | NA | NA* |

*NA = Not available

The results show that forced degradation conditions as used in the Table 12 above did not produce sufficient degradation of the (Z)-endoxifen API in the tablet except for the oxidation conditions. Exposure to 50% $H_2O_2$ for 51 hours caused significant degradation to the (Z)-endoxifen API.

Stability. Stability of the sustained release compositions (e.g., in the form of enteric coated delayed release tablets), placebo and API at 40° C.±2° C./75%±5% RH and at 25±2° C./60%±5% RH were stable for at least 3 m. Stability of the enteric coated delayed release tablets, Placebo and API will be determined for 40° C.±2° C./75%±5% RH) at time points 0, 1, 2, 3, 6 months and at ambient temperature (25±2° C./60%±5% RH) at time points 0, 1, 3, 6, 9, 12, 18, and 24 months. Release testing will be considered as Time Point 0, and will be performed for the remaining time points. Microbial enumeration testing (MET) will be performed for the remaining time points.

Example 8

A Phase I, Randomized, Double-Blinded, Placebo Controlled, Safety and Pharmacokinetic Study of (Z)-Endoxifen in Healthy Female Volunteers The primary objective of the study was to determine and compare the pharmacokinetics of a single oral dose of a previously studied oral (Z)-endoxifen capsule with a sustained release composition in the form of an enteric coated delayed release (Z)-endoxifen tablet ("tablet") in healthy female volunteers. Based on results from Part A (single administration dose, SAD), a multiple dose administration (MAD) in Group A (capsule) and Group B (tablet) or Group B alone was initiated. A secondary objective of the study was to assess the safety and tolerability of each of the oral presentation groups and to assess and compare the side effects associated with (Z)-endoxifen (capsule) or the enteric coated delayed-release (Z)-endoxifen tablet using a questionnaire.

A total of 24 healthy female subjects aged ≥18 years and ≤65 years (inclusive) at the time of screening were randomly assigned and enrolled into two groups (each group n=12) in double-blinded fashion and received the study drug by once daily oral administration. Subjects in Group 1 received either a 4 mg of (Z)-endoxifen capsule (n=9) or a placebo capsule (n=3) whereas subjects in Group 2 received either a 4 mg of (Z)-endoxifen tablet (n=9) or a placebo tablet (n=3). Both groups were dosed in the SAD phase of the study. The safety and PK results from both groups were reviewed to determine if both Groups 1 and 2 were to be dosed in the MAD phase of the study, or if only Group 2 (tablets) were to be dosed in the MAD phase. If the SAD PK results showed equivalence for capsule and tablet, only the tablet group 2 would be dosed in the MAD phase. The subjects then received 14 daily doses in the MAD. Subjects were not required to take the drugs with food.

Healthy females were screened within 28 days prior to commencement of dosing.

Subjects were admitted to the clinical facility on Day 1 for up to 3 days. The first dose of the study drug (active or placebo) was administered on Day 1. Following completion of all safety assessments and sampling for PK analyses, subjects were discharged from the clinical facility on Day 2. Days 2 to 25 were study drug free or daily dosing pause. A safety summary and up to day 6 post dose, PK data were analyzed (blindedly) and reviewed prior to initiation of the MAD regimen in one or both groups.

Each participant returned to the clinical facility for PK blood draws, and safety assessments on study days 4, 6, and 15.

MAD regimen started on Day 26. Depending on the outcome of the safety and PK review, wither Group 1 or both Groups 1 and 2 were to be dosed in the MAD part of the study starting on Day 26. Based on the safety and PK review, both Groups 1 and 2 were dosed in the part of the study starting on Day 26. Subjects in MAD part of the study commenced daily oral administration of the study drug for 14 consecutive days (Days 26 to 39). Subjects were supplied with study drug and instructed to self-administer each morning on empty stomach.

Prior to dose administration on Days 26 and 32, subjects visited the clinical facility for PK blood draws and safety assessments.

Day 39 was the last day of study drug administration. On Day 39, each subject returned to the clinical facility prior to dose administration and were confined to the facility until Day 40 to allow for collection of blood for PK and safety assessment. Subjects were discharged on Day 40 and returned for blood collection for PK and safety assessment on study Days 42, 44, and 46.

A study diary was provided to each participant for the purpose of recording study drug administration (date and time) and adverse events.

Subject's medical history, including evaluation of any on-study adverse events and concomitant medication use was assessed.

Study assessments included taking the subjects' medical history, including evaluation of any on-study adverse events and concomitant medication use; height and weight; physical examination; periodic vital signs (body temperature, heart rate, respiratory rate, blood pressure); periodic 12-lead ECGs. Laboratory tests included hematology, coagulation, urinalysis, serum chemistry, virology, illicit drug screen, alcohol breath test, and pregnancy test.

Specific assessment to evaluate treatment safety included the following: the frequency and type of adverse events, clinical laboratory testing, 12-lead-ECGs and vital signs. A modified FACTES® scoring questionnaire was used to assess symptomatology.

Pharmacokinetics:

SAD: Days 1-2 (during confinement period): Blood was drawn for PK analysis as follows: Day 1 pre-dose, and 0.5, 1, 2, 3, 4, 6, 8, 10, 12 and 24 hours (Day 2) following study drug administration (post dose).

Safety and PK samples was collected during the daily dosing pause on Days 4, 6, 15, and 22.

MAD: Day 26 pre-dose and on Day 32 pre-dose: safety and PK samples was collected. On Days 39-40 during the confinement period: Blood was drawn for PK analysis as follows: Day 39 pre-dose, and 0.5, 1, 2, 3, 4, 6, 8, 10, 12 and 24 hours (Day 40) following study drug administration (post dose). Blood samples was collected following the conclusion of the active study drug administration period for PK analysis on Days 41 (48 hours post Day 39 dose), 42 (72 hours post Day 39 dose), 44 (120 hours post Day 39 dose) and 46 (168 hours post Day 39 dose). Pharmacokinetic parameters determined using Phoenix WinNonlin 8.1. All times used in the calculations of PK parameters were the actual elapsed time from most recent treatment administration, with the exception of pre-dose data which was given the nominal time of 0.00 hr.

One participant withdrew from the study for non-drug-related reasons at the end of SAD part of the study and completed end of Study visit. This participant was replaced by another participant who completed the MAD phase the study only.

Results: The study was conducted as described above and the results are provided below.

Figure 15A:
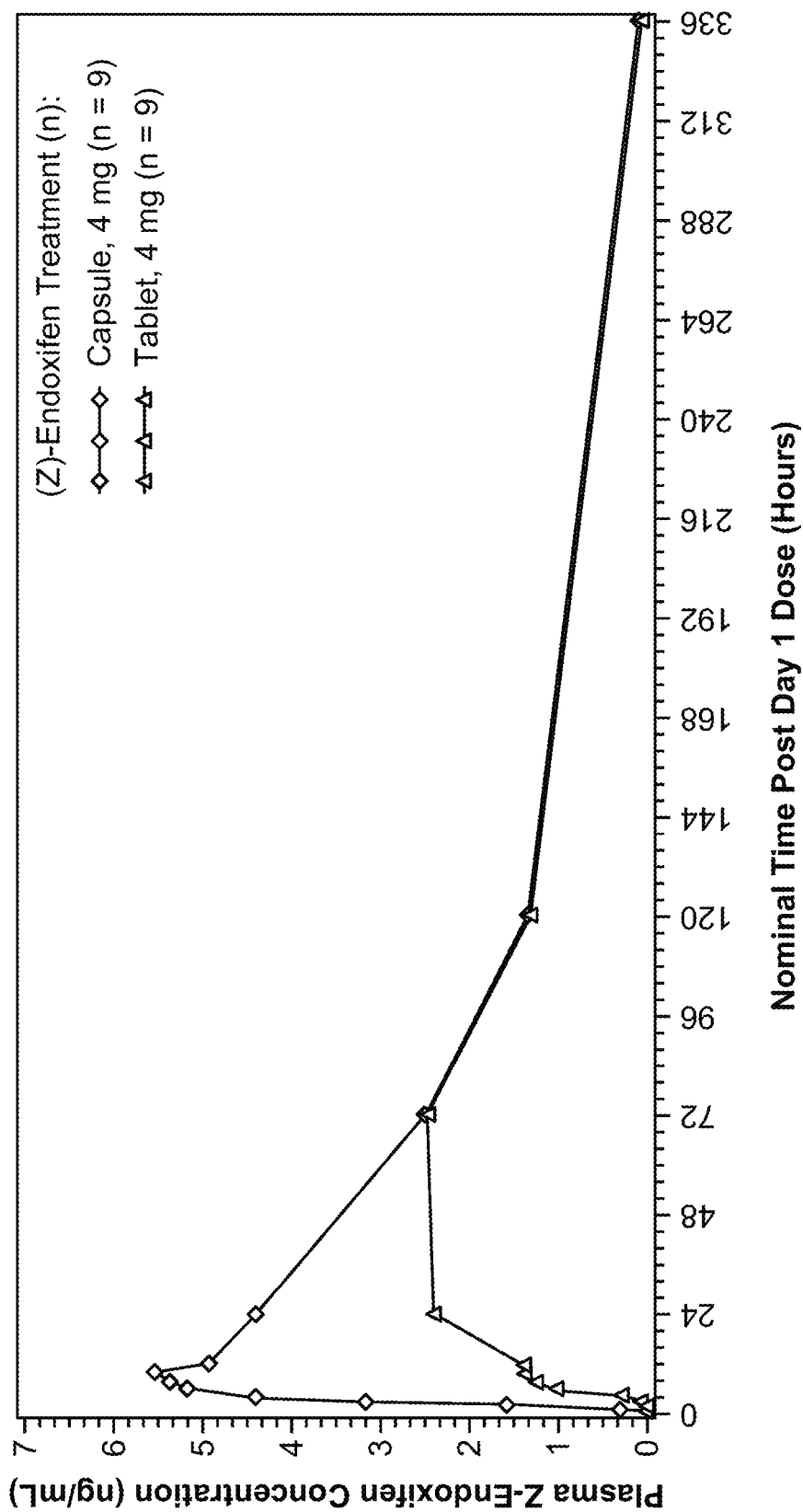
FIG. 15A shows on a linear scale the mean plasma concentrations of (Z)-endoxifen in fasting subjects orally administered a single dose of either a 4 mg delayed release (Z)-endoxifen capsule (Group 1) or a 4 mg enterically coated sustained release tablet having a tablet hardness 13 Kp (Group 2) from time of dose (hour 0) to 336 hours post dose. Mean plasma concentration reflects the uptake and systemic exposure of the subjects to (Z)-endoxifen in the single administration dose phase of the study described in Example 8 as measured in plasma of the subject using a validated HPLC-MS method.
Figure 15B:
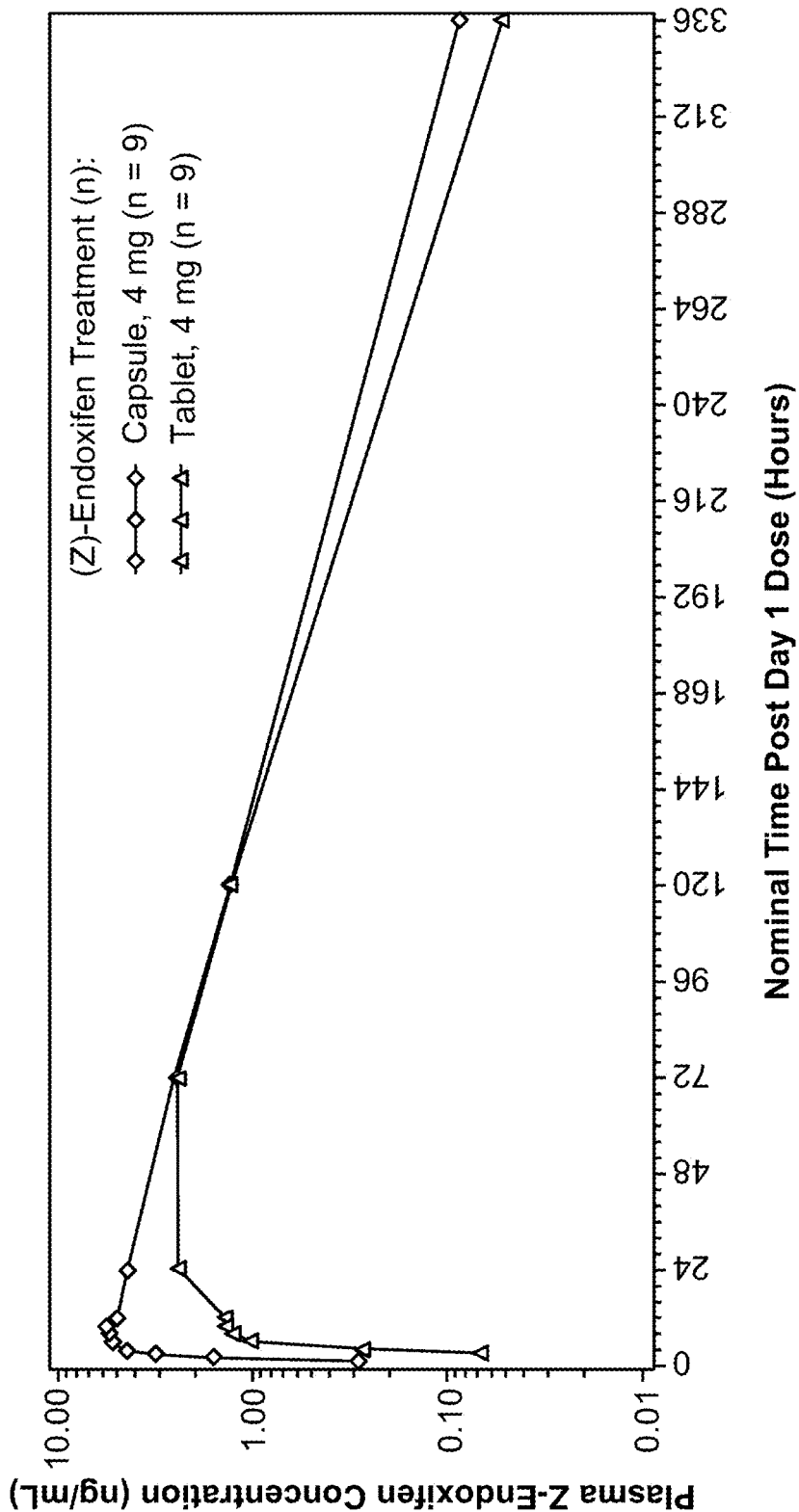
FIG. 15B shows on a semi-logarithmic scale the mean plasma concentrations of (Z)-endoxifen in fasting subjects orally administered a single dose of either a 4 mg delayed release (Z)-endoxifen capsule (Group 1) or a 4 mg enterically coated sustained release tablet having a tablet hardness 13 Kp (Group 2) from time of dose (hour 0) to 336 hours post dose. Mean plasma concentration reflects the uptake and systemic exposure of the subjects to (Z)-endoxifen in the single administration dose phase of the study described in Example 8 as measured in plasma of the subject using a validated high-performance liquid chromatography with mass spectrometry (HPLC-MS) method.

Pharmacokinetics. Mean plasma (Z)-endoxifen concentrations over time after single dose of each formulation in the single administration dose (SAD) regimen or phase of the study is shown in FIG. 15. Results show that (Z)-endoxifen is released from the 4 mg tablets (13 Kp hardness) and appears in subjects' blood primarily as (Z)-endoxifen as detected by the validated HPLC-MS method, peaking between 24 hr to 72 hours, and is still present at 120 hr, i.e., 5 days post-dose at a level that is comparable with the level at about 8 hour post-dose (FIG. 15). (Z)-endoxifen was detectable at 270 hours (approximately 5 half-lives of (Z)-endoxifen) and at 336 hours at the end of the time periods measured (FIG. 15). Subjects' biological samples, serum and plasma isolated from subject's blood, were both tested for (Z)-endoxifen and (E)-endoxifen. (E)-endoxifen levels were undetectable at all the times studied (data not shown). Mean serum (Z)-endoxifen concentrations were consistently approximately 1.1-fold greater than time-point matched mean plasma concentrations.

Figure 16A:
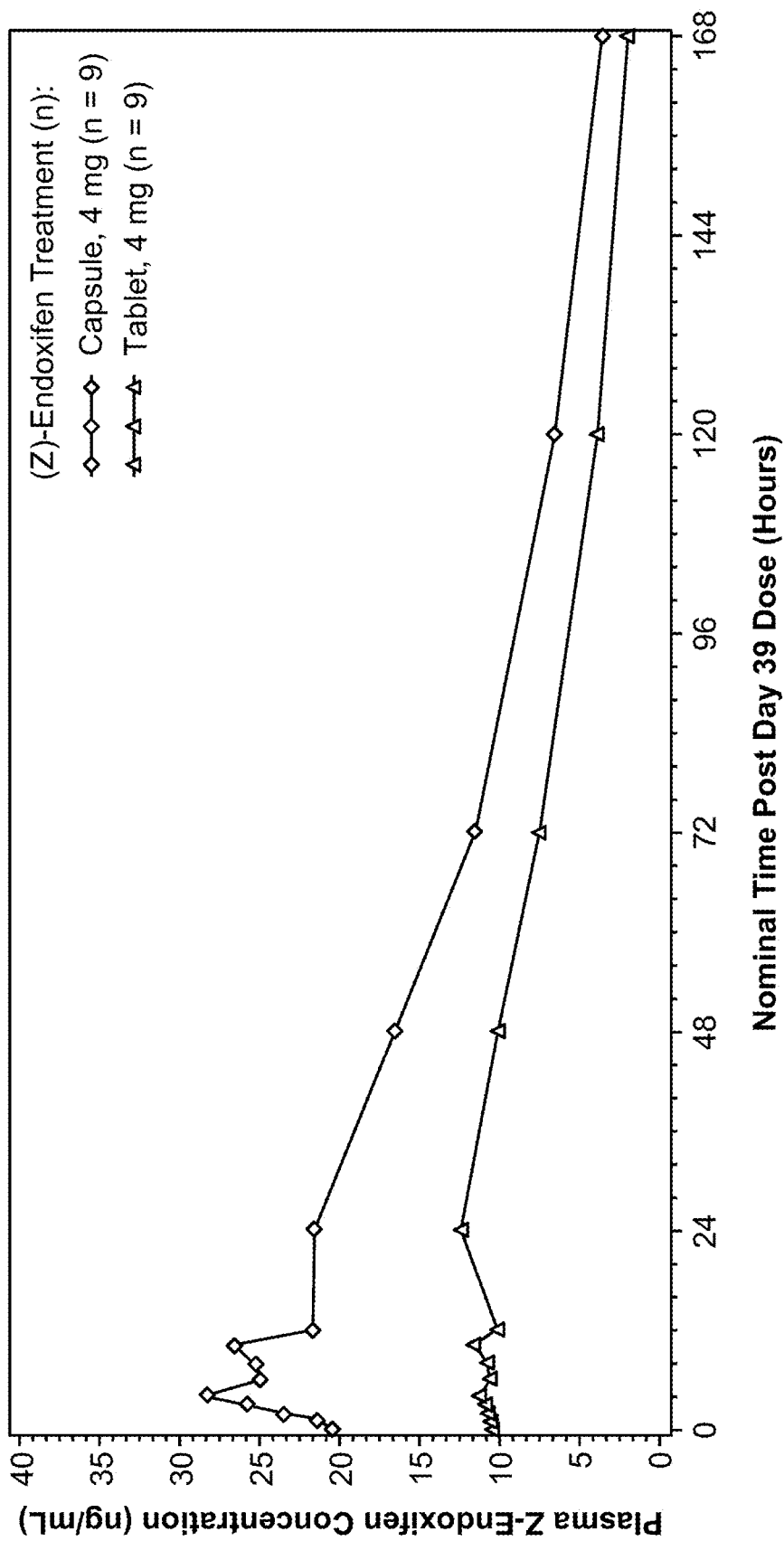
FIG. 16A shows on a linear scale the mean plasma concentration of (Z)-endoxifen in fasting subjects orally administered with a daily dose for 14 consecutive days of either a 4 mg delayed release (Z)-endoxifen capsule (Group 1) or a 4 mg enterically coated sustained release tablet having a tablet hardness 13 Kp (Group 2) in the multiple administration dose (MAD) phase of the clinical study described in Example 8. Day 0 is day 26 of the clinical study of Example 8. Blood samples were drawn between approximately 10 mins to an hour prior to dosing subjects on Day 26 of the study (Day 0 of FIG. 16), Day 32, and Day 39, and at 1, 2, 3, 4, 6, 8, 10, 12, 24, 48, 72, 120 and 168 hours post dose on Day 39 of the study and plasma (Z)-endoxifen and (E)-endoxifen were measured in the plasma of the subject using a validated HPLC-MS method.
Figure 16B:
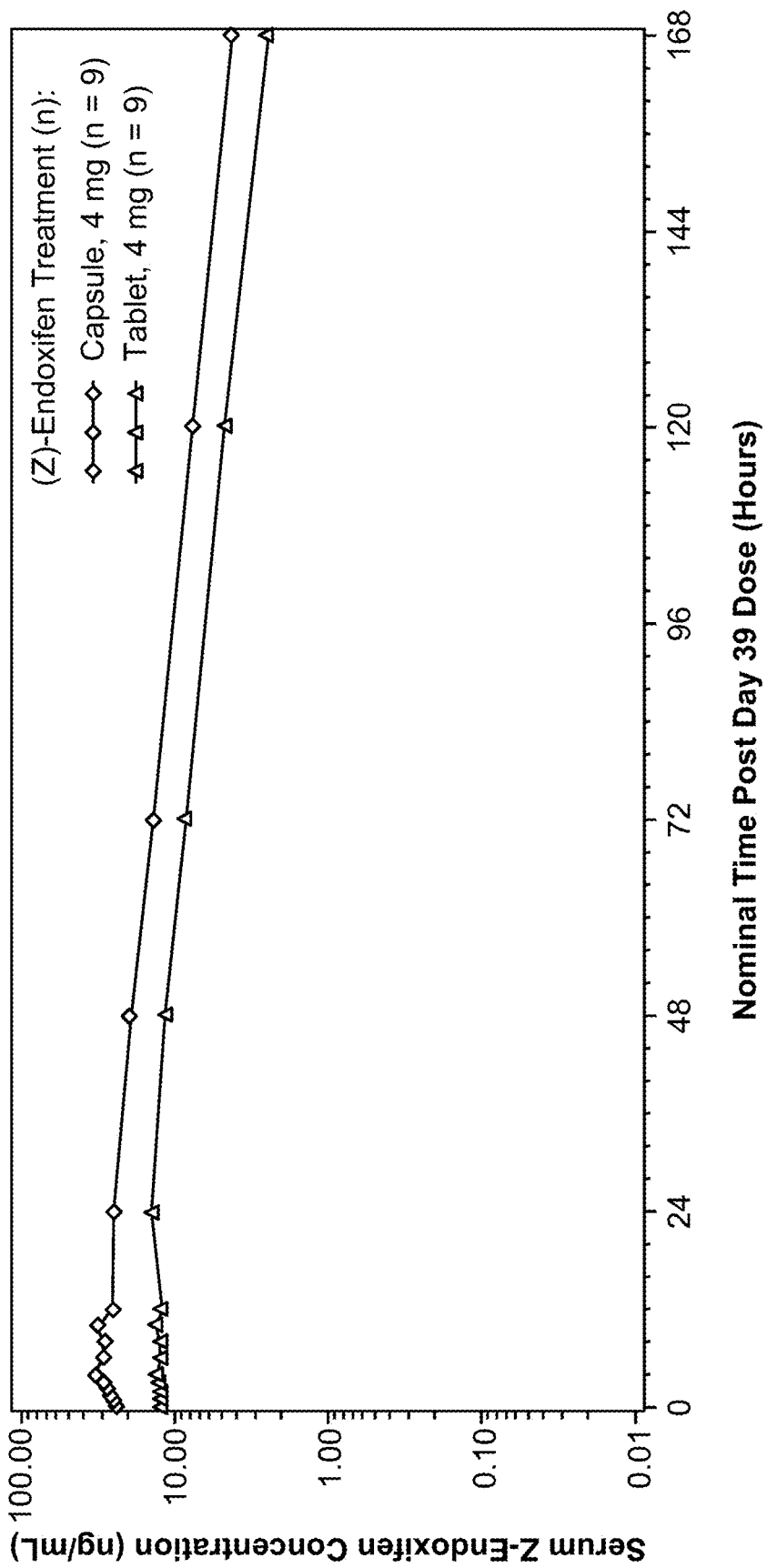
FIG. 16B shows on a semi-logarithmic scale the mean plasma levels of (Z)-endoxifen in fasting subjects orally administered with a daily dose for 14 consecutive days of either a 4 mg delayed release (Z)-endoxifen capsule (Group 1) or a 4 mg enterically coated sustained release tablet having a tablet hardness 13 Kp (Group 2) in the multiple administration dose (MAD) phase of the clinical study described in Example 8.
Figure 17:
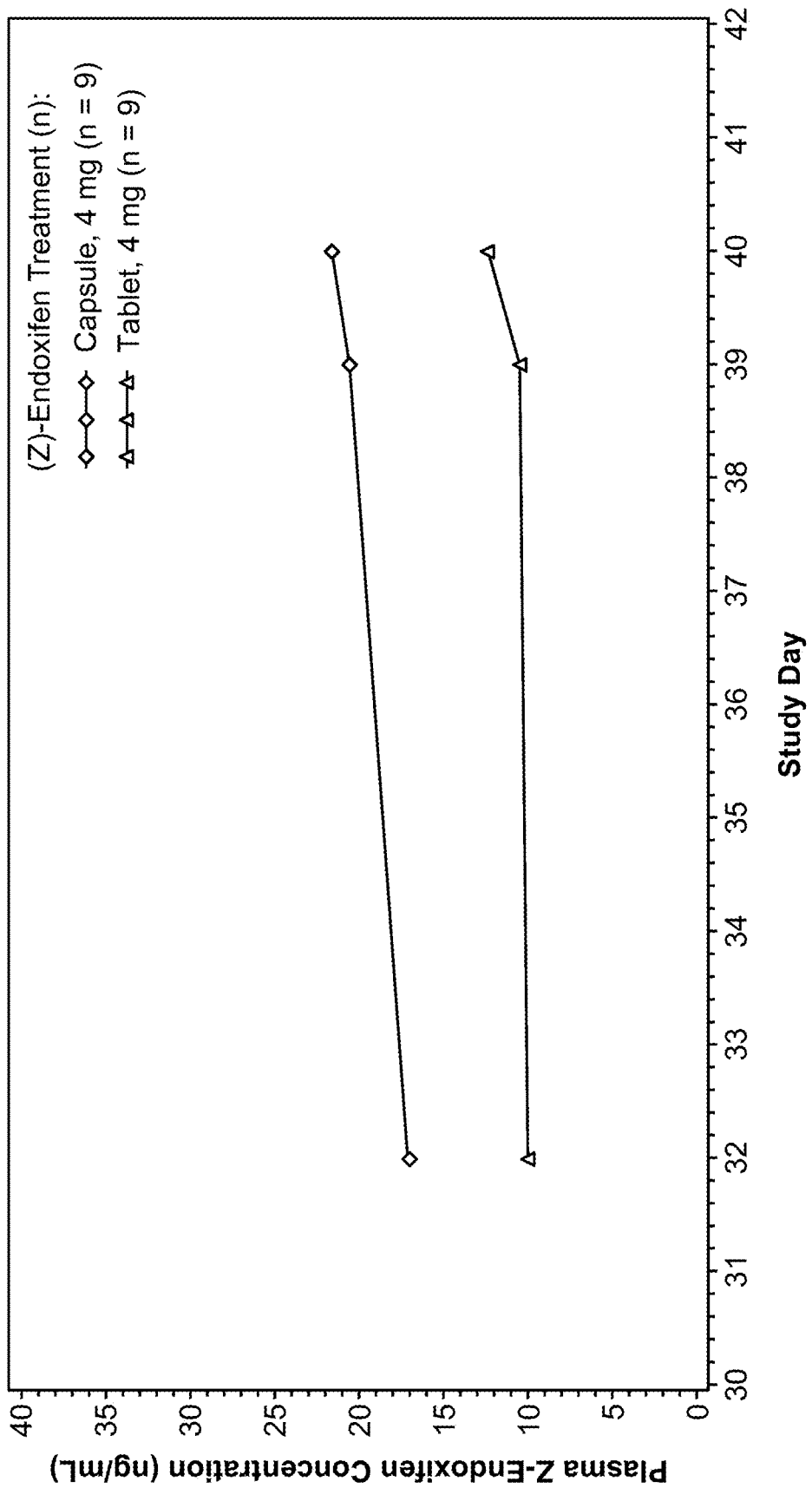
FIG. 17 shows on a linear scale the mean plasma trough concentration of (Z)-endoxifen in fasting subjects orally administered with a daily dose for 14 consecutive days of either a 4 mg delayed release (Z)-endoxifen capsule (Group 1) or a 4 mg enterically coated sustained release tablet having a tablet hardness 13 Kp (Group 2) in the multiple administration dose (MAD) phase of the clinical study described in Example 8.

Mean plasma and mean serum concentrations of (Z)-endoxifen over time after 14 day consecutive days of once-daily (Z)-endoxifen dosing (i.e., after last dose of study day 39) are shown in FIG. 16A and FIG. 16B. Plasma (Z)-endoxifen level was below the detection levels by Day 26 (600 hours post-dose) by the time of beginning of multiple administration dose (MAD) phase (FIG. 16A). Subjects' biological samples, serum and plasma isolated from subject's blood, were both tested for (Z)-endoxifen and (E)-endoxifen. (E)-endoxifen levels were undetectable at all the times studied (data not shown). Results thus show that the subjects are exposed to (Z)-endoxifen starting about 3 hours for a period extending to over 270 hours post administration of a single oral dose of the tablet, peaking at about 72 hours post dose. (Z)-endoxifen released from capsules appears in blood (as tested in serum and plasma) peaking from 6 to 12 hours at higher levels as compared to (Z)-endoxifen from table likely to faster dissolution of the capsules. Mean serum (Z)-endoxifen concentrations were consistently approximately 1.2-fold greater than time-point matched mean plasma concentrations. Individual plasma and serum trough concentrations (~24 hours after previous dose) on study days 32, 39 and 40 were determined and mean plasma trough concentrations for the table and the capsule are presented on a linear concentration scale in FIG. 17 showing that the tablet formulation had less mean plasma concentration fluctuation over the inter-dosing interval at steady-state (22.6%) compared with capsules (40.7%).

TABLE 14

Sustained Release and uptake of (Z)-endoxifen from 4 mg Tablet (13 Kp hardness) and 4 mg Capsule-Single Administration Dose (n = 9)-Mean ± SD

| | Tablets (13 Kp hardness) | | Capsules[§] | |
|---|---|---|---|---|
| Time (hr) | Serum (ng/mL) | Plasma (ng/mL) | Serum (ng/mL) | Plasma (ng/mL) |
| Pre-Dose | ND[‡] | ND | ND | ND |
| 0.5 | ND | ND | ND | ND |
| 1 | ND | ND | 0.32 ± 0.21 | 0.29 ± 0.2 |
| 2 | ND | ND | 1.74 ± 1.29 | 1.58 ± 1.19 |
| 3 | 0.08 ± 0.17 | 0.07 ± 0.15 | 3.39 ± 2.32 | 3.18 ± 2.27 |
| 4 | 0.31 ± 0.34 | 0.28 ± 0.3 | 4.81 ± 2.83 | 4.41 ± 2.63 |
| 6 | 1.16 ± 0.78 | 1.02 ± 0.69 | 5.69 ± 2.8 | 5.17 ± 2.63 |
| 8 | 1.4 ± 1 | 1.26 ± 0.91 | 5.89 ± 2.87 | 5.37 ± 2.68 |
| 10 | 1.54 ± 1 | 1.38 ± 0.93 | 6.22 ± 3.14 | 5.53 ± 2.81 |
| 12 | 1.63 ± 0.84 | 1.39 ± 0.72 | 5.5 ± 3.23 | 4.93 ± 2.98 |
| 24 | 2.63 ± 0.69 | 2.4 ± 0.64 | 4.77 ± 2.51 | 4.41 ± 2.58 |
| 72 | 2.71 ± 1.11 | 2.47 ± 1.04 | 2.79 ± 1.68 | 2.5 ± 1.46 |
| 120 | 1.46 ± 0.55 | 1.31 ± 0.55 | 1.44 ± 1.03 | 1.32 ± 0.97 |
| 336 | 0.07 ± 0.09 | 0.05 ± 0.09 | 0.099 ± 0.17 | 0.09 ± 0.16 |

[‡]ND = Below the lower limit of quantification (LOQ = 0.1 ng/mL)
[§]Capsule. ≥90% (Z)-endoxifen free base was prepared as disclosed in WO2019051416A1 (Methods for making and using endoxifen).

Briefly, (Z)-endoxifen free base as a dry white-to-off-white powder was formulated as stable free-flowing powder and filled neat into a capsule as an API-in-Capsule oral solid dosage form. 4 mg of endoxifen which was at least 90% (Z)-endoxifen was filled neat in a VCaps® Plus enteric capsule using Xcellodose technology (Capsugel). AIC were of size 0, Swedish orange in color. The VCaps® Plus enteric capsules (Capsugel) are made with gluten free, non-animal self-gelling product hypromellose (methyl and hydroxypropyl mixed ether of cellulose), with low-moisture content that is suitable for moisture-sensitive ingredients such as (Z)-endoxifen. The capsules are coated with an enteric coating designed to achieve intestinal targeting (upper GI and colon), by the method of Cole et al. (Cole et al., Int. Journal of Pharmaceutics Vol. 231 83-95, 2002). Eudragit FS D30 is used as enteric coating for colonic targeted release and Eudragit L30 D55 is used as enteric coating for upper gastrointestinal targeted release.

Results from a separate study with a sustained release tablet in the form of an enteric coated delayed release tablet having a tablet hardness of 5 Kp showed similar (Z)-endoxifen slow and prolonged release profile and mean concentration in the blood as measured in the serum and plasma using the validated HPLC-UV method (data not shown).

TABLE 15

Summary of (Z)-Endoxifen Pharmacokinetic Parameters[‡]-Single Administration Dose (n = 9) Mean ± SD

| | Tablet (4 mg) | | Capsule (4 mg) | |
|---|---|---|---|---|
| | Serum | Plasma | Serum | Plasma |
| $C_{max}$ (ng/mL) | 3.09 ± 1.03 | 2.82 ± 0.97 | 6.79 ± 3.36 | 6.22 ± 3.18 |
| $T_{max}$ (hr) | 50.13 ± 28.43 | 50.13 ± 28.43 | 7.33 ± 2.83 | 6.45 ± 2.79 |
| $AUC_{last}$ (hr * ng/mL) | 367 ± 196 | 312 ± 173 | 494 ± 359 | 453 ± 338 |
| $AUC_{0-168h}$ (hr * ng/mL) | 403 ± 114 | 362 ± 135 | 458 ± 259 | 417 ± 244 |

[‡]Pharmacokinetic parameters determined using Phoenix WinNonlin 8.1. AI

Results from this study and the in vitro drug release testing studies suggest that the rate of absorption in to the blood of the subjects is slower and more sustained in subjects ingesting tablet compared to that in subject ingesting Capsules. Systemic exposure for the tablet formulation was reduced compared with the capsule formulation with a geometric mean ratio (confidence interval) of 0.50 (0.33-0.74) and 0.77 (0.47-1.25) for plasma $C_{max}$ and $AUC_{0-last}$, respectively.

Results from this study are similar to the results observed with a similar study conducted in 12 healthy female volunteers ages ≥18 yrs and ≤65 years wherein 9 of 12 subjects received a single dose of active 4 mg enteric-coated delayed release tablet having a tablet hardness of 5 Kp and 3 subjects received placebo (data not shown).

The appearance of the (Z)-endoxifen in the blood stream of the subjects in Group 1 (Capsule, reference product) and Group 2 (tablet), each group administered with 14 once daily doses of either the active therapeutic agent or placebo starting on Day 26 as described above in the MAD phase of the study, was measured by validated HPLC-MS method using subjects' plasma and serum and pharmacokinetic parameters were determined. Results are provided below.

TABLE 16

Summary of Pharmacokinetics Parameters of Multiple Administration Doses (14 daily doses) of Tablet and Capsule (n = 9)-Mean ± SD

|  | Tablet | | Capsule | |
|---|---|---|---|---|
|  | Serum | Plasma | Serum | Plasma |
| $C_{min}$ (ng/mL) | 11.54 ± 2.7 | 9.83 ± 2.73 | 23.04 ± 7.88 | 19.62 ± 6.96 |
| $C_{max}$ (ng/mL) | 14.41 ± 3.17 | 12.24 ± 2.76 | 33.52 ± 11.89 | 28.96 ± 11.79 |
| $T_{max}$ (hr) | 5.13 ± 3.47 | 7.02 ± 7.12 | 5.34 ± 2.66 | 6.45 ± 2.97 |
| $C_{average}$ (ng/mL) | 13.09 ± 3.19 | 11.10 ± 2.87 | 27.19 ± 10.61 | 23.29 ± 9.75 |
| $AUC_{tau}$ (hr * ng/mL) | 314 ± 77 | 266 ± 69 | 653 ± 255 | 559 ± 234 |
| $AUC_{last}$ (hr * ng/mL) | 1383 ± 442 | 1181 ± 406 | 2397 ± 1146 | 2043 ± 1016 |
| Kel ($hr^{-1}$) | 0.013 ± 0.002 | 0.014 ± 0.002 | 0.013 ± 0.003 | 0.013 ± 0.003 |
| $t_{1/2}$ (hr) | 55.03 ± 11.68 | 52.26 ± 11.85 | 54.10 ± 11.32 | 53.81 ± 10.48 |
| CL/F (L/hr) | 13.30 ± 2.71 | 15.75 ± 3.33 | 7 ± 2.92 | 8.27 ± 3.55 |
| $V_z/F$ (L) | 1068 ± 406 | 1205 ± 506 | 529 ± 181 | 621 ± 217 |
| Fluctuation (%) | 22.8 ± 8.8 | 22.6 ± 11.2 | 39.6 ± 8.9 | 40.7 ± 11.9 |
| AI_AUC | 3.94 ± 0.71 | 3.68 ± 0.85 | 5.69 ± 1.83 | 5.3 ± 1.65 |
| AI_$C_{max}$ | 4.93 ± 1.3 | 4.58 ± 1.16 | 6.01 ± 2.49 | 5.77 ± 2.49 |

Pharmacokinetic results (Mean ± SD) from the MAD phase of study are shown in Table 16.

FIG. 16A and FIG. 16B show the mean concentration of (Z)-endoxifen in the plasma of each group in the MAD phase on the linear and semilogarithmic scale. The time to achieve steady state levels of plasma and serum (Z)-endoxifen was approximately 14 days. Results from the MAD phase show that administration of multiple doses (14 once daily 4 mg doses) maintains approximately 13 ng/mL (Z)-endoxifen (>30 nM) in the blood of subjects (FIG. 16A and FIG. 16B).

Relative bioavailability of the drug in plasma and serum from the Tablet and the Capsules was calculated using least square linear regression analysis. Results from bioavailability studies performed using plasma are shown in the Table 17 below. The systemic exposure for the tablet formulation is reduced compared with tablet formulation with a geometric mean ratio (confidence interval) of 0.44 (0.35; 0.56) and 0.50 (0.30; 0.65) for plasma $C_{max}$ and $AUC_{tau}$, respectively.

TABLE 17

Relative Bioavailability Comparison of Tablet (Test Product) and Capsule (Reference Product)

| Parameter (units) | LS Mean‡ Tablet (test product) | LS Mean Capsule (reference product) | Ratio (Tablet/Capsule) |
|---|---|---|---|
| Single Dose (Plasma) | | | |
| $C_{max}$ (ng/mL) | 2.68 | 5.4 | 0.5 |
| $AUC_{last}$ (hr * ng/mL) | 279 | 365 | 0.77 |
| Multiple Dose-Plasma (14 daily doses) | | | |
| $C_{max}$ (ng/mL) | 12 | 27.3 | 0.44 |
| $AUC_{last}$ (hr * ng/mL) | 1135 | 1848 | 0.61 |
| $AUC_{tau}$ (hr * ng/mL) | 260 | 520 | 0.5 |

‡LS Mean = Least Square Mean.

Overall, the PK results from the study show unexpectedly prolonged, i.e. sustained, release of (Z)-endoxifen from the tablet formulation with a median time to maximum plasma concentration that was substantially greater for the tablet (SAD=73.12 hr; MAD=4 hr) compared with the capsule formulation (SAD=6 hr; MAD=4 hr) and substantially reduced systemic exposure after single and multiple dose administration. Approximate steady-state levels are reached by about 14 days of once-daily (Z)-endoxifen dosing for the table and at steady state, the tablet formulation showed less concentration fluctuation over the inter-dosing interval compared with capsule administration, as shown in Table 16. The plasma (Z)-endoxifen concentration were highly correlated with serum concentrations with mean serum concentration generally being 1.1 to 1.2-fold greater than time-point matched mean plasma concentrations for both single and multiple dose administration. Consistent with the differences observed between plasma and serum (Z)-endoxifen concentrations, serum exposure PK parameters (e.g., $C_{max}$ and AUCs) were 1.1 to 1.2-fold greater than corresponding parameter values for both single and multiple dosing.

Safety. There were no unexpected or serious adverse events, no clinically significant adverse safety signals and no clinically significant adverse events in subjects receiving the tablets. There were no apparent differences in safety between (Z)-endoxifen administered as capsule or tablet, and between (Z)-endoxifen and placebo. No subjects withdrew or were removed from the study due to skin rashes and irritation or other adverse effects or side effects.

Tolerability. The tablet was well tolerated by each subject throughout of the study with some subjects reporting in their daily reports during the MAD phase of the study experiencing mild vasomotor symptoms (hot flashes, night sweat, cold sweat, the sensation of "feeling hot" etc.) and headache and nausea.

In the single dose administration phase of the study, hot flash was reported in 2 of 18 subjects (11%) following (Z)-endoxifen (2 subjects following capsule) and in no subjects following (Z)-endoxifen tablets. Hot flash was reported by one subject taking placebo. In the multiple dose study administration phase of the study, hot flash was reported in 4 of the 18 subjects (22%) following (Z)-endoxifen (1 subject following tablet and 3 subjects following capsule) and in 2 of the 6 subject (33%) following placebo. The intensity of the hot flash in subjects taking the tablets and capsules during this study was mild. No subject taking tablets or capsule experienced hot flashes of moderate or high intensity.

Night sweats was reported in the multiple dose administration phase of the study in 2 of 19 subjects (11%) following (Z)-endoxifen (2 subjects following capsule), in no subjects following (Z)-endoxifen tablet or placebo. Results thus show that the intensity and frequency of vasomotor symptoms in these subjects was lower than the reported percentage (78%) of subjects experiencing vasomotor symptoms of mild, moderate and high intensities experienced upon ingesting tamoxifen (Mortimer et al). This is striking and surprising in light of the reported moderate to high intensity of vasomotor symptoms such hot flashes experienced by subjects taking tamoxifen. One of skill in the art could not have predicted this qualitative effect of the sustained release tablets.

Without wishing to be bound by any mechanism of action or any other theory, the present disclosure shows that the sustained release tablets of the present disclosure are an important improvement in development of compositions comprising (Z)-endoxifen, or polymorphs or salts there in the reduction of vasomotor symptoms and tolerance in subjects administered with such sustained release tablets.

Example 9

A Phase I, Randomized, Double-Blinded, Active Controlled, Safety and Pharmacokinetic Study of Sustained Release (Z)-Endoxifen free base in Subjects with Bipolar Disorder A randomized double blinded controlled study will be performed in physically healthy subjects with a mood disorder and will be dosed with varying levels of (Z)-endoxifen for a specified period and moods assessed for effectiveness. The primary objective of the study is to determine and compare the pharmacokinetics of at least two fixed oral doses of a sustained release oral (Z)-endoxifen free base compositions in the form of an enteric coated delayed release tablet ("Tablet") with extended release divalproex (Depakote) (1000 mg) ("Control") and evaluate efficacy and safety of enteric coated delayed release (Z)-endoxifen in bipolar disorder, BPD I, patients with current manic or mixed episode. patients who are diagnosed of BPD I.

Physically healthy male and female subjects, 18 to 65 (both inclusive) years of age who display an acute manic or mixed episode (with or without psychotic features) according to DSM-IV-TR will be selected for the study. Last intake of the medication(s) for BPD I will be within 2-7 days prior to randomization, depending on the individual drug's plasma half-life. All psychotropic medications except, if taking, benzodiazepines (lorazepam/diazepam only) will be discontinued at least 2 days before randomization. The male patients of child-begetting potential and female patients of child-bearing potential, who practice adequate contraception, will be enrolled in the study. The patients with Young Mania Rating Scale (YMRS) total score of 20 and a score of 4 on the Clinical Global Impressions-Severity of Illness (CGI-S) Scale at the time of screening and at randomization (baseline) will be selected.

Before randomization to the 3-week double-blind treatment phase, the subjects will undergo a screening and a washout period of 1 week after signing a written informed consent. Patients entering the study will be randomly assigned 2:1 (endoxifen:divalproex) in randomized and double-blinded fashion for 21 days. Endoxifen will be given orally as enteric coated sustained release tablets at two fixed doses (2 mg/day and 4 mg/day) and extended release tablets of divalproex 1,000 mg for the treatment of BPD I.

Study assessments include taking the subjects medical history, including evaluation of any on-study adverse events and concomitant medication use; height and weight; physical examination; periodic vital signs (body temperature, heart rate, respiratory rate, blood pressure); periodic 12-lead ECGs. Laboratory tests included hematology, coagulation, urinalysis, serum chemistry and biomarker analysis (e.g., CYP2D6, BRCA1/2, Ki-67, tamoxifen metabolites, etc.). Specific assessments to evaluate treatment safety includes the following: the frequency and type of adverse events, clinical laboratory testing, 12-lead ECGs and vital signs. A modified FACT-ES® scoring questionnaire will be used to assess symptomatology.

Pharmacokinetics

Mean and individual (Z)-Endoxifen serum concentration-time curves will be tabulated for each dose cohort, and presented graphically with concentration displayed on a linear and logarithmic scale. Pharmacokinetic parameters will be determined for each participant and summarized by cohort using descriptive statistics (arithmetic means, standard deviations, coefficients of variation, sample size, minimum, maximum and median). In addition, geometric means will be calculated for AUC and $C_{max}$. Analyses using linear models will be performed to assess dose proportionality (both after a single dose and multiple dose), time dependence and accumulation (oral multiple dose), and attainment of steady state (multiple dose).

Parameters determined for the first and last dose includes time to maximum concentration ($T_{max}$), maximum concentration ($C_{max}$), area under the concentration-time curve from time 0 to 24 hours following drug administration ($AUC_{0-24\,h}$), terminal elimination rate constant (kel), terminal half-life ($t_{1/2}$), terminal clearance (CL/F) and volume of distribution ($V_d/F$). Area under the concentration-time curve from time 0 to infinity ($AUC_{0-inf}$) was also determined for the first dose, on Day 1.

The pharmacokinetic parameters will be determined using non-compartmental method(s). Descriptive statistics of pharmacokinetic parameters include mean, standard deviation (SD), and coefficient of variation (CV), minimum (min) and maximum (max). Dose related trends in pharmacokinetic parameters will be assessed.

Mean and individual endoxifen serum concentration-time curves will be tabulated for each dose cohort. Pharmacokinetic parameters will be determined for each subject and summarized by cohort using descriptive statistics (arithmetic means, SD, CV, sample size [N], min, max and median). In addition, geometric means were calculated for AUC and $C_{max}$. Analyses using linear models will be performed to assess dose proportionality (both after a single dose (oral) and multiple dose (topical and oral)). Statistical analysis will be performed on the pharmacokinetic parameters using SAS v9.3 and Phoenix WinNonLin version 7.0 or higher.

Safety endpoints will be summarized by dose cohort, with Control pooled across cohorts. Treatment-emergent AEs will be coded using the latest version of MedDRA by System Organ Class (SOC) and Preferred Term, classified from verbatim terms. The incidence and frequency of AEs, and SAEs, will be summarized by cohort according to SOC and Preferred Terms, and by severity and relationship. The duration of AEs will be determined and included in listings, along with the action taken and outcome. Vital signs, ECG and safety laboratory parameters will be summarized at each scheduled time point using descriptive statistics. Post-dose assessments will be compared with baseline measurements. The incidence of laboratory abnormalities will be summarized.

Example 10

A Phase 2 Clinical Trial of Oral Endoxifen for Treatment of Breast Cancer

A phase 2 clinical trial of (Z)-endoxifen for treatment of breast cancer was performed. Subjects with invasive breast cancer were administered (Z)-endoxifen orally prior to undergoing mastectomy or lumpectomy. The effect of pre-operative oral (Z)-endoxifen treatment on clinical response measured by Ki-67 expression levels was assessed. Ki-67 expression levels were used as a measure of tumor cell proliferation in the subjects. The purpose of this study was to determine the effect of orally administered endoxifen on breast cancer tumor cell proliferation.

Secondary effects of orally administered (Z)-endoxifen were also assessed, namely the effect of pre-operative (Z)-endoxifen treatment on the expression levels of estrogen receptor and progesterone receptor. Additionally, the safety and tolerability of (Z)-Endoxifen in breast cancer patients administered at 4 mg/day for a minimum of 14 to 40 days was evaluated, and expression changes in Ki-67, ER and PgR to (Z)-Endoxifen blood concentration were correlated. Additional exploratory objectives including assessing the effect of pre-operative (Z)-Endoxifen treatment on PCNA (S phase), phospho-Histone H3 (M phase), p16 and p21 (senescence), Beta-Galactosidase (senescence), and TUNEL (apoptosis) markers, and identifying tumor RNA expression changes using RNA sequence.

Subjects were selected who had received an invasive breast cancer diagnosis that required a mastectomy or lumpectomy, in which the cancer was Estrogen Receptor (ER) positive and Human Epidermal growth factor Receptor 2 (HER2) negative.

TABLE 18

Summary of Clinical Trial Enrollment Criteria

Inclusion Criteria

Female, 18 years of age or older

Histologically confirmed invasive breast cancer (stage 1 or 2, ER+ low-grade)

Pathological invasive breast cancer diagnosis requiring mastectomy or lumpectomy Newly diagnosed, tamoxifen naïve Scheduled to undergo mastectomy or lumpectomy for invasive breast cancer at no less than 15 days from commencement of treatment with the study drug Estrogen Receptor positive biopsy, as determined from a biopsy specimen obtained no more than 3 months prior to entry ($\geq 1\%$ of the cells by IHC);

HER2 negative (by Immunohistochemistry and/or Fluorescence in Sit Hybridization (FISH))

Eastern Cooperative Oncology Group (ECOG) score 0-1, an estimated life expectancy of at least 12 months Absolute neutrophil count (ANC) $\geq 1500/\mu L$ Platelets $\geq 100,000/\mu L$ Hemoglobin $\geq 9.0$ g/dL Creatinine $\leq 2$ times upper limit of normal Bilirubin $\leq 2$ times upper limit of normal Transaminases (Aspartate aminotransferase (AST)/Serum Glutamic Oxaloacetic Transaminase (SGOT) and Alanine aminotransferase (ALT)/Serum Glutamate Pyruvate Transaminase (SGPT)) $\leq 2.5$ times upper limit of normal Women with child-bearing potential must have a negative pregnancy test (urine or serum) within 7 days of drug administration and agree to use an acceptable method of birth control to avoid pregnancy for the duration of the study Provide consent for the collection of biopsy material Able to comprehend and sign the informed consent Subjects were excluded from the study if they had been diagnosed with inflammatory breast carcinoma, had stage IV breast cancer, had been diagnosed with a HER2 positive disease, had palpable nodes or clinical suspicion of axillary node positivity, had received concurrent treatment with another anti-estrogen drug, had an infection including ulcerations and fungal infections in the breast to be studied, had coagulopathies, bleeding diatheses, or thrombocytopenia, was currently using anticoagulants, had Child-Pugh Class C or worse hepatic impairment, had prior radiation to the breast or chest wall, had known severe hypersensitivity to any drugs in the study, were pregnant or lactating, had impaired renal function had impaired cardiac function or history of cardiac problems, had a poor nutritional state, had depressed bone marrow, had a serious infection, had ascites, had pleural effusion, had hepatic disease, positive serology or known active disease due to hepatitis B virus, hepatitis C virus, auto-immune liver disease or sclerosing cholangitis, had positive serology or known active disease due to HIV infection, had a major operation or obvious trauma within 28 days prior to enrollment, were concurrently participating in an experimental drug study, concurrent chemotherapy, history of thromboembolitic events, or any other reason for which the investigator considered the volunteer unsuitable for the study.

Subjects with ER positive invasive breast cancer that were scheduled for mastectomy or lumpectomy were considered for the study. Subjects consenting to the study were screened within 28 days prior to commencement of the dosing. Potential subjects were asked to consent to have tissue sections obtained from the biopsy material used for their immunopathology diagnosis. The biopsy material was used to determine baseline expression levels for Ki-67, ER, PgR and the exploratory markers.

An initial group of six subjects was selected. Subjects visited the clinical facility once within 2 days prior to commencement of treatment for study assessments. Subjects were supplied with study drug and were asked to self-administer daily. A study diary was provided to each subject for the purpose of recording study drug administration (date and time) and any adverse events. All subjects received an oral daily dose of 4 mg/day (Z)-Endoxifen until the day preceding their scheduled surgery and for a minimum of 14-days. Subjects were instructed to take each dose in the morning in a fasted state, defined as no food at least 8 hours prior to study medication through to one hour following study medication. Subjects were instructed to self-administer (Z)-Endoxifen orally with a full cup (approximately 240 mL) of noncarbonated room temperature water (additional water is permitted, if needed). There are no restrictions related to water intake. Consecutive doses were administered 24 (±2) hours apart. If a scheduled dose was missed, the dose could be taken up to 6 hours after the scheduled dose.

Each subject returned to the clinical facility for safety assessments on a day during the week preceding their scheduled surgery. The expression of Ki-67, ER, progesterone receptor (PgR), and other exploratory markers, was measured in tumor tissue obtained during the mastectomy (or lumpectomy) and compared to the expression of these markers in pre-operative baseline biopsy material obtained prior to commencement of study treatment. Pharmacodynamic exploratory markers including Proliferating cell nuclear antigen (PCNA, S phase), phosphor-histone H3 (M phase), p16 and p12 (senescence), beta-galactosidase (senescence), Terminal deoxynucleotidyl transferase dUTP nick end labeling (TUNEL, apoptosis), and RNA sequence were assessed. Ki-67, ER, PgR expression were measured using standard immunopathology techniques, and exploratory markers were measured using established laboratory assays. Endoxifen levels in blood measured in blood drawn prior to dosing on day 14 of study treatment administration. Individual and mean serum and plasma concentrations of Endoxifen were tabulated.

Initial results from the group of six subjects indicated a statistically significant reduction in tumor cell proliferation, as measured by Ki-67 levels, which is the recognized standard measurement of breast cancer cell activity, was reduced by an average of 69% in these subjects. Lower Ki-67 levels have been shown to increase disease-free survival (DFS). The 69% reduction of Ki-67 in the tumors of the patients in the study who received oral Endoxifen prior to surgery is considered large and potentially clinically meaningful. Ki-67 was reduce by more than 50% in every patient, with an average reduction of Ki-67 of 69%. Two-thirds of the patients had high or very high Ki-67 levels (high means ~14% to ~25% and very high means over 40%) prior to taking Endoxifen and all had low (defined as less than ~14%) after Endoxifen treatment. Treatment ranged from 16-40 days, with an average of 22 days. There were no safety or tolerability issues, including vasomotor symptoms such as hot flashes and night sweats, which are often a tolerability challenge for patients on tamoxifen.

TABLE 19

Initial Results of Ki-67 Levels in Subjects Receiving Oral Endoxifen

| Subject | CYP2D6 Type | CYP2D6 Phenotype Interpretation | Number of Days on Endoxifen 4 mg | Pre Endoxifen Ki-67% | Surgery Date | Post Endoxifen Ki-67% | Ki-67% reduction |
|---|---|---|---|---|---|---|---|
| R1001 | *1/*2 | Normal Metaboliser | 21 | 5% | May 23, 2019 | 2% | 60% |
| R1002 | *1/*4 | Low Normal Metaboliser | 23 | 20% | Nov. 21, 2019 | 8% | 60% |
| R1003 | *2/*6 | Low Normal Metaboliser | 17 | 90% | Jan. 3, 2020 | 12% | 87% |
| R1004 | *2/*4 | Low Normal Metaboliser | 17 | 22% | Feb. 14, 2020 | 2% | 91% |
| R1005 | Results Pending from MyDNA | TBD | 40 | 25% | Mar. 26, 2020 | 10% | 60% |
| R1006 | *1/*4 | Low Normal Metaboliser | 16 | 12% | Mar. 5, 2020 | 5% | 58% |
| | | AVERAGE | 22.3 | | | AVERAGE | 69% |

Subsequent results showed an average reduction in tumor cell proliferation, as measured by Ki-67, of about 74% over 22 days of dosing for the six subjects. The reduction was statistically significant (p=0.031). All six subjects (100% of subjects) experienced a significant reduction in Ki-67 following treatment with orally administered endoxifen. Ki-67 was reduced by more than 50% in every patient in the window of opportunity between an initial biopsy and surgery. The average overall reduction in Ki-67 was 74%. Four out of the six subjects had high or very high Ki-67 levels prior to taking endoxifen and had low Ki-67 levels after treatment with endoxifen. Low was defined as <14%, high was defined as about 14-40%, and very high was defined as >40%. Following treatment, all six patients had Ki-67 levels below 25%. Ki-67 is an independent prognostic value for predicting overall survival in ER+ breast cancer patients, and a cutoff of 25% is associated with the greatest risk of death with lower expression rate.

Example 11

Safety, Tolerability, and Pharmacokinetics of (Z)-Endoxifen

The safety, tolerability and pharmacokinetics of (Z)-Endoxifen was assessed in healthy female volunteers (Protocol AG-1001-AU-001). Participants were treated with oral (Z)-Endoxifen (1 mg, 2 mg and 4 mg) once daily for a total of fifteen doses (Days 1, and 8-21).

When administered as a single dose and then daily for 14 days (Z)-Endoxifen was well tolerated. There were no clinically significant safety signals in any subjects receiving (Z)-Endoxifen and generally there were no dose-related or treatment-related trends in any of the safety and tolerability end points. Commonly occurring adverse events (AEs) with a relationship of possible or probable and only reported in participants who received (Z)-Endoxifen included upper respiratory infection, hot flush, abdominal distension, dry mouth and menstruation delayed.

There was dose-proportionality in Concentration maximum (peak) ($C_{max}$) and Area Under Curve (24 hrs.) ($AUC_{24\ hr}$) of (Z)-Endoxifen across the three dose levels used in the study. The mean half-life ($t_{1/2}$) by dose level ranged between 42 and 53 hours. Steady state appeared to be attained after approximately 7 days of once daily dosing. Clinical studies conducted with orally administered Endoxifen are summarized in Table 20.

TABLE 20

Summary of Clinical Studies with Orally Administered Endoxifen

| | | | | | (Z)-Endoxifen | | |
| --- | --- | --- | --- | --- | --- | --- | --- |
| | Dose | | | Patient | Exposure | Plasma | | |
| Compound | mg/day | Regimen | Population | Number | (Patient-Days) | (nM) | Outcomes | Source |
| Endoxifen Citrate | 0.5 | Single Dose | Normal Female Subjects | 8 | 32 | 3.8 | No serious or significant adverse events. No abnormal laboratory parameters, vital signs, or EKG measurements. One adverse event (diarrhea) in one subject at 0.5 mg dose judged "not related" to study drug. | Ahmad et al. 2010 |
| | 1 | Single Dose | | 8 | | 10.7 | | |
| | 2 | Single Dose | | 8 | | 18.3 | | |
| | 4 | Single Dose | | 8 | | 40.1 | | |
| Endoxifen Citrate | 2 | 28 days | Metastatic Breast Cancer Patients | 6 | 504 | 66 | "Endoxifen was found to be safe up to 8 mg." | Ahmad et al. 2012 |
| | 4 | 28 days | | 6 | | 205 | | |
| | 8 | 28 days | | 6 | | 362 | | |
| Endoxifen Chloride | 20 | 2; 3 × 28 days | Aromatase Inhibitor Refractory Metastatic Breast Cancer | 2 | 140 | 390 | Gr 2 hot flash (1 patient; first cycle) | Goetz et al. 2013 |
| | 40 | 2; 6 × 28 days | | 2 | 224 | 660 | None; Stable disease (1) | |
| | 60 | 1; 2; 2; 5; 8; 14 × 28 days | | 6 | 896 | 1,010 | Gr 4 Triglycerides (1 pt); Gr 3 thromboembolic event (1 pt); Gr 2 hot flashes, anemia, and hypoalbuminemia | |
| | 80 | 2; 6; 10 × 28 days | | 3 | 504 | 1,610 | Gr 2 Hot flashes | |
| | 100 | 1; 2; 8 × 28 days | | 3 | 308 | 2,480 | Gr 2 nausea (1 pt); Gr 2 irritability (1 pt) | |
| | 120 | 1; 2; 4 × 28 days | | 3 | 196 | 2,180 | Gr 2 hypersomnia, paresthesia, and peripheral sensory neuropathy (1) | |

TABLE 20-continued

Summary of Clinical Studies with Orally Administered Endoxifen

| Compound | Dose mg/day | Regimen | Population | Patient Number | (Z)-Endoxifen Exposure (Patient-Days) | (Z)-Endoxifen Plasma (nM) | Outcomes | Source |
|---|---|---|---|---|---|---|---|---|
| Endoxifen Chloride | 20->160 | 45 months study duration | Aromatase Inhibitor Refractory Metastatic Breast Cancer | 41 | | 3,600 (160 dose) | This report is a continuation of study 3. A maximum tolerated dose was not observed. 1 DLT, a PE, observed at 60 mg in cycle 1. Partial response and stable disease noted in 10 patients. Total and LDL cholesterol decreased in about 50%. | Goetz et al. 2015 |
| Endoxifen Citrate | 4 and 8 | 21 days | Men and women with bipolar disease | 84 | 1764 | 46 and 93 | Nausea, headaches and insomnia in 10% | Ahmad et al 2016 |

Average concentration at steady state ($AUC_{tau}$/tau) were compared to published values.

TABLE 21

Comparison of Average Concentration at Steady State

| (Z)-Endoxifen Dose | Published Literature Result of Average Plasma (Z)-Endoxifen Css | | Study Result of Average Serum (Z)-Endoxifen Css | | % Ratio of Css Study (serum)/ Literature (plasma) |
|---|---|---|---|---|---|
| | ng/mL | nM | ng/mL | nM | |
| 1 mg | 12.4 | 33.1 | 19.1 | 51.1 | 154% |
| 2 mg | 18.6 | 49.8 | 38 | 101.7 | 204% |
| 4 mg | 56.8 | 152.1 | 85.1 | 227.9 | 150% |
| 8 mg | 96.8 | 259.2 | — | — | — |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A sustained release composition comprising a core tablet coated with an enteric coating, wherein the core tablet comprises:
    a therapeutic agent comprising (Z)-endoxifen,
    a sustained release agent comprising not less than 16% and not more than 60% hydroxypropyl methylcellulose by weight relative to total core tablet weight, and
    a hardness of not less than 10 kilopond (Kp) and not more than 16 Kp; and
    wherein the enteric coating comprises a delayed release agent.

2. The sustained release composition of claim 1, wherein the therapeutic agent comprises at least 90% (Z)-endoxifen by weight relative to total therapeutic agent weight.

3. The sustained release composition of claim 1, wherein the core tablet comprises not less than 1% and not more than 40% therapeutic agent by weight relative to total core tablet weight.

4. The sustained release composition of claim 1, wherein the sustained release agent further comprises an hydroxyalkyl cellulose, a cellulosic ether, a gum, an acrylic resin, or a combination thereof.

5. The sustained release composition of claim 4, wherein the hydroxyalkyl cellulose comprises hydroxymethyl cellulose, hydroxyethyl cellulose, or hydroxypropyl cellulose.

6. The sustained release composition of claim 1, wherein the core tablet comprises not less than 20% and not more than 40%, not less than 20% and not more than 50%, or not less than 20% or not more than 60% of sustained release agent by weight relative to total core tablet weight.

7. The sustained release composition of claim 1, wherein the core tablet further comprises a binding agent.

8. The sustained release composition of claim 7, wherein the core tablet comprises not less than 30% and not more than 97%, or not less than 40% and not more than 75% of the binding agent by weight relative to total core tablet weight.

9. The sustained release composition of claim 7, wherein the binding agent comprises a monosaccharide, a disaccharide, a starch, a polyhydric alcohol, mannitol, xylitol, sorbitol, lactose, a polyethylene glycol, a gum, alginic acid, polyvinyl pyrrolidone, methyl cellulose, hydroxypropyl methyl cellulose, crystalline cellulose, microcrystalline cellulose, silicified microcrystalline cellulose, calcium carbonate, calcium phosphate, sodium carbonate, sodium phosphate, anhydrous dibasic calcium phosphate, talc, a dextrate, kaolin, silicic acid, or a combination thereof.

10. The sustained release composition of claim 9, wherein the core tablet comprises not less than 10% and not more than 90% microcrystalline cellulose by weight relative to total core tablet weight.

11. The sustained release composition of claim 1, wherein the core tablet further comprises a lubricant.

12. The sustained release composition of claim 11, wherein the lubricant comprises stearic acid, calcium stearate, magnesium stearate, zinc stearate, potassium stearate, hydrogenated vegetable oil, mineral oil, light mineral oil, glycerin, sorbitol, mannitol, a glycol, polyethylene glycol, sodium lauryl sulfate, magnesium lauryl sulfate, talc, ethyl oleate, ethyl laureate, agar, waxes, or a combination thereof.

13. The sustained release composition of claim 12, wherein the core tablet comprises not less than 0.01% and not more than 5% magnesium stearate by weight relative to total core tablet weight.

14. The sustained release composition of claim 1, wherein the delayed release agent comprises a poly(meth)acrylate polymer.

15. The sustained release composition of claim 14, wherein the enteric coating comprises not less than 60% and not more than 80% of the poly(meth)acrylate polymer by weight relative to total enteric coating weight.

16. The sustained release composition of claim 1, wherein the enteric coating further comprises a plasticizer.

17. The sustained release composition of claim 16, wherein the plasticizer comprises triethyl citrate.

18. The sustained release composition of claim 17, wherein the enteric coating comprises not less than 0.01% and not more than 5% triethyl citrate by weight relative to total enteric coating weight.

19. The sustained release composition of claim 1, wherein the enteric coating further comprises an anti-adherent agent.

20. The sustained release composition of claim 19, wherein the anti-adherent agent comprises talc.

21. The sustained release composition of claim 20, wherein the enteric coating comprises not less than 1% and not more than 40% talc by weight relative to total enteric coating weight.

22. The sustained release composition of claim 1, wherein the enteric coating constitutes not less than 5% and not more than 30%, not less than 5% and not more than 25%, or not less than 5% and not more than 20% by weight of total sustained release composition weight.

23. The sustained release composition of claim 1, wherein the (Z)-endoxifen comprises a (Z)-endoxifen free base, a polymorph of (Z)-endoxifen, a salt of (Z)-endoxifen, or a combination thereof.

24. The sustained release composition of claim 1, wherein the therapeutic agent has a percentage dissolution of less than 20% at 2 hours, less than 40% at 7 hours, at least 30% at 12 hours, or combinations thereof, as measured at 37° C. in simulated gastric fluid at pH 1.2 from hours 0 to 2 and in simulated intestinal fluid at pH 6.8 after 2 hours.

25. The sustained release composition of claim 1, wherein the therapeutic agent has percentage dissolution of less than 35% at 3 hours, at least 50% at 24 hours, or both.

26. The sustained release composition of claim 1, wherein at least 90%, at least 95%, or at least 99% by weight of the therapeutic agent is polymorphic Form I of (Z)-endoxifen polymorphic Form I is characterized by an x-ray powder diffraction pattern comprising major peaks at 16.8±0.3°, 17.1±0.3° and 21.8±0.3° two theta.

27. The sustained release composition of claim 26, wherein polymorphic Form I is characterized by an x-ray powder diffraction pattern further comprising at least one peak selected from 12.3±0.3°, 16.0±0.3°, 18.8±0.3°, 26.5±0.3°, 28.0±0.3° and 29.0±0.3° two theta.

28. A method of treating a disorder in a subject in need thereof, wherein the subject has the disorder or is at risk of having the disorder, the method comprising orally administering to the subject a sustained release composition comprising a core tablet coated with an enteric coating, wherein the core tablet comprises:

a therapeutic agent comprising (Z)-endoxifen, a sustained release agent comprising hydroxypropyl methylcellulose, and a hardness of not less than 10 kilopond (Kp) and not more than 16 Kp; and wherein:

the enteric coating comprises a delayed release agent, and the sustained release composition shows a percentage dissolution ranging from no less than 35% and no more than 55% at 12 hours in a dissolution test according to a 75 RPM USP paddle method and using pH 1.2 at 37° C. for 2 hours in simulated gastric fluid and pH 6.8 at 37° C. for 24 hours in simulated intestinal fluid as a test medium.

29. The method of claim 28, wherein the disorder is a breast disorder, a benign breast disorder, hyperplasia, atypia, atypical ductal hyperplasia, atypical lobular hyperplasia, increased breast density, gynecomastia, ductal carcinoma in situ, lobular carcinoma in situ, breast cancer, precocious puberty, or McCune-Albright Syndrome.

30. The sustained release composition of claim 23, wherein the salt of (Z)-endoxifen comprises acetate, arecoline, benzathine, benzoic, besylate, benzosulfonate, bicarbonate, bitartarate, butylbromide, citrate, camysylate, clemizole, chloroprocaine, choline, diethylamine, diethanolamine, ethylenediamine, formate, fumarate, gluconate, gluconate, glutamate, glycollylarsanilate, hexylresorcinate, hydrabamine, hydrobromide, hydrochloride, hydroxynapthanoate, isethionate, malate, maleate, mandelate, meglumine, mesylate, methylbromide, methylbromide, methylnitrate, methylsulfate, methanesulfonate, mucate, napsylate, nitric, nitrate, oxalate, pamaoate (Embonate), pantothenate, perchloric, phosphate, diphosphate, piperazine, procaine, polygalacuronate, p-toluenesulfonate, salicylate, stearate, succinate, sulfate, sulfonate, sulfuric, tannate, tartarate, teoclate, triethiodide, trifluoroacetate, aluminum, barium, bismuth, lithium, magnesium, potassium, and zinc aluminum, barium, bismuth, lithium, magnesium, potassium, and zinc, or any combination thereof.

31. The sustained release composition of claim 1, wherein the core tablet comprises:

a therapeutic agent comprising not less than 1% and not more than 40% of at least 90% (Z)-endoxifen by weight relative to total core tablet weight, a sustained release agent comprising not less than 16% and not more than 60% of hydroxypropyl methylcellulose by weight relative to total core tablet weight, not less than 10% and not more than 90% microcrystalline cellulose by weight relative to total core tablet weight,
not less than 0.01% and not more than 5% magnesium stearate by weight relative to total core tablet weight, and
a hardness of not less than 10 kilopond (Kp) and not more than 16 Kp.

* * * * *